United States Patent
Hux et al.

(10) Patent No.: US 10,745,665 B2
(45) Date of Patent: Aug. 18, 2020

(54) NUCLEIC ACID MOLECULES ENCODING AN ENGINEERED ANTIGEN RECEPTOR AND AN INHIBITORY NUCLEIC ACID MOLECULE AND METHODS OF USE THEREOF

(71) Applicant: Precision Biosciences, Inc., Durham, NC (US)

(72) Inventors: Joann Hux, Scotland Neck, NC (US); Aaron Martin, Carrboro, NC (US); Derek Jantz, Durham, NC (US); Clayton Beard, Durham, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 16/678,600

(22) Filed: Nov. 8, 2019

(65) Prior Publication Data

US 2020/0063102 A1 Feb. 27, 2020

Related U.S. Application Data

(63) Continuation of application No. PCT/US2018/031674, filed on May 8, 2018.

(60) Provisional application No. 62/579,460, filed on Oct. 31, 2017, provisional application No. 62/503,060, filed on May 8, 2017.

(51) Int. Cl.
| | |
|---|---|
| *C12N 5/0783* | (2010.01) |
| *C07K 14/725* | (2006.01) |
| *C07K 14/74* | (2006.01) |
| *C07K 16/28* | (2006.01) |
| *C12N 15/113* | (2010.01) |

(52) U.S. Cl.
CPC ........ *C12N 5/0636* (2013.01); *C07K 14/7051* (2013.01); *C07K 14/70539* (2013.01); *C07K 16/2803* (2013.01); *C12N 15/1138* (2013.01); *C07K 2319/00* (2013.01); *C12N 2310/14* (2013.01); *C12N 2310/531* (2013.01)

(58) Field of Classification Search
None
See application file for complete search history.

(56) References Cited

U.S. PATENT DOCUMENTS

2007/0036773 A1 2/2007 Cooper et al.

FOREIGN PATENT DOCUMENTS

| WO | WO 2016/069283 A1 | 5/2016 |
|---|---|---|
| WO | WO 2016/196388 A1 | 12/2016 |
| WO | WO 2017/062451 A1 | 4/2017 |
| WO | WO 2017/112859 A1 | 6/2017 |

OTHER PUBLICATIONS

Hu et al (J. Virol. 84(22): 11981-11993, 2010) (Year: 2010).*
https://www.proteinatlas.org/ENSG00000166710-B2M/tissue, downloaded on Jan. 13, 2020 (Year: 2020).*
Iglesias et al. (Retrovirology 2011, 8:92) (Year: 2011).*
Eyquem, J., et al., "Targeting a CAR to the TRAC locus with CRISPR/Cas9 enhances tumour rejection," *Nature*, 2017, vol. 543(7643), pp. 113-117.
Poirot, L., et al., "Multiplex Genome-Edited T-cell Manufacturing Platform for "Off-the-Shelf" Adoptive T-cell Immunotherapies," *Cancer Research*, 2015, vol. 75(18), pp. 3853-3864.
Ren, J., et al., "Multiplex Genome Editing to Generate Universal CAR T Cells Resistant to PD1 Inhibition," *Clinical Cancer Research*, 2016, vol. 23(9), pp. 2255-2266.

* cited by examiner

*Primary Examiner* — Richard A Schnizer
(74) *Attorney, Agent, or Firm* — Womble Bond Dickinson (US) LLP

(57) ABSTRACT

The present disclosure provides nucleic acid molecules encoding an engineered antigen receptor, such as a chimeric antigen receptor or exogenous T cell receptor, and an inhibitory nucleic acid molecule, such as an RNA interference molecule. The present disclosure further relates to nucleic acids, DNA constructs, vectors, pharmaceutical compositions, genetically-modified cells, and methods of treatment that utilize the nucleic acid molecules of the invention.

2 Claims, 37 Drawing Sheets

Specification includes a Sequence Listing.

B2m+ T cells

B2m+ T cells 0.5:1

0:1

FIGURE 2E B2m- T cells
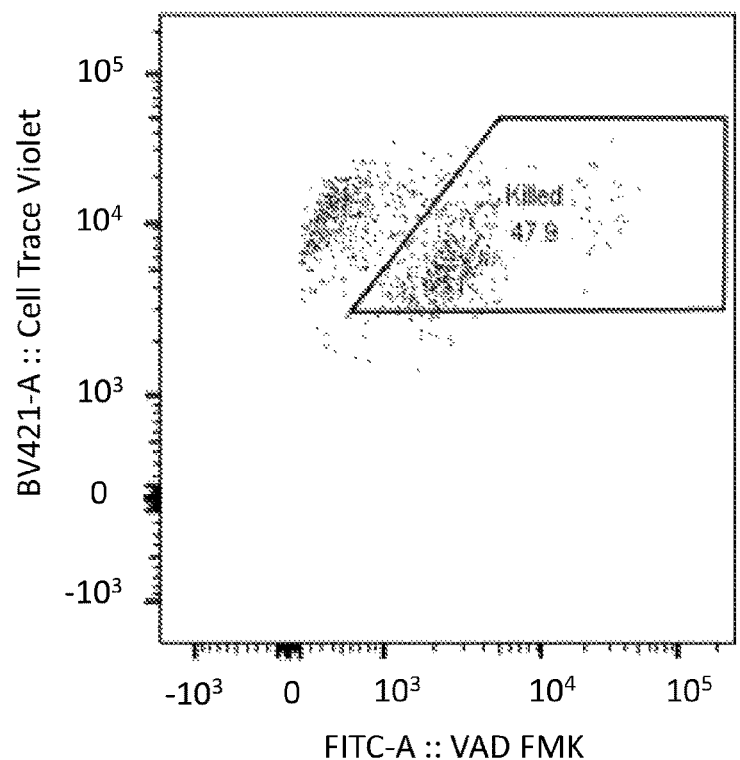
FIGURE 2F
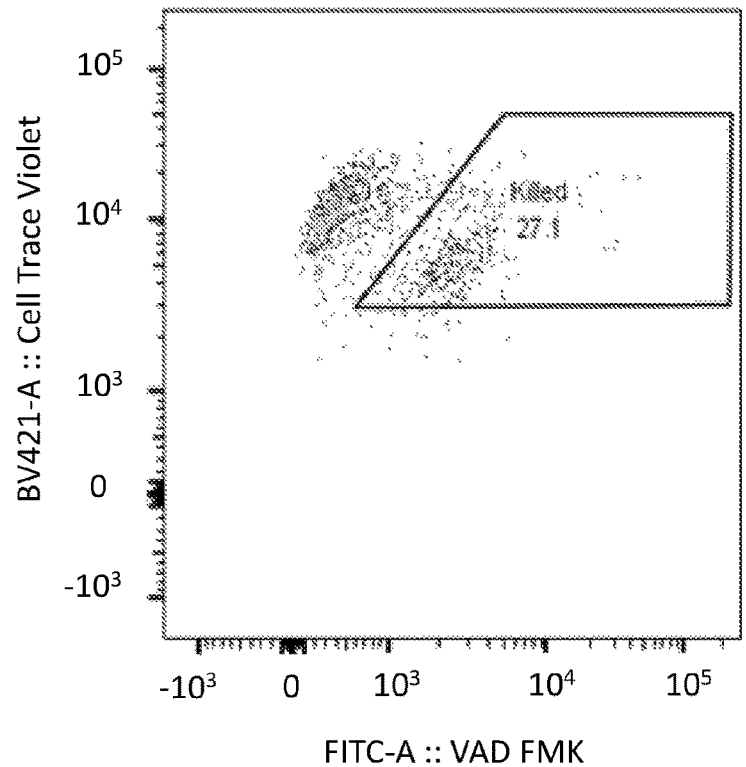

FIGURE 2G <u>B2m- T cells</u>
0.5:1
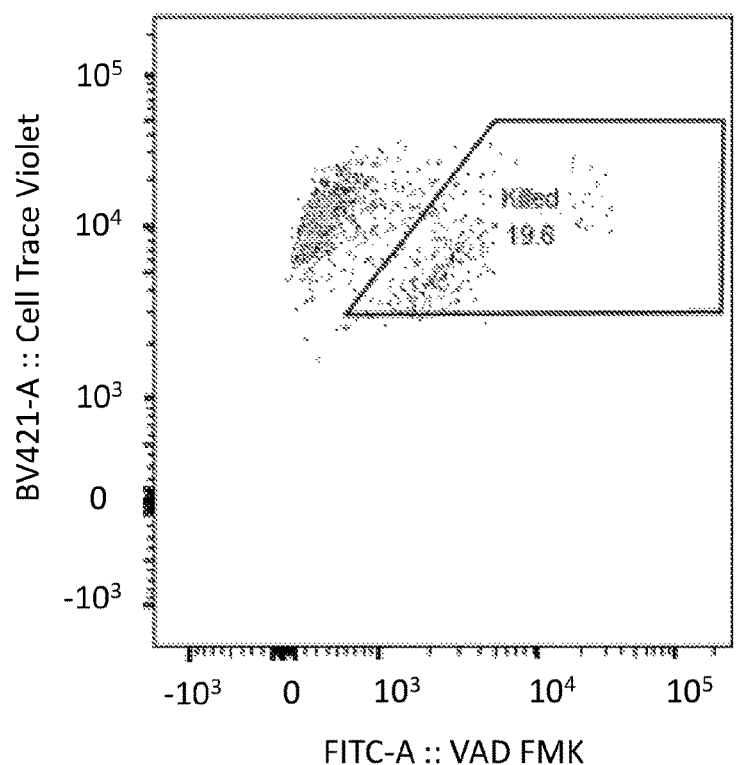
FIGURE 2H   0:1
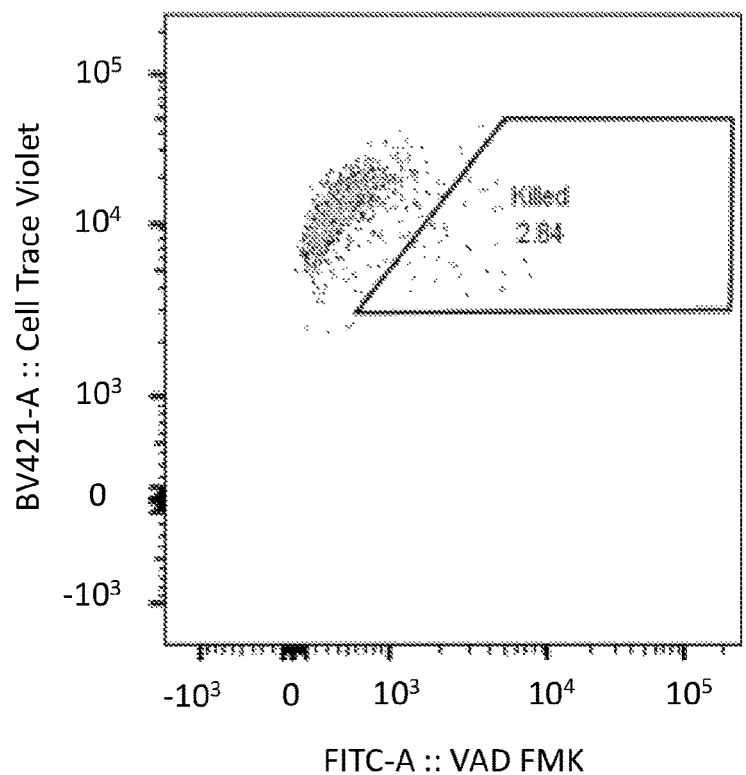

FIGURE 2I  Daudi Class I Neg
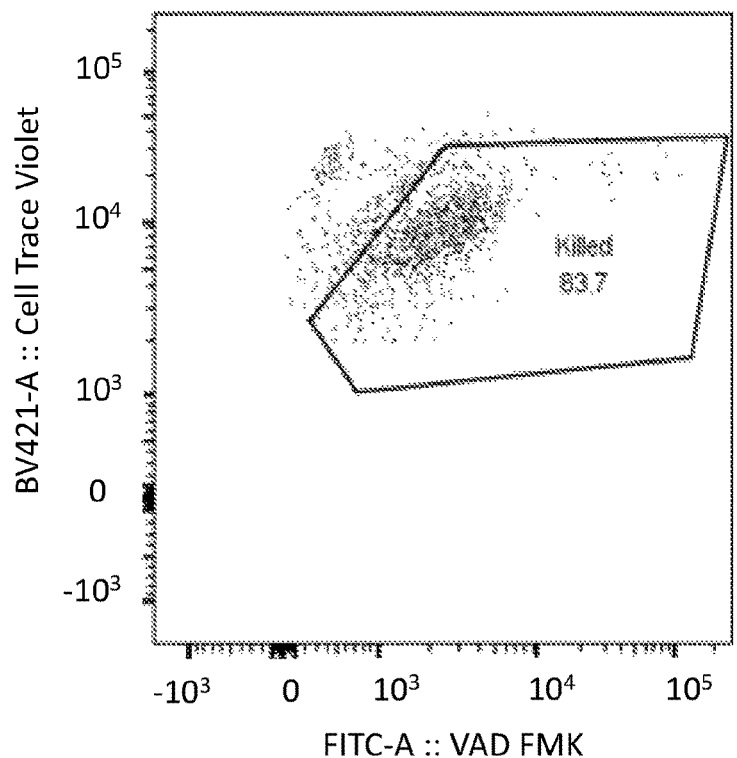
FIGURE 2J
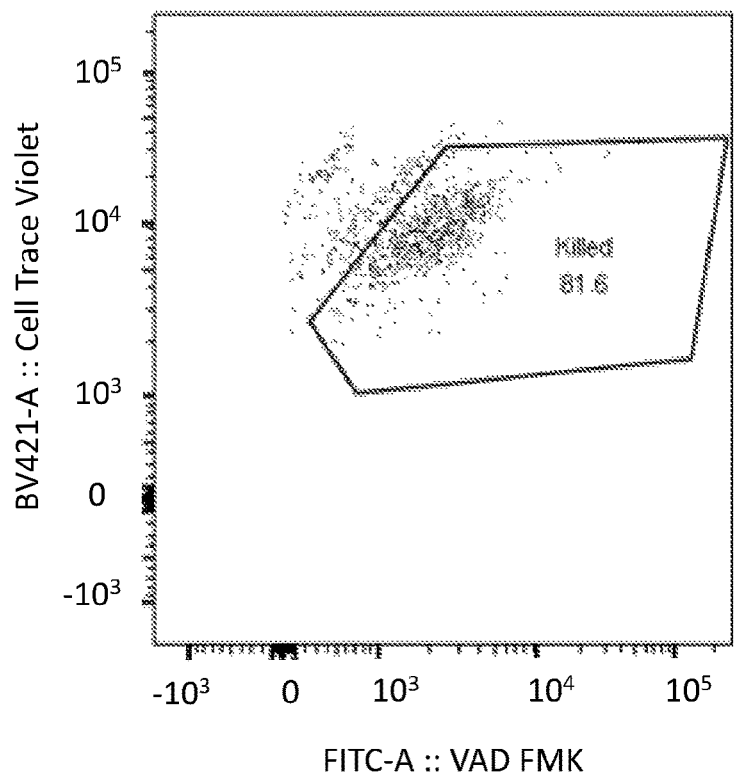

FIGURE 2K  Daudi Class I Neg
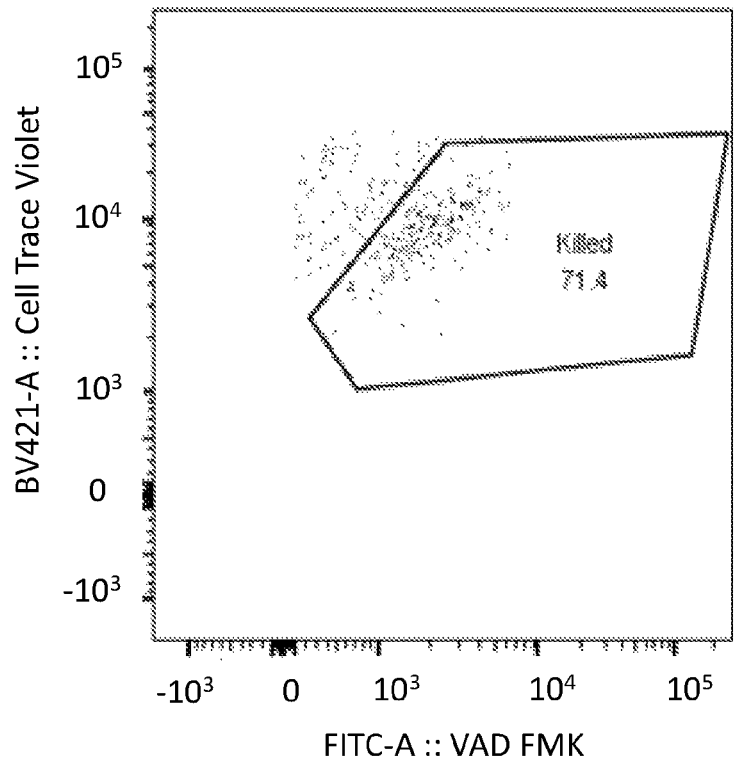
FIGURE 2L
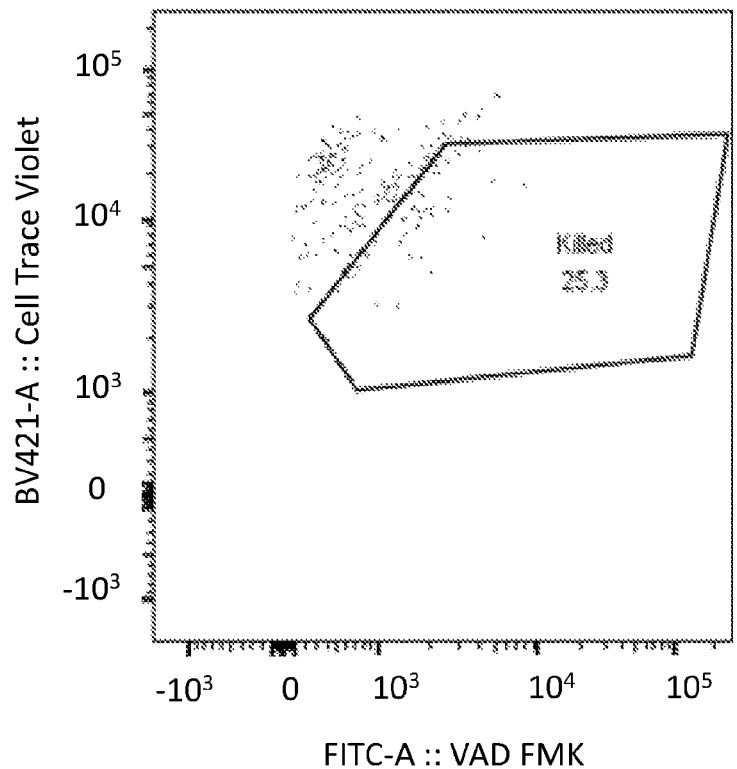

FIGURE 5A K562
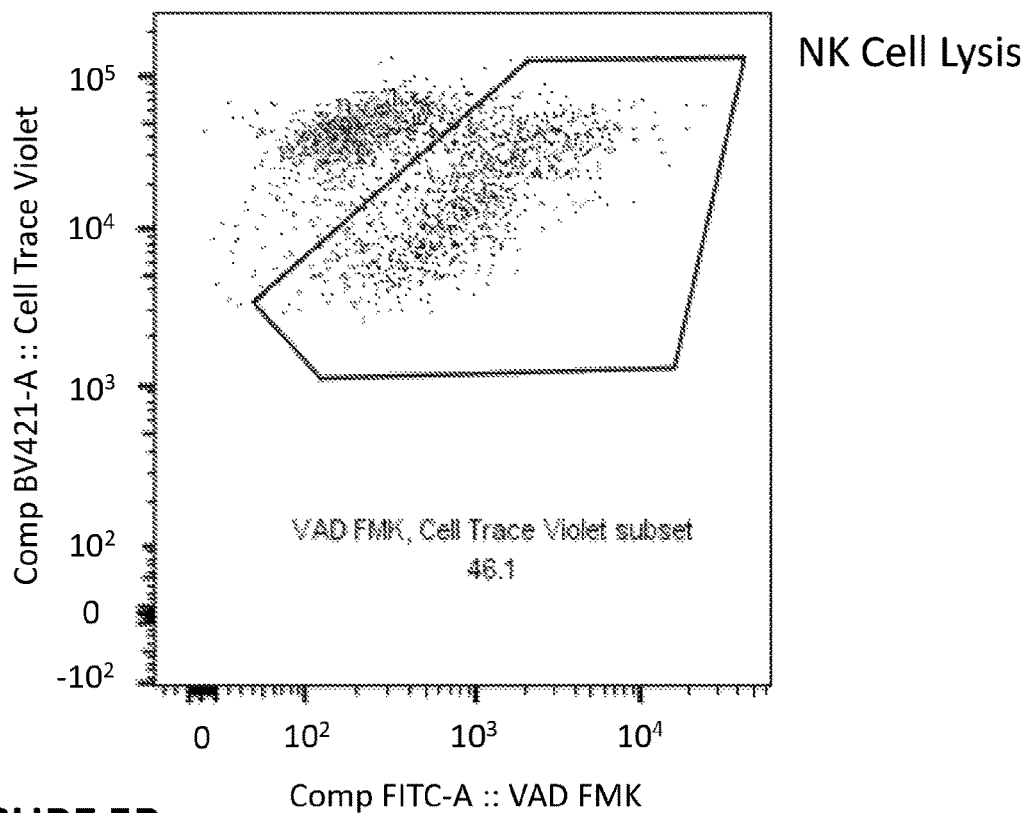
NK Cell Lysis
FIGURE 5B
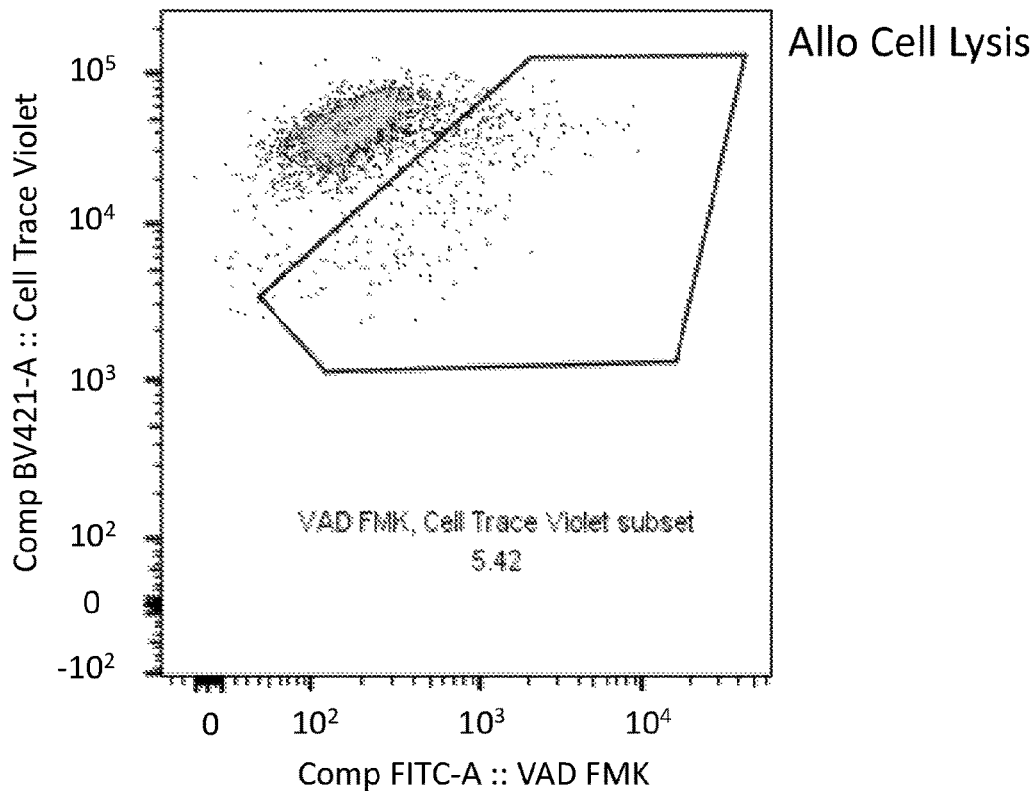
Allo Cell Lysis

FIGURE 5C <u>Mock T cells</u>
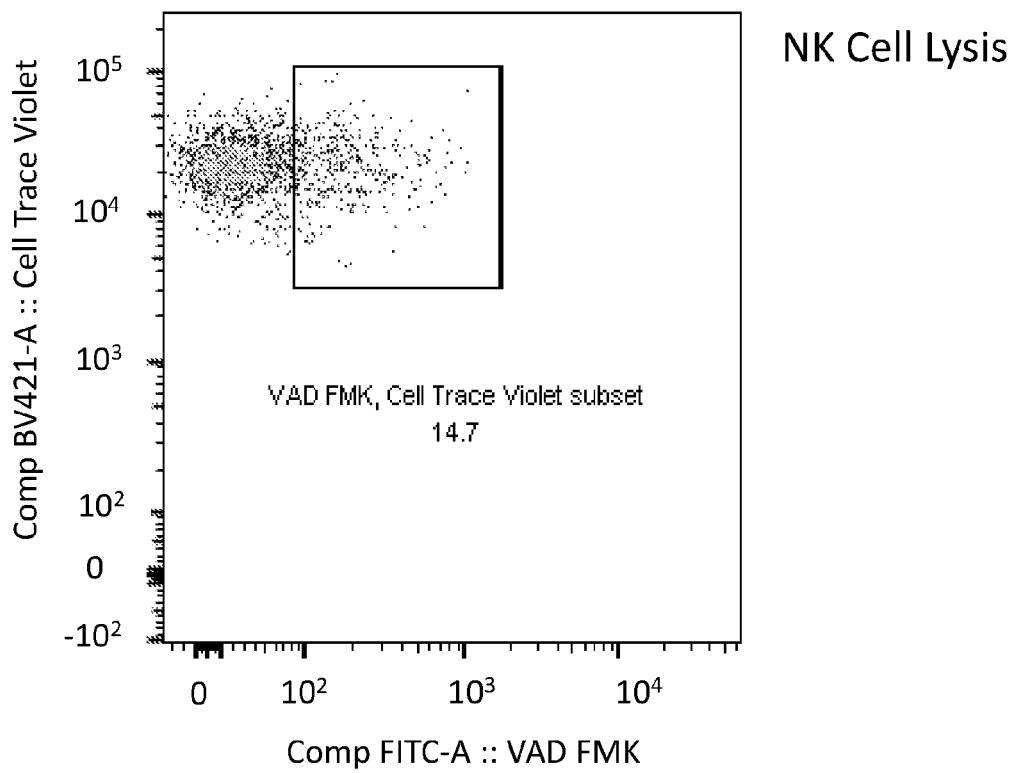
NK Cell Lysis
FIGURE 5D
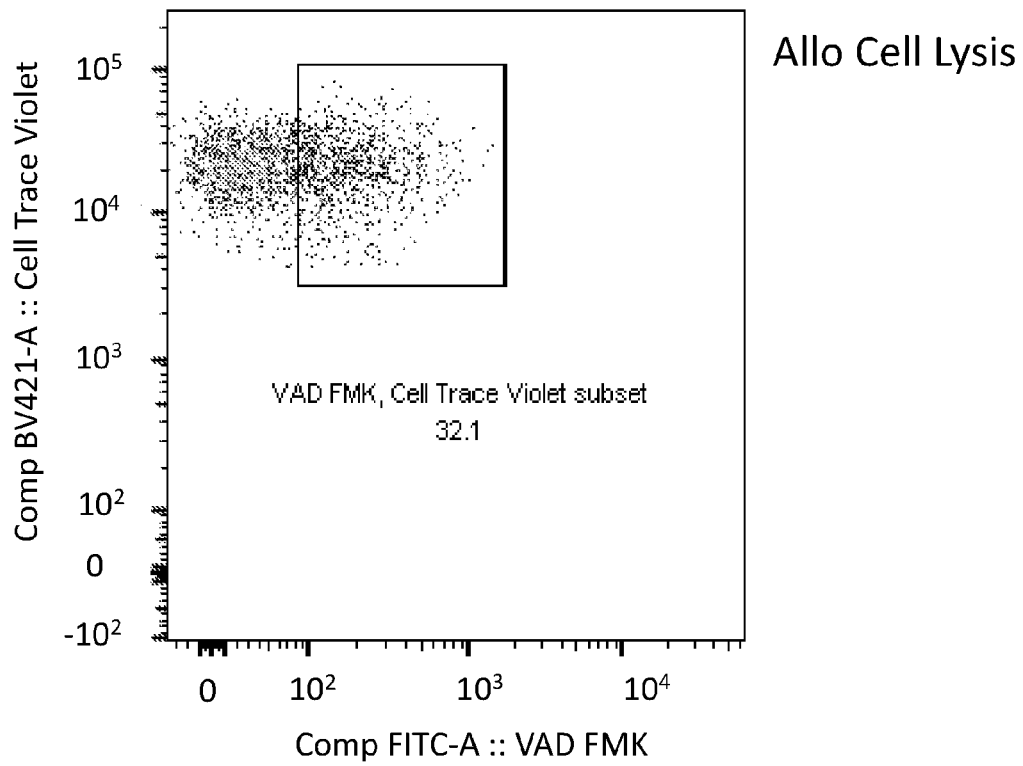
Allo Cell Lysis

FIGURE 6A B2M shRNA 254
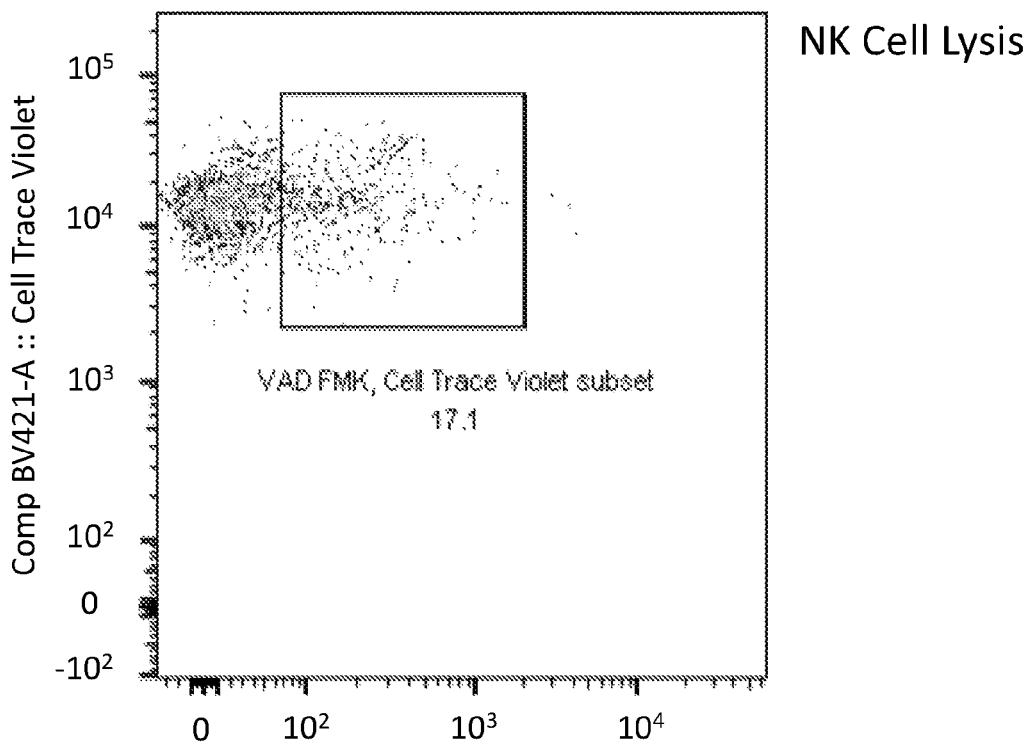
NK Cell Lysis
FIGURE 6B
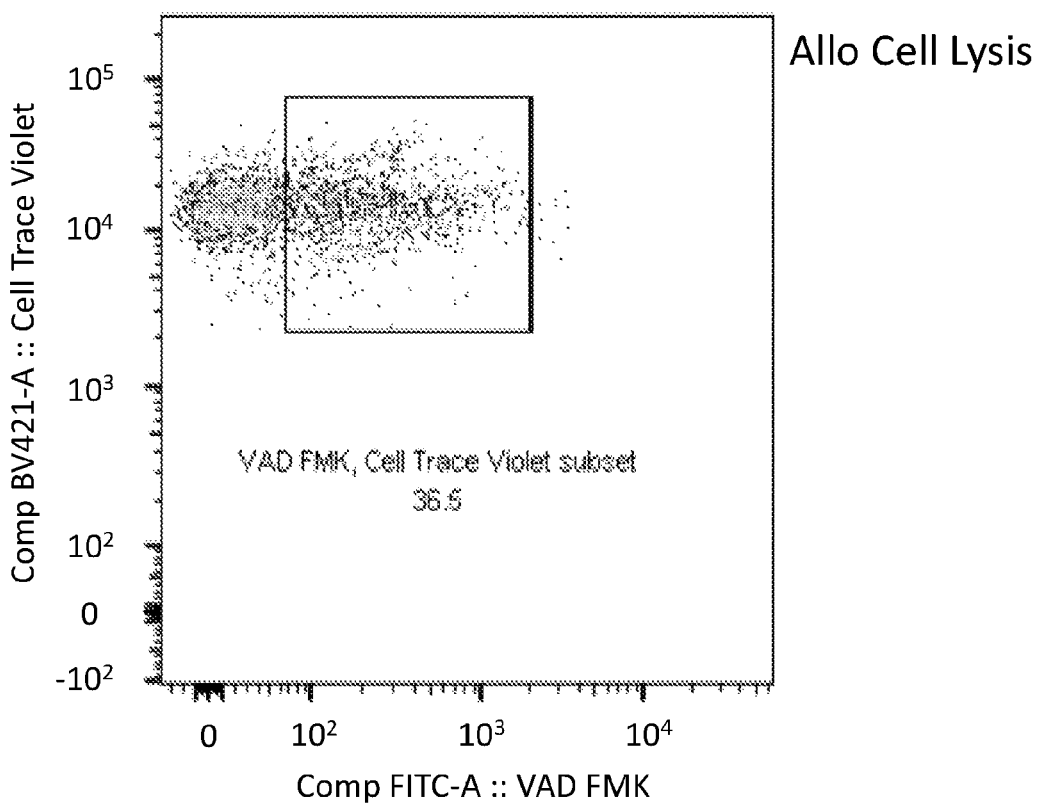
Allo Cell Lysis

FIGURE 6C B2M shRNA 472
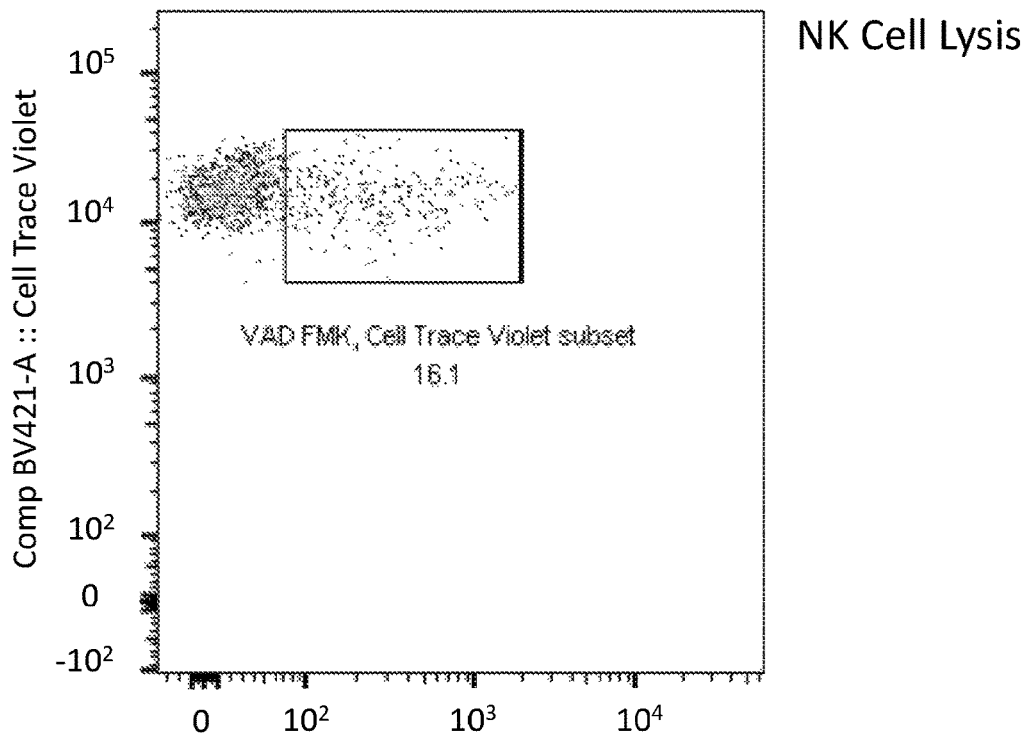
NK Cell Lysis
FIGURE 6D
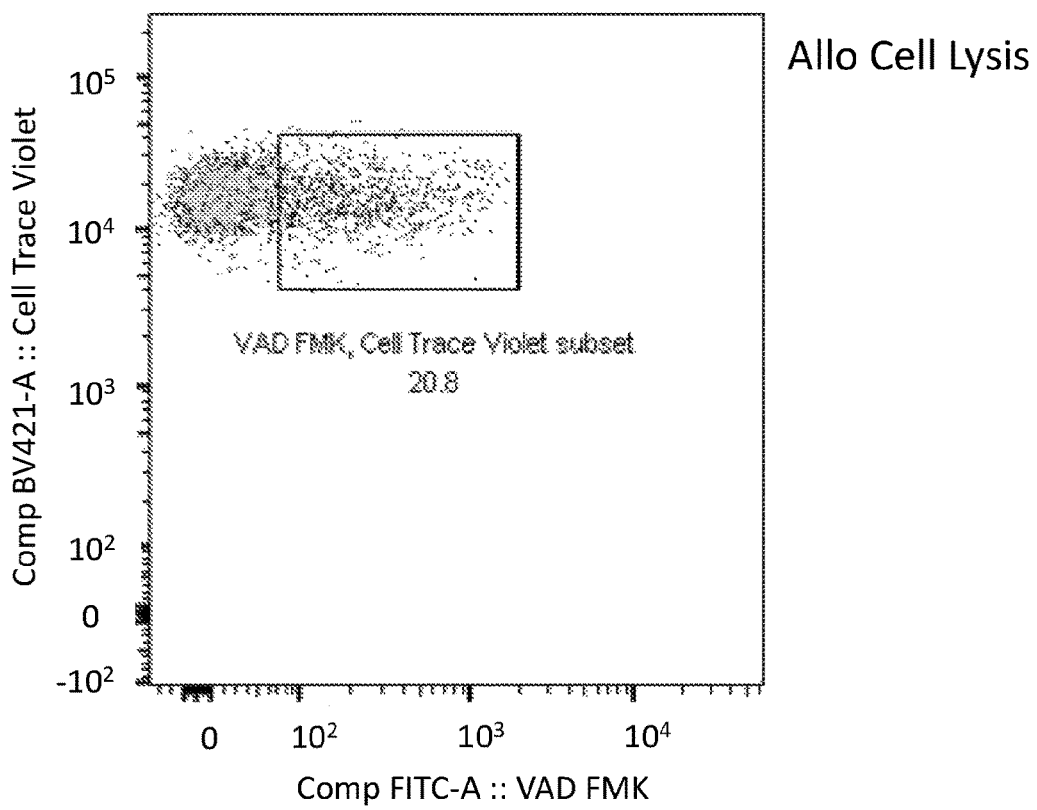
Allo Cell Lysis FL9-A :: B2m R660-APC-A FL9-A :: B2m R660-APC-A shRNA vs no shRNA CAR+ vs CAR- reference

| Subset Name | Mean : FL9-A | Mean : FL13-A |
|---|---|---|
| no shRNA | 6.99E5 | 77582 |
| no edits | 4.66E5 | 39276 |
| KO KI | 41249 | 3699 |

NUCLEIC ACID MOLECULES ENCODING AN ENGINEERED ANTIGEN RECEPTOR AND AN INHIBITORY NUCLEIC ACID MOLECULE AND METHODS OF USE THEREOF

CROSS-REFERENCE TO RELATED APPLICATIONS

This application is a Continuation of PCT/US2018/031674 filed May 8, 2018, which International Application was published by the International Bureau in English on Nov. 15, 2018, and application claims priority from U.S. Provisional Patent Application No. 62/503,060, filed May 8, 2017, and U.S. Provisional Patent Application No. 62/579,460, filed Oct. 31, 2017, which applications are hereby incorporated in their entirety by reference in this application.

FIELD OF THE INVENTION

The present disclosure relates to the field of molecular biology and recombinant nucleic acid technology. In particular, the present disclosure relates to nucleic acid molecules encoding an engineered antigen receptor, such as a chimeric antigen receptor or exogenous T cell receptor, and an inhibitory nucleic acid molecule, such as an RNA interference molecule. The present disclosure further relates to nucleic acids, DNA constructs, viral vectors, pharmaceutical compositions, genetically-modified cells, and methods of treatment that utilize the nucleic acid molecule of the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 8, 2019, is named P89339_1050US_C1_Seq_List, and is 188580 bytes in size.

BACKGROUND OF THE INVENTION

T cell adoptive immunotherapy is a promising approach for cancer treatment. This strategy utilizes isolated human T cells that have been genetically-modified to enhance their specificity for a specific tumor associated antigen. Genetic modification may involve the expression of a chimeric antigen receptor (CAR) or an exogenous T cell receptor to graft antigen specificity onto the T cell. By contrast to exogenous T cell receptors, CARs derive their specificity from the variable domains of a monoclonal antibody. Thus, T cells expressing CARs induce tumor immunoreactivity in a major histocompatibility complex (MHC) non-restricted manner. To date, T cell adoptive immunotherapy has been utilized as a clinical therapy for a number of cancers, including B cell malignancies (e.g., acute lymphoblastic leukemia (ALL), B cell non-Hodgkin lymphoma (NHL), and chronic lymphocytic leukemia), multiple myeloma, neuroblastoma, glioblastoma, advanced gliomas, ovarian cancer, mesothelioma, melanoma, and pancreatic cancer.

Despite its potential usefulness as a cancer treatment, adoptive immunotherapy has been limited, in part, by alloreactivity between host tissues and allogeneic CAR T cells. One cause of alloreactivity arises from the presence of non-host MHC class I molecules on the cell surface of CAR T cells. MHC class I molecules consist of two polypeptide chains, α and β. In humans, the α chain consists of three subunits, α1, α2, and α3, which are encoded by polymorphic human leukocyte antigen (HLA) genes on chromosome 6. The variability of HLA loci, and the encoded α chain subunits, can cause allogeneic CAR T cells to be seen by the host immune system as foreign cells because they bear foreign MHC class I molecules. As a result, CAR T cells administered to a patient can be subject to host versus graft (HvG) rejection, where they are recognized and killed by the host's cytotoxic T cells.

The β chain of MHC class I molecules consists of beta-2 microglobulin, which is encoded by the non-polymorphic beta-2 microglobulin (B2M) gene on chromosome 15 (SEQ ID NO: 1). Beta-2 microglobulin is non-covalently linked to the α3 subunit and is common to all MHC class I molecules. Furthermore, expression of MHC class I molecules at the cell surface requires its association with beta-2 microglobulin. As such, beta-2 microglobulin represents a logical target for suppressing the expression of MHC class I molecules on CAR T cells, which could render the cells invisible to host cytotoxic T cells and reduce alloreactivity. However, complete knockout of beta-2 microglobulin expression may result in NK cell killing of CAR T cells due to the lack of cell surface MHC class I molecules, which could prompt NK cells to recognize them as non-self and initiate cytotoxic action.

Another cause of alloreactivity to CAR T cells is the expression of the endogenous T cell receptor on the cell surface. T cell receptors typically consist of variable α and β chains or, in smaller numbers, variable γ and δ chains. The T cell receptor complexes with accessory proteins, including CD3, and functions with cell surface co-receptors (e.g., CD4 and CD8) to recognize antigens bound to MHC molecules on antigen presenting cells. In the case of allogeneic CAR T cells, expression of endogenous T cell receptors may cause the cell to recognize host MHC antigens following administration to a patient, which can lead to the development of graft-versus-host-disease (GVHD).

To forestall alloreactivity, clinical trials have largely focused on the use of autologous CAR T cells, wherein a donor's T cells are isolated, genetically-modified to incorporate a chimeric antigen receptor, and then re-infused into the same subject. An autologous approach provides immune tolerance to the administered CAR T cells; however, this approach is constrained by both the time and expense necessary to produce patient-specific CAR T cells after a patient's cancer has been diagnosed.

Thus, a need exists in the art for the development of allogeneic CAR T cells which exhibit reduced allogenicity but, at the same time, avoid NK cell killing in vivo.

SUMMARY OF THE INVENTION

In one aspect, the invention provides a nucleic acid molecule comprising: (a) a first expression cassette comprising a nucleic acid sequence encoding an engineered antigen receptor; (b) a second expression cassette comprising a nucleic acid sequence encoding an inhibitory nucleic acid molecule; (c) a 5' homology arm; and (d) a 3' homology arm; wherein the 5' homology arm and the 3' homology arm have homology to chromosomal regions flanking a nuclease recognition sequence in a gene of interest.

In some embodiments, the inhibitory nucleic acid molecule is an RNA interference molecule. In certain embodiments, the RNA interference molecule is a short hairpin RNA (shRNA), a small interfering RNA (siRNA), a hairpin siRNA, a microRNA (miRNA), a precursor miRNA, or an miRNA-adapted shRNA. In particular embodiments, the RNA interference molecule is an shRNA.

In some embodiments the engineered antigen receptor is a chimeric antigen receptor. In other embodiments, the engineered antigen receptor is an exogenous T cell receptor.

In some embodiments, the nuclease recognition sequence is an engineered meganuclease recognition sequence, a TALEN recognition sequence, a zinc finger nuclease (ZFN) recognition sequence, a CRISPR/Cas recognition sequence, a compact TALEN recognition sequence, or a megaTAL recognition sequence. In certain embodiments, the nuclease recognition sequence is an engineered meganuclease recognition sequence.

In some embodiments, the gene of interest is any gene of interest. In certain embodiments, the gene of interest is a human T cell receptor alpha constant region gene. In particular embodiments the nuclease recognition sequence is an engineered meganuclease recognition sequence. In certain embodiments, the engineered meganuclease recognition sequence comprises SEQ ID NO: 1 in a human T cell receptor alpha constant region gene.

In some embodiments, the first expression cassette further comprises a promoter which drives expression of the engineered antigen receptor. In certain embodiments, the promoter is a JeT promoter.

In some embodiments, the second expression cassette further comprises a promoter which drives expression of the inhibitory nucleic acid molecule. In certain embodiments, the promoter is a U6 promoter.

In some embodiments, the first expression cassette comprises a polyadenylation signal to terminate translation of the engineered antigen receptor. In some embodiments, the second expression cassette comprises a central polypurine tract and central terminator sequence (cPPT/CTS) sequence to terminate translation of the inhibitory nucleic acid.

In some embodiments, the first expression cassette and the second expression cassette are in the same orientation in the nucleic acid molecule. In certain embodiments, the first expression cassette and the second expression cassette are in a 5' to 3' orientation relative to the 5' and 3' homology arms. In some such embodiments, the first expression cassette is 5' upstream of the second expression cassette. In other such embodiments, the second expression cassette is 5' upstream of the first expression cassette.

In some embodiments, wherein the first expression cassette and the second expression cassette are in the same orientation in the nucleic acid molecule, the first expression cassette and the second expression cassette are in a 3' to 5' orientation relative to the 5' and 3' homology arms. In some such embodiments, the first expression cassette is 5' upstream of the second expression cassette. In other such embodiments, the second expression cassette is 5' upstream of the first expression cassette.

In some embodiments, the first expression cassette and the second expression cassette are in opposite orientations in the nucleic acid molecule. In some such embodiments, the first expression cassette is in a 3' to 5' orientation and the second expression cassette is in a 5' to 3' orientation relative to the 5' and 3' homology arms. In certain embodiments, the first expression cassette is 5' upstream of the second expression cassette. In other embodiments, the second expression cassette is 5' upstream of the first expression cassette.

In particular embodiments, wherein the first expression cassette and the second expression cassette are in opposite orientations in the nucleic acid molecule, the first expression cassette is in a 5' to 3' orientation and the second expression cassette is in a 3' to 5' orientation relative to the 5' and 3' homology arms. In some such embodiments, the first expression cassette is 5' upstream of the second expression cassette. In other such embodiments, the second expression cassette is 5' upstream of the first expression cassette.

In some embodiments, the nucleic acid molecule comprises multiple copies of the second expression cassette. In some such embodiments, the copies are identical. In further embodiments, the copies include a promoter, a coding sequence for the inhibitory nucleic acid molecule, and a sequence, such as a (cPPT/CTS) sequence, to terminate translation of the inhibitory nucleic acid molecule. In some such embodiments, the copies of the second expression cassette are in tandem in the nucleic acid molecule, and can be in the same orientation, or in opposite orientations. In other such embodiments, the copies may not be in tandem, and can be in the same orientation, or in opposite orientations.

In some embodiments, the nucleic acid molecule further comprises a 5' inverted terminal repeat and a 3' inverted terminal repeat flanking the first expression cassette and the second expression cassette.

In some embodiments, the inhibitory nucleic acid molecule is inhibitory against human beta-2 microglobulin.

In some embodiments, the inhibitory nucleic acid molecule is inhibitory against a component of the MHC class I molecule. In certain embodiments, the inhibitory molecule is inhibitory against an MHC class I alpha-1 ($\alpha$1) domain, alpha-2 ($\alpha$2) domain, alpha-3 ($\alpha$3) domain, or against beta-2 microglobulin.

In some embodiments, the inhibitory nucleic acid molecule is inhibitory against human CD52.

In certain embodiments, the inhibitory nucleic acid molecule is an shRNA inhibitory against beta-2 microglobulin, wherein the shRNA has a sequence comprising any one of SEQ ID NOs: 2-4. In particular embodiments, the shRNA has a sequence comprising SEQ ID NO: 2. In some such embodiments, the first expression cassette and the second expression cassette are in a 3' to 5' orientation relative to the 5' and 3' homology arms, and wherein the first expression cassette is 5' upstream of the second expression cassette. In some such embodiments, the first expression cassette comprises: (i) a nucleic acid sequence encoding a chimeric antigen receptor or an exogenous T cell receptor; (ii) a JeT promoter which drives expression of the chimeric antigen receptor or the exogenous T cell receptor; and (iii) a polyA sequence; and the second expression cassette comprises: (iv) a nucleic acid sequence encoding the shRNA; (v) a U6 promoter which drives expression of the shRNA; and (vi) a central polypurine tract and central terminator sequence (cPPT/CTS) sequence.

In certain embodiments, the inhibitory nucleic acid molecule is an shRNA inhibitory against beta-2 microglobulin, wherein the shRNA has a sequence comprising any one of SEQ ID NOs: 2-4. In particular embodiments, the shRNA has a sequence comprising SEQ ID NO: 2. In some such embodiments, the first expression cassette is in a 3' to 5' orientation and the second expression cassette is in a 5' to 3' orientation relative to the 5' and 3' homology arms, and the first expression cassette is 5' upstream of the second expression cassette. In some such embodiments, the first expression cassette comprises: (i) a nucleic acid sequence encoding a chimeric antigen receptor or an exogenous T cell receptor; (ii) a JeT promoter which drives expression of the chimeric antigen receptor or the exogenous T cell receptor; and (iii) a polyA sequence; and the second expression cassette comprises: (iv) a nucleic acid sequence encoding the shRNA; (v) a U6 promoter which drives expression of the shRNA; and (vi) a central polypurine tract and central terminator sequence (cPPT/CTS) sequence. In some such embodiments, the nucleic acid molecule comprises a first copy and a second copy of the second expression cassette, wherein the first copy and the second copy are identical, and wherein the first copy and the second copy are in tandem, and further wherein the first copy and the second copy are in the same orientation.

In another aspect, the invention provides a recombinant DNA construct comprising any nucleic acid molecule of the invention described herein.

In some embodiments, the recombinant DNA construct encodes a viral vector. In certain embodiments, the viral vector is an adenoviral vector, a lentiviral vector, a retroviral vector, or an adeno-associated viral (AAV) vector. In particular embodiments, the viral vector is a recombinant AAV vector.

In another aspect, the invention provides a viral vector comprising any nucleic acid molecule of the invention described herein. In certain embodiments, the viral vector is an adenoviral vector, a lentiviral vector, a retroviral vector, or an adeno-associated viral (AAV) vector. In particular embodiments, the viral vector is a recombinant AAV vector.

In another aspect, the invention provides a method for producing a genetically-modified eukaryotic cell, the method comprising introducing into a cell any nucleic acid molecule of the invention described herein and: (a) a nucleic acid encoding an engineered nuclease having specificity for the nuclease recognition sequence, wherein the engineered nuclease is expressed in the cell; or (b) an engineered nuclease protein having specificity for the nuclease recognition sequence; wherein the engineered nuclease recognizes and cleaves the nuclease recognition sequence in the genome of the cell to generate a cleavage site, and wherein the nucleic acid molecule of the invention is inserted into the genome of the cell at the cleavage site.

In some embodiments of the method, the genetically-modified eukaryotic cell is a human T cell.

In some embodiments of the method, the engineered nuclease is an engineered meganuclease, a TALEN, a zinc finger nuclease (ZFN), a CRISPR/Cas, a compact TALEN, or a megaTAL. In certain embodiments of the method, the engineered nuclease is an engineered meganuclease.

In some embodiments of the method, the nuclease recognition sequence is in a human T cell receptor alpha constant region gene.

In certain embodiments of the method, the nuclease recognition sequence is an engineered meganuclease recognition sequence. In particular embodiments, wherein the engineered meganuclease recognition sequence is within a human T cell receptor alpha constant region, the nuclease recognition sequence comprises SEQ ID NO: 1.

In some embodiments of the method, wherein the nuclease recognition sequence is within a human T cell receptor alpha constant region, cell surface expression of an endogenous T cell receptor is reduced compared to a control cell.

In some embodiments of the method, the nucleic acid encoding the engineered nuclease is an mRNA. In certain embodiments, the mRNA is a polycistronic mRNA encoding the engineered nuclease and at least one additional polypeptide or nucleic acid molecule.

In some embodiments of the method, the nucleic acid molecule of the invention described herein is introduced into the cell using a viral vector. In certain embodiments of the method, the viral vector is an adenoviral vector, a lentiviral vector, a retroviral vector, or an AAV vector. In particular embodiments of the method, the viral vector is a recombinant AAV vector, such as a recombinant AAV vector previously described herein.

In some embodiments of the method, the nucleic acid molecule of the invention described herein is introduced into the cell using a recombinant DNA construct. In certain embodiments of the method, the recombinant DNA construct is a recombinant DNA construct previously described herein.

In some embodiments of the method, the nucleic acid molecule of the invention described herein is inserted into the genome of the cell at the cleavage site by homologous recombination.

In some embodiments of the method, the engineered antigen receptor is a chimeric antigen receptor. In other embodiments of the method, the engineered antigen receptor is an exogenous T cell receptor.

In some embodiments of the method, the inhibitory nucleic acid molecule is inhibitory against human beta-2 microglobulin. In certain embodiments of the method, cell surface expression of beta-2 microglobulin is between about 1% and about 50% of cell surface beta-2 microglobulin expression on a control cell. In other embodiments of the method, cell surface expression of beta-2 microglobulin is between about 1% and about 25% of cell surface beta-2 microglobulin expression on a control cell. In other embodiments of the method, cell surface expression of beta-2 microglobulin is between about 1% and about 10% of cell surface beta-2 microglobulin expression on a control cell. In other embodiments of the method, cell surface expression of beta-2 microglobulin is between about 1% and about 5% of cell surface beta-2 microglobulin expression on a control cell. In particular embodiments of the method, a control cell is not genetically-modified to reduce cell surface beta-2 microglobulin expression.

In some embodiments of the method, the inhibitory nucleic acid molecule is inhibitory against human beta-2 microglobulin. In certain embodiments of the method, cell surface expression of beta-2 microglobulin is reduced by 10% to 95% compared to cell surface beta-2 microglobulin expression on a control cell. In other embodiments of the method, cell surface expression of beta-2 microglobulin is reduced by 50% to 95% compared to cell surface beta-2 microglobulin expression on a control cell. In other embodiments of the method, cell surface expression of beta-2 microglobulin is reduced by 75% to 95% compared to cell surface beta-2 microglobulin expression on a control cell. In other embodiments of the method, cell surface expression of beta-2 microglobulin is reduced by 90% to 95% compared to cell surface beta-2 microglobulin expression on a control cell. In particular embodiments of the method, a control cell is not genetically-modified to reduce cell surface beta-2 microglobulin expression.

In some embodiments of the method, the inhibitory nucleic acid molecule is inhibitory against a component of the MHC class I molecule. In certain embodiments of the method, cell surface expression of MHC class I molecules is between about 1% and about 50% of expression of MHC class I molecules on a control cell. In certain embodiments of the method, cell surface expression of MHC class I molecules is between about 1% and about 25% of expression of MHC class I molecules on a control cell. In certain embodiments of the method, cell surface expression of MHC class I molecules is between about 1% and about 10% of expression of MHC class I molecules on a control cell. In certain embodiments of the method, cell surface expression of MHC class I molecules is between about 1% and about 5% of expression of MHC class I molecules on a control cell. In particular embodiments of the method, a control cell is not genetically-modified to reduce cell surface expression of MHC class I molecules.

In some embodiments of the method, the inhibitory nucleic acid molecule is inhibitory against a component of the MHC class I molecule. In certain embodiments of the method, cell surface expression of MHC class I molecules is reduced by 10% to 95% compared to expression of MHC class I molecules on a control cell. In certain embodiments of the method, cell surface expression of MHC class I molecules is reduced by 50% to 95% compared to expression of MHC class I molecules on a control cell. In certain embodiments of the method, cell surface expression of MHC class I molecules is reduced by 75% to 95% compared to expression of MHC class I molecules on a control cell. In certain embodiments of the method, cell surface expression of MHC class I molecules is reduced by 90% to 95% compared to expression of MHC class I molecules on a control cell. In particular embodiments of the method, a control cell is not genetically-modified to reduce cell surface expression of MHC class I molecules.

In some embodiments of the method, the inhibitory nucleic acid molecule is inhibitory against human CD52. In certain embodiments of the method, cell surface expression of CD52 is between about 1% and about 50% of cell surface CD52 expression on a control cell. In other embodiments of the method, cell surface expression of CD52 is between about 1% and about 25% of cell surface CD52 expression on a control cell. In other embodiments of the method, cell surface expression of CD52 is between about 1% and about 10% of cell surface CD52 expression on a control cell. In other embodiments of the method, cell surface expression of CD52 is between about 1% and about 5% of cell surface CD52 expression on a control cell. In particular embodiments of the method, a control cell is not genetically-modified to reduce cell surface expression of CD52.

In some embodiments of the method, the inhibitory nucleic acid molecule is inhibitory against human CD52. In certain embodiments of the method, cell surface expression of CD52 is reduced by 10% to 95% compared to cell surface CD52 expression on a control cell. In other embodiments of the method, cell surface expression of CD52 is reduced by 50% to 95% compared to cell surface CD52 expression on a control cell. In other embodiments of the method, cell surface expression of CD52 is reduced by 75% to 95% compared to cell surface CD52 expression on a control cell. In other embodiments of the method, cell surface expression of CD52 is reduced by 90% to 95% compared to cell surface CD52 expression on a control cell. In particular embodiments of the method, a control cell is not genetically-modified to reduce cell surface expression of CD52.

In another aspect the invention provides a genetically-modified eukaryotic cell made by any of the methods described herein above.

In another aspect, the invention provides a genetically-modified eukaryotic cell comprising any nucleic acid molecule of the invention described herein, wherein the engineered antigen receptor and the inhibitory nucleic acid molecule are expressed in the genetically-modified eukaryotic cell.

In some embodiments, the genetically-modified eukaryotic cell is a genetically-modified human T cell.

In some embodiments, the nucleic acid molecule of the invention is inserted into the genome of the genetically-modified eukaryotic cell at the nuclease recognition sequence.

In some embodiments, the gene of interest is a human T cell receptor alpha constant region gene.

In some embodiments, the nuclease recognition sequence is an engineered meganuclease recognition sequence, a TALEN recognition sequence, a zinc finger nuclease (ZFN) recognition sequence, a CRISPR/Cas recognition sequence, a compact TALEN recognition sequence, or a megaTAL recognition sequence. In certain embodiments, the nuclease recognition sequence is an engineered meganuclease recognition sequence.

In particular embodiments, wherein the nuclease recognition sequence is within a human T cell receptor alpha constant region gene, the nuclease recognition sequence is an engineered meganuclease recognition sequence comprising SEQ ID NO: 1.

In some embodiments, cell surface expression of an endogenous T cell receptor is reduced compared to a control cell.

In some embodiments, the inhibitory nucleic acid molecule is inhibitory against human beta-2 microglobulin. In certain embodiments, cell surface expression of beta-2 microglobulin is between about 1% and about 50% of cell surface beta-2 microglobulin expression on a control cell. In other embodiments, cell surface expression of beta-2 microglobulin is between about 1% and about 25% of cell surface beta-2 microglobulin expression on a control cell. In other embodiments, cell surface expression of beta-2 microglobulin is between about 1% and about 10% of cell surface beta-2 microglobulin expression on a control cell. In other embodiments, cell surface expression of beta-2 microglobulin is between about 1% and about 5% of cell surface beta-2 microglobulin expression on a control cell. In particular embodiments, a control cell is not genetically-modified to reduce cell surface beta-2 microglobulin expression.

In some embodiments, the inhibitory nucleic acid molecule is inhibitory against human beta-2 microglobulin. In certain embodiments, cell surface expression of beta-2 microglobulin is reduced by 10% to 95% compared to cell surface beta-2 microglobulin expression on a control cell. In other embodiments, cell surface expression of beta-2 microglobulin is reduced by 50% to 95% compared to cell surface beta-2 microglobulin expression on a control cell. In other embodiments, cell surface expression of beta-2 microglobulin is reduced by 75% to 95% compared to cell surface beta-2 microglobulin expression on a control cell. In other embodiments, cell surface expression of beta-2 microglobulin is reduced by 90% to 95% compared to cell surface beta-2 microglobulin expression on a control cell. In particular embodiments, a control cell is not genetically-modified to reduce cell surface beta-2 microglobulin expression.

In some embodiments, the inhibitory nucleic acid molecule is inhibitory against a component of the MHC class I molecule. In certain embodiments, cell surface expression of MHC class I molecules is between about 1% and about 50% of expression of MHC class I molecules on a control cell. In certain embodiments, cell surface expression of MHC class I molecules is between about 1% and about 25% of expression of MHC class I molecules on a control cell. In certain embodiments, cell surface expression of MHC class I molecules is between about 1% and about 10% of expression of MHC class I molecules on a control cell. In certain embodiments, cell surface expression of MHC class I molecules is between about 1% and about 5% of expression of MHC class I molecules on a control cell. In particular embodiments, a control cell is not genetically-modified to reduce cell surface expression of MHC class I molecules.

In some embodiments, the inhibitory nucleic acid molecule is inhibitory against a component of the MHC class I molecule. In certain embodiments, cell surface expression of MHC class I molecules is reduced by 10% to 95% compared to expression of MHC class I molecules on a control cell. In certain embodiments, cell surface expression of MHC class I molecules is reduced by 50% to 95% compared to expression of MHC class I molecules on a control cell. In certain embodiments, cell surface expression of MHC class I molecules is reduced by 75% to 95% compared to expression of MHC class I molecules on a control cell. In certain embodiments, cell surface expression of MHC class I molecules is reduced by 90% to 95% compared to expression of MHC class I molecules on a control cell. In particular embodiments, a control cell is not genetically-modified to reduce cell surface expression of MHC class I molecules.

In some embodiments, the inhibitory nucleic acid molecule is inhibitory against human CD52. In certain embodiments, cell surface expression of CD52 is between about 1% and about 50% of cell surface CD52 expression on a control cell. In other embodiments, cell surface expression of CD52 is between about 1% and about 25% of cell surface CD52 expression on a control cell. In other embodiments, cell surface expression of CD52 is between about 1% and about 10% of cell surface CD52 expression on a control cell. In other embodiments, cell surface expression of CD52 is between about 1% and about 5% of cell surface CD52 expression on a control cell. In particular embodiments, a control cell is not genetically-modified to reduce cell surface expression of CD52.

In some embodiments, the inhibitory nucleic acid molecule is inhibitory against human CD52. In certain embodiments, cell surface expression of CD52 is reduced by 10% to 95% compared to cell surface CD52 expression on a control cell. In other embodiments, cell surface expression of CD52 is reduced by 50% to 95% compared to cell surface CD52 expression on a control cell. In other embodiments, cell surface expression of CD52 is reduced by 75% to 95% compared to cell surface CD52 expression on a control cell. In other embodiments, cell surface expression of CD52 is reduced by 90% to 95% compared to cell surface CD52 expression on a control cell. In particular embodiments, a control cell is not genetically-modified to reduce cell surface expression of CD52.

In another aspect, the invention provides a genetically-modified eukaryotic cell comprising in its genome a nucleic acid sequence encoding an engineered antigen receptor which is expressed by the genetically-modified eukaryotic cell, wherein cell surface expression of beta-2 microglobulin on the genetically-modified eukaryotic cell is reduced by 10% to 95% compared to cell surface beta-2 microglobulin expression on a control cell. In certain embodiments, cell surface expression of beta-2 microglobulin on the genetically-modified eukaryotic cell is reduced between 50% and 95% compared to cell surface beta-2 microglobulin expression on a control cell. In certain embodiments, cell surface expression of beta-2 microglobulin on the genetically-modified eukaryotic cell is reduced between 75% and 95% compared to cell surface beta-2 microglobulin expression on a control cell. In certain embodiments, cell surface expression of beta-2 microglobulin on the genetically-modified eukaryotic cell is reduced between 90% and 95% compared to cell surface beta-2 microglobulin expression on a control cell. In particular embodiments, the control cell is not genetically-modified to reduce cell surface expression of beta-2 microglobulin.

In some embodiments, cell surface expression of beta-2 microglobulin is between about 1% and about 50% of cell surface beta-2 microglobulin expression on a control cell. In other embodiments, cell surface expression of beta-2 microglobulin is between about 1% and about 25% of cell surface beta-2 microglobulin expression on a control cell. In other embodiments, cell surface expression of beta-2 microglobulin is between about 1% and about 10% of cell surface beta-2 microglobulin expression on a control cell. In other embodiments, cell surface expression of beta-2 microglobulin is between about 1% and about 5% of cell surface beta-2 microglobulin expression on a control cell. In particular embodiments, a control cell is not genetically-modified to reduce cell surface beta-2 microglobulin expression.

In certain embodiments, the genetically-modified eukaryotic cell comprises in its genome a nucleic acid sequence encoding an inhibitory nucleic acid molecule which is inhibitory against beta-2 microglobulin. In particular embodiments, the inhibitory nucleic acid molecule is an RNA interference molecule. In some embodiments, the RNA interference molecule is a short hairpin RNA (shRNA), a small interfering RNA (siRNA), a hairpin siRNA, a microRNA (miRNA), a precursor miRNA, or an miRNA-adapted shRNA. In certain embodiments, the RNA interference molecule is an shRNA. In particular embodiments, the shRNA comprises a sequence of any one of SEQ ID NOs: 2-4. In specific embodiments, the shRNA comprises a sequence of SEQ ID NO: 2.

In some embodiments, the nucleic acid sequence encoding the engineered antigen receptor is integrated at the same location within the genome as the nucleic acid sequence encoding the inhibitory nucleic acid molecule. In particular embodiments, the genetically-modified eukaryotic cell comprises in its genome the nucleic acid molecule of the invention.

In other embodiments, the nucleic acid sequence encoding the engineered antigen receptor is integrated at a different location within the genome than the nucleic acid sequence encoding the inhibitory nucleic acid molecule.

In some embodiments, the genetically-modified eukaryotic cell is less susceptible to endogenous NK cell killing when compared to a control cell, has extended persistence in a subject when compared to a control cell, exhibits enhanced expansion in a subject when compared to a control cell, and/or exhibits reduced allogenicity when compared to a control cell.

In some embodiments, the engineered antigen receptor is a chimeric antigen receptor or an exogenous T cell receptor.

In some embodiments, the genetically-modified eukaryotic cell is a genetically-modified human T cell.

In particular embodiments, the genetically-modified eukaryotic cell is a genetically-modified human T cell, and the engineered antigen receptor is a chimeric antigen receptor or an exogenous T cell receptor.

In another aspect, the invention provides a genetically-modified eukaryotic cell comprising in its genome a nucleic acid sequence encoding an engineered antigen receptor which is expressed by the genetically-modified eukaryotic cell, wherein cell surface expression of MHC class I molecules on the genetically-modified eukaryotic cell is reduced by 10% to 95% compared to cell surface expression of MHC class I molecules on a control cell. In certain embodiments, cell surface expression of MHC class I molecules on the genetically-modified eukaryotic cell is reduced by 50% to 95% compared to cell surface expression of MHC class I molecules on a control cell. In certain embodiments, cell surface expression of MHC class I molecules on the genetically-modified eukaryotic cell is reduced by 75% to 95% compared to cell surface expression of MHC class I molecules on a control cell. In certain embodiments, cell surface expression of MHC class I molecules on the genetically-modified eukaryotic cell is reduced by 90% to 95% compared to cell surface expression of MHC class I molecules on a control cell. In particular embodiments, the control cell is not genetically-modified to reduce cell surface expression of a component of the MHC class I molecule.

In some embodiments, cell surface expression of MHC class I molecules is between about 1% and about 50% of cell surface MHC class I molecule expression on a control cell. In other embodiments, cell surface expression of MHC class I molecules is between about 1% and about 25% of cell surface MHC class I molecule expression on a control cell. In other embodiments, cell surface expression of MHC class I molecules is between about 1% and about 10% of cell surface MHC class I molecule expression on a control cell. In other embodiments, cell surface expression of MHC class I molecules is between about 1% and about 5% of cell surface MHC class I molecule expression on a control cell. In particular embodiments, a control cell is not genetically-modified to reduce cell surface expression of MHC class I molecules.

In certain embodiments, the genetically-modified eukaryotic cell comprises in its genome a nucleic acid sequence encoding an inhibitory nucleic acid molecule which is inhibitory against a component of the MHC class I molecule. In certain embodiments, the inhibitory molecule is inhibitory against an MHC class I alpha-1 (□1) domain, alpha-2 (□2) domain, alpha-3 (□3) domain, or against beta-2 microglobulin. In a particular embodiment, the inhibitory molecule is inhibitory against beta-2 microglobulin.

In particular embodiments, the inhibitory nucleic acid molecule is an RNA interference molecule. In some embodiments, the RNA interference molecule is a short hairpin RNA (shRNA), a small interfering RNA (siRNA), a hairpin siRNA, a microRNA (miRNA), a precursor miRNA, or an miRNA-adapted shRNA. In certain embodiments, the RNA interference molecule is an shRNA.

In certain embodiments, the inhibitory nucleic acid molecule is an shRNA inhibitory against beta-2 microglobulin, wherein the shRNA has a sequence comprising any one of SEQ ID NOs: 2-4. In particular embodiments, the shRNA has a sequence comprising SEQ ID NO: 2. In some such embodiments, the first expression cassette and the second expression cassette are in a 3' to 5' orientation relative to the 5' and 3' homology arms, and wherein the first expression cassette is 5' upstream of the second expression cassette. In some such embodiments, the first expression cassette comprises: (i) a nucleic acid sequence encoding a chimeric antigen receptor or an exogenous T cell receptor; (ii) a JeT promoter which drives expression of the chimeric antigen receptor or the exogenous T cell receptor; and (iii) a polyA sequence; and the second expression cassette comprises: (iv) a nucleic acid sequence encoding the shRNA; (v) a U6 promoter which drives expression of the shRNA; and (vi) a central polypurine tract and central terminator sequence (cPPT/CTS) sequence.

In certain embodiments, the inhibitory nucleic acid molecule is an shRNA inhibitory against beta-2 microglobulin, wherein the shRNA has a sequence comprising any one of SEQ ID NOs: 2-4. In particular embodiments, the shRNA has a sequence comprising SEQ ID NO: 2. In some such embodiments, the first expression cassette is in a 3' to 5' orientation and the second expression cassette is in a 5' to 3' orientation relative to the 5' and 3' homology arms, and the first expression cassette is 5' upstream of the second expression cassette. In some such embodiments, the first expression cassette comprises: (i) a nucleic acid sequence encoding a chimeric antigen receptor or an exogenous T cell receptor; (ii) a JeT promoter which drives expression of the chimeric antigen receptor or the exogenous T cell receptor; and (iii) a polyA sequence; and the second expression cassette comprises: (iv) a nucleic acid sequence encoding the shRNA; (v) a U6 promoter which drives expression of the shRNA; and (vi) a central polypurine tract and central terminator sequence (cPPT/CTS) sequence. In some such embodiments, the nucleic acid molecule comprises a first copy and a second copy of the second expression cassette, wherein the first copy and the second copy are identical, and wherein the first copy and the second copy are in tandem, and further wherein the first copy and the second copy are in the same orientation.

In some embodiments, the nucleic acid sequence encoding the engineered antigen receptor is integrated at the same location within the genome as the nucleic acid sequence encoding the inhibitory nucleic acid molecule. In particular embodiments, the genetically-modified eukaryotic cell comprises in its genome the nucleic acid molecule of the invention.

In other embodiments, the nucleic acid sequence encoding the engineered antigen receptor is integrated at a different location within the genome than the nucleic acid sequence encoding the inhibitory nucleic acid molecule.

In some embodiments, the genetically-modified eukaryotic cell is less susceptible to endogenous NK cell killing when compared to a control cell, has extended persistence in a subject when compared to a control cell, exhibits enhanced expansion in a subject when compared to a control cell, and/or exhibits reduced allogenicity when compared to a control cell.

In some embodiments, the engineered antigen receptor is a chimeric antigen receptor or an exogenous T cell receptor.

In some embodiments, the genetically-modified eukaryotic cell is a genetically-modified human T cell.

In particular embodiments, the genetically-modified eukaryotic cell is a genetically-modified human T cell, and the engineered antigen receptor is a chimeric antigen receptor or an exogenous T cell receptor.

In another aspect, the invention provides a pharmaceutical composition comprising a pharmaceutically-acceptable carrier and a therapeutically effective amount of any genetically-modified eukaryotic cell described herein above.

In some particular embodiments, the genetically-modified eukaryotic cell of the pharmaceutical composition is a genetically-modified human T cell, the engineered antigen receptor is a chimeric antigen receptor or exogenous T cell receptor, and cell surface expression of beta-2 microglobulin is between about 1% and about 50%, about 1% and about 25%, about 1% and about 10%, or about 1% and about 5% of cell surface beta-2 microglobulin expression on a control cell.

In other particular embodiments, the genetically-modified eukaryotic cell of the pharmaceutical composition is a genetically-modified human T cell, the engineered antigen receptor is a chimeric antigen receptor or exogenous T cell receptor, and cell surface expression of beta-2 microglobulin on the genetically-modified human T cell is reduced by 10% to 95%, by 50% to 95%, by 75% to 95%, or by 90% to 95% compared to cell surface expression of beta-2 microglobulin on a control cell.

In some particular embodiments, the genetically-modified eukaryotic cell of the pharmaceutical composition is a genetically-modified human T cell, the engineered antigen receptor is a chimeric antigen receptor or exogenous T cell receptor, and cell surface expression of MHC class I molecules is between about 1% and about 50%, about 1% and about 25%, about 1% and about 10%, or about 1% and about 5% of cell surface expression of MHC class I molecules on a control cell.

In other particular embodiments, the genetically-modified eukaryotic cell of the pharmaceutical composition is a genetically-modified human T cell, the engineered antigen receptor is a chimeric antigen receptor or exogenous T cell receptor, and cell surface expression of MHC class I molecules on the genetically-modified human T cell is reduced by 10% to 95%, by 50% to 95%, by 75% to 95%, or by 90% to 95% compared to cell surface expression of MHC class I molecules on a control cell.

In other particular embodiments, the genetically-modified eukaryotic cell of the pharmaceutical composition is a genetically-modified human T cell, and the engineered antigen receptor is a chimeric antigen receptor, and cell surface expression of CD52 is between about 1% and about 50%, about 1% and about 25%, about 1% and about 10%, or about 1% and about 5% of cell surface CD52 expression on a control cell.

In some embodiments, the genetically-modified eukaryotic cell of the pharmaceutical composition is a genetically-modified human T cell, the engineered antigen receptor is a chimeric antigen receptor or exogenous T cell receptor, and cell surface expression of CD52 on the genetically-modified human T cell is reduced by 10% to 95%, by 50% to 95%, by 75% to 95%, or by 90% to 95% compared to cell surface expression of CD52 on a control cell.

In certain embodiments, the pharmaceutical composition of the invention is for immunotherapy in the treatment of cancer in a subject in need thereof.

In another aspect, the invention provides a population of genetically-modified eukaryotic cells comprising a plurality of any genetically-modified eukaryotic cell described herein.

In some embodiments, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified eukaryotic cell as described herein.

In particular embodiments, the genetically-modified eukaryotic cells of the population are genetically-modified human T cells, or cells derived therefrom, or genetically-modified NK cells, or cells derived therefrom.

In certain embodiments, the genetically-modified eukaryotic cells of the population comprise a cell surface chimeric antigen receptor or exogenous T cell receptor. In some of these embodiments, the chimeric antigen receptor or exogenous T cell receptor comprises an extracellular ligand-binding domain having specificity for a tumor-specific antigen.

In some embodiments, the genetically-modified eukaryotic cells of the population have no cell surface expression of an endogenous T cell receptor when compared to an unmodified control cell. In some embodiments, the genetically-modified eukaryotic cells of the population have reduced cell surface expression of beta-2 microglobulin, MHC class I molecules, or CD52.

In another aspect, the invention provides a method of using immunotherapy to treat a disease in a subject in need thereof, the method comprising administering to the subject a genetically-modified eukaryotic cell described herein; wherein the genetically-modified eukaryotic cell is a genetically-modified human T cell expressing a chimeric antigen receptor or an exogenous T cell receptor; and wherein cell surface expression of beta-2 microglobulin on the genetically-modified human T cell is between about 1% and about 50%, about 1% and about 25%, about 1% and about 10%, or about 1% and about 5% of cell surface beta-2 microglobulin expression on a control cell.

In some embodiments of the method, cell surface expression of beta-2 microglobulin on the genetically-modified human T cell is reduced by 10% to 95%, by 50% to 95%, by 75% to 95%, or by 90% to 95% compared to cell surface beta-2 microglobulin expression on a control cell.

In some embodiments of the method, endogenous NK cell killing of the genetically-modified human T cell is reduced in the subject when compared to a genetically-modified human T cell having no cell surface beta-2 microglobulin expression.

In some embodiments of the method, the subject is administered any pharmaceutical composition described herein in which cell surface beta-2 microglobulin expression is reduced on the genetically-modified human T cell when compared to a control cell.

In some embodiments of the method, the genetically-modified human T cell is allogeneic to the subject.

In some embodiments of the method, persistence of the genetically-modified human T cell is extended in the subject when compared to a genetically-modified human T cell having no cell surface beta-2 microglobulin expression, or when compared to a genetically-modified human T cell having a wild-type level of cell surface expression of beta-2 microglobulin.

In some embodiments of the method, expansion of the genetically-modified human T cell is enhanced in the subject when compared to a genetically-modified human T cell having no cell surface beta-2 microglobulin expression, or when compared to a genetically-modified human T cell having a wild-type level of cell surface expression of beta-2 microglobulin.

In some embodiments of the method, allogenicity of the genetically-modified human T cell is reduced when compared to a genetically-modified human T cell having a wild-type level of cell surface expression of beta-2 microglobulin.

In some embodiments of the method, the disease is cancer.

In some embodiments of the method, the cancer is selected from the group consisting of a cancer of carcinoma, lymphoma, sarcoma, blastomas, and leukemia. In certain embodiments of the method, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In particular embodiments of the method, the cancer of B-cell origin is selected from the group consisting of B-lineage acute lymphoblastic leukemia, B-cell chronic lymphocytic leukemia, and B-cell non-Hodgkin's lymphoma.

In another aspect, the invention provides a method of using immunotherapy to treat a disease in a subject in need thereof, the method comprising administering to the subject a genetically-modified eukaryotic cell described herein; wherein the genetically-modified eukaryotic cell is a genetically-modified human T cell expressing a chimeric antigen receptor or an exogenous T cell receptor; and wherein cell surface expression of MHC class I molecules on the genetically-modified human T cell is between about 1% and about 50%, about 1% and about 25%, about 1% and about 10%, or about 1% and about 5% of cell surface expression of MHC class I molecules on a control cell.

In some embodiments of the method, cell surface expression of MHC class I molecules on the genetically-modified human T cell is reduced by 10% to 95%, by 50% to 95%, by 75% to 95%, or by 90% to 95% compared to cell surface expression of MHC class I molecules on a control cell.

In some embodiments of the method, endogenous NK cell killing of the genetically-modified human T cell is reduced in the subject when compared to a genetically-modified human T cell having no cell surface expression of MHC class I molecules.

In some embodiments of the method, the subject is administered any pharmaceutical composition described herein in which cell surface expression of MHC class I molecules is reduced on the genetically-modified human T cell when compared to a control cell.

In some embodiments of the method, the genetically-modified human T cell is allogeneic to the subject.

In some embodiments of the method, persistence of the genetically-modified human T cell is extended in the subject when compared to a genetically-modified human T cell having no cell surface MHC class I molecule expression, or when compared to a genetically-modified human T cell having a wild-type level of cell surface expression of MHC class I molecules.

In some embodiments of the method, expansion of the genetically-modified human T cell is enhanced in the subject when compared to a genetically-modified human T cell having no cell surface MHC class I molecule expression, or when compared to a genetically-modified human T cell having a wild-type level of cell surface expression of MHC class I molecules.

In some embodiments of the method, allogenicity of the genetically-modified human T cell is reduced when compared to a genetically-modified human T cell having a wild-type level of cell surface expression of MHC class I molecules.

In some embodiments of the method, the disease is cancer.

In some embodiments of the method, the cancer is selected from the group consisting of a cancer of carcinoma, lymphoma, sarcoma, blastomas, and leukemia. In certain embodiments of the method, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In particular embodiments of the method, the cancer of B-cell origin is selected from the group consisting of B-lineage acute lymphoblastic leukemia, B-cell chronic lymphocytic leukemia, and B-cell non-Hodgkin's lymphoma.

In another aspect, the invention provides a method of using immunotherapy to treat cancer in a subject in need thereof, the method comprising administering to the subject a genetically-modified eukaryotic cell described herein; wherein the genetically-modified eukaryotic cell is a genetically-modified human T cell expressing a chimeric antigen receptor or an exogenous T cell receptor; and wherein cell surface expression of CD52 on the genetically-modified human T cell is between 1% and 50%, 1% and 25%, 1% and 10%, or 1% and 5% of cell surface CD52 expression on a control cell.

In some embodiments of the method, cell surface expression of CD52 on the genetically-modified human T cell is reduced by 10% to 95%, by 50% to 95%, by 75% to 95%, or by 90% to 95% compared to cell surface expression of CD52 on a control cell.

In some embodiments of the method, the subject is administered a pharmaceutical composition described herein in which cell surface expression of CD52 is reduced on the genetically-modified human T cell when compared to a control cell.

In some embodiments of the method, the genetically-modified human T cell is allogeneic to the subject.

In some embodiments of the method, the cancer is selected from the group consisting of a cancer of carcinoma, lymphoma, sarcoma, blastomas, and leukemia. In certain embodiments of the method, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In particular embodiments of the method, the cancer of B-cell origin is selected from the group consisting of B-lineage acute lymphoblastic leukemia, B-cell chronic lymphocytic leukemia, and B-cell non-Hodgkin's lymphoma.

In another aspect, the invention provides a method for preparing an enriched population of genetically-modified eukaryotic cells comprising an engineered antigen receptor, the method comprising preparing a population of cells comprising a genetically-modified eukaryotic cell described herein and cells expressing a wild-type level of cell surface CD52, wherein cell surface expression of CD52 on the genetically-modified eukaryotic cell is between about 1% and about 50%, about 1% and about 25%, about 1% and about 10%, or about 1% and about 5% when compared to a control cell, the method comprising: (a) contacting the population of cells with beads conjugated to an anti-CD52 binding molecule, wherein cells expressing a wild-type level of cell surface CD52 are bound to the beads and the genetically-modified eukaryotic cell is not bound to the beads; and (b) removing the beads from the population of cells to produce the enriched population of cells; wherein the enriched population of cells is enriched for the genetically-modified eukaryotic cell.

In some embodiments of the method, cell surface expression of CD52 on the genetically-modified eukaryotic cell is reduced by 10% to 95%, by 50% to 95%, by 75% to 95%, or by 90% to 95% when compared to a control cell.

In some embodiments of the method, the beads are magnetic beads. In certain embodiments of the method, the magnetic beads are removed from the population of cells by magnetic separation.

In some embodiments of the method, at least about 50%, at least about 60%, at least about 70%, at least about 80%, at least about 90%, at least about 95%, or up to 100% of cells in the enriched population are the genetically-modified eukaryotic cell.

In some embodiments of the method, the genetically-modified eukaryotic cell expresses a chimeric antigen receptor. In other embodiments of the method, the genetically-modified eukaryotic cell expresses an exogenous T cell receptor.

In some embodiments of the method, the genetically-modified eukaryotic cell is a genetically-modified human T cell, such as any genetically-modified T cell described herein.

In another aspect, the present disclosure provides a genetically-modified eukaryotic cell described herein for use as a medicament. The present disclosure further provides the use of a genetically-modified eukaryotic cell described herein in the manufacture of a medicament for treating a disease in a subject in need thereof. In one such embodiment, the medicament is useful in the treatment of cancer.

The foregoing and other aspects and embodiments of the present invention can be more fully understood by reference to the following detailed description and claims. Certain features of the invention, which are, for clarity, described in the context of separate embodiments, may also be provided in combination in a single embodiment. All combinations of the embodiments are specifically embraced by the present invention and are disclosed herein just as if each and every combination was individually and explicitly disclosed. Conversely, various features of the invention, which are, for brevity, described in the context of a single embodiment, may also be provided separately or in any suitable sub-combination. All sub-combinations of features listed in the embodiments are also specifically embraced by the present invention and are disclosed herein just as if each and every such sub-combination was individually and explicitly disclosed herein. Embodiments of each aspect of the present invention disclosed herein apply to each other aspect of the invention mutatis mutandis.

BRIEF DESCRIPTION OF THE FIGURES

FIG. 2A-2L shows flow plots which represent NK cell killing of primary human T cells. The indicated ratios represent the ratio of NK cells to T cells (E:T) in each experiment. FIG. 2A shows NK cell killing of B2M+ T cells using a 2:1 ratio. FIG. 2B shows NK cell killing of B2M+ T cells using a 1:1 ratio. FIG. 2C shows NK cell killing of B2M+ T cells using a 0.5:1 ratio. FIG. 2D shows NK cell killing of B2M+ T cells using a 0:1 ratio. FIG. 2E shows NK cell killing of B2M-T cells using a 2:1 ratio. FIG. 2F shows NK cell killing of B2M-T cells using a 1:1 ratio. FIG. 2G shows NK cell killing of B2M-T cells using a 0.5:1 ratio. FIG. 2H shows NK cell killing of B2M-T cells using a 0:1 ratio. FIG. 2I shows NK cell killing of Daudi Class I-negative cells using a 2:1 ratio.

FIG. 2J shows NK cell killing of Daudi Class I-negative cells using a 1:1 ratio. FIG. 2K shows NK cell killing of Daudi Class I-negative cells using a 0.5:1 ratio. FIG. 2L shows NK cell killing of Daudi Class I-negative cells using a 0:1 ratio.

FIGS. 5A-5D show flow diagrams representing NK cell lysis or allogeneic cell lysis of K562 cells or mock-treated primary human T cells. FIG. 5A shows NK cell lysis of K562 cells. FIG. 5B shows allogeneic cell lysis of K562 cells. FIG. 5C shows NK cell lysis of mock-treated primary human T cells. FIG. 5D shows allogeneic cell lysis of mock-treated primary human T cells.

FIGS. 6A-6D show flow diagrams representing NK cell lysis or allogeneic cell lysis of primary human T cells treated with B2M shRNAs. FIG. 6A shows NK cell lysis of primary human T cells treated with shRNA254. FIG. 6B shows allogeneic cell lysis of primary human T cells treated with shRNA254. FIG. 6C shows NK cell lysis of primary human T cells treated with shRNA472. FIG. 6D shows allogeneic cell lysis of primary human T cells treated with shRNA472.

FIG. 7A shows construct 7007 (SEQ ID NO: 18). FIG. 7B shows construct 7217 (SEQ ID NO: 19).

FIG. 7C shows construct 7008 (SEQ ID NO: 20). FIG. 7D shows construct 7218 (SEQ ID NO: 21). FIG. 7E shows construct 7009 (SEQ ID NO: 22). FIG. 7F shows construct 7219 (SEQ ID NO: 23).

FIG. 9 A-C show knockdown of CD52 using shRNA and magnetic enrichment of the knockdown population of primary human T cells by CD52 magnetic depletion.

FIG. 10A shows construct 7005 (SEQ ID NO: 10) which encodes a CAR only. FIG. 10B shows construct 7002 (SEQ ID NO: 11) which encodes a CAR only. FIG. 10C shows construct 7004 (SEQ ID NO: 12). FIG. 10D shows construct 7204 (SEQ ID NO: 13). FIG. 10E shows construct 7013 (SEQ ID NO: 14). FIG. 10F shows construct 7213 (SEQ ID NO: 15). FIG. 10G shows construct 7014 (SEQ ID NO: 16). FIG. 10H shows construct 7214 (SEQ ID NO: 17).

FIG. 11A shows CD52 expression when a CAR is expressed in the absence of a CD52 shRNA. FIG. 11B shows CD52 expression when using the 7013 construct. FIG. 11C shows CD52 expression when using the 7004 construct. FIG. 11D shows CD52 expression when using the 7014 construct.

FIG. 12A shows B2M expression in CAR T cells expressing no B2M shRNA (7002—shaded curve) or a single B2M shRNA cassette (7008—open curve). FIG. 12B shows B2M expression in CAR T cells expressing no B2M shRNA (7002—shaded) or two B2M shRNA cassettes (7029—open). FIG. 12C shows B2M expression in CAR−/

CD3+(i.e. non-edited) populations from cultures electroporated with 7002, 7008, or 7029.

Figure 13A:
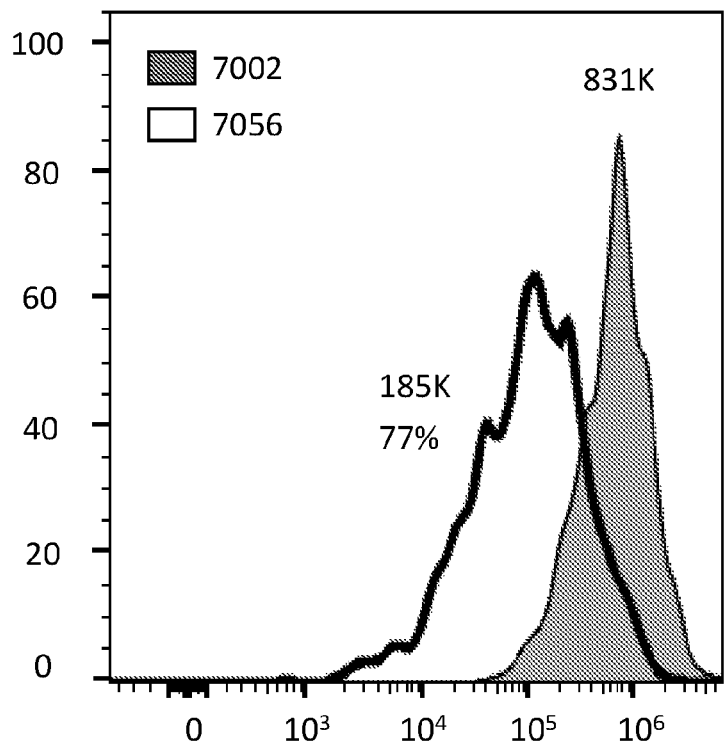
Figure 13B:
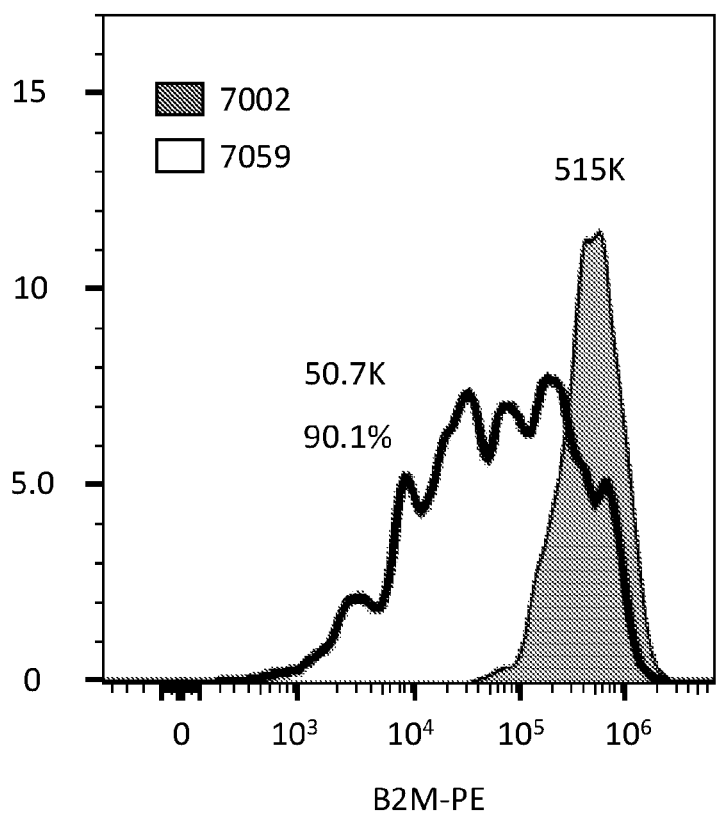
Figure 13C:
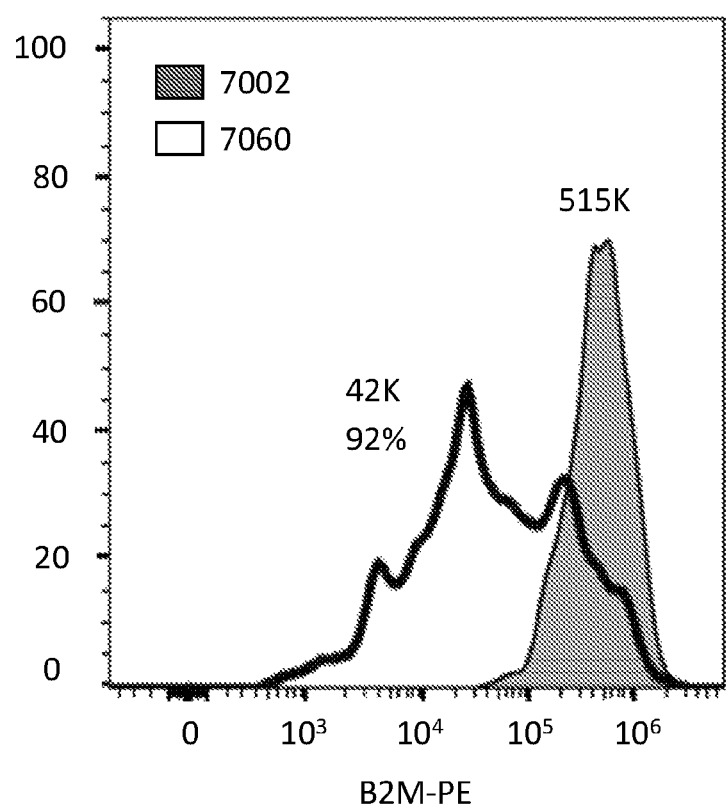

FIG. 13A-13C shows cell surface expression of beta-2 microglobulin on T cells transfected with linearized DNA to express a control CAR-negative construct (7002), CAR constructs expressing a single shRNA472 copy in a 3' to 5' head-to-tail configuration with the CAR (7056), or in a 3' to 5'/5' to 3' tail-to-tail configuration with the CAR (7059), or a CAR construct expressing two shRNA cassette copies in a 3' to 5'/5' to 3' tail-to-tail configuration with the CAR (7060). FIG. 13A shows CART cells expressing the 7002 and 7056 constructs. FIG. 13B shows CART cells expressing the 7002 and 7059 constructs. FIG. 13C shows CART cells expressing the 7002 and 7060 constructs.

FIG. 14 A-D shows beta-2 microglobulin expression or HLA-A, B, and C expression (i.e., MHC class I molecule expression) on T cells transduced with an AAV comprising construct 7056 which expresses a single copy of the shRNA472 in a 3' to 5' head-to-tail configuration with the CAR. FIG. 14A shows the B2M surface levels in CD3-/CAR+ cells compared to meganuclease-edited cells expressing no shRNA from a control culture. FIG. 14B shows B2M levels on CD3-/CAR+ versus CD3+/CAR- populations in the same culture. FIG. 14C shows HLA-ABC (i.e., MHC class I molecule) surface levels in CD3-/CAR+ cells compared to meganuclease-edited cells expressing no shRNA from a control culture. FIG. 14D shows HLA-ABC levels on CD3-/CAR+ versus CD3+/CAR-populations in the same culture.

BRIEF DESCRIPTION OF THE SEQUENCES

SEQ ID NO: 1 sets forth the nucleic acid sequence of the TRC 1-2 recognition sequence.

SEQ ID NO: 2 sets forth the nucleic acid sequence of the anti-beta-2 microglobulin shRNA472.

SEQ ID NO: 3 sets forth the nucleic acid sequence of the anti-beta-2 microglobulin shRNA256.

SEQ ID NO: 4 sets forth the nucleic acid sequence of the anti-beta-2 microglobulin shRNA254.

SEQ ID NO: 5 sets forth the nucleic acid sequence of the anti-CD52 shRNA572.

SEQ ID NO: 6 sets forth the nucleic acid sequence of the anti-CD52 shRNA876.

SEQ ID NO: 7 sets forth the nucleic acid sequence of the anti-CD52 shRNA568.

SEQ ID NO: 8 sets forth the nucleic acid sequence of the anti-CD52 shRNA569.

SEQ ID NO: 9 sets forth the nucleic acid sequence of the anti-CD52 shRNA571.

SEQ ID NO: 10 sets forth the nucleic acid sequence of the CAR 7005 construct.

SEQ ID NO: 11 sets forth the nucleic acid sequence of the CAR 7002 construct.

SEQ ID NO: 12 sets forth the nucleic acid sequence of the CAR 7004 construct.

SEQ ID NO: 13 sets forth the nucleic acid sequence of the CAR 7204 construct.

SEQ ID NO: 14 sets forth the nucleic acid sequence of the CAR 7013 construct.

SEQ ID NO: 15 sets forth the nucleic acid sequence of the CAR 7213 construct.

SEQ ID NO: 16 sets forth the nucleic acid sequence of the CAR 7014 construct.

SEQ ID NO: 17 sets forth the nucleic acid sequence of the CAR 7214 construct.

SEQ ID NO: 18 sets forth the nucleic acid sequence of the CAR 7007 construct.

SEQ ID NO: 19 sets forth the nucleic acid sequence of the CAR 7217 construct.

SEQ ID NO: 20 sets forth the nucleic acid sequence of the CAR 7008 construct.

SEQ ID NO: 21 sets forth the nucleic acid sequence of the CAR 7218 construct.

SEQ ID NO: 22 sets forth the nucleic acid sequence of the CAR 7009 construct.

SEQ ID NO: 23 sets forth the nucleic acid sequence of the CAR 7219 construct.

SEQ ID NO: 24 sets forth the nucleic acid sequence of the CAR 7029 construct.

SEQ ID NO: 25 sets forth the nucleic acid sequence of the CAR 7056 construct.

SEQ ID NO: 26 sets forth the nucleic acid sequence of the CAR 7059 construct.

SEQ ID NO: 27 sets forth the nucleic acid sequence of the CAR 7060 construct.

SEQ ID NO: 28 sets forth the nucleic acid sequence of the cPPT/CTS sequence.

DETAILED DESCRIPTION OF THE INVENTION 1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present disclosure can be embodied in different forms and should not be construed as limited to the embodiments set forth herein. Rather, these embodiments are provided so that this disclosure will be thorough and complete, and will fully convey the scope of the present disclosure to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the present disclosure.

Unless otherwise defined, all technical and scientific terms used herein have the same meaning as commonly understood by one of ordinary skill in the art to which this disclosure belongs. The terminology used in the description of the present disclosure herein is for the purpose of describing particular embodiments only and is not intended to be limiting of the present disclosure.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

The terms "expression cassette," "recombinant DNA construct," "recombinant construct," "expression construct,"

"chimeric construct," "construct," and "recombinant DNA fragment" are used interchangeably herein and are nucleic acid fragments. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant lentiviral or recombinant AAV vectors, or any other vector known in that art suitable for delivering a gene encoding a co-stimulatory domain of the present disclosure to a target cell. The skilled artisan is well aware of the genetic elements that must be present on the vector in order to successfully transform, select and propagate host cells comprising any of the isolated nucleotides or nucleic acid sequences of the present disclosure.

As used herein, a "vector" can also refer to a viral vector. Viral vectors can include, without limitation, retroviral vectors, lentiviral vectors, adenoviral vectors, and adeno-associated viral vectors (AAV).

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the term "RNA interference" or "RNAi" refers to a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559.

The term "siRNA" as used herein refers to small interfering RNA, also known as short interfering RNA or silencing RNA. siRNAs can be, for example, 18 to 30, 20 to 25, 21 to 23 or 21 nucleotide-long double-stranded RNA molecules. An "shRNA" as used herein is a short hairpin RNA, which is a sequence of RNA that makes a tight hairpin turn that can also be used to silence gene expression via RNA interference. shRNA can by operably linked to the U6 promoter expression. The shRNA hairpin structure is cleaved by the cellular machinery into siRNA. shRNA disclosed herein can comprise a sequence complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, or 23 nucleotides of the mRNA a target protein.

As used herein, an "engineered antigen receptor" refers to an exogenous receptor introduced into a cell, such as a chimeric antigen receptor or exogenous T cell receptor, which induces an activating signal in the cell upon stimulation/binding to a ligand or antigen (e.g., a tumor-specific antigen).

As used herein, a "chimeric antigen receptor" or "CAR" refers to an engineered receptor that grafts specificity for an antigen or other ligand or molecule onto an immune effector cell (e.g., a T cell or NK cell). A chimeric antigen receptor typically comprises at least an extracellular ligand-binding domain or moiety and an intracellular domain that comprises one or more signaling domains and/or co-stimulatory domains.

In some embodiments, the extracellular ligand-binding domain or moiety is in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). In some embodiments, the scFv is attached via a linker sequence. In some embodiments, the extracellular ligand-binding domain is specific for any antigen or epitope of interest. In some embodiments, the scFv is humanized. In some embodiments, the extracellular domain of a chimeric antigen receptor comprises an autoantigen (see, Payne et al. (2016) *Science*, Vol. 353 (6295): 179-184), which is recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and the incorporation of one or more co-stimulatory domains described herein into such CAARs is encompassed by the present disclosure.

The extracellular domain of a chimeric antigen receptor can also comprise a naturally-occurring ligand for an antigen of interest, or a fragment of a naturally-occurring ligand which retains the ability to bind the antigen of interest.

Intracellular signaling domains are cytoplasmic domains which transmit an activation signal to the cell following binding of the extracellular domain. An intracellular signaling domain can be any intracellular signaling domain of interest that is known in the art. Such cytoplasmic signaling domains can include, without limitation, CD3 ζ.

In some embodiments, the intracellular domain also includes one or more intracellular co-stimulatory domains, such as those described herein, which transmit a co-stimulatory signal which promotes cell proliferation, cell survival, and/or cytokine secretion after binding of the extracellular domain. As used herein, a "co-stimulatory domain" refers to a polypeptide domain which transmits an intracellular proliferative and/or cell-survival signal upon activation. Activation of a co-stimulatory domain may occur following homodimerization of two co-stimulatory domain polypeptides. Activation may also occur, for example, following activation of a construct comprising the co-stimulatory domain (e.g., a chimeric antigen receptor or an inducible regulatory construct). Generally, a co-stimulatory domain can be derived from a transmembrane co-stimulatory receptor, particularly from an intracellular portion of a co-stimulatory receptor. Such intracellular co-stimulatory domains can be any of those known in the art and can include, without limitation, CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83, N1, N6, or any combination thereof.

As used herein, a "co-stimulatory signal" refers to an intracellular signal induced by a co-stimulatory domain that promotes cell proliferation, expansion of a cell population in vitro and/or in vivo, promotes cell survival, modulates (e.g., upregulates or downregulates) the secretion of cytokines, and/or modulates the production and/or secretion of other immunomodulatory molecules. In some embodiments, a co-stimulatory signal is induced following homodimerization of two co-stimulatory domain polypeptides. In some embodiments, a co-stimulatory signal is induced following activation of a construct comprising the co-stimulatory domain (e.g., a chimeric antigen receptor or an inducible regulatory construct).

A chimeric antigen receptor can further include additional structural elements, including a transmembrane domain that is attached to the extracellular ligand-binding domain via a hinge or spacer sequence. The transmembrane domain can be derived from any membrane-bound or transmembrane protein. For example, the transmembrane polypeptide can be a subunit of the T-cell receptor (i.e., an α, β, γ or ζ polypeptide constituting CD3 complex), IL2 receptor p55 (α chain), p75 (β chain) or γ chain, subunit chain of Fc receptors (e.g., Fcγ receptor III) or CD proteins such as the CD8 alpha chain. Alternatively the transmembrane domain can be synthetic and can comprise predominantly hydrophobic residues such as leucine and valine.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In particular examples, a hinge domain can comprise a part of a human CD8 alpha chain, FcγRIIIa receptor or IgGl.

As used herein, the term "activation" refers to the state of a cell (e.g., a T cell) that has been sufficiently stimulated to induce detectable effector function. In some embodiments, activation is associated with induced cytokine production and/or induced cell proliferation and expansion.

As used herein, an "exogenous T cell receptor" or "exogenous TCR" refers to a TCR whose sequence is introduced into the genome of an immune effector cell (e.g., a human T cell) that may or may not endogenously express the TCR. Expression of an exogenous TCR on an immune effector cell can confer specificity for a specific epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest.

As used herein, with respect to a protein, the term "engineered" or "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring polynucleotide or polypeptide sequence responsible for a given phenotype. Whereas a wild-type allele or polypeptide can confer a normal phenotype in an organism, a mutant or variant allele or polypeptide can, in some instances, confer an altered phenotype.

As used herein with respect to recombinant proteins, the term "modification" means any insertion, deletion or substitution of an amino acid residue in the recombinant sequence relative to a reference sequence (e.g., a wild-type or a native sequence).

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859). A meganuclease as used herein binds to double-stranded DNA as a heterodimer. A meganuclease may also be a "single-chain meganuclease" in which a pair of DNA-binding domains are joined into a single polypeptide using a peptide linker. The term "homing endonuclease" is synonymous with the term "meganuclease." Meganucleases of the present disclosure are substantially non-toxic when expressed in cells, particularly in human T cells, such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit—Linker—C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, any of those encompassed by U.S. Pat. Nos. 8,445,251 and 9,434,931.

As used herein, the term "zinc finger nuclease" or "ZFN" refers to a chimeric protein comprising a zinc finger DNA-binding domain fused to a nuclease domain from an endonuclease or exonuclease, including but not limited to a restriction endonuclease, homing endonuclease, S1 nuclease, mung bean nuclease, pancreatic DNAse I, micrococcal nuclease, and yeast HO endonuclease. Nuclease domains useful for the design of zinc finger nucleases include those from a Type IIs restriction endonuclease, including but not limited to FokI, FoM, and StsI restriction enzyme. Additional Type IIs restriction endonucleases are described in International Publication No. WO 2007/014275, which is incorporated by reference in its entirety. The structure of a zinc finger domain is stabilized through coordination of a zinc ion. DNA binding proteins comprising one or more zinc finger domains bind DNA in a sequence-specific manner. The zinc finger domain can be a native sequence or can be redesigned through rational or experimental means to produce a protein which binds to a pre-determined DNA sequence ~18 basepairs in length, comprising a pair of nine basepair half-sites separated by 2-10 basepairs. See, for example, U.S. Pat. Nos. 5,789,538, 5,925,523, 6,007,988, 6,013,453, 6,200,759, and International Publication Nos. WO 95/19431, WO 96/06166, WO 98/53057, WO 98/54311, WO 00/27878, WO 01/60970, WO 01/88197, and WO 02/099084, each of which is incorporated by reference in its entirety. By fusing this engineered protein domain to a nuclease domain, such as FokI nuclease, it is possible to target DNA breaks with genome-level specificity. The selection of target sites, zinc finger proteins and methods for design and construction of zinc finger nucleases are known to those of skill in the art and are described in detail in U.S. Publications Nos. 20030232410, 20050208489, 2005064474, 20050026157, 20060188987 and International Publication No. WO 07/014275, each of which is incorporated by reference in its entirety. Cleavage by a zinc finger nuclease can create a blunt end or a 5' overhand of variable length (frequently four basepairs).

As used herein, the term "TALEN" refers to an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, S1 nuclease, mung bean nuclease, pancreatic DNAse I, micrococcal nuclease, and yeast HO endonuclease. See, for example, Christian et al. (2010) Genetics 186:757-761, which is incorporated by reference in its entirety. Nuclease domains useful for the design of TALENs include those from a Type IIs restriction endonuclease, including but not limited to FokI, FoM, StsI, HhaI, HindIII, Nod, BbvCI, EcoRl, BglI, and AlwI. Additional Type IIs restriction endonucleases are described in International Publication No. WO 2007/014275. In some embodiments, the nuclease domain of the TALEN is a FokI nuclease domain or an active portion thereof. TAL domain repeats can be derived from the TALE (transcription activator-like effector) family of proteins used in the infection process by plant pathogens of the *Xanthomonas* genus. TAL domain repeats are 33-34 amino acid sequences with divergent 12th and 13th amino acids. These two positions, referred to as the repeat variable dipeptide (RVD), are highly variable and show a strong correlation with specific nucleotide recognition. Each base pair in the DNA target sequence is contacted by a single TAL repeat, with the specificity resulting from the RVD. In some embodiments, the TALEN comprises 16-22 TAL domain repeats. DNA cleavage by a TALEN requires two DNA recognition regions flanking a nonspecific central region (i.e., the "spacer"). The term "spacer" in reference to a TALEN refers to the nucleic acid sequence that separates the two nucleic acid sequences recognized and bound by each monomer constituting a TALEN. The TAL domain repeats can be native sequences from a naturally-occurring TALE protein or can be redesigned through rational or experimental means to produce a protein which binds to a pre-determined DNA sequence (see, for example, Boch et al. (2009) Science 326(5959): 1509-1512 and Moscou and Bogdanove (2009) Science 326(5959):1501, each of which is incorporated by reference in its entirety). See also, U.S. Publication No. 20110145940 and International Publication No. WO 2010/079430 for methods for engineering a TALEN to recognize a specific sequence and examples of RVDs and their corresponding target nucleotides. In some embodiments, each nuclease (e.g., FokI) monomer can be fused to a TAL effector sequence that recognizes a different DNA sequence, and only when the two recognition sites are in close proximity do the inactive monomers come together to create a functional enzyme.

As used herein, the term "compact TALEN" refers to an endonuclease comprising a DNA-binding domain with one or more TAL domain repeats fused in any orientation to any portion of the I-TevI homing endonuclease or any of the endonucleases listed in Table 2 in U.S. Application No. 20130117869 (which is incorporated by reference in its entirety), including but not limited to MmeI, EndA, End1, I-BasI, I-TevII, I-TevIII, I-TwoI, MspI, Mval, NucA, and NucM. Compact TALENs do not require dimerization for DNA processing activity, alleviating the need for dual target sites with intervening DNA spacers. In some embodiments, the compact TALEN comprises 16-22 TAL domain repeats.

As used herein, the term "CRISPR" refers to a caspase-based endonuclease comprising a caspase, such as Cas9, and a guide RNA that directs DNA cleavage of the caspase by hybridizing to a recognition site in the genomic DNA. The caspase component of a CRISPR is an RNA-guided DNA endonuclease. In certain embodiments, the caspase is a class II Cas enzyme. In some of these embodiments, the caspase is a class II, type II enzyme, such as Cas9. In other embodiments, the caspase is a class II, type V enzyme, such as Cpfl. The guide RNA comprises a direct repeat and a guide sequence (often referred to as a spacer in the context of an endogenous CRISPR system), which is complementary to the target recognition site. In certain embodiments, the CRISPR further comprises a tracrRNA (trans-activating CRISPR RNA) that is complementary (fully or partially) to a direct repeat sequence (sometimes referred to as a tracr-mate sequence) present on the guide RNA. In particular embodiments, the caspase can be mutated with respect to a corresponding wild-type enzyme such that the enzyme lacks the ability to cleave one strand of a target polynucleotide, functioning as a nickase, cleaving only a single strand of the target DNA. Non-limiting examples of caspase enzymes that function as a nickase include Cas9 enzymes with a D10A mutation within the RuvC I catalytic domain, or with a H840A, N854A, or N863A mutation.

As used herein, the term "megaTAL" refers to a single-chain nuclease comprising a transcription activator-like effector (TALE) DNA binding domain with an engineered, sequence-specific homing endonuclease.

As used herein, the term "recognition sequence" refers to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a compact TALEN, the recognition sequence comprises a first CNNNGN sequence that is recognized by the I-TevI domain, followed by a nonspecific spacer 4-16 basepairs in length, followed by a second sequence 16-22 bp in length that is recognized by the TAL-effector domain (this sequence typically has a 5' T base). Cleavage by a Compact TALEN produces two basepair 3' overhangs. In the case of a CRISPR, the recognition sequence is the sequence, typically 16-24 basepairs, to which the guide RNA binds to direct cleavage. Full complementarity between the guide sequence and the recognition sequence is not necessarily required to effect cleavage. Cleavage by a CRISPR can produce blunt ends (such as by a class II, type II caspase) or overhanging ends (such as by a class II, type V caspase), depending on the caspase. In those embodiments wherein a Cpfl caspase is utilized, cleavage by the CRISPR complex comprising the same will result in 5' overhangs and in certain embodiments, 5 nucleotide 5' overhangs. Each caspase enzyme also requires the recognition of a PAM (protospacer adjacent motif) sequence that is near the recognition sequence complementary to the guide RNA. The precise sequence, length requirements for the PAM, and distance from the target sequence differ depending on the caspase enzyme, but PAMs are typically 2-5 base pair sequences adjacent to the target/recognition sequence. PAM sequences for particular caspase enzymes are known in the art (see, for example, U.S. Pat. No. 8,697,359 and U.S. Publication No. 20160208243, each of which is incorporated by reference in its entirety) and PAM sequences for novel or engineered caspase enzymes can be identified using methods known in the art, such as a PAM depletion assay (see, for example, Karvelis et al. (2017) Methods 121-122:3-8, which is incorporated herein in its entirety). In the case of a zinc finger, the DNA binding domains typically recognize an 18-bp recognition sequence comprising a pair of nine basepair "half-sites" separated by 2-10 basepairs and cleavage by the nuclease creates a blunt end or a 5' overhang of variable length (frequently four basepairs).

As used herein, the term "target site" or "target sequence" refers to a region of the chromosomal DNA of a cell comprising a recognition sequence for a nuclease.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976).

As used herein, the term "reduced" refers to any reduction in the symptoms or severity of a disease or any reduction in the proliferation or number of cancerous cells. In either case, such a reduction may be up to 5%, 10%, 20%, 30%, 40%, 50%, 60%, 70%, 80%, 90%, 95%, or up to 100%. Accordingly, the term "reduced" encompasses both a partial reduction and a complete reduction of a disease state.

As used herein, the term "reduced" can also refer to a decrease in the cell surface expression of a polypeptide when compared to an appropriate control cell. In the present context, a reduction is distinct from knockout of polypeptide expression, wherein expression is reduced by 100%. Rather, in the present invention, a reduction indicates that expression is decreased but not completely eliminated. Such as a reduction can be, for example, a reduction in cell surface beta-2 microglobulin, MHC class I molecule, or CD52 expression when compared to a control cell which has not been genetically-modified to reduce beta-2 microglobulin, MHC class I molecules, or CD52, respectively. A reduction in expression can be between about 10% and about 99% or any number or range therein. For example, a reduction can be between about 10% and 95%, about 50% and about 95%, about 75% and about 95%, or about 90% and about 95%, when compared to a control cell. A reduction can also be by about 10%, 20%, 30%, 40%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% when compared to a control cell.

As used herein, the term "MHC class I molecule" refers to a major histocompatibility complex (MHC) found on the cell surface which displays peptide fragments of non-self proteins. MHC class I molecules consist of two polypeptide chains. The alpha chain consists of 3 polypeptides referred to as the alpha-1 (☐1), alpha-2 (☐2), and alpha-3 (☐3) domains. The alpha chain is linked non-covalently via the ☐3 domain to a beta chain which consists of beta-2 microglobulin (B2M). The alpha chain is polymorphic and is encoded by the HLA gene (i.e., HLA-A, HLA-B, and HLA-C), whereas beta-2 microglobulin is not polymorphic and it encoded by the B2M gene.

As used herein, the term "beta-2 microglobulin" refers to the beta chain component of MHC class I molecules. Human beta-2 microglobulin is encoded by the B2M gene (e.g., NCBI Gene ID 567). Expression of beta-2 microglobulin is necessary for assembly and function of MHC class I molecules on the cell surface.

As used herein, the term "CD52" refers to the polypeptide encoded by the human CD52 gene (e.g., NCBI gene ID 1043) which is also referred to as cluster of differentiation 52.

As used herein, the term "anti-tumor activity" or "anti-tumor effect" refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the genetically-modified cells of the present disclosure in prevention of the occurrence of tumor in the first place.

The term "effective amount" or "therapeutically effective amount" refers to an amount sufficient to effect beneficial or desirable biological and/or clinical results. The therapeutically effective amount will vary depending on the therapeutic (e.g., genetically-modified cell, CAR T cell, etc.) formulation or composition, the disease and its severity, and the age, weight, physical condition and responsiveness of the subject to be treated. In specific embodiments, an effective amount of a cell comprising a co-stimulatory domain disclosed herein or pharmaceutical compositions disclosed herein reduces at least one symptom or the progression of a disease.

As used herein, the term "treat" or "treatment" means to reduce the frequency or severity of at least one sign or symptom of a disease or disorder experienced by a subject.

As used herein, the term "cancer" should be understood to encompass any neoplastic disease (whether invasive or metastatic) which is characterized by abnormal and uncontrolled cell division causing malignant growth or tumor.

As used herein, the term "carcinoma" refers to a malignant growth made up of epithelial cells.

As used herein, the term "leukemia" refers to malignancies of the hematopoietic organs/systems and is generally characterized by an abnormal proliferation and development of leukocytes and their precursors in the blood and bone marrow.

As used herein, the term "sarcoma" refers to a tumor which is made up of a substance like the embryonic connective tissue and is generally composed of closely packed cells embedded in a fibrillary, heterogeneous, or homogeneous substance.

As used herein, the term "melanoma" refers to a tumor arising from the melanocytic system of the skin and other organs.

As used herein, the term "lymphoma" refers to a group of blood cell tumors that develop from lymphocytes.

As used herein, the term "blastoma" refers to a type of cancer that is caused by malignancies in precursor cells or blasts (immature or embryonic tissue).

As used herein, "transfected" or "transformed" or "transduced" or "nucleofected" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, a "human T cell" or "T cell" refers to a T cell isolated from a human donor. Human T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "human natural killer cell" or "human NK cell" or "natural killer cell" or "NK cell" refers to a type of cytotoxic lymphocyte critical to the innate immune system. The role NK cells play is analogous to that of cytotoxic T-cells in the vertebrate adaptive immune response. NK cells provide rapid responses to virally infected cells and respond to tumor formation, acting at around 3 days after infection.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions, stimuli, or further genetic modifications that would induce expression of altered genotype or phenotype. In particular embodiments, a control cell is otherwise identical to a genetically-modified cell but has not been genetically-modified to reduce cell surface expression of a particular polypeptide (e.g., beta-2 microglobulin, MHC class I molecules, CD52).

As used herein with respect to both amino acid sequences and nucleic acid sequences, the terms "percent identity," "sequence identity," "percentage similarity," "sequence similarity," and the like, refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov), and are described in, for example, Altschul et al. (1990), *J. Mol. Biol.* 215:403-410; Gish and States (1993), *Nature Genet.* 3:266-272; Madden et al. (1996), *Meth. Enzymol.* 266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=-5; gap extension penalty=-2; match reward=1; and mismatch penalty=-3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values and if the variable is inherently continuous.

2.1 Principle of the Invention

The present disclosure is based, in part, on the observation that knockdown of cell surface beta-2 microglobulin, and consequently MHC class I molecules, can reduce allogenicity of genetically-modified cells, such as CAR T cells. Importantly, the inventors have discovered that an incomplete knockdown of beta-2 microglobulin and MHC class I molecules (i.e., to a low percentage of wild-type expression, but not complete knockout) not only reduces allogenicity of genetically-modified cells, but also serves to dramatically reduce killing by NK cells, which can recognize cells that are B2M-negative as non-self and induce a cytotoxic action.

The present invention is also based, in part, on the inventors' discovery that a population of CAR-positive T cells can be enriched by an advantageous negative-selection method when the CAR-encoding construct includes a coding sequence for an RNA interfering molecule against CD52. In this manner, a population of CAR T cells can be contacted with beads conjugated to an anti-CD52 antibody in order to capture CD52-positive cells. Separation of the beads, and thus the CD52-positive cells, results in an enriched population of CAR-positive cells having reduced cell surface expression of CD52.

Accordingly, a nucleic acid molecule is provided comprising a first expression cassette which encodes an engineered antigen receptor, such as a chimeric antigen receptor, and a second expression cassette which encodes an inhibitory nucleic acid molecule, such as an RNA interfering molecule. Further, the nucleic acid molecule is flanked by 5' and 3' homology arms to promote targeted insertion of the nucleic acid into the genome of a cell at a double-strand break, such as a cleavage site produced by an engineered nuclease. In certain embodiments of the invention, the inhibitory nucleic acid molecule can be against human beta-2 microglobulin, a component of the MHC class I molecule, or CD52.

Further disclosed herein are recombinant DNA constructs and viral vectors comprising the nucleic acid molecule, genetically-modified cells comprising the nucleic acid molecule, and pharmaceutical compositions comprising such cells. Also disclosed are genetically-modified cells expressing an engineered antigen receptor (e.g., a CAR or exogenous TCR) which have reduced cell-surface expression of beta-2 microglobulin, MHC class I molecules, or CD52, and may or may not express the particular nucleic acid molecule of the invention.

In some embodiments, administration of genetically-modified cells of the invention reduces the symptoms or severity of diseases, such cancers, which can be targeted by genetically-modified cells of the present disclosure.

Also disclosed herein are methods of immunotherapy for treating cancer in a subject in need thereof comprising administering to the subject a pharmaceutical composition comprising a genetically-modified cell disclosed herein and a pharmaceutically acceptable carrier. In such methods, wherein a CAR is expressed and cell surface beta-2 microglobulin and/or MHC class I molecules is reduced, incomplete knockout leads to a reduction in both allogenicity of the cells and killing of the cells by NK cells.

Further disclosed are methods for producing an enriched population of genetically-modified cells, wherein a CAR is expressed and cell surface CD52 is reduced by RNA interference, allowing for negative selection of CAR-positive cells having reduced CD52 expression.

2.2 Nucleic Acid Molecules

In certain embodiments, the invention provides a nucleic acid molecule comprising: (a) a first expression cassette comprising a nucleic acid sequence encoding an engineered antigen receptor; (b) a second expression cassette comprising a nucleic acid sequence encoding an inhibitory nucleic acid molecule; (c) a 5' homology arm; and (d) a 3' homology arm. The 5' homology arm and the 3' homology arm can be engineered at any suitable length to have homology to chromosomal regions flanking a nuclease recognition sequence in a gene of interest, which can be any desired gene in a target cell in which a suitable recognition sequence is present.

Figure 1:
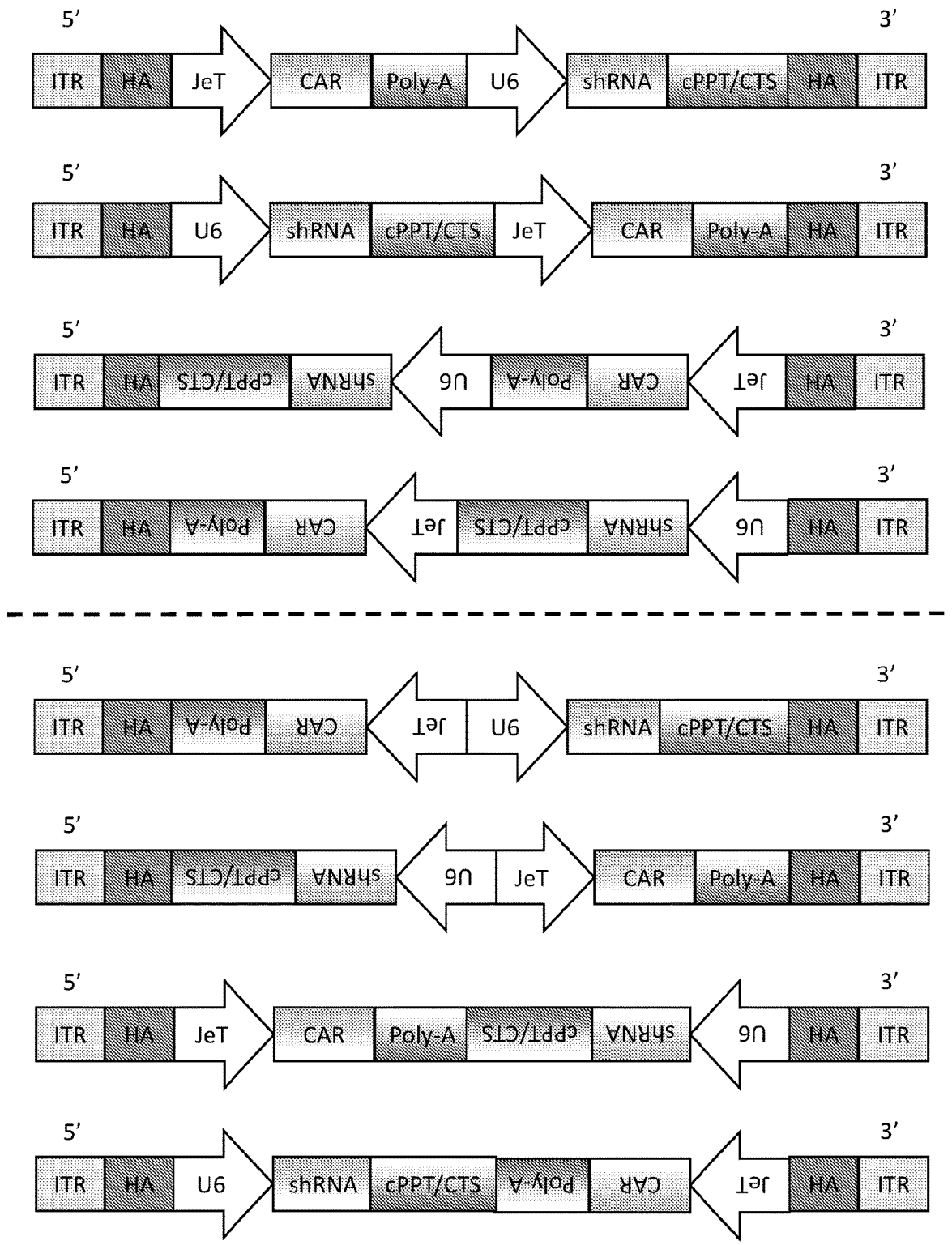
FIG. 1 shows diagrams of various embodiments of the nucleic acid molecule of the invention. The JeT promoter is shown as an example of a promoter driving expression of the engineered antigen receptor. A U6 promoter is shown as an example of a promoter driving expression of the inhibitory nucleic acid molecule. A chimeric antigen receptor (CAR) is shown as an example of an engineered antigen receptor. An shRNA is shown as an example of an inhibitory nucleic acid molecule. A poly-A sequence is shown as an example of a sequence which terminates translation of the engineered antigen receptor. A cPPT/CTS sequence is shown as an example of a sequence which terminates translation of the inhibitory nucleic acid molecule. 5' and 3' homology arms are shown flanking the first expression cassette and second expression cassette of each construct. Optional 5' and 3' inverted terminal repeats are further shown in each construct. Constructs above the dashed line have first and second expression cassettes in the same orientation, whereas constructs below the dashed line have first and second expression cassettes in opposite orientations.
Figure 2A:
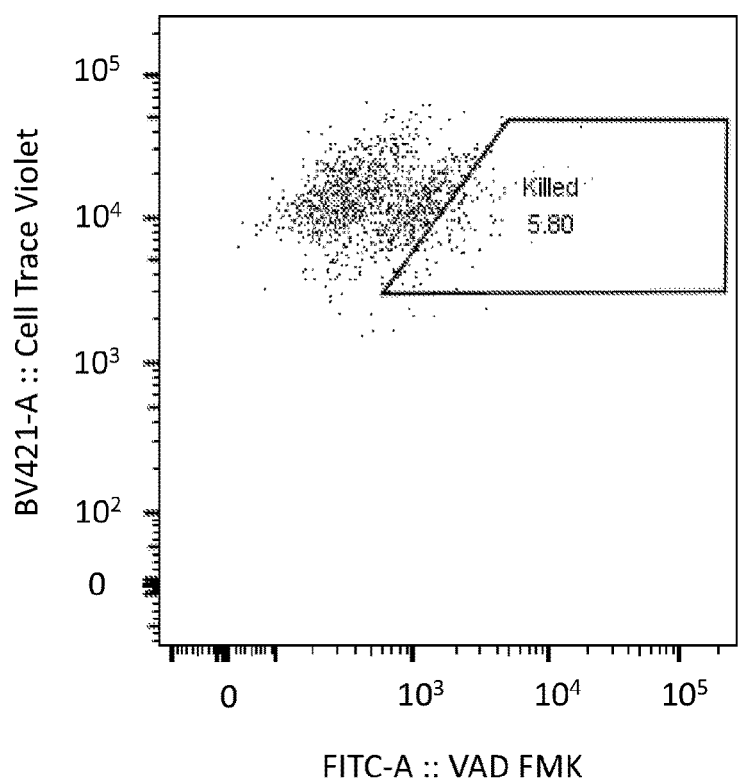
Figure 2B:
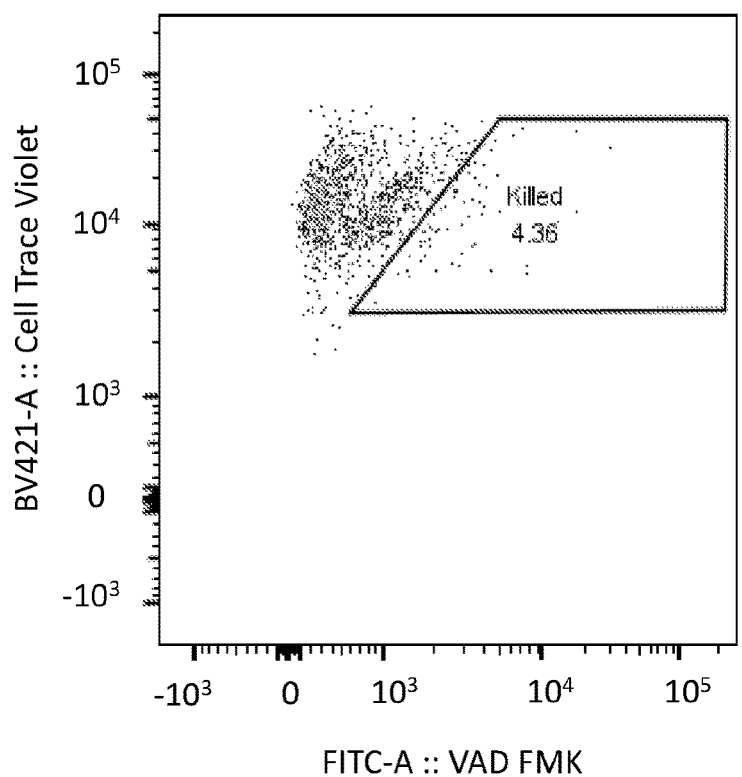
Figure 2C:
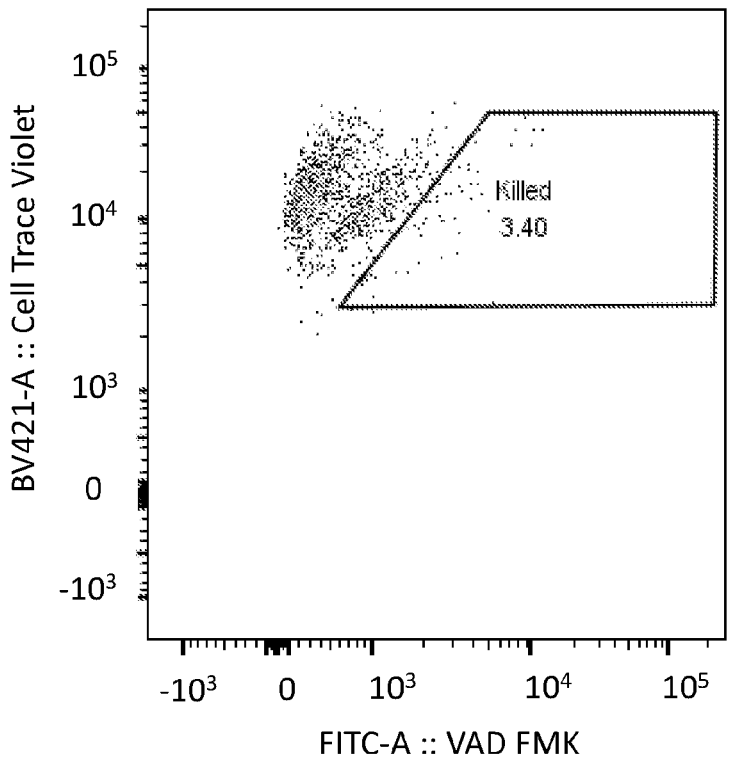
Figure 2D:
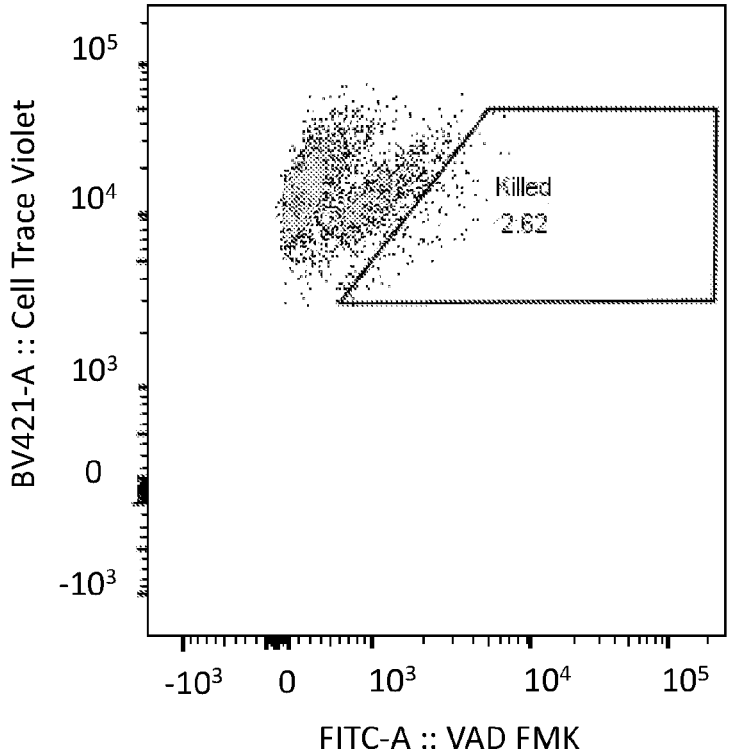

The nucleic acid molecule of the invention can have any number of orientations. Some non-limiting examples illustrated in FIG. 1. In particular embodiments, the first and second expression cassettes can be in the same orientation. This orientation can be either 5' to 3' relative to the homology arms or, alternatively, 3' to 5'. In either case, the first expression cassette may be 5' to the second cassette, or the second cassette may be 5' to the first cassette. In other embodiments, the first and second expression cassettes can be in different orientations in the nucleic acid molecule. For example, the first expression cassette may be oriented 5' to 3', whereas the second expression cassette may be oriented 3' to 5'. Alternatively, the first expression cassette may be oriented 3' to 5' and the second expression cassette may be oriented 5' to 3'.

In embodiments wherein the expression cassettes are in opposite orientations, they may be oriented in a "tail-to-tail" configuration, such that the first expression cassette is oriented 3' to 5' and is positioned 5' to the second expression cassette, which is oriented 5' to 3'. In a similar tail-to-tail embodiment, the second expression cassette is oriented 3' to 5' and is positioned 5' to the first expression cassette, which is oriented 5' to 3'.

In other embodiments wherein the expression cassettes are in opposite orientations, they may be oriented in a "head-to-head" configuration, such that the first expression cassette is oriented 5' to 3' and is positioned 5' to the second expression cassette, which is oriented 3' to 5'. In a similar head-to-head embodiment, the second expression cassette is oriented 5' to 3' and is positioned 5' to the first expression cassette, which is oriented 3' to 5'.

In some embodiments, the nucleic acid molecule can comprise multiple copies of the second expression cassette. The copies of the second expression cassette can be identical or vary from one another. In some cases, the copies can include a promoter, a coding sequence for the inhibitory nucleic acid molecule, and a sequence, such as a (cPPT/CTS) sequence, to terminate translation of the inhibitory nucleic acid molecule. The copies of the second expression cassette can be in tandem to one another in the nucleic acid molecule, and can be in the same orientation, or in opposite orientations. Alternatively, the copies may not be in tandem, and can be in the same orientation, or in opposite orientations.

The expression cassettes of the nucleic acid molecule can include various promoters which drive expression of the engineered antigen receptor and/or the inhibitory nucleic acid molecule. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Synthetic promoters are also contemplated as part of the present disclosure. For example, in particular embodiments, the promoter driving expression of the engineered antigen receptor is a JeT promoter (see, WO/2002/012514).

In some embodiments, the promoters are selected based on the desired outcome. It is recognized that different applications can be enhanced by the use of different promoters in the expression cassettes to modulate the timing, location and/or level of expression of the polynucleotides disclosed herein. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Promoters particularly useful for driving expression of an RNA interference molecule are well known in the art and can include, without limitation, pol III promoters, such as U6 or H1.

The 5' and 3' homology arms of the nucleic acid molecule have sequence homology to corresponding sequences 5' upstream and 3' downstream of the nuclease recognition sequence in the genome. The homology arms promote insertion of the nucleic acid molecule into the cleavage site generated by the nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

In order to assess the expression of an engineered antigen receptor (e.g. a CAR or exogenous T cell receptor) in a genetically-modified cell, the nucleic acid molecule of the invention can optionally comprise an epitope which can be used to detect the presence of the encoded cell surface protein. In some examples described herein, a CAR coding sequence may include a QBend10 epitope which allows for detection using an anti-CD34 antibody (see, WO2013/153391).

In other examples, an expression cassette can also contain either a selectable marker gene or a reporter gene, or both, to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes and fluorescent marker genes.

Expression may also be assessed by determining protein expression of the polypeptide targeted by the inhibitory nucleic acid sequence. For example, expression of beta-2 microglobulin and CD52 can be detected on the cell surface by a number of techniques known in the art. Expression can also be determined by positive or negative selection procedures which purify particular populations of cells expressing, or lacking expression, of the cell surface polypeptides.

Also provided herein are vectors comprising the nucleic acid molecules of the present disclosure. In some embodiments, the nucleic acid molecule is cloned into a vector including, but not limited to a plasmid, a phagemid, a phage derivative, an animal virus, or a cosmid. Vectors of particular interest include expression vectors, replication vectors, probe generation vectors, and sequencing vectors.

In other embodiments, nucleic acid molecules of the invention are provided on viral vectors, such as retroviral vectors, lentiviral vectors, adenoviral vectors, and adeno-associated viral (AAV) vectors. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193). Where the nucleic acid of the invention is provided in a viral vector that promotes random integration into the genome, and does not require the presence of 5' and 3' homology arms for homologous recombination, the nucleic acid of the invention can be provided without 5' and 3' homology arms.

2.3 Chimeric Antigen Receptors (CARs)

Provided herein are genetically-modified cells expressing an engineered antigen receptor. In some embodiments, the engineered antigen receptor is a chimeric antigen receptor (CAR). Generally, a CAR of the present disclosure will comprise at least an extracellular domain and an intracellular domain. In some embodiments, the extracellular domain comprises a target-specific binding element otherwise referred to as a ligand-binding domain or moiety. In some embodiments, the intracellular domain, or cytoplasmic domain, comprises at least one co-stimulatory domain and one or more signaling domains. In other embodiments, the CAR may only comprise a signaling domain, such as CD3□, and the cell may comprise one or more co-stimulatory domains on another construct expressed in the cell.

In some embodiments, a CAR comprises an extracellular, target-specific binding element otherwise referred to as a ligand-binding domain or moiety. The choice of ligand-binding domain depends upon the type and number of ligands that define the surface of a target cell. For example, the ligand-binding domain may be chosen to recognize a ligand that acts as a cell surface marker on target cells associated with a particular disease state. Thus, examples of cell surface markers that may act as ligands for the ligand-binding domain in the CAR of the present disclosure can include those associated with viral, bacterial and parasitic infections, autoimmune disease, and cancer cells. In some embodiments, the CAR of the present disclosure is engineered to target a tumor antigen of interest by way of engineering a desired ligand-binding moiety that specifically binds to an antigen on a tumor cell. In the context of the present disclosure, "tumor antigen" refers to antigens that are common to specific hyperproliferative disorders such as cancer.

In some embodiments, the extracellular ligand-binding domain of the CAR is specific for any antigen or epitope of interest, particularly any tumor antigen or epitope of interest. As non-limiting examples, in some embodiments the antigen of the target is a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD22, CD30, CD40, CLL-1, disialoganglioside GD2, ductal-epithelial mucine, gp36, TAG-72, glycosphingolipids, glioma-associated antigen, B-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, insulin growth factor (IGF1)-1, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD38, CD123, CD133, CD138, CTLA-4, B7-1 (CD80), B7-2 (CD86), endoglin, a major histocompatibility complex (MHC) molecule, BCMA (CD269, TNFRSF 17), CS1, or a virus-specific surface antigen such as an HIV-specific antigen (such as HIV gp120); an EBV-specific antigen, a CMV-specific antigen, a HPV-specific antigen such as the E6 or E7 oncoproteins, a Lasse Virus-specific antigen, an Influenza Virus-specific antigen, as well as any derivate or variant of these surface markers. In a particular embodiment of the present disclosure, the ligand-binding domain is specific for CD19.

In some embodiments, the extracellular domain of a chimeric antigen receptor further comprises an autoantigen (see, Payne et al. (2016) Science, Vol. 353 (6295): 179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and the incorporation of one or more co-stimulatory domains described herein into such CAARs is encompassed by the present disclosure.

In some embodiments, the extracellular domain of a chimeric antigen receptor can comprise a naturally-occurring ligand for an antigen of interest, or a fragment of a naturally-occurring ligand which retains the ability to bind the antigen of interest.

In some embodiments, a CAR comprises a transmembrane domain which links the extracellular ligand-binding domain or autoantigen with the intracellular signaling and co-stimulatory domains via a hinge or spacer sequence. The transmembrane domain can be derived from any membrane-bound or transmembrane protein. For example, the transmembrane polypeptide can be a subunit of the T-cell receptor (i.e., an α, β, γ or ζ, polypeptide constituting CD3 complex), IL2 receptor p55 (α chain), p75 (β chain) or γ chain, subunit chain of Fc receptors (e.g., Fcγ receptor III) or CD proteins such as the CD8 alpha chain. Alternatively the transmembrane domain can be synthetic and can comprise predominantly hydrophobic residues such as leucine and valine. In particular examples, the transmembrane domain is a CD8☐ transmembrane polypeptide.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In particular examples, a hinge domain can comprise a part of a human CD8 alpha chain, FcγRIIIa receptor or IgG1.

The intracellular signaling domain of a CAR of the present disclosure is responsible for activation of at least one of the normal effector functions of the cell in which the CAR has been placed and/or activation of proliferative and cell survival pathways. The term "effector function" refers to a specialized function of a cell. Effector function of a T cell, for example, may be cytolytic activity or helper activity including the secretion of cytokines. An intracellular signaling domain, such as CD3☐, can provide an activation signal to the cell in response to binding of the extracellular domain. As discussed, the activation signal can induce an effector function of the cell such as, for example, cytolytic activity or cytokine secretion.

The intracellular domain of the CAR can include one or more intracellular co-stimulatory domains which transmit a co-stimulatory signal to promote cell proliferation, cell survival, and/or cytokine secretion after binding of the extracellular domain. Such intracellular co-stimulatory domains include those known in the art such as, without limitation, CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83, N1, or N6.

The CAR can be specific for any type of cancer cell. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin's lymphoma. In certain embodiments, cancers of B cell origin include, without limitation, B lineage acute lymphoblastic leukemia, B cell chronic lymphocytic leukemia, B cell non-Hodgkin's lymphoma, and multiple myeloma.

2.4 Methods for Producing Recombinant Viral Vectors

In some embodiments, the present disclosure provides recombinant AAV vectors for use in the methods of the present disclosure. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) Curr. Gene Ther. 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient. Accordingly, methods are provided herein for producing recombinant AAV vectors comprising the nucleic acid molecules of the invention described herein.

In some embodiments, genetic transfer is accomplished via lentiviral vectors. Lentiviruses, in contrast to other retroviruses, in some contexts may be used for transducing certain non-dividing cells. Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif, vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In specific embodiments, lentiviral vectors are prepared using a first plasmid encoding the gag, pol, tat, and rev genes cloned from human immunodeficiency virus (HIV) and a second plasmid encoding the envelope protein from vesicular stomatitis virus (VSV-G) used to pseudotype viral particles. A transfer vector, such as the pCDH-EF1-MCS vector, can be used with a suitable promoter. All three plasmids can then be transfected into lentivirus cells, such as the Lenti-X-293T cells, and lentivirus can then be harvested, concentrated and screened after a suitable incubation time. Accordingly, methods are provided herein for producing recombinant lentiviral vectors comprising the nucleic acid molecule of the invention described herein.

2.5 Genetically-Modified Cells

Provided herein are cells genetically-modified to comprise the nucleic acid molecule of the invention described herein. Further provided are genetically-modified cells (e.g., human T cells expressing a CAR or exogenous TCR) with reduced cell-surface expression of beta-2 microglobulin, MHC class I molecules, and or CD52, which do not necessarily comprise the particular nucleic acid molecule of the invention.

In different variations of the present disclosure, a nucleic acid molecule of the invention is present within the genome of the genetically-modified cell or, alternatively, is not integrated into the genome of the cell. In particular embodiments, the nucleic acid molecule of the invention is inserted into the genome of a cell by targeted insertion at a cleavage site produced by a double-strand break, such as that produced by an engineered nuclease. The presence of 5' and 3' homology arms flanking the first and second expression cassettes of the nucleic acid molecule promote homologous recombination of the nucleic acid molecule into the cleavage site, resulting in targeted insertion.

In some embodiments where the nucleic acid molecule is not integrated into the genome, the nucleic acid molecule can be present in the genetically-modified cell in a recombinant DNA construct, in an mRNA, in a viral genome, or other nucleic acid which is not integrated into the genome of the cell.

In specific embodiments, the cells comprising the nucleic acid molecule of the invention, and other genetically-modified cells of the invention, are eukaryotic cells. In particular embodiments, such cells are T cells or NK cells, particularly human T cells or NK cells. In some embodiments, the cells are primary T cells or primary NK cells.

T cells and NK cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell and NK cell lines available in the art may be used. In some embodiments of the present disclosure, T cells and NK cells are obtained from a unit of blood collected from a subject using any number of techniques known to the skilled artisan. In one embodiment, cells from the circulating blood of an individual are obtained by apheresis.

Genetically-modified cells comprising the nucleic acid molecule disclosed herein, and other genetically-modified cells of the invention, can exhibit a number of functional properties dependent upon which polypeptide is reduced in the cell and/or targeted by the inhibitory nucleic acid molecule. For example, in some genetically-modified cells of the invention, beta-2 microglobulin is reduced, or the inhibitory nucleic acid molecule is against human beta-2 microglobulin, and cell surface beta-2 microglobulin expression is reduced, to a small percentage of wild-type expression. Such genetically-modified cells can be less susceptible to endogenous NK cell killing, have extended persistence time in a subject, exhibit enhanced expansion in a subject, and/or have reduced allogenicity than cells with wild-type levels of B2M or cells which are completely B2M-negative. Reductions in beta-2 microglobulin consequently result in a reduction in cell surface expression of MHC class I molecules, because beta-2 microglobulin is necessary for their assembly and function. Therefore, the same properties are also applicable to genetically-modified cells of the invention which have reduced cell surface expression of MHC class I molecules.

Susceptibility to NK cell killing can be determined by methods known in the art such as those described further herein. Reductions in NK cell killing can be by about 5%, 10%, 20%, 30%, 40%, 50% 55%, 60%, 65%, 70%, 75%, 80%, 85%, 86%, 87%, 88%, 89%, 90%, 91%, 92%, 93% 94%, 95%, 96, 97%, 98%, 99%, or up to 100% when compared to a control cell.

The genetically-modified cells of the invention are capable of expansion in a subject following administration. Here, expansion is considered an increase in cell number resulting from proliferation and division in vivo. The degree of expansion depends, in part, on the subject's response to the cells; for example, if the cells are identified as allogeneic and/or non-self, the subject's immune system may reduce the ability of the cells to expand and further reduce persistence of the cells post-administration. Thus, in some examples, genetically-modified cells of the invention can exhibit an increase in expansion in a subject that is about 5%, 10%, 20%, 30%, 40%, 50%, 60%, 70%, 80%, 90%, 100% 150%, 200%, 250%, 200%, 350%, 400%, 450%, 500%, up to 1000%, or more, when compared to a control cell. Expansion in vivo can be determined post-administration by any method known in the art. Persistence time of a genetically-modified cell in a subject can be considered, for example, as the amount of time post-administration of the cell that it can be detected in the subject by any method known in the art. In some examples, a genetically-modified cell of the invention will have an increase in persistence time that is up to about 1 week, 2 weeks, 3, weeks, 4 weeks, 5 weeks, 6 weeks, 7 weeks, 2 months, 3 months, 4 months, 5 months, 6 months, 1 year, or more, longer than a control cell.

Allogenicity can be determine by any method known in the art, such as those methods described further herein. The genetically-modified cells of the invention can exhibit a reduction in allogenicity of about 5%, 10%, 20%, 30%, 40%, 50% 55%, 60%, 65%, 70%, 75%, 80%, 85%, 86%, 87%, 88%, 89%, 90%, 91%, 92%, 93% 94%, 95%, 96, 97%, 98%, 99%, or up to 100% when compared to a control cell.

2.6 Methods for Producing Genetically-Modified Cells

The present disclosure provides methods for producing genetically-modified cells comprising the nucleic acid molecule of the invention described herein. In specific embodiments, methods are provided for modifying the cell to comprise the nucleic acid molecule. In different aspects of the present disclosure, the nucleic acid molecule is integrated into the genome of the cell or, alternatively, is not integrated into the genome of the cell.

In some embodiments, the nucleic acid molecule is introduced into a cell using any technology known in the art. In specific embodiments, vectors or expression cassettes comprising the nucleic acid molecule disclosed herein is introduced into a cell using a viral vector. Such vectors are known in the art and include lentiviral vectors, adenoviral vectors, and adeno-associated virus (AAV) vectors (reviewed in Vannucci, et al. (2013 New Microbiol. 36:1-22). Recombinant AAV vectors useful in the present disclosure can have any serotype that allows for transduction of the virus into the cell and insertion of the nuclease gene into the cell and, in particular embodiments, into the cell genome. In particular embodiments, recombinant AAV vectors have a serotype of AAV2, AAV6, or AAV8. Recombinant AAV vectors can also be self-complementary such that they do not require second-strand DNA synthesis in the host cell (McCarty, et al. (2001) *Gene Ther.* 8:1248-54).

In some embodiments, nucleic acid molecules disclosed herein are delivered into a cell in the form of DNA (e.g., circular or linearized plasmid DNA or PCR products) and/or via a viral vector. In some embodiments, the nucleic acid molecule disclosed herein is coupled covalently or non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 □m, preferably <100 nm. Such nanoparticles may be designed using a core composed of metal, lipid, polymer, or biological macromolecule, and multiple copies of the nucleic acid molecules can be attached to or encapsulated with the nanoparticle core. This increases the copy number of the DNA that is delivered to each cell and, so, increases the intracellular expression to maximize the likelihood that the encoded products will be expressed. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell surface receptors and the natural ligands (or portions of the natural ligands) for cell surface receptors.

In some embodiments, the nucleic acid molecule disclosed herein can be encapsulated within liposomes or complexed using cationic lipids (see, e.g., LIPO-FECTAMINE, Life Technologies Corp., Carlsbad, Calif.; Zuris et al. (2015) Nat Biotechnol. 33: 73-80; Mishra et al. (2011) *J Drug Deliv.* 2011:863734). The liposome and lipoplex formulations can protect the payload from degradation, and facilitate cellular uptake and delivery efficiency through fusion with and/or disruption of the cellular membranes of the cells.

In some embodiments, the nucleic acid molecule disclosed herein can be encapsulated within polymeric scaffolds (e.g., PLGA) or complexed using cationic polymers (e.g., PEI, PLL) (Tamboli et al. (2011) *Ther Deliv.* 2(4): 523-536). In some embodiments, the nucleic acid molecule disclosed herein can be combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions outside of the cell.

In some embodiments, the nucleic acid molecule disclosed herein can be formulated as an emulsion for delivery to the cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, the nucleic acid molecule disclosed herein can be covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size, and can provide a high payload capacity. Moreover, display of multiple surface groups can be leveraged to improve stability and reduce nonspecific interactions.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection. Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

2.7 Pharmaceutical Compositions

In some embodiments, the present disclosure provides a pharmaceutical composition comprising a genetically-modified cell, or a population of genetically-modified cells, of the present disclosure and a pharmaceutically-acceptable carrier. Such pharmaceutical compositions can be prepared in accordance with known techniques. See, e.g., Remington, *The Science And Practice of Pharmacy* (21st ed. 2005). In the manufacture of a pharmaceutical formulation according to the present disclosure, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the present disclosure further comprises one or more additional agents useful in the treatment of a disease in the subject. In additional embodiments, where the genetically-modified cell is a genetically-modified human T cell or NK cell (or a cell derived therefrom), pharmaceutical compositions of the present disclosure further include biological molecules, such as cytokines (e.g., IL-2, IL-7, IL-15, and/or IL-21), which promote in vivo cell proliferation and engraftment. Pharmaceutical compositions comprising genetically-modified cells of the present disclosure can be administered in the same composition as an additional agent or biological molecule or, alternatively, can be co-administered in separate compositions.

In some embodiments, the pharmaceutical compositions of the present disclosure are useful for treating any disease state that can be targeted by T cell adoptive immunotherapy. In a particular embodiment, the pharmaceutical compositions of the present disclosure are useful as immunotherapy in the treatment of cancer. Such cancers can include, without limitation, carcinoma, lymphoma, sarcoma, blastomas, leukemia, cancers of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In certain embodiments, cancers of B-cell origin include, without limitation, B-lineage acute lymphoblastic leukemia, B-cell chronic lymphocytic leukemia, and B-cell non-Hodgkin's lymphoma. Non-limiting examples of cancer which may be treated with the pharmaceutical compositions and medicaments of the present disclosure are carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, and B-cell non-Hodgkin's lymphoma.

In some of these embodiments wherein cancer is treated with the presently disclosed genetically-modified cells, the subject administered the genetically-modified cells is further administered an additional therapeutic, such as radiation, surgery, or a chemotherapeutic agent.

The invention further provides a population of genetically-modified cells comprising a plurality of genetically-modified cells described herein. Such genetically-modified cells can comprise in their genome a nucleic acid molecule encoding an engineered antigen receptor, such as a chimeric antigen receptor or exogenous T cell receptor, and an inhibitory nucleic acid molecule, such as an RNA interference molecule. Such genetically-modified cells can also comprise in their genome a nucleic acid molecule encoding an engineered antigen receptor, such as a chimeric antigen receptor or exogenous T cell receptor, and have reduced cell surface expression of beta-2 microglobulin, MHC class I molecules, or CD52, without necessarily comprising the particular nucleic acid molecule of the invention. Thus, in various embodiments of the invention, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified cell described herein.

2.8 Methods of Administering Genetically-Modified Cells

Another aspect disclosed herein is the administration of the genetically-modified cells of the present disclosure to a subject in need thereof. In particular embodiments, the pharmaceutical compositions described herein are administered to a subject in need thereof For example, an effective amount of a genetically-modified cell or population of genetically-modified cells of the invention which express a cell surface chimeric antigen receptor or exogenous T cell receptor, can be administered to a subject having a disease. In particular embodiments, the disease can be cancer, such as a cancer of B-cell origin. Thus, the present disclosure also provides a method for providing a T cell-mediated immune response to a target cell population or tissue in a mammal, comprising the step of administering to the mammal a CAR T cell, wherein the CAR comprises an extracellular ligand-binding domain that specifically interacts with a predetermined target, such as a tumor antigen, and an intracellular domain that comprises at least one signaling domain, such as CD3, and optionally one or more co-stimulatory signaling domains. The administered CAR T cells are able to reduce the proliferation, reduce the number, or kill target cells in the recipient. Unlike antibody therapies, genetically-modified cells of the present disclosure are able to replicate and expand in vivo, resulting in long-term persistence that can lead to sustained control of a disease.

In examples wherein the inhibitory nucleic acid molecule is against human beta-2 microglobulin or a component of the MHC class I molecule, or wherein beta-2 microglobulin or MHC class I molecules are otherwise reduced, expansion and/or persistence of such CAR T cells can be enhanced in the subject when compared to a CAR T cell having wild-type levels of beta-2 microglobulin or MHC class I molecules, or no cell surface beta-2 microglobulin or MHC class I expression. Further, allogenicity of the CAR T cell can be reduced when compared to a CAR T cell having a wild-type level of cell surface expression of beta-2 microglobulin and MHC class I molecules. These advantageous characteristics result from the incomplete reduction of cell surface beta-2 microglobulin (and consequently MHC class I molecules) to a small percentage of wild-type expression, which allows for reduced allogenicity but avoidance of NK cells which would otherwise target a beta-2 microglobulin-negative cell.

Examples of possible routes of administration include parenteral, (e.g., intravenous (IV), intramuscular (IM), intradermal, subcutaneous (SC), or infusion) administration. Moreover, the administration may be by continuous infusion or by single or multiple boluses. In specific embodiments, one or both of the agents is infused over a period of less than about 12 hours, 6 hours, 4 hours, 3 hours, 2 hours, or 1 hour. In still other embodiments, the infusion occurs slowly at first and then is increased over time.

In some embodiments, a genetically-modified eukaryotic cell or population thereof of the present disclosure targets a tumor antigen for the purposes of treating cancer. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin's lymphoma. In specific embodiments, cancers and disorders include but are not limited to pre-B ALL (pediatric indication), adult ALL, mantle cell lymphoma, diffuse large B cell lymphoma, salvage post allogenic bone marrow transplantation, and the like. These cancers can be treated using a combination of CARs that target, for example, CD19, CD20, CD22, and/or ROR1. In some non-limiting examples, a genetically-modified eukaryotic cell or population thereof of the present disclosure targets carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, multiple myeloma, and B-cell non-Hodgkin's lymphoma.

When an "effective amount" or "therapeutic amount" is indicated, the precise amount of the compositions of the present disclosure to be administered can be determined by a physician with consideration of individual differences in age, weight, tumor size (if present), extent of infection or metastasis, and condition of the patient (subject). In some embodiments, a pharmaceutical composition comprising the genetically-modified cells described herein is administered at a dosage of 104 to 109 cells/kg body weight, including all integer values within those ranges. In further embodiments, the dosage is 105 to 106 cells/kg body weight, including all integer values within those ranges. In some embodiments, cell compositions are administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In some embodiments, administration of genetically-modified cells of the present disclosure reduce at least one symptom of a target disease or condition. For example, administration of genetically-modified cells of the present disclosure can reduce at least one symptom of a cancer, such as cancers of B-cell origin. Symptoms of cancers, such as cancers of B-cell origin, are well known in the art and can be determined by known techniques.

EXPERIMENTAL

This disclosure is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

NK Cell Killing of B2M Knockout Primary Human T Cells

1. Methods and Materials

Primary human T cells were stimulated for 3 days using ImmunoCult anti-CD2/CD3/CD28 (StemCell Technologies) in the presence of IL-2 (Gibco) in XVIVO-15 medium (Lonza) supplemented with 5% fetal bovine serum. RNA encoding B2M13-14×479 nuclease was introduced into the T cells using the 4D Nucleofector (Lonza). Cells were cultured in the presence of IL-2 for 6 days before magnetic depletion of remaining B2M+ cells using biotinylated anti-human B2M (BioLegend) and a Biotin Selection Kit (StemCell Technologies). NK cells were isolated from PBMC samples of the same donor using a CD56 positive selection kit (StemCell Technologies). Daudi cells were purchased from ATCC. Daudi cells are naturally B2M$^-$ and are reported to be highly sensitive to NK cytolysis. All target cells were labeled with luM CellTrace Violet (LifeTechnologies) to distinguish them from effectors in mixed cultures. Isolated NK cells were mixed with either autologous B2M$^+$ T cell targets (negative control for NK cytolysis), Daudi targets (positive control for NK cytolysis), or autologous B2M KO T cell targets (experimental sample) at effector: target ratios of 2:1, 1:1, 0.5:1, and 0:1. Killing was assessed after 2 h of co-culture. Killing by NK cells was measured by staining with CaspACE-VAD-FMK (Promega).

2. Results

Figure 3:
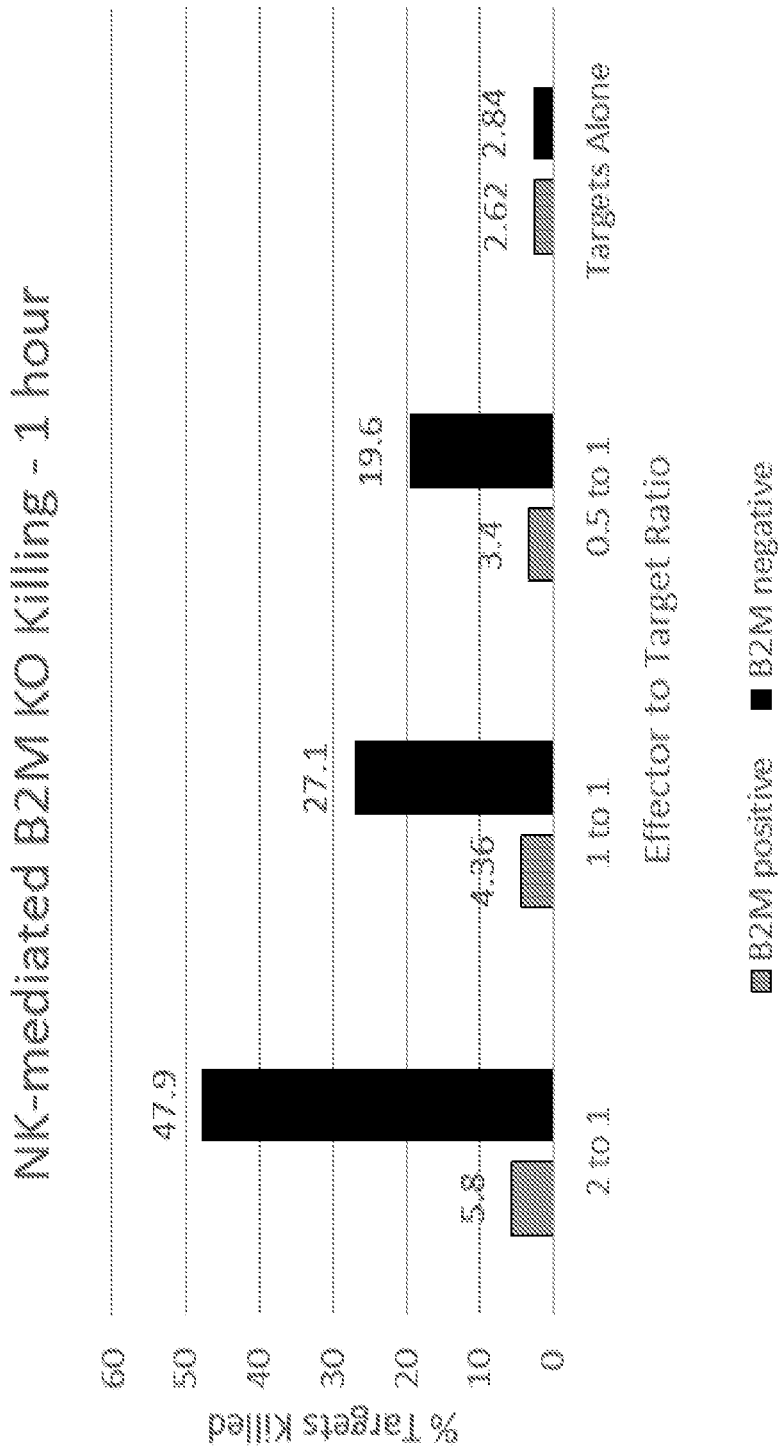
FIG. 3 shows a chart summarizing NK cell killing of B2M+ and B2M-cells at different ratios.

NK cells elicited only dim VAD-FMK signals in autologous B2M$^+$ targets, indicating low levels of apoptosis induction by active caspases (FIGS. 2A-2D). In comparison, high VAD-FMK signals were induced in large percentages of Class I-Daudi cells (71-83%, FIGS. 2I-2L), indicating extensive caspase cascade activation. Similarly, B2M$^-$ autologous T cells returned high VAD-FMK signals in response to NK encounter (19-47%, FIG. 2 E-H), indicative of caspase-mediated apoptosis induction. A graphical summary of these results appears in FIG. 3.

3. Conclusions

Complete knockout of cell surface B2M using engineered meganucleases sensitizes primary human T cells to NK cell attack and killing.

Example 2

Characterization of Candidate shRNAs Against B2M and Effect of B2M Knockdown on NK Cell Killing of Primary Human T Cells 1. Materials and Methods Five Mission-shRNA lentiviral transfer plasmids encoding different B2M targeting sequences were purchased from Sigma-Aldrich. Second-generation lentiviral vectors were produced in-house using Lenti-X 293T cells (ClonTech) and a triple transfection method (Lipofectamine 2000—ThermoFisher). T cells were prepared for lentiviral transduction by stimulating for 3 days with ImmunoCult anti-CD2/CD3/CD28 as in Example 1. Transduction was carried out in the presence of 5 uM polybrene (Sigma-Aldritch) and transduced cells were selected with puromycin (InVivoGen) beginning at 48 h post-transduction and concluding 72 h following drug addition. Selected cells were expanded for 5 days in IL-2 supplemented medium before a flow cytometric analysis of B2M surface expression to determine the extent of knockdown. Cultures receiving B2M shRNAs were used as targets in NK and CTL killing assays. The NK killing assays were carried out as described in Example 1, but the K562 cell line was used as the positive control for NK cytolysis. For the CTL killing assay, CD8+ T cells from a donor unrelated to the donor of the target cells were isolated and used as effectors. The NK killing assay was carried out for 2 h and the CTL assay was carried out for 6 h. For both assays, target cells were labeled with luM CellTrace Violet (Life Technologies), and killing was measured using CaspACE-VAD-FMK (Promega).

2. Results

Figure 4:
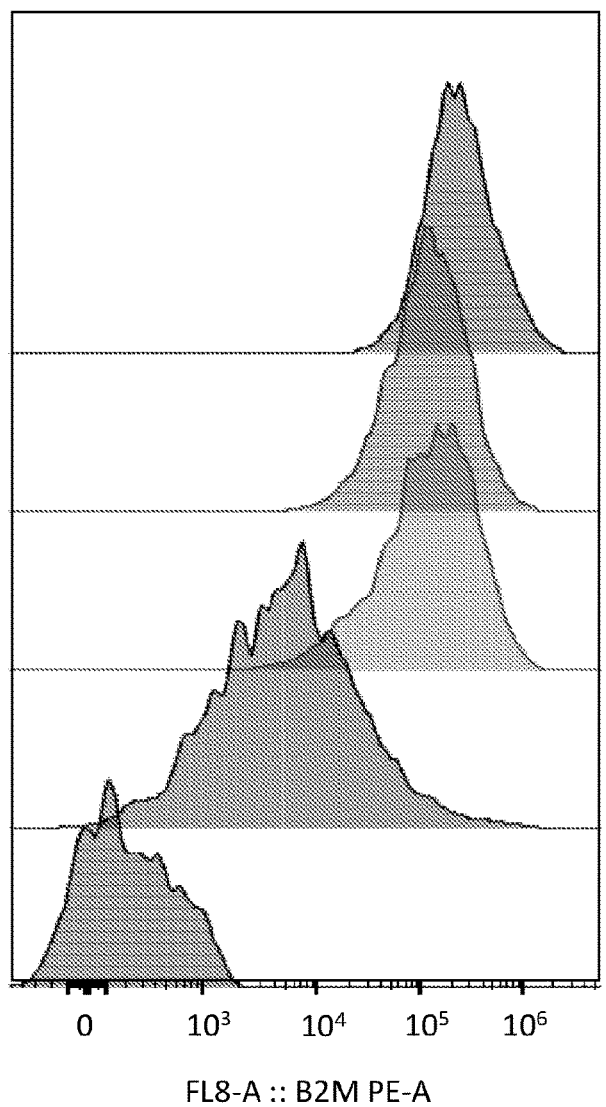
FIG. 4 shows percentage knockdown of human B2M in primary human T cells by three candidate B2M shRNAs.
Figure 7A:
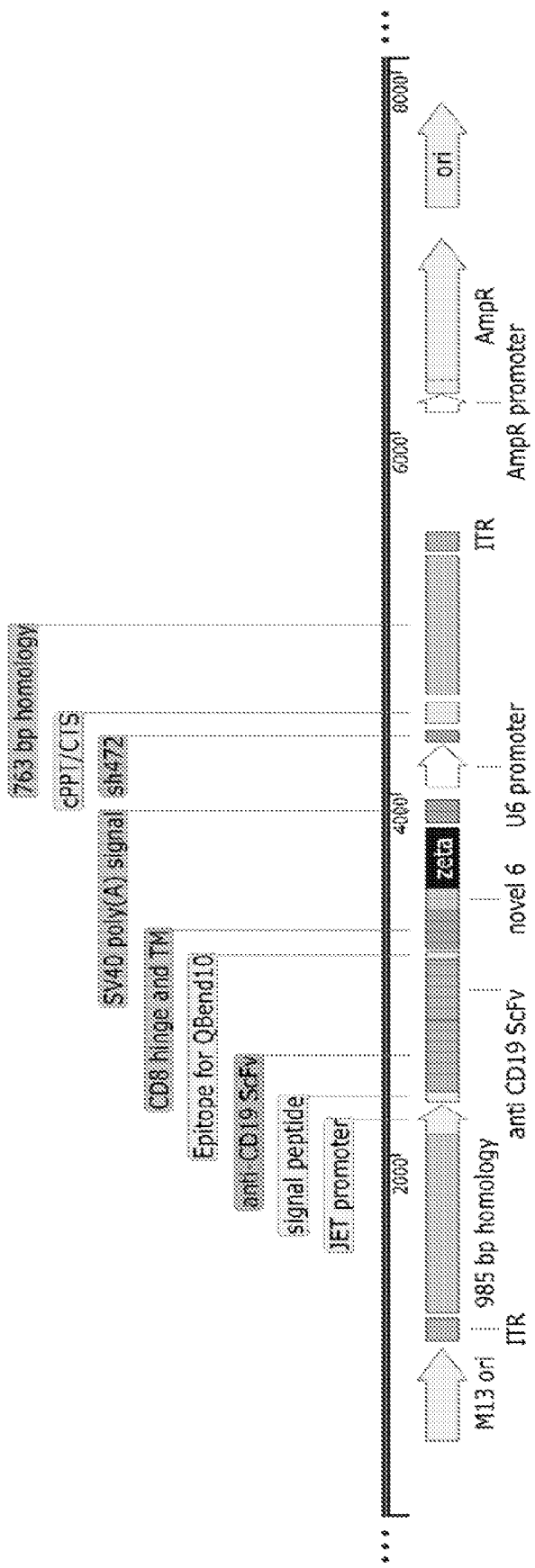
FIGS. 7A-7F show diagrams of various nucleic acid molecule constructs encoding a chimeric antigen receptor and an shRNA against beta-2 microglobulin.
Figure 7B:
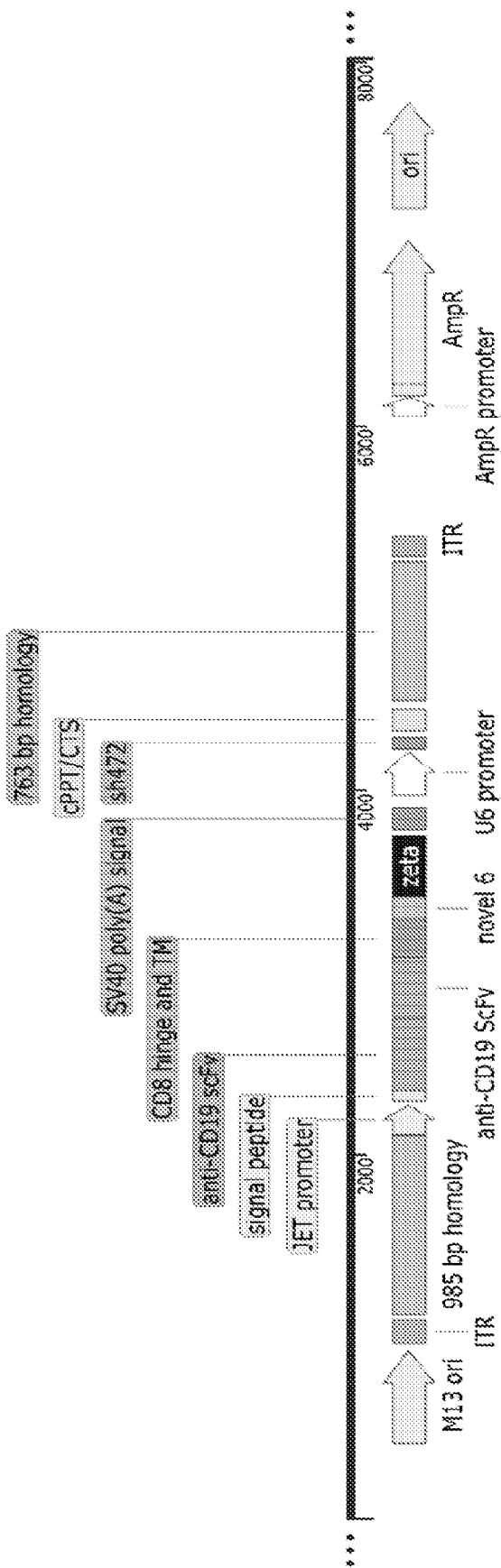
Figure 7C:
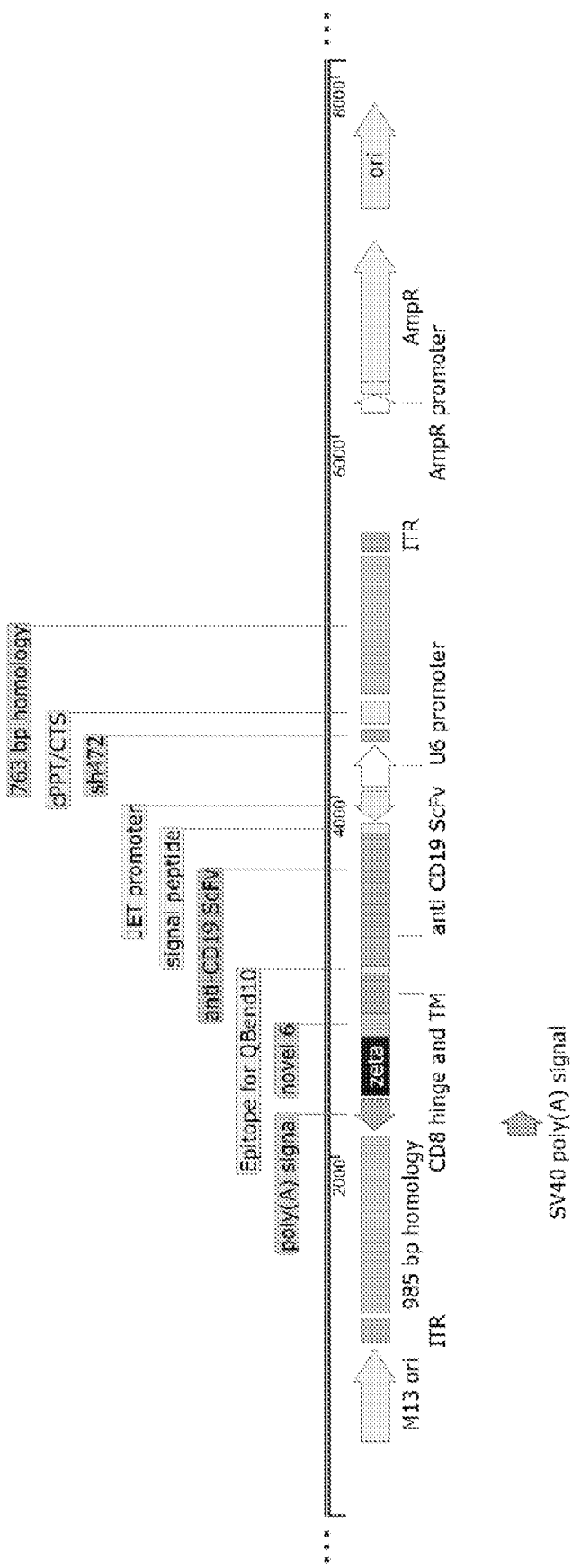
Figure 7D:
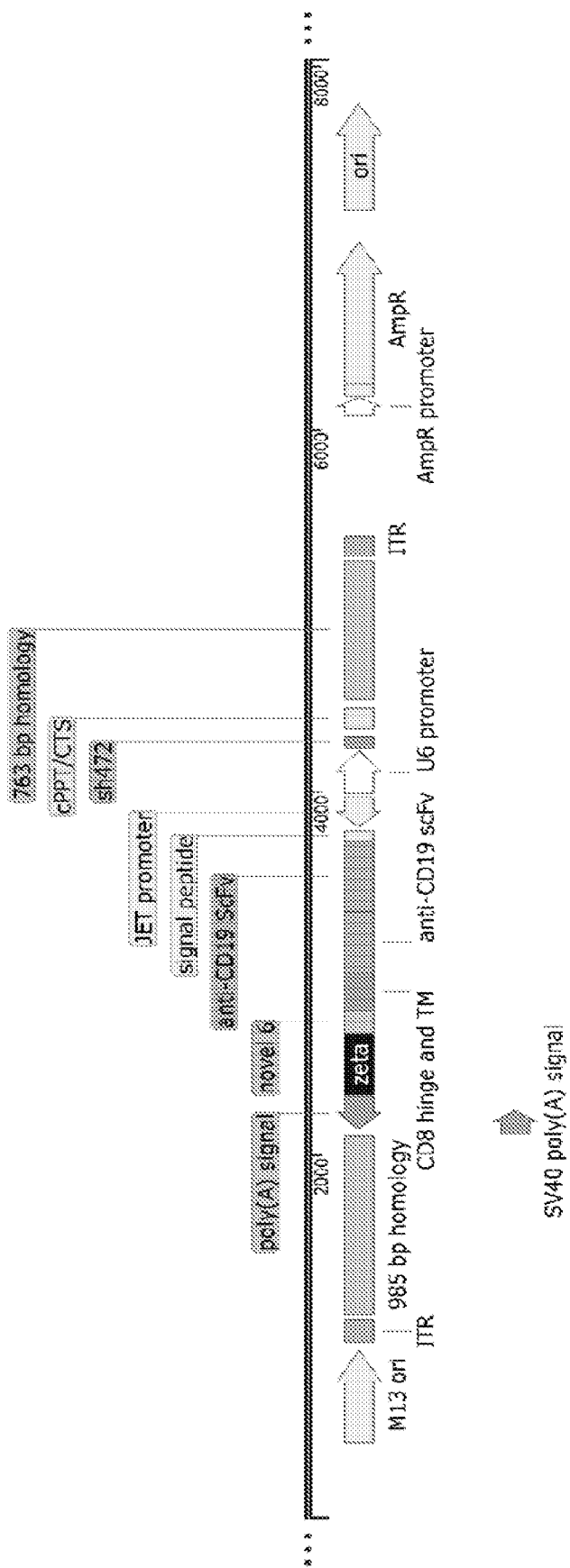
Figure 7E:
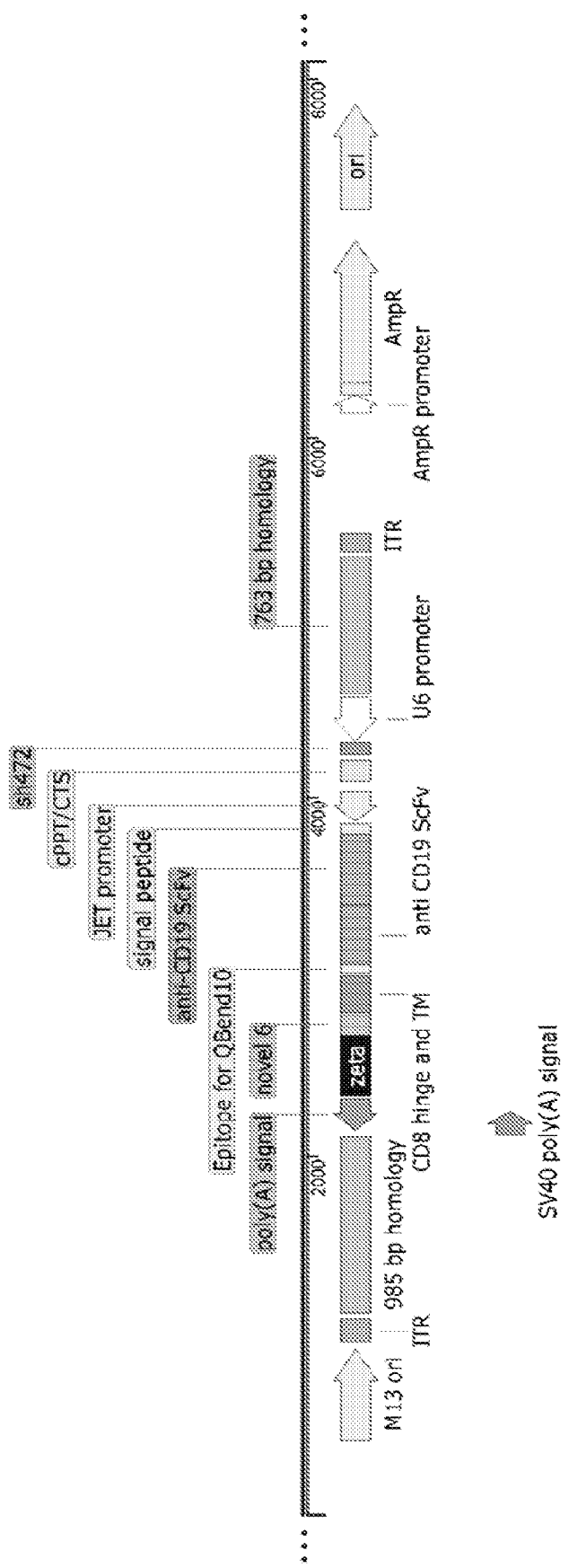
Figure 7F:
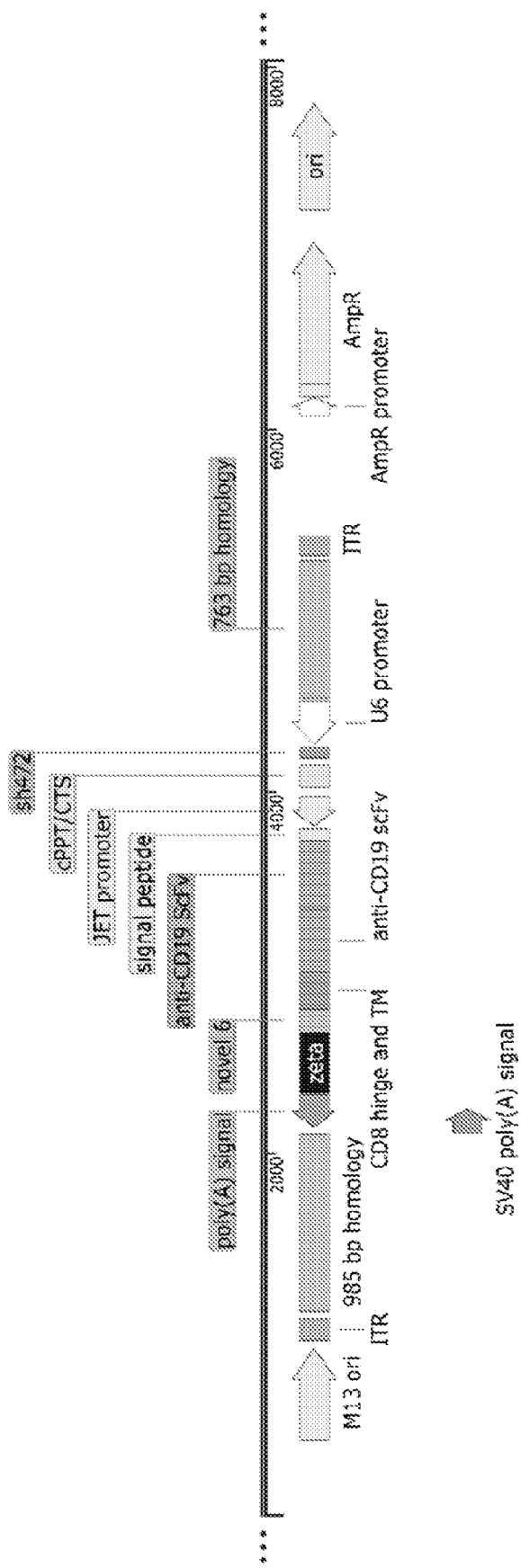

Five shRNAs were screened in human T cells for interference with B2M expression. Two sequences did not reduce the mean fluorescence intensity of B2M in a cytometric analysis (not shown). Three shRNA sequences did reduce the MFI of B2M expression, with sequence 254 and 255 reducing MFI by approximately 50% and sequence 472 reducing the MFI by approximately 95% (FIG. 4).

CTL and NK killing of targets exhibiting altered B2M expression was next measured. NK cells, but not CTLs induced caspase activation (measured by VAD-FMK signal) in Class I deficient K562 cells (46% vs. 5%—FIGS. 5A and 5B). Conversely, CTLs induced caspase activation (32%) in mismatched B2M$^+$ T cells while NK cells induced a signal in a lower frequency of mismatched T cells (14%) (FIGS. 5C and 5D). In T cell targets exhibiting a 50% reduction in B2M antigen density, NK cells elicited caspase activity in 17% of targets while mismatched CTLs did so in 36% of targets (FIGS. 6A and 6B). In T cell targets exhibiting a 95% knockdown of B2M levels, NK cells elicited caspase activation in 16% of targets, while mismatched CTLs did so in 20.8% of targets (FIGS. 5 C and D).

3. Conclusions

B2M expression can be effectively knocked down using shRNA delivered by a viral vector. Using caspase (VAD-FMK) activity to measure apoptosis induction in target cells by NK cells or CTLs, it was determined that B2M knockdown does not alter a target's susceptibility to NK cytolysis, as both B2M knockdown targets exhibited the same VAD-FMK frequency as un-manipulated targets, and less VAD-FMK signal than K562 targets. In addition, B2M knockdown confers some protection against CTL cytolysis, as the frequency of VAD-FMK+ targets in the shRNA 472 group was approximately half the frequency observed in the positive control. In fact, there was a direct relationship between the degree of knockdown and the degree of protection against CTL activity from NK cells.

Example 3

Production and Characterization of CAR T Cells Utilizing shRNA to Reduce Cell Surface Expression of B2M 1. Materials and Methods A number of constructs were prepared comprising an anti-CD19 CAR coding sequence and an shRNA against B2M. These are illustrated in FIG. 7A-7F and are provided in SEQ ID NOs: 18-23. CAR constructs 7007 and 7217 (SEQ ID NOs: 18 and 19) comprise the CAR coding sequence and the shRNA472 sequence in the same 5' to 3' orientation. CAR constructs 7008 and 7218 (SEQ ID NOs: 20 and 21) comprise the CAR coding sequence in the 3' to 5' orientation, and shRNA472 sequence in the 5' to 3' orientation (i.e., tail-to-tail). CAR constructs 7009 and 7219 (SEQ ID NOs: 22 and 23) comprise both the CAR coding sequence and the shRNA472 sequence in the 3' to 5' orientation. The 5' and 3' homology arms flanking the CAR coding sequence and the shRNA472 sequence have homology to regions upstream and downstream of the TRC 1-2 recognition sequence in the TRAC locus.

CAR T cells will be prepared using primary donor human T cells transduced with recombinant AAV vectors comprising one of the CAR/shRNA constructs above, with simultaneous nucleofection of mRNA encoding the TRC 1-2x.87EE to induce a double-strand break at the TRC 1-2 recognition sequence and promote targeted insertion of the construct into the genome of the T cells. Beta-2 microglobulin expression will be determined as described above to determine which orientation of the first and second expression cassettes will result in the highest and/or the most consistent CAR expression, along with the most consistent level of B2M knockdown on the cell surface.

CAR T cells produced with certain constructs will be evaluated in both the allogenicity and NK cell killing assays previously described above. Further, CAR T cells produced using the disclosed constructs will be evaluated in various stress tests, in which the CAR T cells are repeatedly exposed to antigen in order to determine changes in cell proliferation/expansion and cytotoxic potential. CAR T cells produced using the disclosed constructs will also be utilized with in vivo tumor models to determine their ability to clear tumor cells in an animal and to evaluate their ability to persist in vivo. It is expected, based on the Examples described herein, that CAR T cells having a reduced but incomplete knockdown of cell surface beta-2 microglobulin will have greater persistence and/or enhanced expansion in vivo when compared to CAR T cells which are completely B2M-negative and may be susceptible to NK cell killing.

In a particular study, CAR T cells were prepared that are TCR-negative, CAR-positive, and have reduced cell surface expression of B2M. CAR T cells were prepared using donor templates that comprise a promoter-driven CAR coding sequence, a T2A element, and one or multiple promoter-driven B2M shRNA cassettes. In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28—Stem Cell Technologies) in X-VIVO 15 medium (Lonza) supplemented with 5% fetal bovine serum and 10 ng/ml IL-2 (Gibco). After 3 days of stimulation, cells were collected and samples of 1e6 cells were electroporated with the following mixture of nucleic acid species using the Lonza 4D NucleoFector.

1 µg mRNA encoding the TRC 1-2x.87EE meganuclease which produces a double-strand break in Exon 1 of the T cell receptor alpha constant region gene 1.5 µl of 100 mM siRNA specific for TMEM173 (STING)

1 µg of linearized plasmid DNA comprising a donor template

In this experiment, three different CAR constructs were analyzed for their ability to knock down B2M surface expression. All three constructs use homology to genomic regions flanking the TRC 1-2x.87EE binding site (referred to as the TRC 1-2 recognition site) to direct targeted insertion into the T cell receptor alpha constant region locus, and they all express a CAR that comprises a CD34 epitope tag (for detection). Construct 7002 (SEQ ID NO: 11) does not encode an shRNA gene. Construct 7008 (SEQ ID NO: 20) encodes one copy of shRNA472. Construct 7029 (SEQ ID NO: 24) encodes two copies of this shRNA cassette. Expression from each shRNA cassette is driven by a U6 promoter.

Cell cultures were maintained for 10 additional days in X-VIVO15 medium supplemented with 5% FBS and 30 ng/ml of IL-2. On d4, 7, and 10 post-nucleofection, the cultures were sampled and analyzed for surface expression of CD3 (anti-CD3-BV711, BioLegend), CD34 (anti-CD34-PE, LifeTechnologies), and B2M (anti-B2M-APC, BioLegend). Flow cytometry data were acquired on a Beckman-Coulter CytoFLEX-LX.

2. Results

Figure 12A:
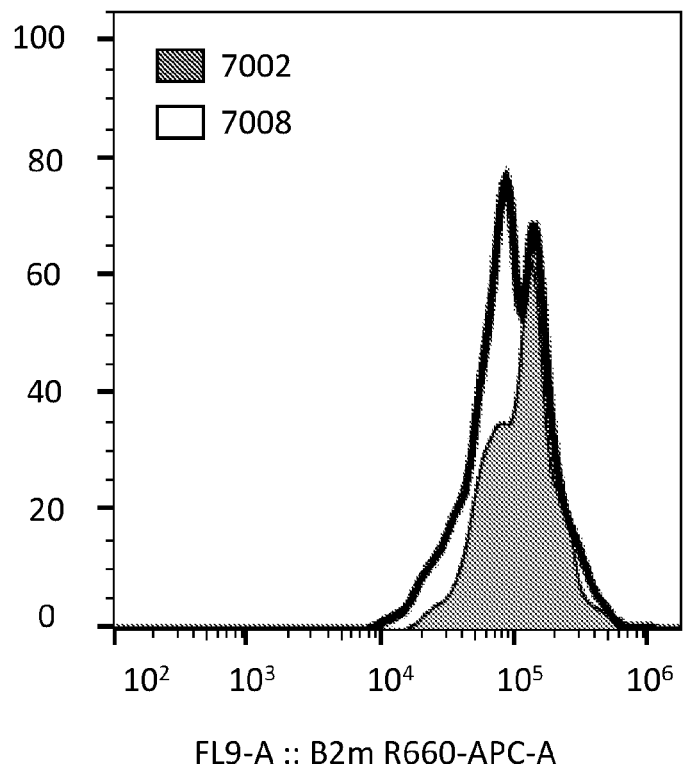
FIG. 12A-12C shows B2M knockdown on CAR T cells using CAR/B2M shRNA constructs having one or multiple shRNA cassettes.
Figure 12B:
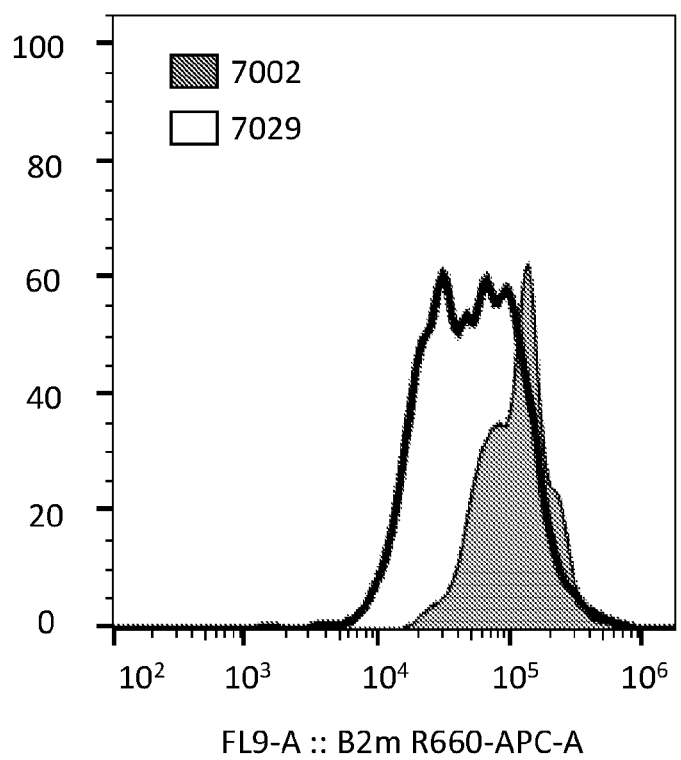
Figure 12C:
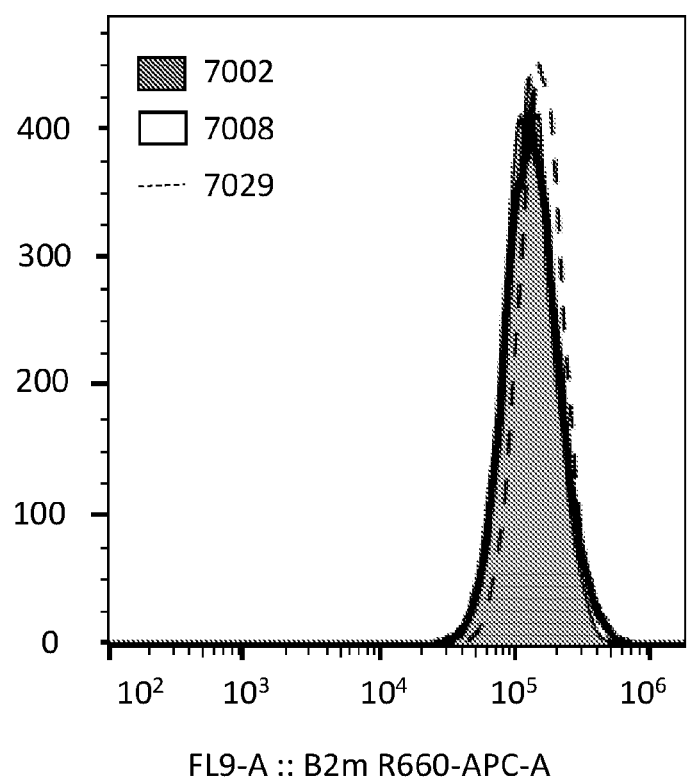

B2M surface levels were measured in samples nucleofected with a control CAR construct (7002) or with CAR constructs expressing one (7008) or two (7029) copies of B2M-specific shRNA (FIG. 12). When comparing the CD3-/CD34+ populations in 7002 (control) and 7008 (single shRNA) expressing cells, 7008 expressing cells were observed to display slightly lower levels of surface B2M (FIG. 12A). Notably, cells nucleofected with construct 7029 (two shRNA copies) displayed approximately half of the amount of B2M displayed on the surface of control cells (7002) (FIG. 12B). This observation was specific to the CD3-/CD34+ population, but was not observed in the CD3-/CD34- population (FIG. 12C).

3. Conclusions

A pre-screened B2M-targeting shRNA can knock down B2M expression levels on the surface of cells into which the construct has been delivered (via targeted insertion into the T cell receptor alpha constant region locus). Due to the high abundance of B2M transcripts, these data suggest that a single shRNA copy can be sufficient for low levels of B2M knockdown, whereas multiple copies of the shRNA cassette may be required to achieve more significant knockdown.

Example 4

Production and Characterization of CAR T Cells Utilizing shRNA to Reduce Cell Surface Expression of B2M

1. Materials and Methods

A number of constructs were prepared comprising an anti-CD19 CAR coding sequence and an shRNA against B2M. These are illustrated in FIG. 7A-7F and are provided in SEQ ID NOs: 18-23. CAR constructs 7007 and 7217 (SEQ ID NOs: 18 and 19) comprise the CAR coding sequence and the shRNA472 sequence in the same 5' to 3' orientation. CAR constructs 7008 and 7218 (SEQ ID NOs: 20 and 21) comprise the CAR coding sequence in the 3' to 5' orientation, and shRNA472 sequence in the 5' to 3' orientation (i.e., tail-to-tail). CAR constructs 7009 and 7219 (SEQ ID NOs: 22 and 23) comprise both the CAR coding sequence and the shRNA472 sequence in the 3' to 5' orientation. CAR constructs 7056, 7059, and 7060 contain modified versions of the U6-shRNA gene cassette. A cloning site that was located between the U6 promoter and the hairpin sequence in constructs 7007-7009, and in 7217-7219 was removed. Construct 7056 comprises the CAR coding sequence and the shRNA472 sequence in the 3' to 5' orientation. Construct 7056 comprises the CAR coding sequence in 3' to 5' orientation, and the shRNA472 sequence in the 5' to 3' orientation (tail-to-tail). Construct 7060 comprises the CAR coding sequence in 3' to 5' orientation and two copies of the U6-shRNA472 sequence in 5' to 3' orientation. The 5' and 3' homology arms flanking the CAR coding sequence and the shRNA472 sequence have homology to regions upstream and downstream of the TRC 1-2 recognition sequence in the T cell receptor alpha constant locus.

In a particular study, CAR T cells were prepared that are TCR-negative, CAR-positive, and have reduced cell surface expression of B2M. CAR T cells were prepared using donor templates that comprise a promoter-driven CAR coding sequence, and one or multiple promoter-driven B2M shRNA cassettes. In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28—Stem Cell Technologies) in X-VIVO 15 medium (Lonza) supplemented with 5% fetal bovine serum and 10 ng/ml IL-2 (Gibco). After 3 days of stimulation, cells were collected and samples of 1e6 cells were electroporated with the following mixture of nucleic acid species using the Lonza 4D NucleoFector.

- 1 ug mRNA encoding the TRC 1-2x.87EE meganuclease which produces a double-strand break in Exon 1 of the T cell receptor alpha constant region gene
- 1.5 µl of 100 mM siRNA specific for TMEM173 (STING)
- 1 µg of linearized plasmid DNA comprising a donor template In this experiment, four different CAR constructs were analyzed for their ability to knock down B2M surface expression. All four constructs use homology to genomic regions flanking the TRC 1-2x.87EE recognition site to direct targeted insertion into the T cell receptor alpha constant region locus, and they all express a CAR that comprises a CD34 epitope tag (for detection). Construct 7002 (SEQ ID NO: 11) does not encode an shRNA gene. Construct 7056 (SEQ ID NO: 25) encodes one copy of shRNA472, and both cassettes are in the 3' to 5' orientation (head-to-tail). Construct 7059 (SEQ ID NO: 26) encodes one copy of this shRNA cassette, with the CAR expression cassette in a 3' to 5' orientation, and the shRNA472 cassette in a 5' to 3' orientation (tail-to-tail). Construct 7060 (SEQ ID NO: 27) is in the same orientation as construct 7059 but encodes two copies of the shRNA472 cassette (tail-to-tail). Expression from each shRNA cassette is driven by a U6 promoter. Cell cultures were maintained for up to 10 additional days in X-VIVO15 medium supplemented with 5% FBS and 30 ng/ml of IL-2. On d4, 7, and/or 10 post-nucleofection, the cultures were sampled and analyzed for surface expression of CD3 (anti-CD3-BV711, BioLegend), CD34 (anti-CD34-PE, or APC, LifeTechnologies), B2M (anti-B2M-APC, or PE, BioLegend), and/or HLA-A, B, and C (clone W6/32, BV605). Flow cytometry data were acquired on a Beckman-Coulter CytoFLEX-LX.

2. Results

B2M surface levels were measured in samples nucleofected with a control CAR construct (7002) or with CAR constructs expressing one (7056 or 7059) or two (7060) copies of B2M-specific shRNA in either head-to-tail (7056) or tail-to-tail (7059, 7060) configurations. A restriction digest site that was present in previous constructs between the U6 promoter and the shRNA sequence was been removed from these shRNA472 vectors. It was hypothesized that the palindromic restriction digest site interfered with the efficacy of the constructs and the ability of the shRNA to knock down B2M.

When comparing the CD3-/CD34+ populations in 7002 (control) and 7056 (single shRNA) expressing cells, 7056 expressing cells were observed to display lower levels of surface B2M (77% knockdown) (FIG. 13A). Cells nucleofected with 7059 (single copy, tail-to-tail) displayed a 90.1% knockdown of B2M relative to 7002 control cells (FIG. 13B), while 7060 nucleofection (two copies, tail-to-tail) resulted in a 92% knockdown relative to 7002 controls (FIG. 13C).

3. Conclusions

A pre-screened B2M-targeting shRNA can knock down B2M expression levels on the surface of cells into which the construct has been delivered (via targeted insertion into the T cell receptor alpha constant region locus). Removing the cloning site between the U6 promoter and the hairpin sequence improves the efficiency with which B2M is knocked down. 7008 (tail-to-tail, one shRNA472 cassette—FIG. 12A) supports minimal B2M knockdown while 7059 (one cassette, tail-to-tail—FIG. 13B) supports greater than 90% knockdown. As was observed using a CD52-specific shRNA, superior knockdown was observed when the CAR promoter and the shRNA promoter were oriented in different directions (tail-to-tail configuration). Adding a second shRNA sequence did not provide any noticeable benefit (92% versus 90.1% knockdown).

Example 5

Production and Characterization of CAR T Cells Utilizing shRNA to Reduce Cell Surface Expression of B2M

1. Materials and Methods

In this study, an apheresis sample was drawn from a healthy, informed, and compensated donor, and the T cells were enriched using the CD3 positive selection kit II in accord with the manufacturer's instructions (Stem Cell Technologies). T cells were activated using ImmunoCult T cell stimulator (anti-CD2/CD3/CD28—Stem Cell Technologies) in X-VIVO 15 medium (Lonza) supplemented with 5% fetal bovine serum and 10 ng/ml IL-2 (Gibco). After 3 days of stimulation, cells were collected and samples of 1e6 cells were electroporated with 1 ug of RNA encoding the TRC 1-2L.1592 meganuclease, which recognizes and cleaves the TRC 1-2 recognition sequence in the T cell receptor alpha constant locus, and were transduced with AAV packaged with construct 7056 at an MOI of 25000 viral genomes/cell.

Cell cultures were maintained for up to 10 additional days in X-VIVO15 medium supplemented with 5% FBS and 30 ng/ml of IL-2. On day 4, 7, and/or 10 post-nucleofection, the cultures were sampled and analyzed for surface expression of CD3 (anti-CD3-PE, BioLegend), (anti-FMC63 anti-CAR clone VM16 conjugated to AlexaFluor488), B2M (anti-B2M-APC, or PE, BioLegend), and HLA-A, B, and C (clone W6/32, BV605). Flow cytometry data were acquired on a Beckman-Coulter CytoFLEX-LX.

2. Results

Figure 14A:
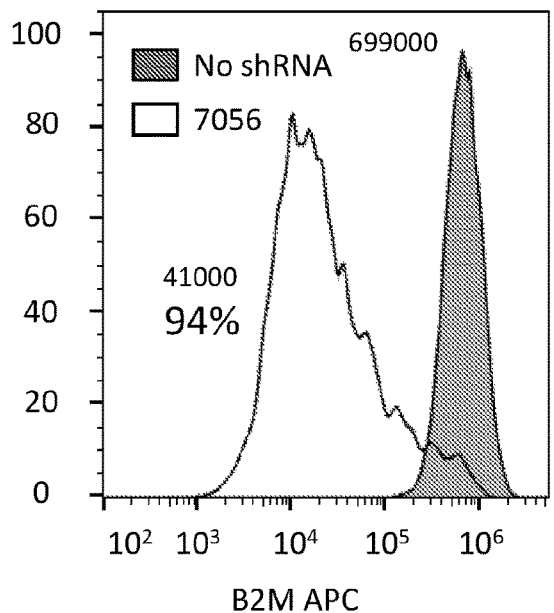
Figure 14B:
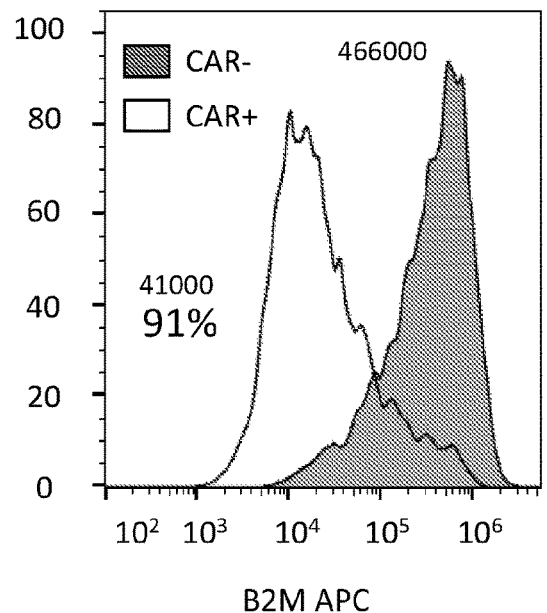
Figure 14C:
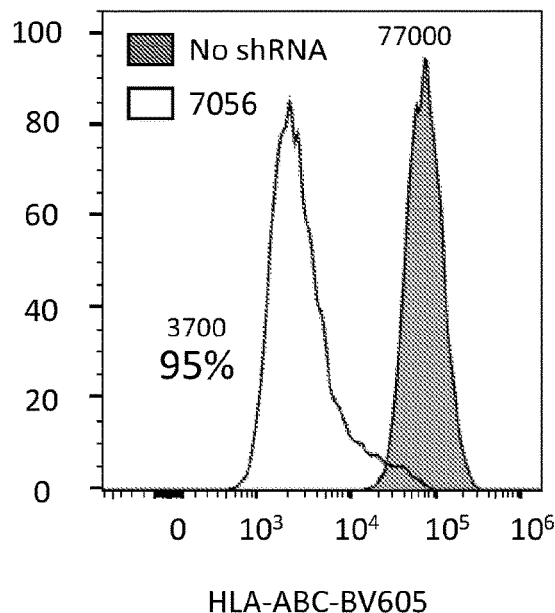
Figure 14D:
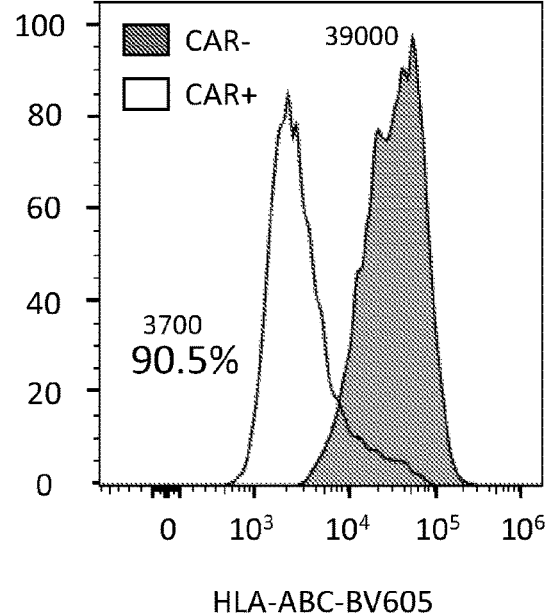

B2M and HLA-ABC levels were measured in samples expressing construct 7056 and control populations. FIG. 14A shows the B2M surface levels in CD3−/CAR+ cells compared to TRAC-edited cells expressing no shRNA from a control culture. FIG. 14B shows B2M levels on CD3−/CAR+ versus CD3+/CAR− populations in the same culture. FIGS. 14C and 14D make the same respective comparisons in displays of HLA-ABC surface levels. The CD3−/CAR+ fraction of cells transduced with AAV-7056 displayed levels of B2M and HLA-ABC that are reduced by greater than 90% compared to control populations.

3. Conclusions

A pre-screened B2M-targeting shRNA can knock down B2M expression levels on the surface of cells into which the construct has been delivered (via targeted insertion into the T cell receptor alpha constant region locus). This effect is specific to CAR+ populations (i.e., cells in which targeted integration into the TRAC locus has occurred). This experiment demonstrates that B2M can be efficiently knocked down using a single copy of shRNA472 co-delivered to the TRAC locus with the CAR gene on the same AAV template.

Example 6

Characterization of Candidate shRNAs Against CD52 in Primary Human T Cells

1. Materials and Methods

Five Mission-shRNA lentiviral transfer plasmids encoding different CD52 targeting sequences were purchased from Sigma-Aldrich. Second-generation lentiviral vectors were produced in-house using Lenti-X 293T cells (ClonTech) and a triple transfection method (Lipofectamine 2000—Thermo-Fisher). T cells were prepared for lentiviral transduction by stimulating for 3 days with ImmunoCult anti-CD2/CD3/CD28 as in Example 1. Transduction was carried out in the presence of 5 uM polybrene (Sigma-Aldritch) and transduced cells were expanded for 5 days in IL-2 supplemented medium before a flow cytometric analysis of CD52 surface levels. Cells were not selected with puromycin because a heterogeneous population was desired for downstream attempts at magnetic depletion of CD52Hi cells. Cells transduced with a lentivirus encoding shRNA 568 were labeled with biotinylated anti-CD52 (Miltenyi Biotec), and magnetic separation was performed using a Biotin Positive Selection Kit (StemCell Technologies). A post-separation analysis of surface CD52 was performed.

2. Results

Figure 8:
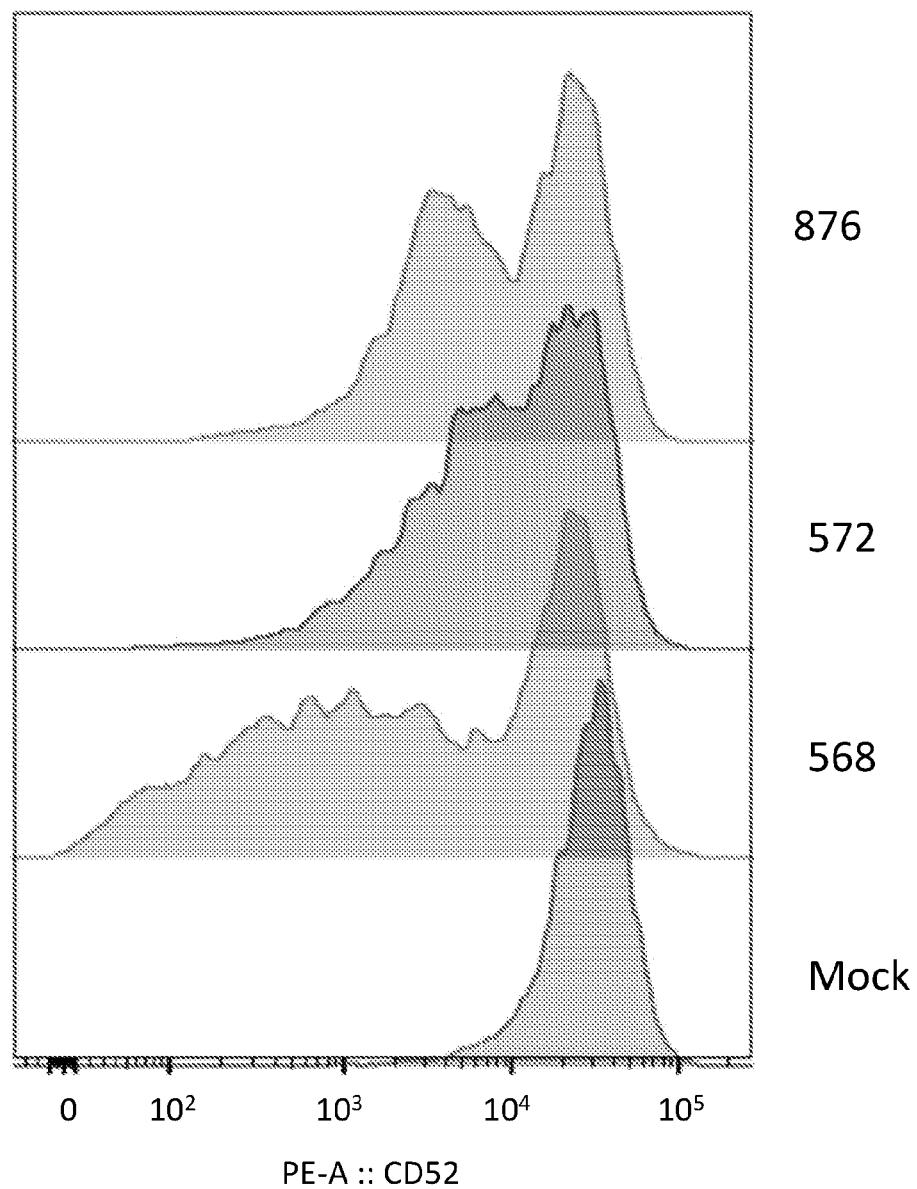
FIG. 8 shows percentage knockdown of human CD52 in primary human T cells by three different candidate CD52 shRNAs.
Figure 9A:
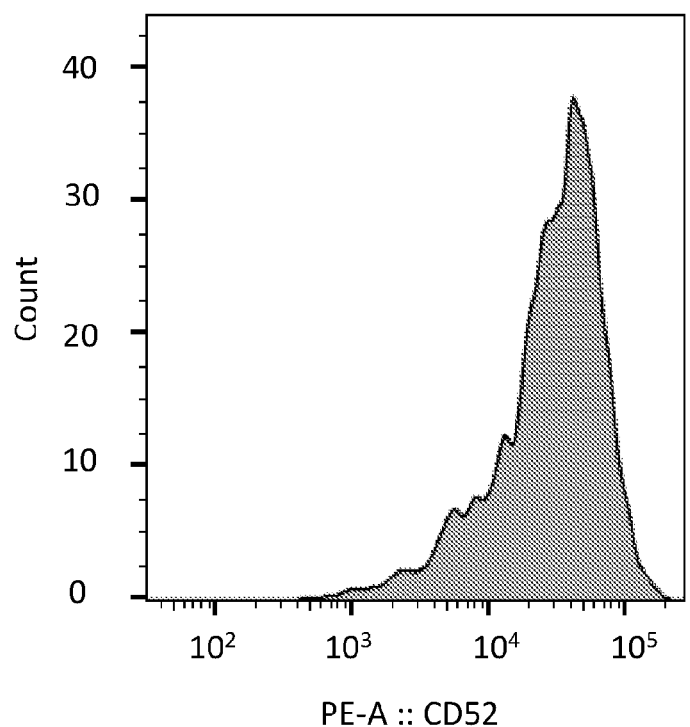
FIG. 9A shows T cells that were mock transduced.
Figure 9B:
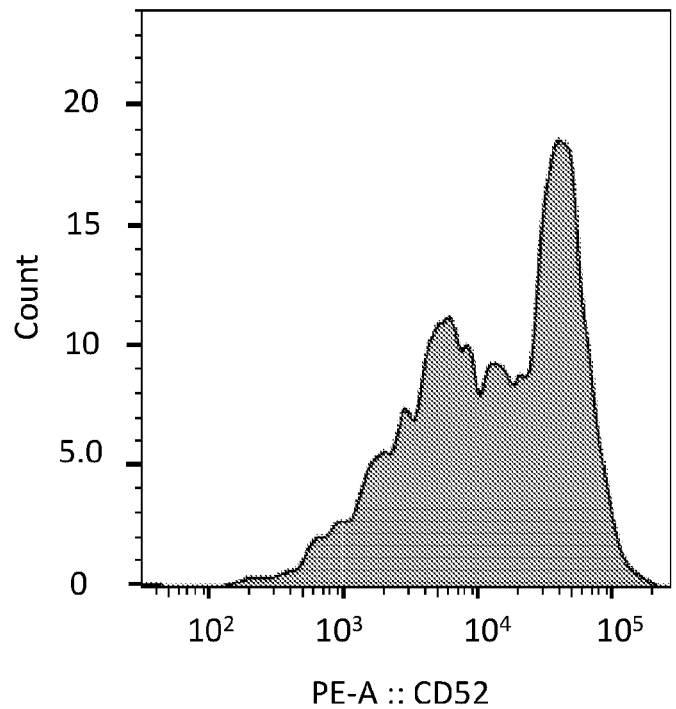
FIG. 9B shows T cells transduced with an shRNA-568 lentivirus.
Figure 9C:
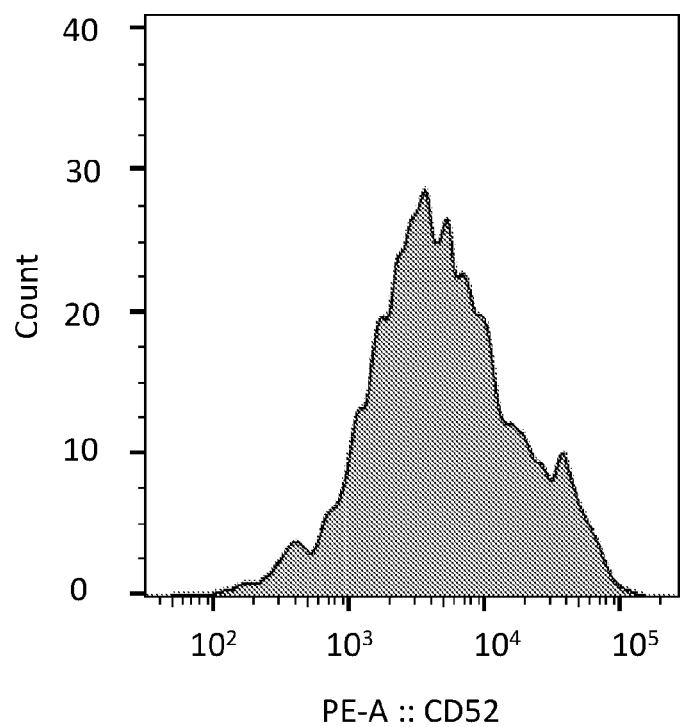
FIG. 9C shows lentivirus-shRNA568 transduced cells that have undergone a CD52 magnetic depletion.
Figure 10A:
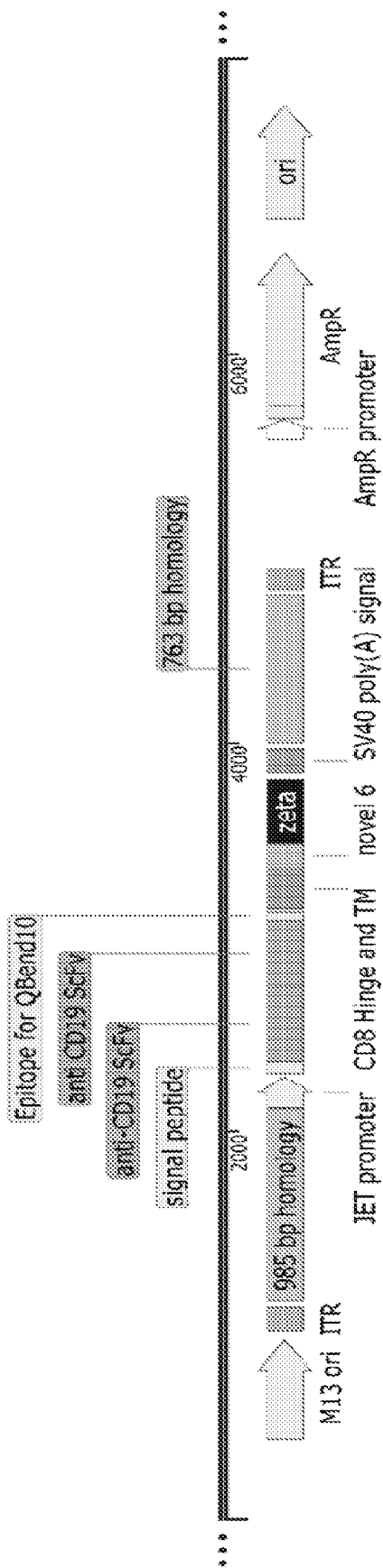
FIGS. 10A-10H shows diagrams of nucleic acid molecule constructs encoding a chimeric antigen receptor and an shRNA against CD52.
Figure 10B:
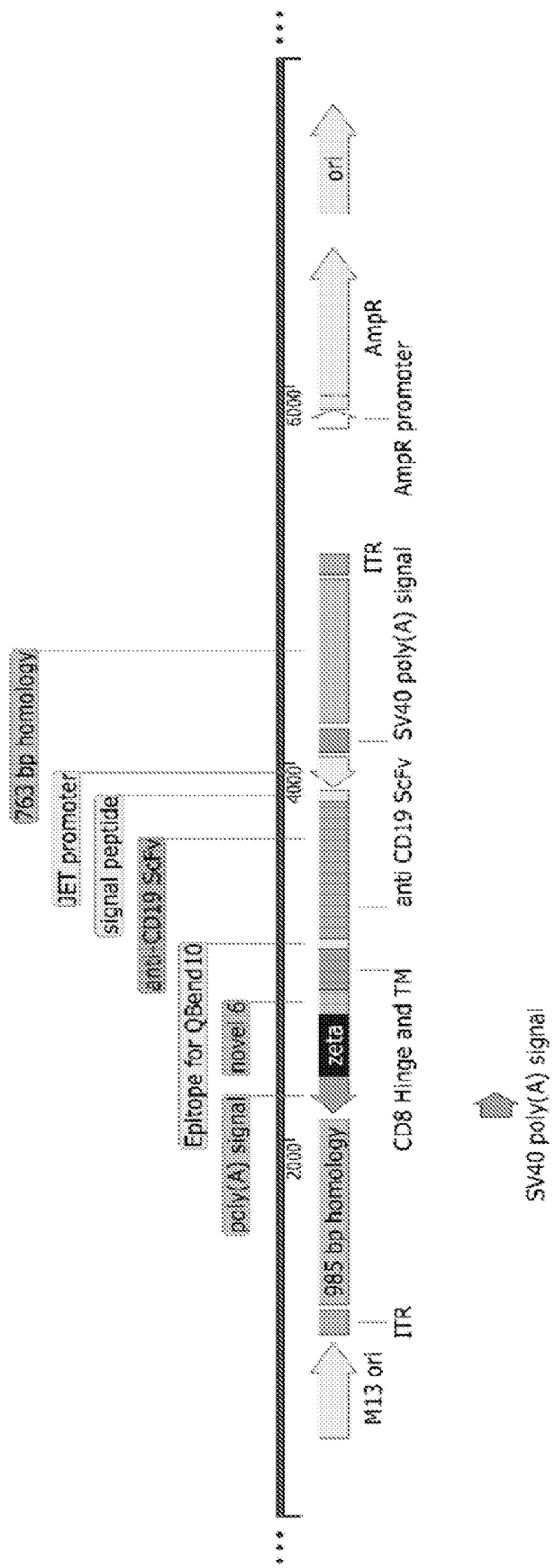
Figure 10C:
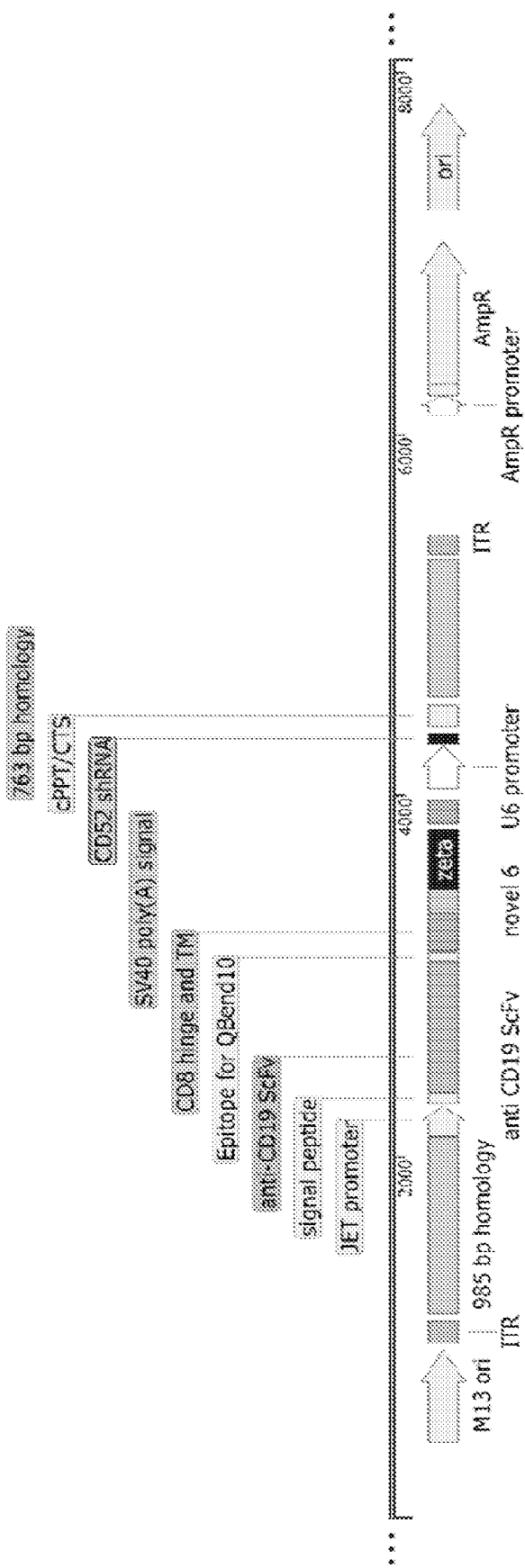
Figure 10D:
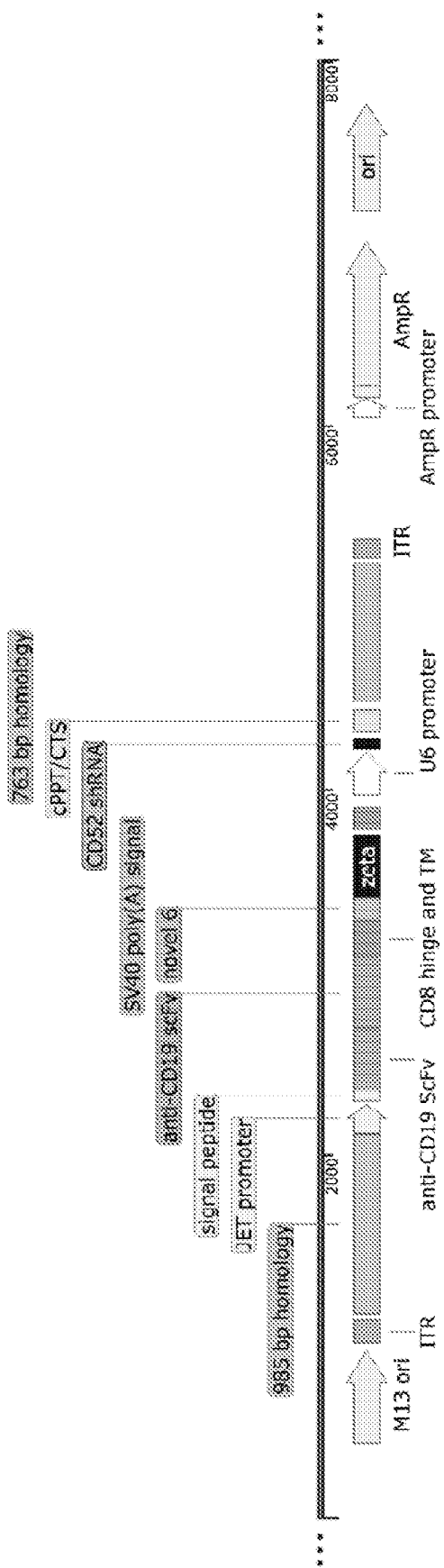
Figure 10E:
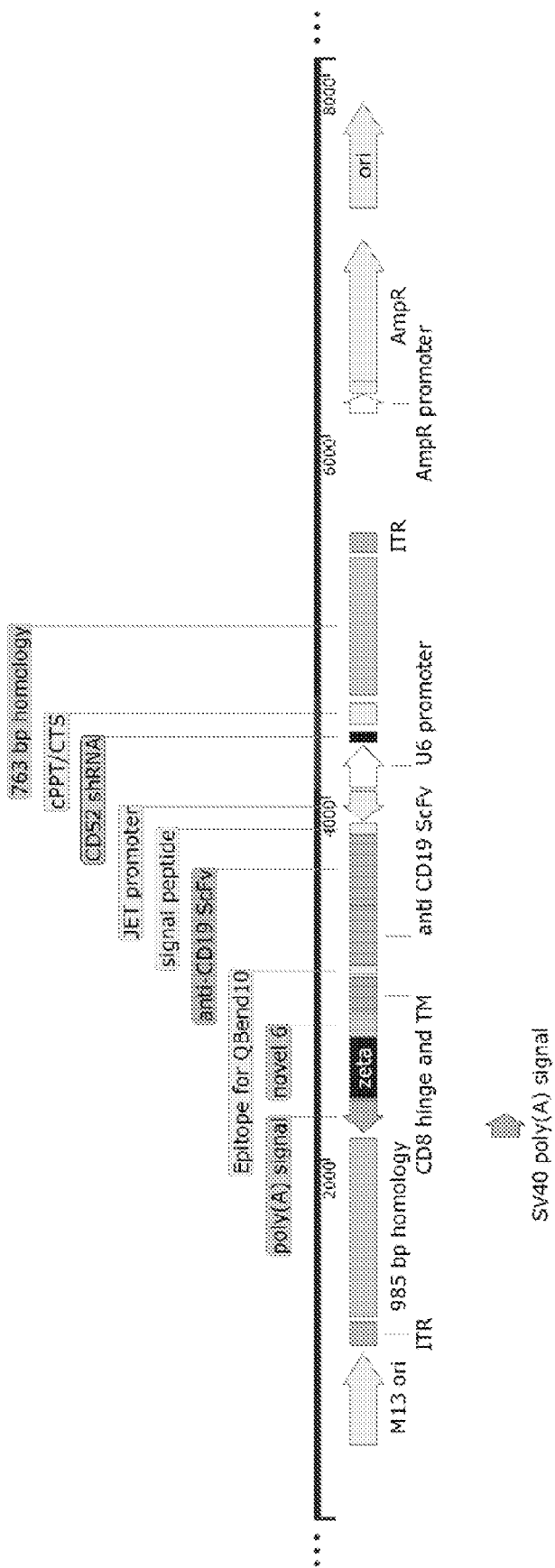
Figure 10F:
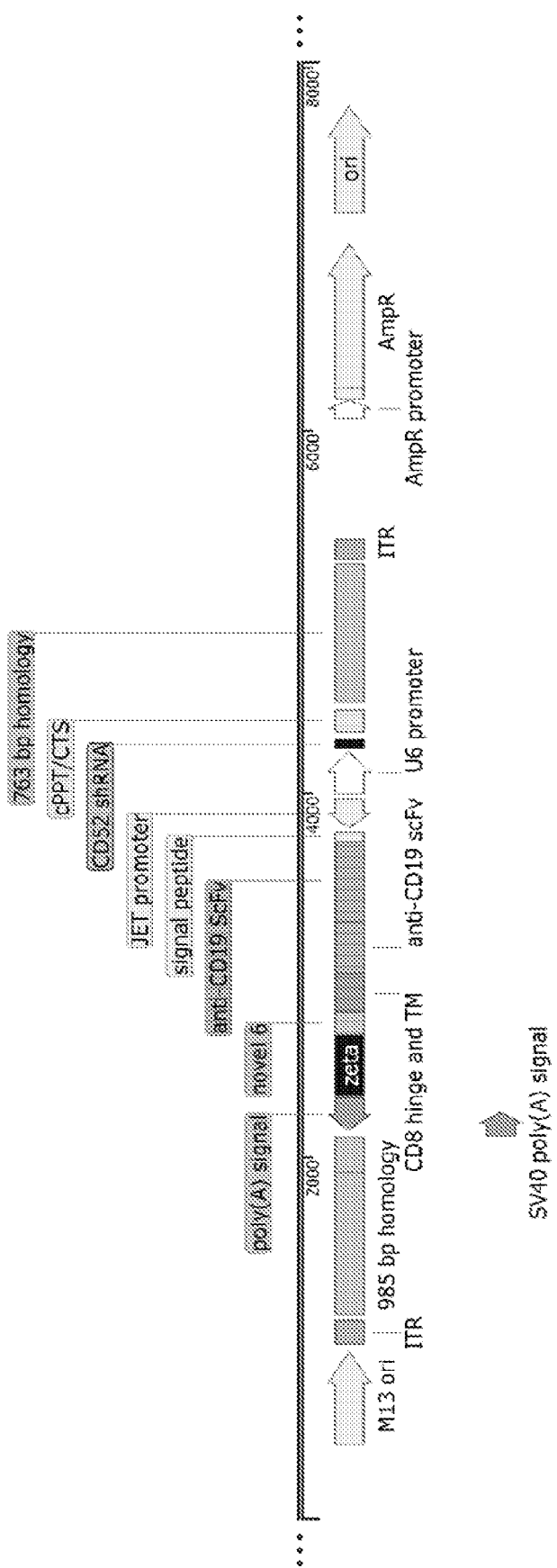
Figure 10G:
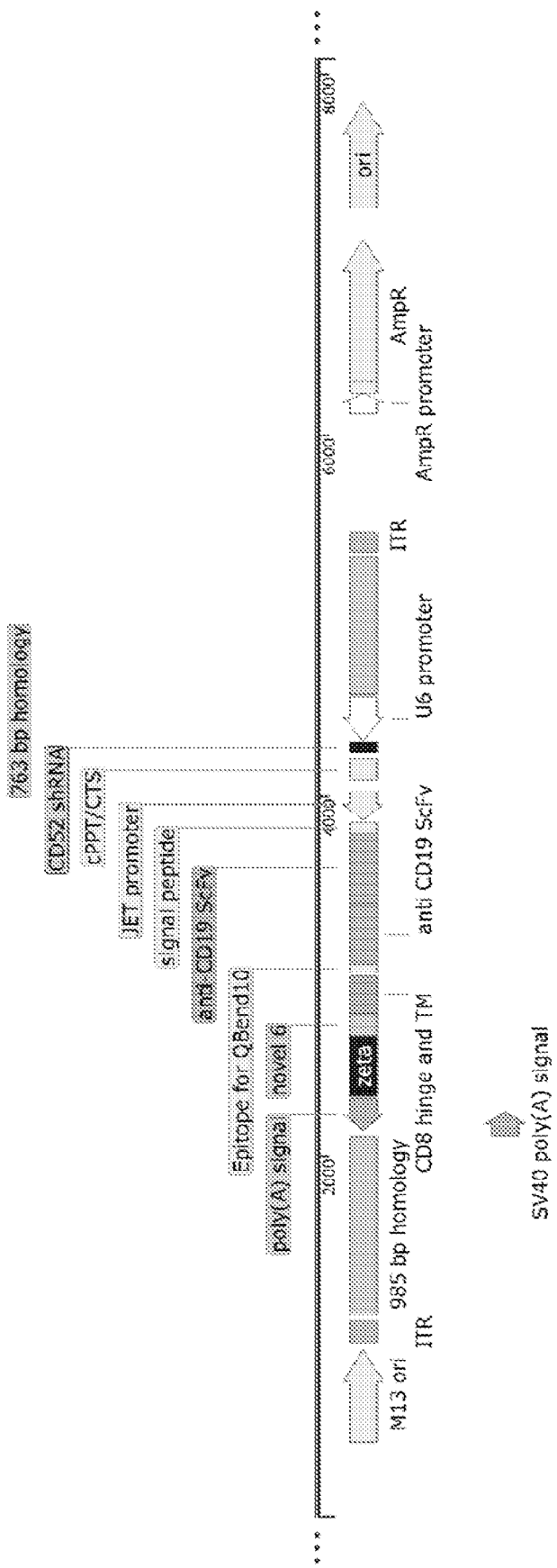
Figure 10H:
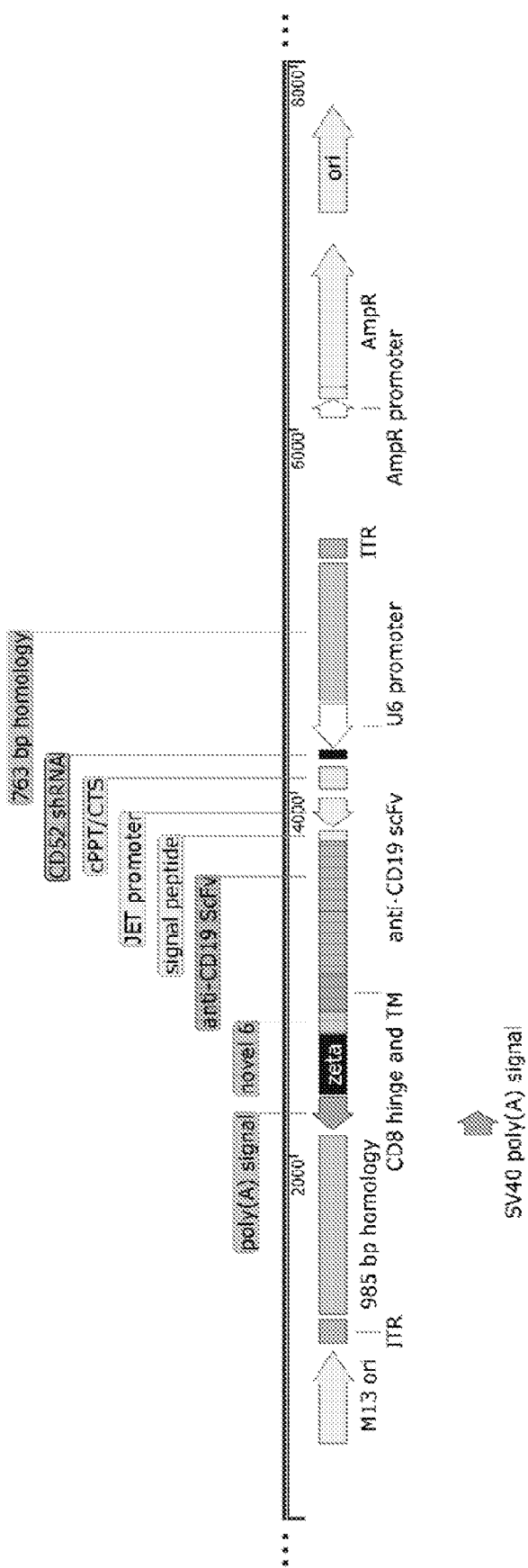

Of the 5 shRNA sequences screened, 3 (shRNA568, shRNA572, and shRNA876) interfered with CD52 expression. CD52 surface expression profiles are displayed in FIG. 8. Levels of CD52 displayed on the surface of T cells are shown in FIG. 9 for mock transduced T cells (9A), T cells transduced with an shRNA-568 lentivirus (9B), and LV-shRNA568 transduced cells that have undergone a CD52 magnetic depletion (9C).

3. Conclusions

CD52 antigen density on the surface of cells can be reduced using shRNA delivered by a viral vector. Sequence 568 exhibited the highest degree of CD52 knockdown. Knockdown of CD52 using this shRNA sequence was sufficient to allow for magnetic depletion of non-transduced CD52 Hi cells.

Example 7

CD52 Knockdown Profiles Using CAR/CD52 Constructs with Different Orientations

1. Materials and Methods

T cells were stimulated for 3 days using ImmunoCult anti-CD2/CD3/CD28 as described in EXAMPLE 1. After 3 days, TRC 1-2x.87EE mRNA, STING siRNA, and linearized AAV transfer vector encoding different CAR constructs (FIG. 10) were delivered to the T cells using the 4-D Nucleofector (Lonza). Cultures of nucleofected T cells were carried for 10 days in medium supplemented with IL-2 prior to flow cytometric analyses of CD3, CAR (CD34 epitope-tagged), and CD52.

2. Results

Figure 11A:
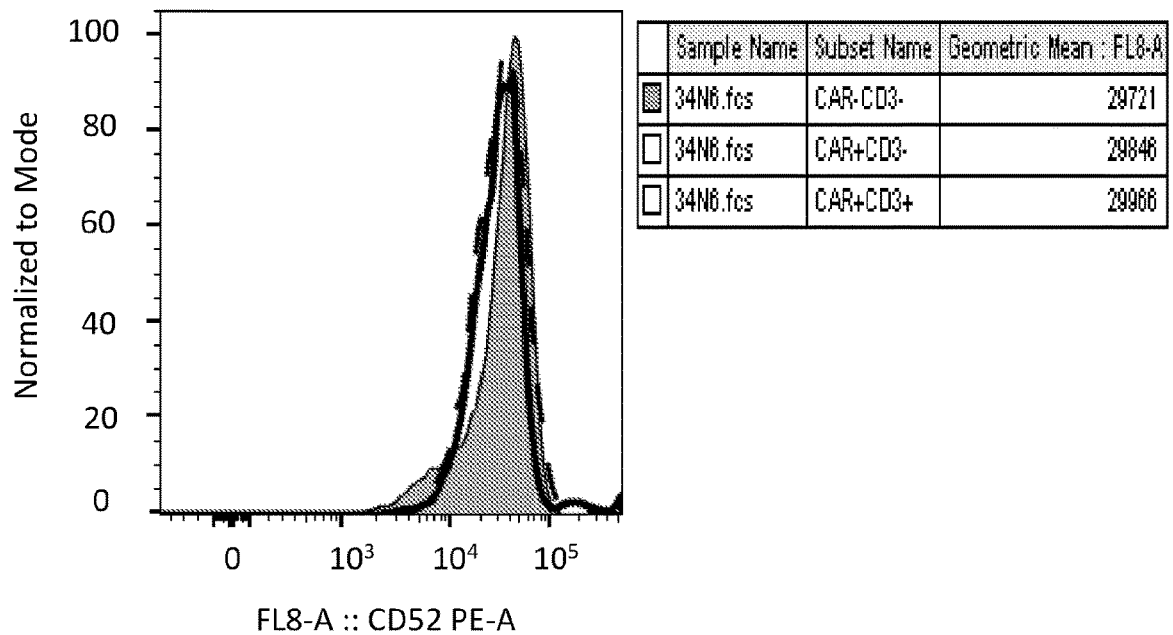
FIG. 11A-11D shows CD52 knockdown profiles using CAR/CD52 shRNA constructs with different orientations.
Figure 11B:
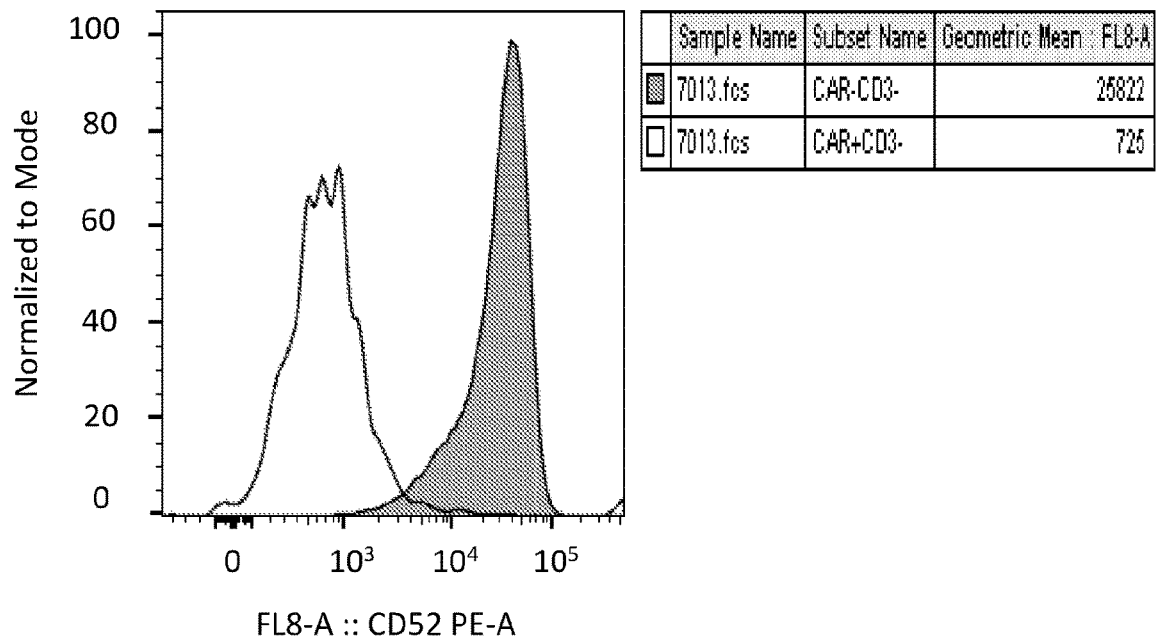
Figure 11C:
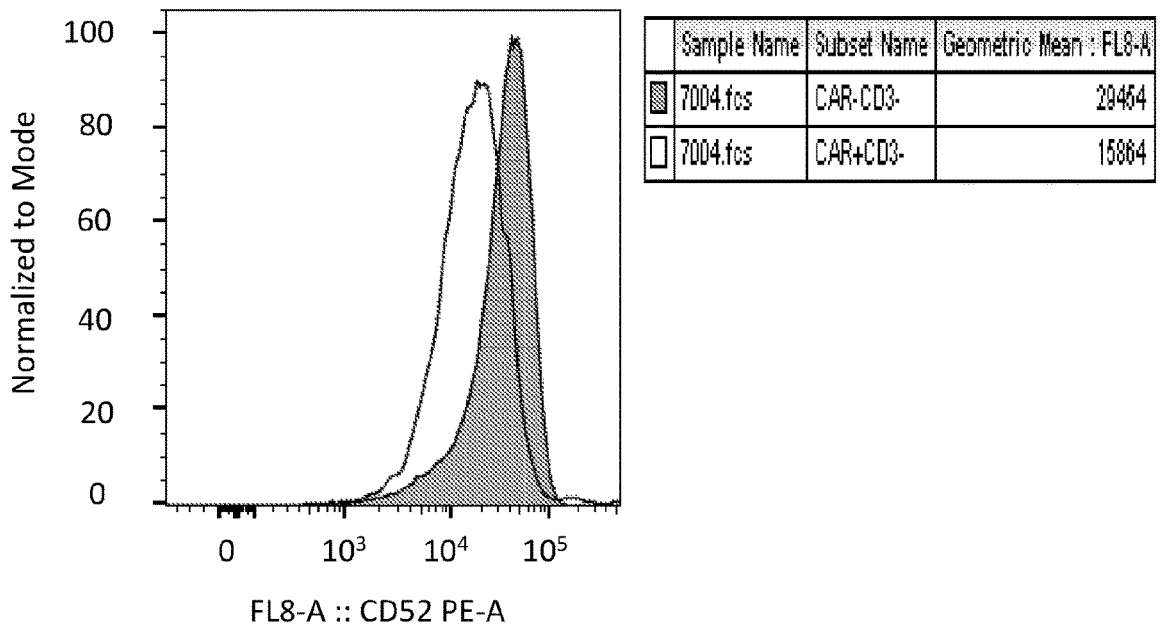
Figure 11D:
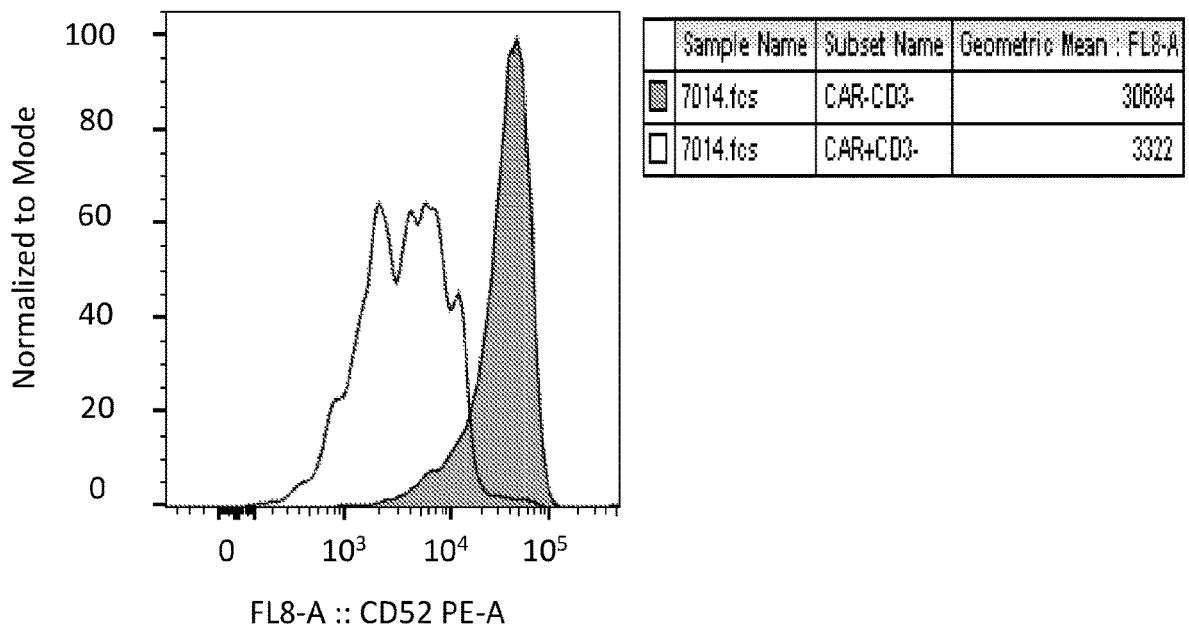

To demonstrate un-manipulated levels of CD52 surface display on TRAC-edited CART cells, a TRC 1-2x.87EE nuclease and a CD34-tagged CAR construct encoding no shRNA sequence were delivered. CD52 levels on TCR KO cells, TCR KO CAR+ cells and nonedited cells are overlaid in the histogram in FIG. 11A. Three CAR constructs encoding a U6 promoter-controlled CD52 shRNA were evaluated for ability to knock down CD52 when integrated into the TRAC locus. When the CAR gene and the shRNA cassette are both in forward orientation, CD52 antigen density is reduced by approximately 50% (FIG. 11C; construct 7004). Reversing the transcriptional orientation of the CAR gene alone (i.e., a tail-to-tail configuration) reduces the amount of CD52 displayed on the surface by approximately 95% (FIG. 11B; construct 7013), while reversing the orientation of both the CAR gene and the U6-shRNA element reduces the CD52 signal by approximately 90% (FIG. 11D; construct 7014).

3. Conclusions

The CD52 specific shRNA sequence 568 can interfere with CD52 expression when only one copy is delivered by targeted insertion into the TRAC locus. Altering the transcriptional orientation of either the CAR gene only (i.e., tail-to-tail configuration) or both the CAR and shRNA genes can influence the efficiency of target gene knockdown. Reversing only the CAR gene's orientation resulted in the most efficient knockdown.

4. Further Studies

A number of constructs were prepared comprising an anti-CD19 CAR coding sequence and an shRNA against CD52. These are illustrated in FIG. 10A-10H and are provided in SEQ ID NOs: 10-17. As described above, CAR constructs 7004 (SEQ ID NO: 12), 7013 (SEQ ID NO: 14), and 7014 (SEQ ID NO: 16) were previously evaluated for their ability to reduce CD52 expression while expressing a CAR. The 5' and 3' homology arms flanking the CAR coding sequence and the shRNA sequence have homology to regions upstream and downstream of the TRC 1-2 recognition sequence in the TRAC locus.

In additional studies, CAR T cells will be prepared using primary donor human T cells transduced with recombinant AAV vectors comprising one of the CAR/shRNA constructs above, with simultaneous nucleofection of mRNA encoding the TRC 1-2x.87EE to induce a double-strand break at the TRC 1-2 recognition sequence and promote targeted insertion of the construct into the genome of the T cells. CD52 expression will be determined as described above to determine which orientation of the first and second expression cassettes will result in the highest and/or the most consistent CAR expression, along with the most consistent level of CD52 knockdown on the cell surface.

CAR T cells produced with certain constructs will be evaluated in both the allogenicity and NK cell killing assays previously described above. Further, CAR T cells produced using the disclosed constructs will be evaluated in various stress tests, in which the CAR T cells are repeatedly exposed to antigen in order to determine changes in cell proliferation/expansion and cytotoxic potential. CAR T cells produced using the disclosed constructs will also be utilized with in vivo tumor models to determine their ability to clear tumor cells in an animal and to evaluate their ability to persist in vivo. It is expected, based on the Examples described herein, that enriched populations of CAR T cells can be produced for in vivo use by an advantageous negative-selection for CAR T cells having reduced cell surface expression of CD52.

The invention claimed is:

1. A genetically-modified T cell comprising in its genome an exogenous nucleic acid sequence comprising:

(a) a first nucleic acid sequence encoding a chimeric antigen receptor that is expressed by said genetically-modified T cell, wherein said first nucleic acid sequence further comprises a first promoter that drives expression of said chimeric antigen receptor and a polyadenylation signal to terminate translation of said chimeric antigen receptor;

(b) a second nucleic acid sequence encoding a short hairpin RNA (shRNA) that is expressed by said genetically-modified T cell, wherein said shRNA is inhibitory against beta-2 microglobulin and comprises SEQ ID NO: 2, and wherein said second nucleic acid sequence further comprises a U6 promoter that drives expression of said shRNA and a central polypurine tract and central terminator sequence (cPPT/CTS) sequence comprising SEQ ID NO: 28;

wherein, relative to the T cell receptor alpha constant region coding sequence, said first nucleic acid sequence is in a 3' to 5' orientation and said second nucleic acid sequence is in a 5' to 3' orientation, and wherein said first nucleic acid sequence is 5' upstream of said second nucleic acid sequence;

wherein said exogenous nucleic acid sequence is positioned in the genome within a nuclease recognition sequence in a T cell receptor alpha constant region gene, wherein said recognition sequence comprises SEQ ID NO: 1.

2. The genetically-modified T cell of claim 1, wherein an endogenous T cell receptor is not detectable on the cell surface of said genetically-modified human T cell.

* * * * *

```
                      SEQUENCE LISTING

<160> NUMBER OF SEQ ID NOS: 28

<210> SEQ ID NO 1
<211> LENGTH: 22
<212> TYPE: DNA
<213> ORGANISM: Homo sapiens

<400> SEQUENCE: 1
tggcctggag caacaaatct ga                                          22

<210> SEQ ID NO 2
<211> LENGTH: 62
<212> TYPE: DNA
<213> ORGANISM: Artificial Sequence
<220> FEATURE:
<223> OTHER INFORMATION: Synthesized

<400> SEQUENCE: 2
gtaccggagg tttgaagatg ccgcatttct cgagaaatgc ggcatcttca aaccttttt    60 tg                                                                62

<210> SEQ ID NO 3
<211> LENGTH: 58
<212> TYPE: DNA
<213> ORGANISM: Artificial Sequence
<220> FEATURE:
<223> OTHER INFORMATION: Synthesized

<400> SEQUENCE: 3
ccggctggtc tttctatctc ttgtactcga gtacaagaga tagaaagacc agtttttg    58

<210> SEQ ID NO 4
<211> LENGTH: 58
<212> TYPE: DNA
<213> ORGANISM: Artificial Sequence
<220> FEATURE:
<223> OTHER INFORMATION: Synthesized

<400> SEQUENCE: 4
ccggcagcag agaatggaaa gtcaactcga gttgactttc cattctctgc tgttttg     58

<210> SEQ ID NO 5
<211> LENGTH: 58
<212> TYPE: DNA
<213> ORGANISM: Artificial Sequence
<220> FEATURE:
<223> OTHER INFORMATION: Synthesized

<400> SEQUENCE: 5
```
ccggcagata caaactggac tctcactcga gtgagagtcc agtttgtatc tgtttttg    58

<210> SEQ ID NO 6
<211> LENGTH: 59
<212> TYPE: DNA
<213> ORGANISM: Artificial Sequence
<220> FEATURE:
<223> OTHER INFORMATION: Synthesized

<400> SEQUENCE: 6
ccggccacca tcactcgcaa gagaactcga gttctcttgc gagtgatggt ggtttttg    59

<210> SEQ ID NO 7
<211> LENGTH: 58
<212> TYPE: DNA
<213> ORGANISM: Artificial Sequence
<220> FEATURE:
<223> OTHER INFORMATION: Synthesized

<400> SEQUENCE: 7
ccggcctcct ggttatggta cagatctcga gatctgtacc ataaccagga ggttttg    58

<210> SEQ ID NO 8
<211> LENGTH: 58
<212> TYPE: DNA
<213> ORGANISM: Artificial Sequence
<220> FEATURE:
<223> OTHER INFORMATION: Synthesized

<400> SEQUENCE: 8
ccggcaatgc cataatccac ctcttctcga gaagaggtgg attatggcat tgttttg    58

<210> SEQ ID NO 9
<211> LENGTH: 58
<212> TYPE: DNA
<213> ORGANISM: Artificial Sequence
<220> FEATURE:
<223> OTHER INFORMATION: Synthesized

<400> SEQUENCE: 9
ccgggcagca tgagcggagg catttctcga gaaatgcctc cgctcatgct gctttttg    58

<210> SEQ ID NO 10
<211> LENGTH: 7524
<212> TYPE: DNA
<213> ORGANISM: Artificial Sequence
<220> FEATURE:
<223> OTHER INFORMATION: Synthesized

<400> SEQUENCE: 10
cagcagctgg cgtaatagcg aagaggcccg caccgatcgc ccttcccaac agttgcgcag    60
cctgaatggc gaatggaatt ccagacgatt gagcgtcaaa atgtaggtat ttccatgagc    120
gtttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540

```
cacgttcgcc ggctttcccc gtcaagctct aaatcggggg ctcccttag ggttccgatt      600
tagtgcttta cggcacctcg accccaaaaa acttgattag ggtgatggtt cacgtagtgg      660
gccatcgccc tgatagacgg ttttcgccc tttgacgttg gagtccacgt tctttaatag      720
tggactcttg ttccaaactg gaacaacact caaccctatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900
cctgttttg gggcttttct gattatcaac cggggtacat atgattgaca tgctagtttt      960
acggcgcgcc gggttggcca ctccctctct gcgcgctcgc tcgctcactg aggccgggcg     1020
accaaaggtc gcccgacgcc cgggctttgc ccggcggcc tcagtgagcg agcgagcgcg      1080
cagagaggga gtggccaact ccatcactag gggttcctac gcgtagatct catattctgg     1140
cagggtcagt ggctccaact aacatttgtt tggtacttta cagtttatta aatagatgtt     1200
tatatggaga agctctcatt tctttctcag aagagcctgg ctaggaaggt ggatgaggca     1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc caacttaat      1440
gccaacatac cataaacctc ccattctgct aatgcccagc ctaagttggg gagaccactc     1500
cagattccaa gatgtacagt ttgctttgct gggcctttt cccatgcctg cctttactct      1560
gccagagtta tattgctggg gttttgaaga agatcctatt aaataaaaga ataagcagta     1620
ttattaagta gccctgcatt tcaggttcc ttgagtggca ggccaggcct ggccgtgaac      1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc cccgcccttg tccatcactg gcatctggac tccagcctgg     1860
gttgggcaa agaggaaat gagatcatgt cctaaccctg atcctcttgt cccacagata      1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg     2040
tgtatatcac agacaaaact gtgctagaca tgaggtctat ggacttcaag agcaacagtg     2100
ctgtggcctg gagcaactag tgggcggagt tagggcggag ccaatcagcg tgcgccgttc     2160
cgaaagttgc cttttatggc tgggcggaga atgggcggtg aacgccgatg attatataag     2220
gacgcgccgg gtgtggcaca gctagttccg tcgcagccgg gatttgggtc gcggttcttg     2280
tttgttccgg aaagccacca tggcgctccc agtgacagcc ttacttttac ctctggcgtt     2340
attattgcac gcggctcgtc ctgacataca gatgactcag actacctctt ccctatctgc     2400
ttctttaggc gaccgagtaa caatatcttg ccgggccagc caggacatct caaaatactt     2460
aaactggtat cagcagaagc cggacggaac agttaagttg ctcatttacc acacgtcgag     2520
attacactca ggcgttccta gccgattttc gggttccggt tccggtacgg actacagcct     2580
gacaatcagt aaccttgagc aggaggacat cgccacctac ttctgtcagc agggcaacac     2640
gctcccgtac acattcggtg ggggaactaa gctggagatt accggaggcg gtggcagcgg     2700
tggcggcggc agcgggggtg gcggctcgga ggtcaagtta caggagagcg gacccggctt     2760
ggtcgcacct agccagagcc tctcagtcac gtgcactgtg tctggagtca gtctcccaga     2820
ctacgggta tcatggatac gacagccgcc tagaaagggc ttagagtggc tgggggttat     2880
ctgggaagt gaaaccacat actacaactc agctctcaag agccgcctca ccatcattaa      2940
```

```
ggacaacagt aagtcgcagg ttttcttaaa gatgaactct ctccagactg acgacaccgc    3000
tatttactac tgcgcgaagc actactacta cggcgggagt tacgcaatgg actactgggg    3060
tcagggcact tctgtgaccg tatccagcga gttacctacc cagggaacat tttcaaatgt    3120
ttctacaaat gtatcccccag cgaagcccac tactacccca gccccacgtc cccccacgcc    3180
agctccaacg atagcaagtc agcccttatc tcttcgccct gaggcttgca ggcccgcggc    3240
gggcggcgcc gttcacacgc gaggactaga cttcgcctgc gacatctaca tctgggcacc    3300
actagccggg acttgcggag tgttgttgtt gagcttggta ataacgctct actgcaaagc    3360
gagccgcaaa aaagcggcgg cggcggctaa agcccgtttg cgagcccgg cgagcagcgc    3420 gcaggaagaa gatgcgagca gctgccgcgc gccgagcgaa gaagaaggca gctgcgaact    3480
gagagtgaag ttctctcgct ccgcggacgc acccgcttac cagcagggtc agaaccagct    3540
atacaacgag ttaaacctgg ggcgccggga ggagtacgac gtgttagaca agcgtagagg    3600
tagggacccg gagatgggag gcaagcctcg gagaaagaac ccccaggagg gcctgtacaa    3660
cgaactccag aaggacaaga tggctgaggc gtactcggag attggtatga agggcgagag    3720
acgtcgcgga aagggacacg acggcttata ccagggggtt tccaccgcga ccaaggacac    3780
atacgacgcg ctgcacatgc aagccttacc acctcgatga ggtaccagcg gccgcttcga    3840
gcagacatga taagatacat tgatgagttt ggacaaacca caactagaat gcagtgaaaa    3900
aaatgcttta tttgtgaaat ttgtgatgct attgctttat ttgtaaccat tataagctgc    3960
aataaacaag ttaacaacaa caattcgaat ttaaatcgga tccgcaacaa atctgacttt    4020
gcatgtgcaa acgccttcaa caacagcatt attccagaag acaccttctt ccccagccca    4080
ggtaagggca gctttggtgc cttcgcaggc tgtttccttg cttcaggaat ggccaggttc    4140
tgcccagagc tctggtcaat gatgtctaaa actcctctga ttggtggtct cggccttatc    4200
cattgccacc aaaaccctct ttttactaag aaacagtgag ccttgttctg gcagtccaga    4260
gaatgacacg ggaaaaaagc agatgaagag aaggtggcag gagagggcac gtggcccagc    4320
ctcagtctct ccaactgagt tcctgcctgc ctgcctttgc tcagactgtt tgccccttac    4380
tgctcttcta ggcctcattc taagcccctt ctccaagttg cctctcctta tttctccctg    4440
tctgccaaaa aatctttccc agctcactaa gtcagtctca cgcagtcact cattaaccca    4500
ccaatcactg attgtgccgg cacatgaatg caccaggtgt tgaagtggag gaattaaaaa    4560
gtcagatgag gggtgtgccc agaggaagca ccattctagt tgggggagcc catctgtcag    4620
ctgggaaaag tccaaataac ttcagattgg aatgtgtttt aactcagggt tgagaaaaca    4680
gccaccttca ggacaaaagt cagggaaggg ctctctgaag aaatgctact tgaagatacc    4740
agccctacca agggcaggga gaggaccaat tgatggagtt ggccactccc tctctgcgcg    4800
ctcgctcgct cactgaggcc gcccgggcaa agcccgggcg tcgggcgacc tttggtcgcc    4860
cggcctcagt gagcgagcga gcgcgcagag agggagtggc caacgcgcg cctgcaggtc    4920 tcaaaaatag ctaccctctc cggcatgaat ttatcagcta gaacggttga atatcatatt    4980
gatggtgatt tgactgtctc cggcctttct cacccgtttg aatctttacc tacacattac    5040
tcaggcattg catttaaaat atatgagggt tctaaaaatt tttatccttg cgttgaaata    5100
aaggcttctc ccgcaaaagt attacagggt cataatgttt ttggtacaac cgatttagct    5160
ttatgctctg aggctttatt gcttaatttt gctaattctt tgccttgcct gtatgattta    5220
ttggatgttg gaattcctga tgcggtattt tctccttacg catctgtgcg gtatttcaca    5280
```

```
ccgcatatgg tgcactctca gtacaatctg ctctgatgcc gcatagttaa gccagccccg    5340
acacccgcca acaccgctg acgcgccctg acgggcttgt ctgctcccgg catccgctta     5400
cagacaagct gtgaccgtct ccgggagctg catgtgtcag aggttttcac cgtcatcacc    5460
gaaacgcgcg agacgaaagg gcctcgtgat acgcctattt ttataggtta atgtcatgat    5520
aataatggtt tcttagacgt caggtggcac ttttcgggga aatgtgcgcg gaaccctat     5580 ttgtttattt ttctaaatac attcaaatat gtatccgctc atgagacaat aaccctgata   5640
aatgcttcaa taatattgaa aaggaagag tatgagtatt caacatttcc gtgtcgccct     5700 tattccctt tttgcggcat tttgccttcc tgttttttgct cacccagaaa cgctggtgaa    5760
agtaaaagat gctgaagatc agttgggtgc acagtgggt tacatcgaac tggatctcaa     5820
cagcggtaag atccttgaga gttttcgccc cgaagaacgt tttccaatga tgagcacttt    5880
taaagttctg ctatgtggcg cggtattatc ccgtattgac gccgggcaag agcaactcgg    5940
tcgccgcata cactattctc agaatgactt ggttgagtac tcaccagtca cagaaaagca   6000
tcttacggat ggcatgacag taagagaatt atgcagtgct gccataacca tgagtgataa    6060
cactgcggcc aacttacttc tgacaacgat cggaggaccg aaggagctaa ccgcttttt     6120 gcacaacatg ggggatcatg taactcgcct tgatcgttgg gaaccggagc tgaatgaagc    6180
cataccaaac gacgagcgtg acaccacgat gcctgtagca atggcaacaa cgttgcgcaa    6240
actattaact ggcgaactac ttactctagc ttcccggcaa caattaatag actggatgga    6300
ggcggataaa gttgcaggac cacttctgcg ctcggccctt ccggctggct ggtttattgc    6360
tgataaatct ggagccggtg agcgtgggtc tcgcggtatc attgcagcac tggggccaga    6420
tggtaagccc tcccgtatcg tagttatcta cacgacgggg agtcaggcaa ctatggatga    6480
acgaaataga cagatcgctg agataggtgc ctcactgatt aagcattggt aactgtcaga    6540
ccaagtttac tcatatatac tttagattga tttaaaactt cattttaat ttaaaggat     6600 ctaggtgaag atcctttttg ataatctcat gaccaaaatc ccttaacgtg agttttcgtt    6660
ccactgagcg tcagaccccg tagaaaagat caaaggatct tcttgagatc ctttttttct    6720
gcgcgtaatc tgctgcttgc aaacaaaaaa accaccgcta ccagcggtgg tttgtttgcc    6780
ggatcaagag ctaccaactc tttttccgaa ggtaactggc ttcagcagag cgcagatacc    6840
aaatactgtc cttctagtgt agccgtagtt aggccaccac ttcaagaact ctgtagcacc    6900
gcctacatac ctcgctctgc taatcctgtt accagtggct gctgccagtg gcgataagtc    6960
gtgtcttacc gggttggact caagacgata gttaccggat aaggcgcagc ggtcgggctg    7020
aacggggggt tcgtgcacac agcccagctt ggagcgaacg acctacaccg aactgagata    7080
cctacagcgt gagctatgag aaagcgccac gcttcccgaa gggagaaagg cggacaggta    7140
tccggtaagc ggcagggtcg aacaggaga gcgcacgagg gagcttccag ggggaaacgc     7200
ctggtatctt tatagtcctg tcgggtttcg ccacctctga cttgagcgtc gatttttgtg    7260
atgctcgtca ggggggcgga gcctatgaa aaacgccagc aacgcggcct ttttacggtt     7320
cctggccttt tgctggcctt ttgctcacat gttctttcct gcgttatccc ctgattctgt    7380
ggataaccgt attaccgcct ttgagtgagc tgataccgct cgccgcagcc gaacgaccga    7440
gcgcagcgag tcagtgagcg aggaagcgga agagcgccca atacgcaaac cgcctctccc    7500
cgcgcgttgg ccgattcatt aatg                                          7524
```

<210> SEQ ID NO 11
<211> LENGTH: 7739

<212> TYPE: DNA
<213> ORGANISM: Artificial Sequence
<220> FEATURE:
<223> OTHER INFORMATION: Synthesized

<400> SEQUENCE: 11

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttttcgcc tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900
cctgtttttg ggcttttct gattatcaac cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc tggtaatgt gatagatttc caacttaat    1440
gccaacatac cataaacctc ccattctgct aatgcccagc ctaagttggg gagaccactc    1500
cagattccaa gatgtacagt ttgctttgct gggcctttt cccatgcctg cctttactct    1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttggggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgatccagac atgataagat acattgatga gtttggacaa    2160
```

```
accacaacta gaatgcagtg aaaaaaatgc tttatttgtg aaatttgtga tgctattgct    2220
ttatttgtaa ccattataag ctgcaataaa caagttaaca acaacaattg cattcatttt    2280
atgtttcagg ttcagggga ggtgtgggag gttttttaaa gcaagtaaac tggtacctca    2340
tcgaggtggt aaggcttgca tgtgcagcgc gtcgtatgtg tccttggtcg cggtggaaag    2400
cccctggtat aagccgtcgt gtccctttcc gcgacgtctc tcgcccttca taccaatctc    2460
cgagtacgcc tcagccatct tgtccttctg gagttcgttg tacaggccct cctgggggtt    2520 cttttctccga ggcttgcctc ccatctccgg gtccctacct ctacgcttgt ctaacacgtc    2580
gtactcctcc cggcgcccca ggtttaactc gttgtatagc tggttctgac cctgctggta    2640
agcgggtgcg tccgcggagc gagagaactt cactctcagt tcgcagctgc cttcttcttc    2700
gctcggcgcg cggcagctgc tcgcatcttc ttcctgcgcg ctgctcgccg ggctcgcaaa    2760 cgggcttta gccgccgccg ccgcttttt gcggctcgct ttgcagtaga gcgttattac    2820
caagctcaac aacaacactc cgcaagtccc ggctagtggt gcccagatgt agatgtcgca    2880
ggcgaagtct agtcctcgcg tgtgaacgg gccgcccgcc gcgggcctgc aagcctcagg    2940
gcgaagagat aagggctgac ttgctatcgt tggagctggc gtgggggac gtgggctgg    3000 ggtagtagtg ggcttcgctg gggatacatt tgtagaaaca tttgaaaatg ttccctgggt    3060
aggtaactcg ctggatacgg tcacagaagt gccctgaccc cagtagtcca ttgcgtaact    3120
cccgccgtag tagtagtgct tcgcgcagta gtaaatagcg gtgtcgtcag tctggagaga    3180
gttcatcttt aagaaaacct gcgacttact gttgtcctta atgatggtga ggcggctctt    3240
gagagctgag ttgtagtatg tggtttcact tccccagata accccagcc actctaagcc    3300 cttttctaggc ggctgtcgta tccatgatac cccgtagtct gggagactga ctccagacac    3360
agtgcacgtg actgagaggc tctggctagg tgcgaccaag cccggtccgc tctcctgtaa    3420
cttgacctcc gagccgccac ccccgctgcc gccgccaccg ctgccaccgc tccggtaat    3480 ctccagctta gttcccccac cgaatgtgta cgggagcgtg ttgccctgct gacagaagta    3540
ggtggcgatg tcctcctgct caaggttact gattgtcagg ctgtagtccg taccggaacc    3600
ggaacccgaa aatcggctag gaacgcctga gtgtaatctc gacgtgtggt aaatgagcaa    3660
cttaactgtt ccgtccggct tctgctgata ccagttttaag tattttgaga tgtcctggct    3720
ggcccggcaa gatattgtta ctcggtcgcc taaagaagca gatagggaag aggtagtctg    3780
agtcatctgt atgtcaggac gagccgcgtg caataataac gccagaggta aaagtaaggc    3840
tgtcactggg agcgccatgg tggctttccg gaacaaacaa gaaccgcgac ccaaatcccg    3900
gctgcgacgg aactagctgt gccacacccg gcgcgtcctt atataatcat cggcgttcac    3960
cgcccattct ccgcccagcc ataaaaggca actttcggaa cggcgcacgc tgattggctc    4020
cgccctaact ccgcccacta gtgcggccgc ttcgagcaga catgataaga tacattgatg    4080
agtttggaca aaccacaact agaatgcagt gaaaaaaatg cttttatttgt gaaatttgtg    4140 atgctattgc tttatttgta accattataa gctgcaataa acaagttaac aacaacaatt    4200
cgaatttaaa tcggatccgc aacaaatctg actttgcatg tgcaaacgcc ttcaacaaca    4260
gcattattcc agaagacacc ttcttcccca gcccaggtaa gggcagcttt ggtgccttcg    4320
caggctgttt ccttgcttca ggaatggcca ggttctgccc agagctctgg tcaatgatgt    4380
ctaaaactcc tctgattggt ggtctcggcc ttatccattg ccaccaaaac cctcttttta    4440
ctaagaaaca gtgagccttg ttctggcagt ccagagaatg acacgggaaa aaagcagatg    4500
aagagaaggt ggcaggagag ggcacgtggc ccagcctcag tctctccaac tgagttcctg    4560
```

```
cctgcctgcc tttgctcaga ctgtttgccc cttactgctc ttctaggcct cattctaagc    4620
cccttctcca agttgcctct ccttatttct ccctgtctgc caaaaaatct ttcccagctc    4680
actaagtcag tctcacgcag tcactcatta acccaccaat cactgattgt gccggcacat    4740
gaatgcacca ggtgttgaag tggaggaatt aaaaagtcag atgagggtg tgcccagagg     4800 aagcaccatt ctagttgggg gagcccatct gtcagctggg aaaagtccaa ataacttcag    4860
attggaatgt gttttaactc agggttgaga aaacagccac cttcaggaca aaagtcaggg    4920
aagggctctc tgaagaaatg ctacttgaag ataccagccc taccaagggc agggagagga    4980
ccaattgatg gagttggcca ctccctctct gcgcgctcgc tcgctcactg aggccgcccg    5040
ggcaaagccc gggcgtcggg cgacctttgg tcgcccggcc tcagtgagcg agcgagcgcg    5100
cagagaggga gtggccaacg gcgcgcctgc aggtctcaaa aatagctacc ctctccggca    5160
tgaatttatc agctagaacg gttgaatatc atattgatgg tgatttgact gtctccggcc    5220
tttctcaccc gtttgaatct ttacctacac attactcagg cattgcattt aaaatatatg    5280
agggttctaa aaatttttat ccttgcgttg aaataaaggc ttctcccgca aaagtattac    5340
agggtcataa tgttttttggt acaaccgatt tagctttatg ctctgaggct ttattgctta    5400
attttgctaa ttctttgcct tgcctgtatg atttattgga tgttggaatt cctgatgcgg    5460
tattttctcc ttacgcatct gtgcggtatt tcacaccgca tatggtgcac tctcagtaca    5520
atctgctctg atgccgcata gttaagccag ccccgacacc cgccaacacc cgctgacgcg    5580
ccctgacggg cttgtctgct cccggcatcc gcttacagac aagctgtgac cgtctccggg    5640
agctgcatgt gtcagaggtt ttcaccgtca tcaccgaaac gcgcgagacg aaagggcctc    5700
gtgatacgcc tatttttata ggttaatgtc atgataataa tggtttctta gacgtcaggt    5760
ggcacttttc ggggaaatgt gcgcggaacc cctatttgtt tatttttcta aatacattca    5820
aatatgtatc cgctcatgag acaataaccc tgataaatgc ttcaataata ttgaaaaagg    5880
aagagtatga gtattcaaca tttccgtgtc gcccttattc ccttttttgc ggcattttgc    5940
cttcctgttt ttgctcaccc agaaacgctg gtgaaagtaa agatgctgaa gatcagttg     6000 ggtgcacgag tgggttacat cgaactggat ctcaacagcg gtaagatcct tgagagtttt    6060
cgccccgaag aacgttttcc aatgatgagc acttttaaag ttctgctatg tggcgcggta    6120
ttatcccgta ttgacgccgg gcaagagcaa ctcggtcgcc gcatacacta ttctcagaat    6180
gacttggttg agtactcacc agtcacagaa aagcatctta cggatggcat gacagtaaga    6240
gaattatgca gtgctgccat aaccatgagt gataacactg cggccaactt acttctgaca    6300
acgatcggag gaccgaagga gctaaccgct tttttgcaca acatggggga tcatgtaact    6360
cgccttgatc gttgggaacc ggagctgaat gaagccatac caaacgacga gcgtgacacc    6420
acgatgcctg tagcaatggc aacaacgttg cgcaaactat taactggcga actacttact    6480
ctagcttccc ggcaacaatt aatagactgg atggaggcgg ataaagttgc aggaccactt    6540
ctgcgctcgg cccttccggc tggctggttt attgctgata aatctggagc cggtgagcgt    6600
gggtctcgcg gtatcattgc agcactgggg ccagatggta agccctcccg tatcgtagtt    6660
atctacacga cggggagtca ggcaactatg gatgaacgaa atagacagat cgctgagata    6720
ggtgcctcac tgattaagca ttggtaactg tcagaccaag tttactcata tatactttag    6780
attgatttaa aacttcattt ttaatttaaa aggatctagg tgaagatcct ttttgataat    6840
ctcatgacca aaatccctta acgtgagttt tcgttccact gagcgtcaga ccccgtagaa    6900
```

| | |
|---|---|
| aagatcaaag gatcttcttg agatcctttt tttctgcgcg taatctgctg cttgcaaaca | 6960 |
| aaaaaaccac cgctaccagc ggtggtttgt ttgccggatc aagagctacc aactcttttt | 7020 |
| ccgaaggtaa ctggcttcag cagagcgcag ataccaaata ctgtccttct agtgtagccg | 7080 |
| tagttaggcc accacttcaa gaactctgta gcaccgccta catacctcgc tctgctaatc | 7140 |
| ctgttaccag tggctgctgc cagtggcgat aagtcgtgtc ttaccgggtt ggactcaaga | 7200 |
| cgatagttac cggataaggc gcagcggtcg ggctgaacgg ggggttcgtg cacacagccc | 7260 |
| agcttggagc gaacgaccta caccgaactg agataccta<br>c agcgtgagct atgagaaagc | 7320 |
| gccacgcttc ccgaagggag aaaggcggac aggtatccgg taagcggcag gtcggaaca | 7380 |
| ggagagcgca cgagggagct tccaggggga aacgcctggt atctttatag tcctgtcggg | 7440 |
| tttcgccacc tctgacttga gcgtcgattt ttgtgatgct cgtcaggggg gcggagccta | 7500 |
| tggaaaaacg ccagcaacgc ggccttttta cggttcctgg ccttttgctg gccttttgct | 7560 |
| cacatgttct ttcctgcgtt atcccctgat tctgtggata accgtattac cgcctttgag | 7620 |
| tgagctgata ccgctcgccg cagccgaacg accgagcgca gcgagtcagt gagcgaggaa | 7680 |
| gcggaagagc gcccaatacg caaaccgcct ctccccgcgc gttggccgat tcattaatg | 7739 |

<210> SEQ ID NO 12
<211> LENGTH: 8073
<212> TYPE: DNA
<213> ORGANISM: Artificial Sequence
<220> FEATURE:
<223> OTHER INFORMATION: Synthesized

<400> SEQUENCE: 12

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gtttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctccctttag ggttccgatt | 600 |
| tagtgcttta cggcacctcg accccaaaaa acttgattag ggtgatggtt cacgtagtgg | 660 |
| gccatcgccc tgatagacgg ttttt<br>cgccc tttgacgttg gagtccacgt tctttaatag | 720 |
| tggactcttg ttccaaactg gaacaacact caaccctatc tcggtctatt cttttgattt | 780 |
| ataagggatt ttgccgattt cggcctattg gttaaaaaat gagctgattt aacaaaaatt | 840 |
| taacgcgaat tttaacaaaa tattaacgtt acaatttaa atatttgctt atacaatctt | 900 |
| cctgtttttg ggcttttct gattatcaac cggggtacat atgattgaca tgctagtttt | 960 |
| acggcgcgcc gggttggcca ctccctctct gcgcgctcgc tcgctcactg aggccgggcg | 1020 |
| accaaaggtc gcccgacgcc cgggctttgc ccgggcggcc tcagtgagcg agcgagcgcg | 1080 |
| cagagaggga gtggccaact ccatcactag gggttcctac gcgtagatct catattctgg | 1140 |
| cagggtcagt ggctccaact aacatttgtt tggtacttta cagtttatta aatagatgtt | 1200 |
| tatatggaga agctctcatt tcttttctcag aagagcctgg ctaggaaggt ggatgaggca | 1260 |

```
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc ctggtaatgt gatagatttc ccaacttaat    1440
gccaacatac cataaacctc ccattctgct aatgcccagc ctaagttggg gagaccactc    1500
cagattccaa gatgtacagt ttgctttgct gggccttttt cccatgcctg cctttactct    1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttggggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgggcggagt tagggcggag ccaatcagcg tgcgccgttc    2160
cgaaagttgc cttttatggc tgggcggaga atgggcggtg aacgccgatg attatataag    2220
gacgcgccgg gtgtggcaca gctagttccg tcgcagccgg gatttgggtc gcggttcttg    2280
tttgttccgg aaagccacca tggcgctccc agtgacagcc ttacttttac ctctggcgtt    2340
attattgcac gcggctcgtc ctgacataca gatgactcag actacctctt ccctatctgc    2400
ttctttaggc gaccgagtaa caatatcttg ccgggccagc caggacatct caaaatactt    2460
aaactggtat cagcagaagc cggacggaac agttaagttg ctcatttacc acacgtcgag    2520
attacactca ggcgttccta gccgattttc gggttccggt tccggtacgg actacagcct    2580
gacaatcagt aaccttgagc aggaggacat cgccacctac ttctgtcagc agggcaacac    2640
gctcccgtac acattcggtg ggggaactaa gctggagatt accggaggcg gtggcagcgg    2700
tggcggcggc agcggggggtg gcggctcgga ggtcaagtta caggagagcg gacccggctt    2760
ggtcgcacct agccagagcc tctcagtcac gtgcactgtg tctggagtca gtctcccaga    2820 ctacgggta tcatggatac gacagccgcc tagaaagggc ttagagtggc tgggggttat    2880
ctggggaagt gaaaccacat actacaactc agctctcaag agccgcctca ccatcattaa    2940
ggacaacagt aagtcgcagg ttttcttaaa gatgaactct ctccagactg acgacaccgc    3000
tatttactac tgcgcgaagc actactacta cggcgggagt tacgcaatgg actactgggg    3060
tcagggcact tctgtgaccg tatccagcga gttacctacc cagggaacat ttcaaatgt    3120 ttctacaaat gtatccccag cgaagcccac tactaccccca gccccacgtc cccccacgcc    3180
agctccaacg atagcaagtc agcccttatc tcttcgccct gaggcttgca ggcccgcggc    3240
gggcggcgcc gttcacacgc gaggactaga cttcgcctgc gacatctaca tctgggcacc    3300
actagccggg acttgcggag tgttgttgtt gagcttggta ataacgctct actgcaaagc    3360
gagccgcaaa aaagcggcgg cggcggctaa aagcccgttt gcgagcccgg cgagcagcgc    3420
gcaggaagaa gatgcgagca gctgccgcgc gccgagcgaa gaagaaggca gctgcgaact    3480
gagagtgaag ttctctcgct ccgcggacgc acccgcttac cagcagggtc agaaccagct    3540
atacaacgag ttaaacctgg ggcgccggga ggagtacgac gtgttagaca agcgtagagg    3600
```

```
tagggacccg gagatgggag gcaagcctcg gagaaagaac ccccaggagg gcctgtacaa    3660
cgaactccag aaggacaaga tggctgaggc gtactcggag attggtatga agggcgagag    3720
acgtcgcgga aagggacacg acggcttata ccaggggctt ccaccgcga ccaaggacac     3780 atacgacgcg ctgcacatgc aagccttacc acctcgatga ggtaccagcg ccgcttcga     3840 gcagacatga taagatacat tgatgagttt ggacaaacca caactagaat gcagtgaaaa    3900
aaatgcttta tttgtgaaat ttgtgatgct attgctttat ttgtaaccat tataagctgc    3960
aataaacaag ttaacaacaa caattcgaag gatctcgacg gtatcgatca cgagactagc    4020
ctcgagcggc cgcccccttc accgagggcc tatttcccat gattccttca tatttgcata    4080
tacgatacaa ggctgttaga gagataattg gaattaattt gactgtaaac acaaagatat    4140
tagtacaaaa tacgtgacgt agaaagtaat aatttcttgg gtagtttgca gttttaaaat    4200
tatgttttaa aatggactat catatgctta ccgtaacttg aaagtatttc gatttcttgg    4260
ctttatatat cttgtggaaa ggacgaaaca ccggcctcct ggttatggta cagatctcga    4320
gatctgtacc ataaccagga ggttttgaa ttctcgaccct cgagacaaat ggcagtattc     4380
atccacaatt ttaaaagaaa agggggggatt gggggggtaca gtgcagggga aagaatagta    4440
gacataatag caacagacat acaaactaaa gaattacaaa aacaaattac aaaaattcaa    4500
aattttcggg tttattacag ggacagcaga gatccacttt ggccgcggat ccgcaacaaa    4560
tctgactttg catgtgcaaa cgccttcaac aacagcatta ttccagaaga caccttcttc    4620
cccagcccag gtaagggcag ctttggtgcc ttcgcaggct gtttccttgc ttcaggaatg    4680
gccaggttct gcccagagct ctggtcaatg atgtctaaaa ctcctctgat tggtggtctc    4740
ggccttatcc attgccacca aaaccctctt tttactaaga aacagtgagc cttgttctgg    4800
cagtccagag aatgacacgg gaaaaaagca gatgaagaga aggtggcagg agagggcacg    4860
tggcccagcc tcagtctctc caactgagtt cctgcctgcc tgcctttgct cagactgttt    4920
gccccttact gctcttctag gcctcattct aagccccttc tccaagttgc ctctccttat    4980
ttctccctgt ctgccaaaaa atctttccca gctcactaag tcagtctcac gcagtcactc    5040
attaacccac caatcactga ttgtgccggc acatgaatgc accaggtgtt gaagtggagg    5100
aattaaaaag tcagatgagg ggtgtgccca gaggaagcac cattctagtt gggggagccc    5160
atctgtcagc tggaaaaagt ccaaataact tcagattgga atgtgtttta actcagggtt    5220
gagaaaacag ccaccttcag gacaaaagtc agggaagggc tctctgaaga aatgctactt    5280
gaagatacca gccctaccaa gggcagggag aggaccaatt gatggagttg ccactccct    5340 ctctgcgcgc tcgctcgctc actgaggccg cccgggcaaa gcccgggcgt cgggcgacct    5400
ttggtcgccc ggcctcagtg agcgagcgag cgcgcagaga gggagtggcc aacgcgcgc    5460 ctgcaggtct caaaaatagc taccctctcc ggcatgaatt tatcagctag aacggttgaa    5520
tatcatattg atggtgattt gactgtctcc ggcctttctc acccgtttga atctttacct    5580
acacattact caggcattgc atttaaaata tatgaggggt ctaaaaattt ttatccttgc    5640
gttgaaataa aggcttctcc cgcaaaagta ttacagggtc ataatgtttt tggtacaacc    5700
gatttagctt tatgctctga ggcttttattg cttaattttg ctaattcttt gcttgcctg    5760 tatgatttat tggatgttgg aattcctgat gcggtatttt ctccttacgc atctgtgcgg    5820
tatttcacac cgcatatggt gcactctcag tacaatctgc tctgatgccg catagttaag    5880
ccagccccga cacccgccaa cacccgctga cgcgccctga cgggcttgtc tgctcccggc    5940
atccgcttac agacaagctg tgaccgtctc cgggagctgc atgtgtcaga ggttttcacc    6000
```

```
gtcatcaccg aaacgcgcga gacgaaaggg cctcgtgata cgcctatttt tataggttaa    6060
tgtcatgata taatggttt cttagacgtc aggtggcact tttcggggaa atgtgcgcgg     6120
aaccccctatt tgtttatttt tctaaataca ttcaaatatg tatccgctca tgagacaata   6180
accctgataa atgcttcaat aatattgaaa aggaagagt atgagtattc aacatttccg     6240
tgtcgccctt attccctttt ttgcggcatt ttgccttcct gtttttgctc acccagaaac    6300
gctggtgaaa gtaaaagatg ctgaagatca gttgggtgca cgagtgggtt acatcgaact    6360
ggatctcaac agcggtaaga tccttgagag ttttcgcccc gaagaacgtt ttccaatgat    6420
gagcactttt aaagttctgc tatgtggcgc ggtattatcc cgtattgacg ccgggcaaga    6480
gcaactcggt cgccgcatac actattctca gaatgacttg gttgagtact caccagtcac   6540
agaaaagcat cttacggatg gcatgacagt aagagaatta tgcagtgctg ccataaccat    6600
gagtgataac actgcggcca acttacttct gacaacgatc ggaggaccga aggagctaac    6660
cgcttttttg cacaacatgg gggatcatgt aactcgcctt gatcgttggg aaccggagct    6720
gaatgaagcc ataccaaacg acgagcgtga caccacgatg cctgtagcaa tggcaacaac    6780
gttgcgcaaa ctattaactg gcgaactact tactctagct tcccggcaac aattaataga    6840
ctggatggag gcggataaag ttgcaggacc acttctgcgc tcggcccttc cggctggctg    6900
gtttattgct gataaatctg gagccggtga gcgtgggtct cgcggtatca ttgcagcact    6960
ggggccagat ggtaagccct cccgtatcgt agttatctac acgacgggga gtcaggcaac    7020
tatggatgaa cgaaatagac agatcgctga gataggtgcc tcactgatta agcattggta    7080
actgtcagac caagtttact catatatact ttagattgat ttaaaacttc attttttaatt   7140
taaaaggatc taggtgaaga tcctttttga taatctcatg accaaaatcc cttaacgtga    7200
gttttcgttc cactgagcgt cagacccgt agaaaagatc aaaggatctt cttgagatcc     7260
ttttttctg cgcgtaatct gctgcttgca acaaaaaaa ccaccgctac cagcggtggt     7320
ttgtttgccg gatcaagagc taccaactct ttttccgaag gtaactggct tcagcagagc    7380
gcagatacca aatactgtcc ttctagtgta gccgtagtta ggccaccact tcaagaactc    7440
tgtagcaccg cctacatacc tcgctctgct aatcctgtta ccagtggctg ctgccagtgg    7500
cgataagtcg tgtcttaccg ggttggactc aagacgatag ttaccggata aggcgcagcg    7560
gtcgggctga acggggggtt cgtgcacaca gcccagcttg gagcgaacga cctacaccga    7620
actgagatac ctacagcgtg agctatgaga aagcgccacg cttcccgaag ggagaaaggc    7680
ggacaggtat ccggtaagcg gcagggtcgg aacaggagag cgcacgaggg agcttccagg    7740
gggaaacgcc tggtatcttt atagtcctgt cgggtttcgc cacctctgac ttgagcgtcg    7800
atttttgtga tgctcgtcag gggggcggag cctatgaaaa acgccagca acgcggcctt     7860
tttacggttc ctggcctttt gctggccttt tgctcacatg ttctttcctg cgttatcccc    7920
tgattctgtg gataaccgta ttaccgcctt tgagtgagct gataccgctc gccgcagccg    7980
aacgaccgag cgcagcgagt cagtgagcga ggaagcggaa gagcgcccaa tacgcaaacc    8040
gcctctcccc gcgcgttggc cgattcatta atg                                8073
```

<210> SEQ ID NO 13
<211> LENGTH: 8013
<212> TYPE: DNA
<213> ORGANISM: Artificial Sequence
<220> FEATURE:
<223> OTHER INFORMATION: Synthesized

<400> SEQUENCE: 13

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gttttttcctg ttgcaatggc tggcggtaat attgttctgg atattaccag caaggccgat    180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc tttgacgttg gagtccacgt tctttaatag      720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900
cctgtttttg ggcttttct gattatcaac cggggtacat atgattgaca tgctagtttt      960
acggcgcgcc gggttggcca ctccctctct gcgcgctcgc tcgctcactg aggccgggcg     1020
accaaaggtc gcccgacgcc cgggctttgc ccgggcggcc tcagtgagcg agcgagcgcg     1080
cagagaggga gtggccaact ccatcactag gggttcctac gcgtagatct catattctgg     1140
cagggtcagt ggctccaact aacatttgtt tggtacttta cagtttatta aatagatgtt     1200
tatatggaga agctctcatt tcttttctcag aagagcctgg ctaggaaggt ggatgaggca    1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc ccaacttaat     1440
gccaacatac cataaacctc ccattctgct aatgcccagc ctaagttggg gagaccactc     1500
cagattccaa gatgtacagt tgctttgct gggccttttt cccatgcctg cctttactct      1560
gccagagtta tattgctggg gttttgaaga agatcctatt aaataaaaga ataagcagta    1620
ttattaagta gccctgcatt tcaggttttcc ttgagtggca ggccaggcct ggccgtgaac    1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc cccgcccttg tccatcactg gcatctggac tccagcctgg     1860
gttgggcaa agagggaaat gagatcatgt cctaaccctg atcctcttgt cccacagata     1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgggcggagt tagggcggag ccaatcagcg tgcgccgttc     2160
cgaaagttgc cttttatggc tgggcggaga atgggcggtg aacgccgatg attatataag     2220
gacgcgccgg gtgtggcaca gctagttccg tcgcagccgg gatttgggtc gcggttcttg     2280
tttgttccgg aaagccacca tggcgctccc agtgacagcc ttactttac ctctggcgtt      2340
```

```
attattgcac gcggctcgtc ctgacataca gatgactcag actacctctt ccctatctgc    2400
ttctttaggc gaccgagtaa caatatcttg ccgggccagc caggacatct caaaatactt    2460
aaactggtat cagcagaagc cggacggaac agttaagttg ctcatttacc acacgtcgag    2520
attacactca ggcgttccta gccgattttc gggttccggt tccggtacgg actacagcct    2580
gacaatcagt aaccttgagc aggaggacat cgccacctac ttctgtcagc agggcaacac    2640
gctcccgtac acattcggtg ggggaactaa gctggagatt accggaggcg gtggcagcgg    2700
tggcggcggc agcggggggtg gcggctcgga ggtcaagtta caggagagcg gaccgggctt    2760
ggtcgcacct agccagagcc tctcagtcac gtgcactgtg tctggagtca gtctcccaga    2820
ctacggggta tcatggatac gacagccgcc tagaaagggc ttagagtggc tgggggttat    2880
ctggggaagt gaaaccacat actacaactc agctctcaag agccgcctca ccatcattaa    2940
ggacaacagt aagtcgcagg tttcttaaa gatgaactct ctccagactg acgacaccgc    3000
tatttactac tgcgcgaagc actactacta cggcgggagt tacgcaatgg actactgggg    3060
tcagggcact tctgtgaccg tatccagcac tactacccca gccccacgtc ccccacgcc     3120 agctccaacg atagcaagtc agcccttatc tcttcgccct gaggcttgca ggcccgcggc    3180
gggcggcgcc gttcacacgc gaggactaga cttcgcctgc gacatctaca tctgggcacc    3240
actagccggg acttgcggag tgttgttgtt gagcttggta ataacgctct actgcaaagc    3300
gagccgcaaa aaagcggcgg cggcggcgaa aagcccgttt gcgagcccgg cgagcagcgc    3360
gcaggaagaa gatgcgagca gctgccgcgc gccgagcgaa aagaaggca gctgcgaact    3420 gagagtgaag ttctctcgct ccgcggacgc acccgcttac cagcagggtc agaaccagct    3480
atacaacgag ttaaacctgg ggcgccggga ggagtacgac gtgttagaca agcgtagagg    3540
tagggacccg gagatgggag gcaagcctcg gagaaagaac ccccaggagg gcctgtacaa    3600
cgaactccag aaggacaaga tggctgaggc gtactcggag attggtatga agggcgagag    3660
acgtcgcgga aagggacacg acggcttata ccagggcctt ccaccgcga ccaaggacac    3720 atacgacgcg ctgcacatgc aagccttacc acctcgatga ggtaccagcg gccgcttcga    3780
gcagacatga taagatacat tgatgagttt ggacaaacca caactagaat gcagtgaaaa    3840
aaatgcttta tttgtgaaat ttgtgatgct attgctttat ttgtaaccat tataagctgc    3900
aataaacaag ttaacaacaa caattcgaag gatctcgacg gtatcgatca cgagactagc    3960
ctcgagcggc cgcccccttc accgagggcc tatttcccat gattccttca tatttgcata    4020
tacgatacaa ggctgttaga gagataattg gaattaattt gactgtaaac acaaagatat    4080
tagtacaaaa tacgtgacgt agaaagtaat aatttcttgg gtagtttgca gttttaaaat    4140
tatgttttaa aatggactat catatgctta ccgtaacttg aaagtatttc gatttcttgg    4200
ctttatatat cttgtggaaa ggacgaaaca ccggcctcct ggttatggta cagatctcga    4260
gatctgtacc ataaccagga ggtttttgaa ttctcgacct cgagacaaat ggcagtattc    4320
atccacaatt ttaaaagaaa aggggggatt ggggggtaca gtgcagggga agaatagta    4380 gacataatag caacagacat acaaactaaa gaattacaaa acaaattac aaaaattcaa    4440 aattttcggg tttattacag ggacagcaga gatccacttt ggccgcgat ccgcaacaaa    4500 tctgactttg catgtgcaaa cgccttcaac aacagcatta ttccagaaga caccttcttc    4560
cccagcccag gtaagggcag cttggtgcc ttcgcaggc gtttccttgc ttcaggaatg    4620
gccaggttct gcccagagct ctggtcaatg atgtctaaaa ctcctctgat tggtggtctc    4680
```

```
ggccttatcc attgccacca aaaccctctt tttactaaga aacagtgagc cttgttctgg    4740
cagtccagag aatgacacgg gaaaaaagca gatgaagaga aggtggcagg agagggcacg    4800
tggcccagcc tcagtctctc caactgagtt cctgcctgcc tgccttttgct cagactgttt   4860
gccccttact gctcttctag gcctcattct aagccccttc tccaagttgc ctctccttat    4920
ttctccctgt ctgccaaaaa atctttccca gctcactaag tcagtctcac gcagtcactc    4980
attaacccac caatcactga ttgtgccggc acatgaatgc accaggtgtt gaagtggagg    5040
aattaaaaag tcagatgagg ggtgtgccca gaggaagcac cattctagtt gggggagccc    5100
atctgtcagc tgggaaaagt ccaaataact tcagattgga atgtgtttta actcagggtt    5160
gagaaaacag ccaccttcag gacaaaagtc agggaagggc tctctgaaga aatgctactt    5220
gaagatacca gccctaccaa gggcagggag aggaccaatt gatggagttg ccactccct    5280
ctctgcgcgc tcgctcgctc actgaggccg cccgggcaaa gcccgggcgt cgggcgacct    5340
ttggtcgccc ggcctcagtg agcgagcgag cgcgcagaga gggagtggcc aacggcgcgc    5400
ctgcaggtct caaaaatagc taccctctcc ggcatgaatt tatcagctag aacgttgaa     5460
tatcatattg atggtgattt gactgtctcc ggcctttctc acccgtttga atctttacct    5520
acacattact caggcattgc atttaaaata tatgagggt ctaaaatttt ttatccttgc     5580
gttgaaataa aggcttctcc cgcaaaagta ttacagggtc ataatgtttt tggtacaacc    5640
gatttagctt tatgctctga ggcttttattg cttaattttg ctaattcttt gccttgcctg    5700
tatgatttat tggatgttgg aattcctgat gcggtatttt ctccttacgc atctgtgcgg    5760
tatttcacac cgcatatggt gcactctcag tacaatctgc tctgatgccg catagttaag    5820
ccagccccga cacccgccaa cacccgctga cgcgccctga cgggcttgtc tgctcccggc    5880
atccgcttac agacaagctg tgaccgtctc cgggagctgc atgtgtcaga ggttttcacc    5940
gtcatcaccg aaacgcgcga acgaaaggg cctcgtgata cgcctatttt tataggttaa     6000
tgtcatgata ataatggttt cttagacgtc aggtggcact tttcggggaa atgtgcgcgg    6060
aacccctatt tgtttatttt tctaaataca ttcaaatatg tatccgctca tgagacaata    6120
accctgataa atgcttcaat aatattgaaa aaggaagagt atgagtattc aacatttccg    6180
tgtcgccctt attccctttt ttgcggcatt ttgccttcct gttttttgctc acccagaaac    6240
gctggtgaaa gtaaaagatg ctgaagatca gttgggtgca cgagtgggtt acatcgaact    6300
ggatctcaac agcggtaaga tccttgagag ttttcgcccc gaagaacgtt ttccaatgat    6360
gagcactttt aaagttctgc tatgtggcgc ggtattatcc cgtattgacg ccgggcaaga    6420
gcaactcggt cgccgcatac actattctca gaatgacttg gttgagtact caccagtcac    6480
agaaaagcat cttacggatg gcatgacagt aagagaatta tgcagtgctg ccataaccat    6540
gagtgataac actgcggcca acttacttct gacaacgatc ggaggaccga aggagctaac    6600
cgcttttttg cacaacatgg gggatcatgt aactcgcctt gatcgttggg aaccggagct    6660
gaatgaagcc ataccaaacg acgagcgtga ccacgatgcc tgtagcaa tggcaacaac     6720
gttgcgcaaa ctattaactg gcgaactact tactctagct tcccggcaac aattaataga    6780
ctggatggag gcggataaag ttgcaggacc acttctgcgc tcggcccttc cggctggctg    6840
gtttattgct gataaatctg gagccggtga gcgtgggtct cgcggtatca ttgcagcact    6900
ggggccagat ggtaagccct cccgtatcgt agttatctac acgacgggga gtcaggcaac    6960
tatggatgaa cgaaatagac agatcgctga gataggtgcc tcactgatta agcattggta    7020
actgtcagac caagtttact catatatact ttagattgat ttaaaacttc attttaatt    7080
```

```
taaaaggatc taggtgaaga tccttttttga taatctcatg accaaaatcc cttaacgtga    7140
gttttcgttc cactgagcgt cagacccgt  agaaaagatc aaaggatctt cttgagatcc    7200 ttttttctg  cgcgtaatct gctgcttgca acaaaaaaaa ccaccgctac cagcggtggt    7260
ttgtttgccg gatcaagagc taccaactct ttttccgaag gtaactggct tcagcagagc    7320
gcagatacca aatactgtcc ttctagtgta gccgtagtta ggccaccact tcaagaactc    7380
tgtagcaccg cctacatacc tcgctctgct aatcctgtta ccagtggctg ctgccagtgg    7440
cgataagtcg tgtcttaccg ggttggactc aagacgatag ttaccggata aggcgcagcg    7500
gtcgggctga acggggggtt cgtgcacaca gcccagcttg gagcgaacga cctacaccga    7560
actgagatac ctacagcgtg agctatgaga aagcgccacg cttcccgaag ggagaaaggc    7620
ggacaggtat ccggtaagcg gcagggtcgg aacaggagag cgcacgaggg agcttccagg    7680
gggaaacgcc tggtatcttt atagtcctgt cgggtttcgc cacctctgac ttgagcgtcg    7740
atttttgtga tgctcgtcag gggggcgag  cctatggaaa aacgccagca acgcggcctt    7800
tttacggttc ctggcctttt gctggccttt tgctcacatg ttctttcctg cgttatcccc    7860
tgattctgtg gataaccgta ttaccgcctt tgagtgagct gataccgctc gccgcagccg    7920
aacgaccgag cgcagcgagt cagtgagcga ggaagcggaa gagcgcccaa tacgcaaacc    7980
gcctctcccc gcgcgttggc cgattcatta atg                                8013

<210> SEQ ID NO 14
<211> LENGTH: 8090
<212> TYPE: DNA
<213> ORGANISM: Artificial Sequence
<220> FEATURE:
<223> OTHER INFORMATION: Synthesized

<400> SEQUENCE: 14
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttcctg  ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc  tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900
cctgtttttg ggcttttctg attatcaac  cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
```

-continued

```
cagagaggga gtggccaact ccatcactag gggttcctac gcgtagatct catattctgg     1140
cagggtcagt ggctccaact aacatttgtt tggtacttta cagtttatta aatagatgtt     1200
tatatggaga agctctcatt tctttctcag aagagcctgg ctaggaaggt ggatgaggca     1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc ccaacttaat     1440
gccaacatac cataaacctc ccattctgct aatgcccagc ctaagttggg gagaccactc     1500
cagattccaa gatgtacagt ttgctttgct gggccttttt cccatgcctg cctttactct     1560
gccagagtta tattgctggg gttttgaaga agatcctatt aaataaaaga ataagcagta     1620
ttattaagta gccctgcatt tcaggtttcc ttgagtggca ggccaggcct ggccgtgaac     1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc cccgcccttg tccatcactg gcatctggac tccagcctgg     1860
gttggggcaa agagggaaat gagatcatgt cctaaccctg atcctcttgt cccacagata     1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg     2040
tgtatatcac agacaaaact gtgctagaca tgaggtctat ggacttcaag agcaacagtg     2100
ctgtggcctg gagcaactag tgatccagac atgataagat acattgatga gtttggacaa     2160
accacaacta gaatgcagtg aaaaaaatgc tttatttgtg aaatttgtga tgctattgct     2220
ttatttgtaa ccattataag ctgcaataaa caagttaaca acaacaattg cattcatttt     2280
atgtttcagg ttcaggggga ggtgtgggag gttttttaaa gcaagtaaac tggtacctca     2340
tcgaggtggt aaggcttgca tgtgcagcgc gtcgtatgtg tccttggtcg cggtggaaag     2400
cccctggtat aagccgtcgt gtcccttttcc gcgacgtctc tcgcccttca taccaatctc     2460
cgagtacgcc tcagccatct tgtccttctg gagttcgttg tacaggccct cctgggggtt     2520
ctttctccga ggcttgcctc ccatctccgg gtccctacct ctacgcttgt ctaacacgtc     2580
gtactcctcc cggcgcccca ggtttaactc gttgtatagc tggttctgac cctgctggta     2640
agcgggtgcg tccgcggagc gagagaactt cactctcagt tcgcagctgc cttcttcttc     2700
gctcggcgcg cggcagctgc tcgcatcttc ttcctgcgcg ctgctcgccg ggctcgcaaa     2760
cgggctttta gccgccgccg ccgcttttttt gcggctcgct ttgcagtaga gcgttattac     2820
caagctcaac aacaacactc cgcaagtccc ggctagtggt gcccagatgt agatgtcgca     2880
ggcgaagtct agtcctcgcg tgtgaacggc gccgccgcc gcgggcctgc aagcctcagg     2940
gcgaagagat aagggctgac ttgctatcgt tggagctggc gtgggggac gtgggctgg     3000 ggtagtagtg ggcttcgctg gggatacatt tgtagaaaca tttgaaaatg ttccctgggt     3060
aggtaactcg ctggatacgg tcacagaagt gccctgaccc cagtagtcca ttgcgtaact     3120
cccgccgtag tagtagtgct tcgcgcagta gtaaatagcg gtgtcgtcag tctggagaga     3180
gttcatcttt aagaaaacct gcgacttact gttgtcctta atgatggtga ggcggctctt     3240
gagagctgag ttgtagtatg tggtttcact tccccagata accccagcc actctaagcc     3300 cttttctaggc ggctgtcgta tccatgatac cccgtagtct gggagactga ctccagacac     3360
agtgcacgtg actgagaggc tctggctagg tgcgaccaag cccggtccgc tctcctgtaa     3420
cttgacctcc gagccgccac ccccgctgcc gccgccaccg ctgccaccgc ctccggtaat     3480
```

```
ctccagctta gttcccccac cgaatgtgta cgggagcgtg ttgccctgct gacagaagta   3540
ggtggcgatg tcctcctgct caaggttact gattgtcagg ctgtagtccg taccggaacc   3600
ggaacccgaa aatcggctag gaacgcctga gtgtaatctc gacgtgtggt aaatgagcaa   3660
cttaactgtt ccgtccggct tctgctgata ccagtttaag tattttgaga tgtcctggct   3720
ggcccggcaa gatattgtta ctcggtcgcc taaagaagca gatagggaag aggtagtctg   3780
agtcatctgt atgtcaggac gagccgcgtg caataataac gccagaggta aaagtaaggc   3840
tgtcactggg agcgccatgg tggctttccg gaacaaacaa gaaccgcgac ccaaatcccg   3900
gctgcgacgg aactagctgt gccacacccg gcgcgtcctt atataatcat cggcgttcac   3960
cgcccattct ccgcccagcc ataaaaggca actttcggaa cggcgcacgc tgattggctc   4020
cgccctaact ccgcccacta gtgcggccgc ccccttcacc gagggcctat ttcccatgat   4080
tccttcatat ttgcatatac gatacaaggc tgttagagag ataattggaa ttaatttgac   4140
tgtaaacaca aagatattag tacaaaatac gtgacgtaga aagtaataat ttcttgggta   4200
gtttgcagtt ttaaaattat gttttaaaat ggactatcat atgcttaccg taacttgaaa   4260
gtatttcgat ttcttggctt tatatatctt gtggaaagga cgaaacaccg gcctcctggt   4320
tatggtacag atctcgagat ctgtaccata accaggaggt ttttgaattc tcgacctcga   4380
gacaaatggc agtattcatc cacaatttta aagaaaagg ggggattggg gggtacagtg   4440
caggggaaag aatagtagac ataatagcaa cagacataca aactaaagaa ttacaaaaac   4500
aaattacaaa aattcaaaat tttcgggttt attacaggga cagcagagat ccactttggc   4560
cgcggatccg caacaaatct gactttgcat gtgcaaacgc cttcaacaac agcattattc   4620
cagaagacac cttcttcccc agcccaggta agggcagctt tggtgccttc gcaggctgtt   4680
tccttgcttc aggaatggcc aggttctgcc cagagctctg gtcaatgatg tctaaaactc   4740
ctctgattgg tggtctcggc cttatccatt gccaccaaaa ccctcttttt actaagaaac   4800
agtgagcctt gttctggcag tccagagaat gacacgggaa aaaagcagat gaagagaagg   4860
tggcaggaga gggcacgtgg cccagcctca gtctctccaa ctgagttcct gcctgcctgc   4920
cttttgctcag actgtttgcc ccttactgct cttctaggcc tcattctaag cccttctcc   4980
aagttgcctc tccttatttc tccctgtctg ccaaaaaatc tttcccagct cactaagtca   5040
gtctcacgca gtcactcatt aacccaccaa tcactgattg tgccggcaca tgaatgcacc   5100
aggtgttgaa gtggaggaat taaaaagtca gatgagggt gtgcccagag gaagcaccat   5160
tctagtgggg ggagcccatc tgtcagctgg gaaaagtcca aataacttca gattggaatg   5220
tgttttaact cagggttgag aaaacagcca ccttcaggac aaaagtcagg gaagggctct   5280
ctgaagaaat gctacttgaa gataccagcc ctaccaaggg cagggagagg accaattgat   5340
ggagttggcc actccctctc tgcgcgctcg ctcgctcact gaggccgccc gggcaaagcc   5400
cgggcgtcgg gcgacctttg gtcgcccggc ctcagtgagc gagcgagcgc gcagagaggg   5460
agtggccaac ggcgcgcctg caggtctcaa aaatagctac cctctccggc atgaatttat   5520
cagctagaac ggttgaatat catattgatg gtgatttgac tgtctccggc ctttctcacc   5580
cgtttgaatc tttacctaca cattactcag gcattgcatt taaatatat gagggttcta   5640
aaaattttta tccttgcgtt gaaataaagg cttctcccgc aaaagtatta cagggtcata   5700
atgtttttgg tacaaccgat ttagctttat gctctgaggc tttattgctt aattttgcta   5760
attctttgcc ttgcctgtat gatttattgg atgttggaat tcctgatgcg gtattttctc   5820
```

```
cttacgcatc tgtgcggtat ttcacaccgc atatggtgca ctctcagtac aatctgctct    5880
gatgccgcat agttaagcca gccccgacac ccgccaacac ccgctgacgc gccctgacgg    5940
gcttgtctgc tcccggcatc cgcttacaga caagctgtga ccgtctccgg gagctgcatg    6000
tgtcagaggt tttcaccgtc atcaccgaaa cgcgcgagac gaaagggcct cgtgatacgc    6060
ctatttttat aggttaatgt catgataata atggtttctt agacgtcagg tggcacttt    6120
cggggaaatg tgcgcggaac ccctatttgt ttatttttct aaatacattc aaatatgtat    6180
ccgctcatga gacaataacc ctgataaatg cttcaataat attgaaaaag gaagagtatg    6240
agtattcaac atttccgtgt cgcccttatt ccctttttg cggcattttg ccttcctgtt    6300
tttgctcacc cagaaacgct ggtgaaagta aaagatgctg aagatcagtt gggtgcacga    6360
gtgggttaca tcgaactgga tctcaacagc ggtaagatcc ttgagagttt tcgccccgaa    6420
gaacgttttc caatgatgag cacttttaaa gttctgctat gtggcgcggt attatcccgt    6480
attgacgccg ggcaagagca actcggtcgc cgcatacact attctcagaa tgacttggtt    6540
gagtactcac cagtcacaga aaagcatctt acggatggca tgacagtaag agaattatgc    6600
agtgctgcca taaccatgag tgataacact gcggccaact tacttctgac aacgatcgga    6660
ggaccgaagg agctaaccgc ttttttgcac aacatggggg atcatgtaac tcgccttgat    6720
cgttgggaac cggagctgaa tgaagccata ccaaacgacg agcgtgacac cacgatgcct    6780
gtagcaatgg caacaacgtt gcgcaaacta ttaactggcg aactacttac tctagcttcc    6840
cggcaacaat taatagactg gatggaggcg gataaagttg caggaccact tctgcgctcg    6900
gcccttccgg ctggctggtt tattgctgat aaatctggag ccggtgagcg tgggtctcgc    6960
ggtatcattg cagcactggg gccagatggt aagccctccc gtatcgtagt tatctacacg    7020
acggggagtc aggcaactat ggatgaacga atagacaga tcgctgagat aggtgcctca    7080
ctgattaagc attggtaact gtcagaccaa gtttactcat atatacttta gattgattta    7140
aaacttcatt tttaatttaa aaggatctag gtgaagatcc tttttgataa tctcatgacc    7200
aaaatccctt aacgtgagtt ttcgttccac tgagcgtcag accccgtaga aagatcaaa    7260
ggatcttctt gagatccttt ttttctgcgc gtaatctgct gcttgcaaac aaaaaaacca    7320
ccgctaccag cggtggtttg tttgccggat caagagctac caactctttt tccgaaggta    7380
actggcttca gcagagcgca gataccaaat actgtccttc tagtgtagcc gtagttaggc    7440
caccacttca agaactctgt agcaccgcct acatacctcg ctctgctaat cctgttacca    7500
gtggctgctg ccagtggcga taagtcgtgt cttaccgggt tggactcaag acgatagtta    7560
ccggataagg cgcagcggtc gggctgaacg gggggttcgt gcacacagcc cagcttggag    7620
cgaacgacct acaccgaact gagatacccta cagcgtgagc tatgagaaag cgccacgctt    7680
cccgaaggga gaaaggcgga caggtatccg gtaagcggca gggtcggaac aggagagcgc    7740
acgagggagc ttccaggggg aaacgcctgg tatctttata gtcctgtcgg gtttcgccac    7800
ctctgacttg agcgtcgatt tttgtgatgc tcgtcagggg gcggagcct atggaaaaac    7860
gccagcaacg cggccttttt acggttcctg gccttttgct ggccttttgc tcacatgttc    7920
tttcctgcgt tatcccctga ttctgtggat aaccgtatta ccgcctttga gtgagctgat    7980
accgctcgcc gcagccgaac gaccgagcgc agcgagtcag tgagcgagga agcggaagag    8040
cgcccaatac gcaaaccgcc tctccccgcg cgttggccga ttcattaatg              8090
```

<210> SEQ ID NO 15
<211> LENGTH: 8030

```
<212> TYPE: DNA
<213> ORGANISM: Artificial Sequence
<220> FEATURE:
<223> OTHER INFORMATION: Synthesized

<400> SEQUENCE: 15
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctcccnttag ggttccgatt     600
tagtgcttta cggcacctcg acccccaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caacccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900
cctgttttg gggcttttct gattatcaac cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc ctggtaatgt gatagatttc ccaacttaat    1440
gccaacatac cataaacctc ccattctgct aatgcccagc ctaagttggg gagaccactc    1500
cagattccaa gatgtacagt ttgctttgct gggccttttt cccatgcctg cctttactct    1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttggggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgatccagac atgataagat acattgatga gtttggacaa    2160
```

```
accacaacta gaatgcagtg aaaaaaatgc tttatttgtg aaatttgtga tgctattgct   2220
ttatttgtaa ccattataag ctgcaataaa caagttaaca acaacaattg cattcatttt   2280
atgtttcagg ttcaggggga ggtgtgggag gttttttaaa gcaagtaaac tggtacctca   2340
tcgaggtggt aaggcttgca tgtgcagcgc gtcgtatgtg tccttggtcg cggtggaaag   2400
cccctggtat aagccgtcgt gtcccttttcc gcgacgtctc tcgcccttca taccaatctc   2460
cgagtacgcc tcagccatct tgtccttctg gagttcgttg tacaggccct cctgggggtt   2520 cttttctccga ggcttgcctc ccatctccgg gtccctacct ctacgcttgt ctaacacgtc   2580
gtactcctcc cggcgcccca ggtttaactc gttgtatagc tggttctgac cctgctggta   2640
agcgggtgcg tccgcggagc gagagaactt cactctcagt tcgcagctgc cttcttcttc   2700
gctcggcgcg cggcagctgc tcgcatcttc ttcctgcgcg ctgctcgccg ggctcgcaaa   2760
cgggcttttc gccgccgccg ccgctttttt gcggctcgct ttgcagtaga gcgttattac   2820
caagctcaac aacaacactc cgcaagtccc ggctagtggt gcccagatgt agatgtcgca   2880
ggcgaagtct agtcctcgcg tgtgaacggc gccgcccgcc gcgggcctgc aagcctcagg   2940
gcgaagagat aagggctgac ttgctatcgt tggagctggc gtgggggggac gtgggggctgg   3000 ggtagtagtg ctggatacgg tcacagaagt gccctgaccc cagtagtcca ttgcgtaact   3060
cccgccgtag tagtagtgct tcgcgcagta gtaaatagcg gtgtcgtcag tctggagaga   3120
gttcatcttt aagaaaacct gcgacttact gttgtcctta atgatggtga ggcggctctt   3180
gagagctgag ttgtagtatg tggtttcact tccccagata accccagcc actctaagcc    3240 cttttctaggc ggctgtcgta tccatgatac cccgtagtct gggagactga ctccagacac   3300
agtgcacgtg actgagaggc tctggctagg tgcgaccaag cccggtccgc tctcctgtaa   3360
cttgacctcc gagccgccac ccccgctgcc gccgccaccg ctgccaccgc ctccggtaat   3420
ctccagctta gttcccccac cgaatgtgta cgggagcgtg ttgccctgct gacagaagta   3480
ggtggcgatg tcctcctgct caaggttact gattgtcagg ctgtagtccg taccggaacc   3540
ggaacccgaa aatcggctag gaacgcctga gtgtaatctc gacgtgtggt aaatgagcaa   3600
cttaactgtt ccgtccggct tctgctgata ccagtttaag tattttgaga tgtcctggct   3660
ggcccggcaa gatattgtta ctcggtcgcc taaagaagca gatagggaag aggtagtctg   3720
agtcatctgt atgtcaggac gagccgcgtg caataataac gccagaggta aaagtaaggc   3780
tgtcactggg agcgccatgg tggctttccg gaacaaacaa gaaccgcgac ccaaatcccg   3840
gctgcgacgg aactagctgt gccacacccg gcgcgtcctt atataatcat cggcgttcac   3900
cgcccattct ccgcccagcc ataaaaggca actttcggaa cggcgcacgc tgattggctc   3960
cgccctaact ccgcccacta gtgcggccgc ccccttcacc gagggcctat ttcccatgat   4020
tccttcatat ttgcatatac gatacaaggc tgttagagag ataattggaa ttaatttgac   4080
tgtaaacaca aagatattag tacaaaatac gtgacgtaga aagtaataat ttcttgggta   4140
gtttgcagtt ttaaaattat gttttaaaat ggactatcat atgcttaccg taacttgaaa   4200
gtatttcgat tcttggctt tatatatctt gtggaaagga cgaaacaccg gcctcctggt    4260
tatggtacag atctcgagat ctgtaccata accaggaggt ttttgaattc tcgacctcga   4320
gacaaatggc agtattcatc cacaatttta aaagaaaagg ggggattggg gggtacagtg   4380
caggggaaag aatagtagac ataatagcaa cagacataca aactaaagaa ttacaaaaac   4440
aaattacaaa aattcaaaat tttcgggttt attacaggga cagcagagat ccactttggc   4500
cgcggatccg caacaaatct gactttgcat gtgcaaacgc cttcaacaac agcattattc   4560
```

```
cagaagacac cttcttcccc agcccaggta agggcagctt tggtgccttc gcaggctgtt    4620
tccttgcttc aggaatggcc aggttctgcc cagagctctg gtcaatgatg tctaaaactc    4680
ctctgattgg tggtctcggc cttatccatt gccaccaaaa ccctcttttt actaagaaac    4740
agtgagcctt gttctggcag tccagagaat gacacgggaa aaagcagat gaagagaagg    4800 tggcaggaga gggcacgtgg cccagcctca gtctctccaa ctgagttcct gcctgcctgc    4860
ctttgctcag actgtttgcc ccttactgct cttctaggcc tcattctaag ccccttctcc    4920
aagttgcctc tccttatttc tccctgtctg ccaaaaaatc tttcccagct cactaagtca    4980
gtctcacgca gtcactcatt aacccaccaa tcactgattg tgccggcaca tgaatgcacc    5040
aggtgttgaa gtggaggaat taaaaagtca gatgaggggt gtgcccagag aagcaccat    5100 tctagttggg ggagcccatc tgtcagctgg gaaaagtcca ataacttca gattggaatg    5160 tgttttaact cagggttgag aaaacagcca ccttcaggac aaaagtcagg gaagggctct    5220
ctgaagaaat gctacttgaa gataccagcc ctaccaaggg cagggagagg accaattgat    5280
ggagttggcc actccctctc tgcgcgctcg ctcgctcact gaggccgccc gggcaaagcc    5340
cgggcgtcgg gcgacctttg gtcgcccggc ctcagtgagc gagcgagcgc gcagagaggg    5400
agtggccaac ggcgcgcctg caggtctcaa aaatagctac cctctccggc atgaatttat    5460
cagctagaac ggttgaatat catattgatg gtgatttgac tgtctccggc ctttctcacc    5520
cgtttgaatc tttacctaca cattactcag gcattgcatt taaaatatat gagggttcta    5580
aaaattttta tccttgcgtt gaaataaagg cttctcccgc aaaagtatta cagggtcata    5640 atgttttgg tacaaccgat ttagcttat gctctgaggc tttattgctt aattttgcta    5700
attctttgcc ttgcctgtat gatttattgg atgttggaat tcctgatgcg gtattttctc    5760
cttacgcatc tgtgcggtat ttcacaccgc atatggtgca ctctcagtac aatctgctct    5820
gatgccgcat agttaagcca gccccgacac ccgccaacac ccgctgacgc gccctgacgg    5880
gcttgtctgc tcccggcatc cgcttacaga caagctgtga ccgtctccgg gagctgcatg    5940
tgtcagaggt tttcaccgtc atcaccgaaa cgcgcgagac gaaagggcct cgtgatacgc    6000
ctatttttat aggttaatgt catgataata atggtttctt agacgtcagg tggcactttt    6060
cggggaaatg tgcgcggaac ccctatttgt ttatttttct aaatacattc aaatatgtat    6120
ccgctcatga gacaataacc ctgataaatg cttcaataat attgaaaaag gaagagtatg    6180
agtattcaac atttccgtgt cgcccttatt ccctttttg cggcattttg ccttcctgtt    6240
tttgctcacc cagaaacgct ggtgaaagta aaagatgctg aagatcagtt gggtgcacga    6300
gtgggttaca tcgaactgga tctcaacagc ggtaagatcc ttgagagttt cgccccgaa    6360 gaacgttttc caatgatgag cactttaaa gttctgctat gtggcgcggt attatcccgt    6420
attgacgccg ggcaagagca actcggtcgc cgcatacact attctcagaa tgacttggtt    6480
gagtactcac cagtcacaga aaagcatctt acgatggca tgacagtaag agaattatgc    6540
agtgctgcca taaccatgag tgataacact gcggccaact tacttctgac aacgatcgga    6600
ggaccgaagg agctaaccgc ttttttgcac aacatggggg atcatgtaac tcgccttgat    6660
cgttgggaac cggagctgaa tgaagccata ccaaacgacg agcgtgacac cacgatgcct    6720
gtagcaatgg caacaacgtt gcgcaaacta ttaactggcg aactacttac tctagcttcc    6780
cggcaacaat taatagactg gatggaggcg gataaagttg caggaccact tctgcgctcg    6840
gcccttccgg ctggctggtt tattgctgat aaatctggag ccggtgagcg tgggtctcgc    6900
```

```
ggtatcattg cagcactggg gccagatggt aagccctccc gtatcgtagt tatctacacg      6960
acggggagtc aggcaactat ggatgaacga aatagacaga tcgctgagat aggtgcctca      7020
ctgattaagc attggtaact gtcagaccaa gtttactcat atatacttta gattgattta      7080
aaacttcatt tttaatttaa aaggatctag gtgaagatcc ttttgataa tctcatgacc       7140 aaaatccctt aacgtgagtt ttcgttccac tgagcgtcag accccgtaga aaagatcaaa      7200
ggatcttctt gagatccttt ttttctgcgc gtaatctgct gcttgcaaac aaaaaaacca      7260
ccgctaccag cggtggtttg tttgccggat caagagctac caactctttt tccgaaggta      7320
actggcttca gcagagcgca gataccaaat actgtccttc tagtgtagcc gtagttaggc      7380
caccacttca agaactctgt agcaccgcct acatacctcg ctctgctaat cctgttacca      7440
gtggctgctg ccagtggcga taagtcgtgt cttaccgggt tggactcaag acgatagtta      7500
ccggataagg cgcagcggtc gggctgaacg gggggttcgt gcacacagcc agcttggag       7560 cgaacgacct acaccgaact gagataccta cagcgtgagc tatgagaaag cgccacgctt      7620
cccgaaggga aaaggcgga caggtatccg gtaagcggca gggtcggaac aggagagcgc       7680
acgagggagc ttccaggggg aaacgcctgg tatctttata gtcctgtcgg gtttcgccac      7740
ctctgacttg agcgtcgatt tttgtgatgc tcgtcagggg ggcggagcct atggaaaaac      7800
gccagcaacg cggccttttt acggttcctg gccttttgct ggccttttgc tcacatgttc      7860
tttcctgcgt tatcccctga ttctgtggat aaccgtatta ccgcctttga gtgagctgat      7920
accgctcgcc gcagccgaac gaccgagcgc agcgagtcag tgagcgagga agcggaagag      7980
cgcccaatac gcaaaccgcc tctccccgcg cgttggccga ttcattaatg                8030

<210> SEQ ID NO 16
<211> LENGTH: 8089
<212> TYPE: DNA
<213> ORGANISM: Artificial Sequence
<220> FEATURE:
<223> OTHER INFORMATION: Synthesized

<400> SEQUENCE: 16
cagcagctgg cgtaatagcg aagaggcccg caccgatcgc ccttcccaac agttgcgcag        60
cctgaatggc gaatggaatt ccagacgatt gagcgtcaaa atgtaggtat ttccatgagc       120
gtttttcctg ttgcaatggc tggcggtaat attgttctgg atattaccag caaggccgat       180
agtttgagtt cttctactca ggcaagtgat gttattacta atcaaagaag tattgcgaca       240
acggttaatt tgcgtgatgg acagactctt ttactcggtg gcctcactga ttataaaaac      300
acttctcagg attctggcgt accgttcctg tctaaaatcc ctttaatcgg cctcctgttt      360
agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
cgctacactt gccagcgccc tagcgcccgc tcctttcgct ttcttccctt cctttctcgc      540
cacgttcgcc ggctttcccc gtcaagctct aaatcggggg ctccctttag ggttccgatt      600
tagtgcttta cggcacctcg accccaaaaa acttgattag ggtgatggtt cacgtagtgg      660
gccatcgccc tgatagacgg ttttcgccc tttgacgttg gagtccacgt tctttaatag      720
tggactcttg ttccaaactg gaacaacact caaccctatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900 cctgttttg gggcttttct gattatcaac cggggtacat atgattgaca tgctagtttt      960
```

```
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc ctggtaatgt gatagatttc ccaacttaat    1440
gccaacatac cataaacctc ccattctgct aatgcccagc taagttggg agaccactc     1500 cagattccaa gatgtacagt ttgctttgct gggccttttt cccatgcctg cctttactct    1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860 gttgggcaa agagggaaat gagatcatgt cctaaccctg atcctcttgt cccacagata     1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgatccagac atgataagat acattgatga gtttggacaa    2160
accacaacta gaatgcagtg aaaaaaatgc tttatttgtg aaatttgtga tgctattgct    2220
ttatttgtaa ccattataag ctgcaataaa caagttaaca acaacaattg cattcatttt    2280
atgtttcagg ttcaggggga ggtgtgggag gttttttaaa gcaagtaaac tggtacctca    2340
tcgaggtggt aaggcttgca tgtgcagcgc gtcgtatgtg tccttggtcg cggtggaaag    2400
cccctggtat aagccgtcgt gtcccttttcc gcgacgtctc tcgcccttca taccaatctc    2460
cgagtacgcc tcagccatct tgtccttctg gagttcgttg tacaggccct cctgggggtt    2520 cttttctccga ggcttgcctc ccatctccgg gtccctacct ctacgcttgt ctaacacgtc    2580
gtactcctcc cggcgcccca ggtttaactc gttgtatagc tggttctgac cctgctggta    2640
agcgggtgcg tccgcggagc gagagaactt cactctcagt tcgcagctgc cttcttcttc    2700
gctcggcgcg cggcagctgc tcgcatcttc ttcctgcgcg ctgctcgccg ggctcgcaaa    2760
cgggctttta gccgccgccg ccgctttttt gcggctcgct ttgcagtaga gcgttattac    2820
caagctcaac aacaacactc cgcaagtccc ggctagtggt gcccagatgt agatgtcgca    2880
ggcgaagtct agtcctcgcg tgtgaacggc gccgccgcc gcgggcctgc aagcctcagg     2940
gcgaagagat aagggctgac ttgctatcgt tggagctggc gtgggggac gtgggctgg      3000 ggtagtagtg ggcttcgctg gggatacatt tgtagaaaca tttgaaaatg ttccctgggt    3060
aggtaactcg ctggatacgg tcacagaagt gccctgaccc cagtagtcca ttgcgtaact    3120
cccgccgtag tagtagtgct tcgcgcagta gtaaatagcg gtgtcgtcag tctggagaga    3180
gttcatcttt aagaaaacct gcgacttact gttgtcctta atgatggtga gcggctctt    3240 gagagctgag ttgtagtatg tggtttcact tccccagata accccagcc actctaagcc     3300
```

```
ctttctaggc ggctgtcgta tccatgatac cccgtagtct gggagactga ctccagacac      3360
agtgcacgtg actgagaggc tctggctagg tgcgaccaag cccggtccgc tctcctgtaa      3420
cttgacctcc gagccgccac ccccgctgcc gccgccaccg ctgccaccgc ctccggtaat      3480
ctccagctta gttcccccac cgaatgtgta cgggagcgtg ttgccctgct gacagaagta      3540
ggtggcgatg tcctcctgct caaggttact gattgtcagg ctgtagtccg taccggaacc      3600
ggaacccgaa aatcggctag gaacgcctga gtgtaatctc gacgtgtggt aaatgagcaa      3660
cttaactgtt ccgtccggct tctgctgata ccagtttaag tattttgaga tgtcctggct      3720
ggcccggcaa gatattgtta ctcggtcgcc taaagaagca gatagggaag aggtagtctg      3780
agtcatctgt atgtcaggac gagccgcgtg caataataac gccagaggta aaagtaaggc      3840
tgtcactggg agcgccatgg tggctttccg gaacaaacaa gaaccgcgac ccaaatcccg      3900
gctgcgacgg aactagctgt gccacacccg gcgcgtcctt atataatcat cggcgttcac      3960
cgcccattct ccgcccagcc ataaaaggca actttcggaa cggcgcacgc tgattggctc      4020
cgccctaact ccgcccacta gtgcggccgc gcggccaaag tggatctctg ctgtccctgt      4080
aataaacccg aaaattttga attttttgtaa tttgtttttg taattcttta gtttgtatgt      4140
ctgttgctat tatgtctact attctttccc ctgcactgta ccccccaatc cccccttttc      4200
ttttaaaatt gtggatgaat actgccattt gtctcgaggt cgagaattca aaaacctcct      4260
ggttatggta cagatctcga gatctgtacc ataaccagga ggccggtgtt tcgtcctttc      4320
cacaagatat ataaagccaa gaaatcgaaa tactttcaag ttacggtaag catatgatag      4380 tccatttttaa aacataattt taaaactgca aactacccaa gaaattatta ctttctacgt      4440
cacgtatttt gtactaatat ctttgtgttt acagtcaaat taattccaat tatctctcta      4500
acagccttgt atcgtatatg caaatatgaa ggaatcatgg gaaataggcc ctcggtgaag      4560
ggggatccgc aacaaatctg actttgcatg tgcaaacgcc ttcaacaaca gcattattcc      4620
agaagacacc ttcttcccca gcccaggtaa gggcagcttt ggtgccttcg caggctgttt      4680
ccttgcttca ggaatggcca ggttctgccc agagctctgg tcaatgatgt ctaaaactcc      4740
tctgattggt ggtctcggcc ttatccattg ccaccaaaac cctctttta ctaagaaaca      4800 gtgagccttg ttctggcagt ccagagaatg acacgggaaa aaagcagatg aagagaaggt      4860
ggcaggagag ggcacgtggc ccagcctcag tctctccaac tgagttcctg cctgcctgcc      4920
tttgctcaga ctgtttgccc cttactgctc ttctaggcct cattctaagc cccttctcca      4980
agttgcctct ccttatttct ccctgtctgc caaaaaatct ttcccagctc actaagtcag      5040
tctcacgcag tcactcatta acccaccaat cactgattgt gccggcacat gaatgcacca      5100
ggtgttgaag tggaggaatt aaaaagtcag atgaggggtg tgcccagagg aagcaccatt      5160
ctagttgggg gagcccatct gtcagctggg aaaagtccaa ataacttcag attggaatgt      5220
gttttaactc agggttgaga aaacagccac cttcaggaca aaagtcaggg aagggctctc      5280
tgaagaaatg ctacttgaag ataccagccc taccaagggc agggagagga ccaattgatg      5340
gagttggcca ctccctctct gcgcgctcgc tcgctcactg aggccgcccg gcaaagccc      5400 gggcgtcggg cgacctttgg tcgcccggcc tcagtgagcg agcgagcgcg cagagaggga      5460
gtggccaacg gcgcgcctgc aggtctcaaa aatagctacc ctctccggca tgaatttatc      5520
agctagaacg gttgaatatc atattgatgg tgatttgact gtctccggcc tttctcaccc      5580
gtttgaatct ttacctacac attactcagg cattgcattt aaaatatatg agggttctaa      5640
aaatttttat ccttgcgttg aaataaaggc ttctcccgca aaagtattac agggtcataa      5700
```

```
tgttttttggt acaaccgatt tagctttatg ctctgaggct ttattgctta attttgctaa    5760
ttctttgcct tgcctgtatg atttattgga tgttggaatt cctgatgcgg tattttctcc    5820
ttacgcatct gtgcggtatt tcacaccgca tatggtgcac tctcagtaca atctgctctg    5880
atgccgcata gttaagccag ccccgacacc cgccaacacc cgctgacgcg ccctgacggg    5940
cttgtctgct cccggcatcc gcttacagac aagctgtgac cgtctccggg agctgcatgt    6000
gtcagaggtt ttcaccgtca tcaccgaaac gcgcgagacg aaagggcctc gtgatacgcc    6060
tatttttata ggttaatgtc atgataataa tggtttctta dacgtcaggt ggcacttttc    6120
ggggaaatgt gcgcggaacc cctatttgtt tatttttcta atacattca aatatgtatc    6180
cgctcatgag acaataaccc tgataaatgc ttcaataata ttgaaaaagg aagagtatga    6240
gtattcaaca tttccgtgtc gcccttattc cctttttgc ggcattttgc cttcctgttt    6300
ttgctcaccc agaaacgctg gtgaaagtaa aagatgctga agatcagttg ggtgcacgag    6360
tgggttacat cgaactggat ctcaacagcg gtaagatcct tgagagtttt cgccccgaag    6420
aacgttttcc aatgatgagc acttttaaag ttctgctatg tggcgcggta ttatcccgta    6480
ttgacgccgg gcaagagcaa ctcggtcgcc gcatacacta ttctcagaat gacttggttg    6540
agtactcacc agtcacagaa aagcatctta cggatggcat gacagtaaga gaattatgca    6600
gtgctgccat aaccatgagt gataacactg cggccaactt acttctgaca acgatcggag    6660
gaccgaagga gctaaccgct ttttgcaca acatggggga tcatgtaact cgccttgatc    6720
gttgggaacc ggagctgaat gaagccatac caaacgacga gcgtgacacc acgatgcctg    6780
tagcaatggc aacaacgttg cgcaaactat taactggcga actacttact ctagcttccc    6840
ggcaacaatt aatagactgg atggaggcgg ataaagttgc aggaccactt ctgcgctcgg    6900
cccttccggc tggctggttt attgctgata atctggagc cggtgagcgt gggtctcgcg    6960
gtatcattgc agcactgggg ccagatggta agccctcccg tatcgtagtt atctacacga    7020
cggggagtca ggcaactatg gatgaacgaa atagacagat cgctgagata ggtgcctcac    7080
tgattaagca ttggtaactg tcagaccaag tttactcata tatactttag attgatttaa    7140
aacttcattt ttaatttaaa aggatctagg tgaagatcct ttttgataat ctcatgacca    7200
aaatccctta acgtgagttt tcgttccact gagcgtcaga ccccgtagaa aagatcaaag    7260
gatcttcttg agatcctttt tttctgcgcg taatctgctg cttgcaaaca aaaaaaccac    7320
cgctaccagc ggtggtttgt ttgccggatc aagagctacc aactcttttt ccgaaggtaa    7380
ctggcttcag cagagcgcag ataccaaata ctgtccttct agtgtagccg tagttaggcc    7440
accacttcaa gaactctgta gcaccgccta catacctcgc tctgctaatc ctgttaccag    7500
tggctgctgc cagtggcgat aagtcgtgtc ttaccgggtt ggactcaaga cgatagttac    7560
cggataaggc gcagcggtcg ggctgaacgg ggggttcgtg cacacagccc agcttggagc    7620
gaacgaccta caccgaactg agatacctac agcgtgagct atgagaaagc gccacgcttc    7680
ccgaagggag aaaggcggac aggtatccgg taagcggcag ggtcggaaca ggagagcgca    7740
cgagggagct tccagggga aacgcctggt atctttatag tcctgtcggg tttcgccacc    7800
tctgacttga gcgtcgattt ttgtgatgct cgtcaggggg gcggagccta tggaaaaacg    7860
ccagcaacgc ggcctttta cggttcctgg ccttttgctg gccttttgct cacatgttct    7920
ttcctgcgtt atcccctgat tctgtggata accgtattac cgcctttgag tgagctgata    7980
ccgctcgccg cagccgaacg accgagcgca gcgagtcagt gagcgaggaa gcggaagagc    8040
```
gcccaatacg caaaccgcct ctccccgcgc gttggccgat tcattaatg        8089

<210> SEQ ID NO 17
<211> LENGTH: 8029
<212> TYPE: DNA
<213> ORGANISM: Artificial Sequence
<220> FEATURE:
<223> OTHER INFORMATION: Synthesized

<400> SEQUENCE: 17
cagcagctgg cgtaatagcg aagaggcccg caccgatcgc ccttcccaac agttgcgcag        60
cctgaatggc gaatgaatt ccagacgatt gagcgtcaaa atgtaggtat ttccatgagc       120
gttttcctg ttgcaatggc tggcggtaat attgttctgg atattaccag caaggccgat       180
agtttgagtt cttctactca ggcaagtgat gttattacta atcaaagaag tattgcgaca       240
acggttaatt tgcgtgatgg acagactctt ttactcggtg gcctcactga ttataaaaac       300
acttctcagg attctggcgt accgttcctg tctaaaatcc ctttaatcgg cctcctgttt       360
agctcccgct ctgattctaa cgaggaaagc acgttatacg tgctcgtcaa agcaaccata       420
gtacgcgccc tgtagcggcg cattaagcgc ggcgggtgtg gtggttacgc gcagcgtgac       480
cgctacactt gccagcgccc tagcgcccgc tcctttcgct ttcttccctt cctttctcgc       540
cacgttcgcc ggctttcccc gtcaagctct aaatcggggg ctcccttag ggttccgatt       600
tagtgcttta cggcacctcg accccaaaaa acttgattag ggtgatggtt cacgtagtgg       660
gccatcgccc tgatagacgg ttttcgccc tttgacgttg gagtccacgt tctttaatag       720
tggactcttg ttccaaactg gaacaacact caacccatc tcggtctatt cttttgattt       780
ataagggatt tgccgatt cggcctattg gttaaaaaat gagctgattt aacaaaaatt       840
taacgcgaat tttaacaaaa tattaacgtt acaatttaa atatttgctt atacaatctt       900
cctgttttg gggcttttct gattatcaac cggggtacat atgattgaca tgctagtttt       960
acggcgcgcc gggttggcca ctccctctct gcgcgctcgc tcgctcactg aggccgggcg      1020
accaaaggtc gcccgacgcc cgggctttgc ccgggcggcc tcagtgagcg agcgagcgcg      1080
cagagaggga gtggccaact ccatcactag gggttcctac gcgtagatct catattctgg      1140
cagggtcagt ggctccaact aacatttgtt tggtacttta cagtttatta aatagatgtt      1200
tatatggaga agctctcatt tctttctcag aagagcctgg ctaggaaggt ggatgaggca      1260
ccatattcat tttgcaggtg aaattcctga gatgtaagga gctgctgtga cttgctcaag      1320
gccttatatc gagtaaacgg tagcgctggg gcttagacgc aggtgttctg atttatagtt      1380
caaaacctct atcaatgaga gagcaatctc ctggtaatgt gatagatttc ccaacttaat      1440
gccaacatac cataaacctc ccattctgct aatgcccagc ctaagttggg gagaccactc      1500
cagattccaa gatgtacagt ttgctttgct gggccttttt cccatgcctg cctttactct      1560
gccagagtta tattgctggg gttttgaaga agatcctatt aaataaaaga ataagcagta      1620
ttattaagta gccctgcatt tcaggtttcc ttgagtggca ggccaggcct ggccgtgaac      1680
gttcactgaa atcatggcct cttggccaag attgatagct tgtgcctgtc cctgagtccc      1740
agtccatcac gagcagctgg tttctaagat gctatttccc gtataaagca tgagaccgtg      1800
acttgccagc cccacagagc cccgcccttg tccatcactg gcatctggac tccagcctgg      1860
gttggggcaa agagggaaat gagatcatgt cctaaccctg atcctcttgt cccacagata      1920
tccagaaccc tgaccctgcc gtgtaccagc tgagagactc taaatccagt gacaagtctg      1980
tctgcctatt caccgatttt gattctcaaa caaatgtgtc acaaagtaag gattctgatg      2040

```
tgtatatcac agacaaaact gtgctagaca tgaggtctat ggacttcaag agcaacagtg    2100
ctgtggcctg gagcaactag tgatccagac atgataagat acattgatga gtttggacaa    2160
accacaacta gaatgcagtg aaaaaaatgc tttatttgtg aaatttgtga tgctattgct    2220
ttatttgtaa ccattataag ctgcaataaa caagttaaca acaacaattg cattcatttt    2280
atgtttcagg ttcagggggga ggtgtgggag ggtttttaaa gcaagtaaac tggtacctca    2340
tcgaggtggt aaggcttgca tgtgcagcgc gtcgtatgtg tccttggtcg cggtggaaag    2400
cccctggtat aagccgtcgt gtcccttttcc gcgacgtctc tcgcccttca taccaatctc    2460
cgagtacgcc tcagccatct tgtccttctg gagttcgttg tacaggccct cctgggggtt    2520
ctttctccga ggcttgcctc ccatctccgg gtccctacct ctacgcttgt ctaacacgtc    2580
gtactcctcc cggcgcccca ggtttaactc gttgtatagc tggttctgac cctgctggta    2640
agcgggtgcg tccgcggagc gagagaactt cactctcagt tcgcagctgc cttcttcttc    2700
gctcggcgcg cggcagctgc tcgcatcttc ttcctgcgcg ctgctcgccg ggctcgcaaa    2760
cgggcttttc gccgccgccg ccgcttttt gcggctcgct ttgcagtaga gcgttattac    2820
caagctcaac aacaacactc cgcaagtccc ggctagtggt gcccagatgt agatgtcgca    2880
ggcgaagtct agtcctcgcg tgtgaacggc gccgcccgcc gcgggcctgc aagcctcagg    2940
gcgaagagat aagggctgac ttgctatcgt tggagctggc gtgggggggac gtggggctgg    3000 ggtagtagtg ctggatacgg tcacagaagt gccctgaccc cagtagtcca ttgcgtaact    3060
cccgccgtag tagtagtgct tcgcgcagta gtaaatagcg gtgtcgtcag tctggagaga    3120
gttcatcttt aagaaaacct gcgacttact gttgtcctta atgatggtga ggcggctctt    3180
gagagctgag ttgtagtatg tggtttcact tcccccagata accccagcc actctaagcc    3240 cttttctaggc ggctgtcgta tccatgatac cccgtagtct gggagactga ctccagacac    3300
agtgcacgtg actgagaggc tctggctagg tgcgaccaag cccggtccgc tctcctgtaa    3360
cttgacctcc gagccgccac cccgctgcc gccgccaccg ctgccaccgc ctccggtaat    3420
ctccagctta gttcccccac cgaatgtgta cgggagcgtg ttgccctgct gacagaagta    3480
ggtggcgatg tcctcctgct caaggttact gattgtcagg ctgtagtccg taccggaacc    3540
ggaacccgaa aatcggctag gaacgcctga gtgtaatctc gacgtgtggt aaatgagcaa    3600
cttaactgtt ccgtccggct tctgctgata ccagttttaag tattttgaga tgtcctggct    3660
ggcccggcaa gatattgtta ctcggtcgcc taaagaagca gatagggaag aggtagtctg    3720
agtcatctgt atgtcaggac gagccgcgtg caataataac gccagaggta aaagtaaggc    3780
tgtcactggg agcgccatgg tggctttccg gaacaaacaa gaaccgcgac ccaaatcccg    3840
gctgcgacgg aactagctgt gccacacccg gcgcgtcctt atataatcat cggcgttcac    3900
cgcccattct ccgcccagcc ataaaaggca actttcggaa cggcgcacgc tgattggctc    3960
cgccctaact ccgcccacta gtgcggccgc gcggccaaag tggatctctg ctgtccctgt    4020
aataaacccg aaaattttga attttttgtaa tttgttttttg taattcttta gtttgtatgt    4080
ctgttgctat tatgtctact attctttccc ctgcactgta ccccccaatc ccccttttc    4140 ttttaaaatt gtggatgaat actgccattt gtctcgaggt cgagaattca aaaacctcct    4200
ggttatggta cagatctcga gatctgtacc ataaccagga ggccggtgtt tcgtcctttc    4260
cacaagatat ataagccaa gaaatcgaaa tactttcaag ttacggtaag catatgatag    4320
tccattttaa aacataattt taaaactgca aactacccaa gaaattatta ctttctacgt    4380
```

| | |
|---|---|
| cacgtatttt gtactaatat ctttgtgttt acagtcaaat taattccaat tatctctcta | 4440 |
| acagccttgt atcgtatatg caaatatgaa ggaatcatgg gaaataggcc ctcggtgaag | 4500 |
| ggggatccgc aacaaatctg actttgcatg tgcaaacgcc ttcaacaaca gcattattcc | 4560 |
| agaagacacc ttcttcccca gcccaggtaa gggcagcttt ggtgccttcg caggctgttt | 4620 |
| ccttgcttca ggaatggcca ggttctgccc agagctctgg tcaatgatgt ctaaaactcc | 4680 |
| tctgattggt ggtctcggcc ttatccattg ccaccaaaac cctcttttta ctaagaaaca | 4740 |
| gtgagccttg ttctggcagt ccagagaatg acacgggaaa aaagcagatg aagagaaggt | 4800 |
| ggcaggagag ggcacgtggc ccagcctcag tctctccaac tgagttcctg cctgcctgcc | 4860 |
| tttgctcaga ctgtttgccc cttactgctc ttctaggcct cattctaagc cccttctcca | 4920 |
| agttgcctct ccttatttct ccctgtctgc caaaaatct ttcccagctc actaagtcag | 4980 |
| tctcacgcag tcactcatta acccaccaat cactgattgt gccggcacat gaatgcacca | 5040 |
| ggtgttgaag tggaggaatt aaaaagtcag atgaggggtg tgcccagagg aagcaccatt | 5100 |
| ctagttgggg gagcccatct gtcagctggg aaaagtccaa ataacttcag attggaatgt | 5160 |
| gttttaactc agggttgaga aaacagccac cttcaggaca aaagtcaggg aagggctctc | 5220 |
| tgaagaaatg ctacttgaag ataccagccc taccaagggc agggagagga ccaattgatg | 5280 |
| gagttggcca ctccctctct gcgcgctcgc tcgctcactg aggccgcccg gcaaagccc | 5340 |
| gggcgtcggg cgacctttgg tcgcccggcc tcagtgagcg agcgagcgcg cagagaggga | 5400 |
| gtggccaacg gcgcgcctgc aggtctcaaa atagctacc ctctccggca tgaatttatc | 5460 |
| agctagaacg gttgaatatc atattgatgg tgatttgact gtctccggcc tttctcaccc | 5520 |
| gtttgaatct ttacctacac attactcagg cattgcattt aaaatatatg agggttctaa | 5580 |
| aaattttat ccttgcgttg aaataaaggc ttctcccgca aaagtattac agggtcataa | 5640 |
| tgttttggt acaaccgatt tagctttatg ctctgaggct ttattgctta attttgctaa | 5700 |
| ttctttgcct tgcctgtatg atttattgga tgttggaatt cctgatgcgg tattttctcc | 5760 |
| ttacgcatct gtgcggtatt tcacaccgca tatggtgcac tctcagtaca atctgctctg | 5820 |
| atgccgcata gttaagccag ccccgacacc cgccaacacc cgctgacgcg ccctgacggg | 5880 |
| cttgtctgct cccggcatcc gcttacagac aagctgtgac cgtctccggg agctgcatgt | 5940 |
| gtcagaggtt ttcaccgtca tcaccgaaac gcgcgagacg aaagggcctc gtgatacgcc | 6000 |
| tatttttata ggttaatgtc atgataataa tggtttctta gacgtcaggt ggcactttc | 6060 |
| ggggaaatgt gcgcggaacc cctatttgtt tatttttcta aatacattca aatatgtatc | 6120 |
| cgctcatgag acaataaccc tgataaatgc ttcaataata ttgaaaaagg aagagtatga | 6180 |
| gtattcaaca tttccgtgtc gcccttattc ccttttttgc ggcattttgc cttcctgttt | 6240 |
| ttgctcaccc agaaacgctg gtgaaagtaa aagatgctga agatcagttg ggtgcacgag | 6300 |
| tgggttacat cgaactggat ctcaacagcg gtaagatcct tgagagtttt cgccccgaag | 6360 |
| aacgttttcc aatgatgagc acttttaaag ttctgctatg tggcgcggta ttatcccgta | 6420 |
| ttgacgccgg gcaagagcaa ctcggtcgcc gcatacacta ttctcagaat gacttggttg | 6480 |
| agtactcacc agtcacagaa aagcatctta cggatggcat gacagtaaga gaattatgca | 6540 |
| gtgctgccat aaccatgagt gataacactg cggccaactt acttctgaca acgatcggag | 6600 |
| gaccgaagga gctaaccgct ttttgcaca acatggggga tcatgtaact cgccttgatc | 6660 |
| gttgggaacc ggagctgaat gaagccatac caaacgacga gcgtgacacc acgatgcctg | 6720 |
| tagcaatggc aacaacgttg cgcaaactat taactggcga actacttact ctagcttccc | 6780 |

```
ggcaacaatt aatagactgg atggaggcgg ataaagttgc aggaccactt ctgcgctcgg    6840
cccttccggc tggctggttt attgctgata atctggagc cggtgagcgt gggtctcgcg    6900
gtatcattgc agcactgggg ccagatggta agccctcccg tatcgtagtt atctacacga    6960
cggggagtca ggcaactatg gatgaacgaa atagacagat cgctgagata ggtgcctcac    7020
tgattaagca ttggtaactg tcagaccaag tttactcata tatactttag attgatttaa    7080
aacttcattt ttaatttaaa aggatctagg tgaagatcct ttttgataat ctcatgacca    7140
aaatccctta acgtgagttt tcgttccact gagcgtcaga ccccgtagaa aagatcaaag    7200
gatcttcttg agatcctttt tttctgcgcg taatctgctg cttgcaaaca aaaaaaccac    7260
cgctaccagc ggtggtttgt ttgccggatc aagagctacc aactctttt ccgaaggtaa    7320 ctggcttcag cagagcgcag ataccaaata ctgtccttct agtgtagccg tagttaggcc    7380
accacttcaa gaactctgta gcaccgccta catacctcgc tctgctaatc ctgttaccag    7440
tggctgctgc cagtggcgat aagtcgtgtc ttaccgggtt ggactcaaga cgatagttac    7500
cggataaggc gcagcggtcg ggctgaacgg ggggttcgtg cacacagccc agcttggagc    7560
gaacgaccta caccgaactg agatacctac agcgtgagct atgagaaagc gccacgcttc    7620
ccgaagggag aaaggcggac aggtatccgg taagcggcag gtcggaaca ggagagcgca    7680 cgagggagct ccaggggga aacgcctggt atctttatag tcctgtcggg tttcgccacc    7740
tctgacttga gcgtcgattt tgtgatgct cgtcagggg gcggagccta tggaaaaacg    7800
ccagcaacgc ggccttttta cggttcctgg ccttttgctg ccttttgct cacatgttct    7860 ttcctgcgtt atcccctgat tctgtggata accgtattac cgcctttgag tgagctgata    7920
ccgctcgccg cagccgaacg accgagcgca gcgagtcagt gagcgaggaa gcggaagagc    7980
gcccaatacg caaaccgcct ctccccgcgc gttggccgat tcattaatg                8029
```

<210> SEQ ID NO 18
<211> LENGTH: 8082
<212> TYPE: DNA
<213> ORGANISM: Artificial Sequence
<220> FEATURE:
<223> OTHER INFORMATION: Synthesized

<400> SEQUENCE: 18

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120
gtttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcgggg ctcccttag ggttccgatt     600 tagtgcttta cggcacctcg accccaaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caaccctatc tcggtctatt cttttgattt     780
```

```
ataagggatt ttgccgattt cggcctattg gttaaaaaat gagctgattt aacaaaaatt    840
taacgcgaat tttaacaaaa tattaacgtt tacaatttaa atatttgctt atacaatctt    900
cctgttttg gggcttttct gattatcaac cggggtacat atgattgaca tgctagtttt    960
acggcgcgcc gggttggcca ctccctctct gcgcgctcgc tcgctcactg aggccgggcg   1020
accaaaggtc gcccgacgcc cgggctttgc ccggcggcc tcagtgagcg agcgagcgcg   1080
cagagaggga gtggccaact ccatcactag gggttcctac gcgtagatct catattctgg   1140
cagggtcagt ggctccaact aacatttgtt tggtacttta cagtttatta aatagatgtt   1200
tatatggaga agctctcatt tctttctcag aagagcctgg ctaggaaggt ggatgaggca   1260
ccatattcat tttgcaggtg aaattcctga gatgtaagga gctgctgtga cttgctcaag   1320
gccttatatc gagtaaacgg tagcgctggg gcttagacgc aggtgttctg atttatagtt   1380
caaaacctct atcaatgaga gagcaatctc ctggtaatgt gatagatttc ccaacttaat   1440
gccaacatac cataaacctc ccattctgct aatgcccagc ctaagttggg gagaccactc   1500
cagattccaa gatgtacagt ttgctttgct gggccttttt cccatgcctg cctttactct   1560
gccagagtta tattgctggg gttttgaaga agatcctatt aaataaaaga ataagcagta   1620
ttattaagta gccctgcatt tcaggtttcc ttgagtggca ggccaggcct ggccgtgaac   1680
gttcactgaa atcatggcct cttggccaag attgatagct tgtgcctgtc cctgagtccc   1740
agtccatcac gagcagctgg tttctaagat gctatttccc gtataaagca tgagaccgtg   1800
acttgccagc cccacagagc cccgcccttg tccatcactg gcatctggac tccagcctgg   1860
gttggggcaa agagggaaat gagatcatgt cctaaccctg atcctcttgt cccacagata   1920
tccagaaccc tgaccctgcc gtgtaccagc tgagagactc taaatccagt gacaagtctg   1980
tctgcctatt caccgatttt gattctcaaa caaatgtgtc acaaagtaag gattctgatg   2040
tgtatatcac agacaaaact gtgctagaca tgaggtctat ggacttcaag agcaacagtg   2100
ctgtggcctg gagcaactag tgggcggagt tagggcggag ccaatcagcg tgcgccgttc   2160
cgaaagttgc cttttatggc tgggcggaga atgggcggtg aacgccgatg attatataag   2220
gacgcgccgg gtgtggcaca gctagttccg tcgcagccgg gatttgggtc gcggttcttg   2280
tttgttccgg aaagccacca tggcgctccc agtgacagcc ttactttac ctctggcgtt   2340
attattgcac gcggctcgtc ctgacataca gatgactcag actacctctt ccctatctgc   2400
ttctttaggc gaccgagtaa caatatcttg ccgggccagc caggacatct caaaatactt   2460
aaactggtat cagcagaagc cggacggaac agttaagttg ctcatttacc acacgtcgag   2520
attacactca ggcgttccta gccgattttc gggttccggt tccggtacgg actacagcct   2580
gacaatcagt aaccttgagc aggaggacat cgccacctac ttctgtcagc agggcaacac   2640
gctcccgtac acattcggtg ggggaactaa gctggagatt accggaggcg gtggcagcgg   2700
tggcggcggc agcggggtg gcggctcgga ggtcaagtta caggagagcg gacccgggctt   2760
ggtcgcacct agccagagcc tctcagtcac gtgcactgtg tctggagtca gtctcccaga   2820
ctacggggta tcatggatac gacagccgcc tagaaagggc ttagagtggc tgggggttat   2880
ctggggaagt gaaaccacat actacaactc agctctcaag agccgcctca ccatcattaa   2940
ggacaacagt aagtcgcagg ttttcttaaa gatgaactct ctccagactg acgacaccgc   3000
tatttactac tgcgcgaagc actactacta cggcggagt tacgcaatgg actactgggg   3060
tcagggcact tctgtgaccg tatccagcga gttacctacc cagggaacat ttcaaatgt   3120
ttctacaaat gtatccccag cgaagcccac tactacccca gccccacgtc ccccacgcc   3180
```

```
agctccaacg atagcaagtc agcccttatc tcttcgccct gaggcttgca ggcccgcggc    3240
gggcggcgcc gttcacacgc gaggactaga cttcgcctgc acatctaca tctgggcacc     3300
actagccggg acttgcggag tgttgttgtt gagcttggta ataacgctct actgcaaagc    3360
gagccgcaaa aaagcggcgg cggcggctaa agcccgtttt gcgagcccgg cgagcagcgc    3420
gcaggaagaa gatgcgagca gctgccgcgc gccgagcgaa gaagaaggca gctgcgaact    3480
gagagtgaag ttctctcgct ccgcggacgc acccgcttac cagcagggtc agaaccagct    3540
atacaacgag ttaaacctgg ggcgccggga ggagtacgac gtgttagaca agcgtagagg    3600
tagggacccg gagatgggag gcaagcctcg gagaaagaac ccccaggagg gcctgtacaa    3660
cgaactccag aaggacaaga tggctgaggc gtactcggag attggtatga agggcgagag    3720
acgtcgcgga aagggacacg acggcttata ccaggggctt tccaccgcga ccaaggacac    3780
atacgacgcg ctgcacatgc aagccttacc acctcgatga ggtaccagcg gccgcttcga    3840
gcagacatga taagatacat tgatgagttt ggacaaacca caactagaat gcagtgaaaa    3900
aaatgcttta tttgtgaaat ttgtgatgct attgctttat ttgtaaccat tataagctgc    3960
aataaacaag ttaacaacaa caattcgaag gatctcgacg gtatcgatca cgagactagc    4020
ctcgagcggc cgcccccttc accgagggcc tatttcccat gattccttca tatttgcata    4080
tacgatacaa ggctgttaga gagataattg gaattaattt gactgtaaac acaaagatat    4140
tagtacaaaa tacgtgacgt agaaagtaat aatttcttgg gtagtttgca gttttaaaat    4200
tatgttttaa aatggactat catatgctta ccgtaacttg aaagtatttc gatttcttgg    4260
ctttatatat cttgtggaaa ggacgaaaca ccggtgtacc ggaggtttga agatgccgca    4320
tttctcgaga atgcggcat cttcaaacct tttttgaat tctcgaccta gggacaaatg      4380
gcagtattca tccacaattt taaaagaaaa ggggggattg ggggtacag tgcaggggaa      4440
agaatagtag acataatagc aacagacata caaactaaag aattacaaaa acaaattaca    4500
aaaattcaaa attttcgggt ttattacagg gacagcagag atccactttg gccgcggatc    4560
cgcaacaaat ctgactttgc atgtgcaaac gccttcaaca acagcattat tccagaagac    4620
accttcttcc ccagcccagg taagggcagc tttggtgcct tcgcaggctg tttccttgct    4680
tcaggaatgg ccaggttctg cccagagctc tggtcaatga tgtctaaaac cctctgatt     4740
ggtggtctcg gccttatcca ttgccaccaa acccctcttt ttactaagaa acagtgagcc    4800
ttgttctggc agtccagaga atgacacggg aaaaagcag atgaagagaa ggtggcagga    4860
gagggcacgt ggcccagcct cagtctctcc aactgagttc ctgcctgcct gcctttgctc    4920
agactgtttg ccccttactg ctcttctagg cctcattcta agcccttct ccaagttgcc     4980
tctccttatt tctccctgtc tgccaaaaaa tctttcccag ctcactaagt cagtctcacg    5040
cagtcactca ttaacccacc aatcactgat tgtgccggca catgaatgca ccaggtgttg    5100
aagtggagga attaaaaagt cagatgaggg gtgtgcccag aggaagcacc attctagttg    5160
ggggagccca tctgtcagct gggaaaagtc caaataactt cagattggaa tgtgttttaa    5220
ctcagggttg agaaaacagc caccttcagg acaaaagtca gggaagggct ctctgaagaa    5280
atgctacttg aagataccag ccctaccaag ggcagggaga ggaccaattg atggagttgg    5340
ccactccctc tctgcgcgct cgctcgctca ctgaggccgc ccgggcaaag cccgggcgtc    5400
gggcgacctt tggtcgcccg gcctcagtga gcgagcgagc gcgcagagag ggagtggcca    5460
acggcgcgcc tgcaggtctc aaaaatagct accctctccg gcatgaattt atcagctaga    5520
```

```
acggttgaat atcatattga tggtgatttg actgtctccg gcctttctca cccgtttgaa    5580
tctttaccta cacattactc aggcattgca tttaaaatat atgagggttc taaaaatttt    5640
tatccttgcg ttgaaataaa ggcttctccc gcaaaagtat tacagggtca taatgttttt    5700
ggtacaaccg atttagcttt atgctctgag gctttattgc ttaattttgc taattctttg    5760
ccttgcctgt atgatttatt ggatgttgga attcctgatg cggtattttc tccttacgca    5820
tctgtgcggt atttcacacc gcatatggtg cactctcagt acaatctgct ctgatgccgc    5880
atagttaagc cagccccgac acccgccaac acccgctgac gcgccctgac gggcttgtct    5940
gctcccggca tccgcttaca gacaagctgt gaccgtctcc gggagctgca tgtgtcagag    6000
gttttcaccg tcatcaccga aacgcgcgag acgaaagggc ctcgtgatac gcctattttt    6060
ataggttaat gtcatgataa taatggtttc ttagacgtca ggtggcactt ttcggggaaa    6120
tgtgcgcgga acccctattt gtttattttt ctaaatacat tcaaatatgt atccgctcat    6180
gagacaataa ccctgataaa tgcttcaata atattgaaaa aggaagagta tgagtattca    6240
acatttccgt gtcgccctta ttcccttttt tgcggcattt tgccttcctg tttttgctca    6300
cccagaaacg ctggtgaaag taaaagatgc tgaagatcag ttgggtgcac gagtgggtta    6360
catcgaactg gatctcaaca gcggtaagat ccttgagagt tttcgccccg aagaacgttt    6420
tccaatgatg agcactttta aagttctgct atgtggcgcg gtattatccc gtattgacgc    6480
cgggcaagag caactcggtc gccgcataca ctattctcag aatgacttgg ttgagtactc    6540
accagtcaca gaaaagcatc ttacggatgg catgacagta agagaattat gcagtgctgc    6600
cataaccatg agtgataaca ctgcggccaa cttacttctg acaacgatcg gaggaccgaa    6660
ggagctaacc gcttttttgc acaacatggg ggatcatgta actcgccttg atcgttggga    6720
accggagctg aatgaagcca taccaaacga cgagcgtgac accacgatgc ctgtagcaat    6780
ggcaacaacg ttgcgcaaac tattaactgg cgaactactt actctagctt cccggcaaca    6840
attaatagac tggatggagg cggataaagt tgcaggacca cttctgcgct cggcccttcc    6900
ggctggctgg tttattgctg ataaatctgg agccggtgag cgtgggtctc gcggtatcat    6960
tgcagcactg gggccagatg gtaagccctc ccgtatcgta gttatctaca cgacggggag    7020
tcaggcaact atggatgaac gaaatagaca gatcgctgag ataggtgcct cactgattaa    7080
gcattggtaa ctgtcagacc aagtttactc atatatactt tagattgatt taaaacttca    7140
tttttaattt aaaaggatct aggtgaagat cctttttgat aatctcatga ccaaaatccc    7200
ttaacgtgag ttttcgttcc actgagcgtc agaccccgta gaaaagatca aaggatcttc    7260
ttgagatcct ttttttctgc gcgtaatctg ctgcttgcaa acaaaaaaac caccgctacc    7320
agcggtggtt tgtttgccgg atcaagagct accaactctt tttccgaagg taactggctt    7380
cagcagagcg cagataccaa atactgtcct tctagtgtag ccgtagttag gccaccactt    7440
caagaactct gtagcaccgc ctacatacct cgctctgcta atcctgttac cagtggctgc    7500
tgccagtggc gataagtcgt gtcttaccgg gttggactca agacgatagt taccggataa    7560
ggcgcagcgg tcgggctgaa cggggggttc gtgcacacag cccagcttgg agcgaacgac    7620
ctacaccgaa ctgagatacc tacagcgtga gctatgagaa agcgccacgc ttcccgaagg    7680
gagaaaggcg gacaggtatc cggtaagcgg cagggtcgga acaggagagc gcacgaggga    7740
gcttccaggg ggaaacgcct ggtatcttta tagtcctgtc gggtttcgcc acctctgact    7800
tgagcgtcga tttttgtgat gctcgtcagg ggggcggagc ctatggaaaa acgccagcaa    7860
cgcggccttt ttacggttcc tggccttttg ctggcctttt gctcacatgt tctttcctgc    7920
```

```
gttatccccct gattctgtgg ataaccgtat taccgccttt gagtgagctg ataccgctcg    7980
ccgcagccga acgaccgagc gcagcgagtc agtgagcgag gaagcggaag agcgcccaat    8040
acgcaaaccg cctctccccg cgcgttggcc gattcattaa tg                       8082
```

<210> SEQ ID NO 19
<211> LENGTH: 8022
<212> TYPE: DNA
<213> ORGANISM: Artificial Sequence
<220> FEATURE:
<223> OTHER INFORMATION: Synthesized

<400> SEQUENCE: 19

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttttcctg ttgcaatggc tggcggtaat attgttctgg atattaccag caaggccgat    180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctcccttag ggttccgatt     600 tagtgcttta cggcacctcg accccaaaaa acttgattag ggtgatggtt cacgtagtgg     660
gccatcgccc tgatagacgg ttttttcgccc tttgacgttg gagtccacgt tctttaatag     720
tggactcttg ttccaaactg gaacaacact caaccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900 cctgttttttg ggcttttctt gattatcaac cgggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtactttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc ctggtaatgt gatagatttc ccaacttaat    1440
gccaacatac cataaacctc ccattctgct aatgcccagc ctaagttggg gagaccactc    1500
cagattccaa gatgtacagt tgctttgct gggcctttt cccatgcctg cctttactct       1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
```

-continued

```
gttggggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgggcggagt tagggcggag ccaatcagcg tgcgccgttc    2160
cgaaagttgc cttttatggc tgggcggaga atgggcggtg aacgccgatg attatataag    2220
gacgcgccgg gtgtggcaca gctagttccg tcgcagccgg gatttgggtc gcggttcttg    2280
tttgttccgg aaagccacca tggcgctccc agtgacagcc ttactttac ctctggcgtt     2340 attattgcac gcggctcgtc ctgacataca gatgactcag actacctctt ccctatctgc    2400
ttctttaggc gaccgagtaa caatatcttg ccgggccagc caggacatct caaaatactt    2460
aaactggtat cagcagaagc cggacggaac agttaagttg ctcatttacc acacgtcgag    2520
attacactca ggcgttccta gccgattttc gggttccggt tccggtacgg actacagcct    2580
gacaatcagt aaccttgagc aggaggacat cgccacctac ttctgtcagc agggcaacac    2640
gctcccgtac acattcggtg ggggaactaa gctggagatt accggaggcg gtggcagcgg    2700
tggcggcggc agcgggggtg gcggctcgga ggtcaagtta caggagagcg gacgggcgtt    2760
ggtcgcacct agccagagcc tctcagtcac gtgcactgtg tctggagtca gtctcccaga    2820
ctacggggta tcatggatac gacagccgcc tagaaagggc ttagagtggc tgggggttat    2880
ctggggaagt gaaaccacat actacaactc agctctcaag agccgcctca ccatcattaa    2940
ggacaacagt aagtcgcagg ttttcttaaa gatgaactct ctccagactg acgacaccgc    3000
tatttactac tgcgcgaagc actactacta cggcgggagt tacgcaatgg actactgggg    3060
tcagggcact tctgtgaccg tatccagcac tactacccca gccccacgtc ccccacgcc     3120 agctccaacg atagcaagtc agcccttatc tcttcgccct gaggcttgca ggcccgcggc    3180
gggcggcgcc gttcacacgc gaggactaga cttcgcctgc gacatctaca tctgggcacc    3240
actagccggg acttgcggag tgttgttgtt gagcttggta ataacgctct actgcaaagc    3300
gagccgcaaa aaagcggcgg cggcggcgaa aagcccgttt gcgagcccgg cgagcagcgc    3360
gcaggaagaa gatgcgagca gctgccgcgc gccgagcgaa gaagaaggca gctgcgaact    3420
gagagtgaag ttctctcgct ccgcggacgc acccgcttac cagcagggtc agaaccagct    3480
atacaacgag ttaaacctgg ggcgccggga ggagtacgac gtgttagaca gcgtagagg     3540 tagggacccg gagatgggag gcaagcctcg gagaaagaac ccccaggagg gcctgtacaa    3600
cgaactccag aaggacaaga tggctgaggc gtactcggag attggtatga agggcgagag    3660
acgtcgcgga aagggacacg acggcttata ccagggggctt tccaccgcga ccaaggacac    3720
atacgacgcg ctgcacatgc aagccttacc acctcgatga ggtaccagcg gccgcttcga    3780
gcagacatga taagatacat tgatgagttt ggacaaacca caactagaat gcagtgaaaa    3840
aaatgcttta tttgtgaaat ttgtgatgct attgctttat ttgtaaccat tataagctgc    3900
aataaacaag ttaacaacaa caattcgaag atctcgacg gtatcgatca cgagactagc     3960
ctcgagcggc cgcccccttc accgagggcc tatttcccat gattccttca tatttgcata    4020
tacgatacaa ggctgttaga gagataattg gaattaattt gactgtaaac acaaagatat    4080
tagtacaaaa tacgtgacgt agaaagtaat aatttcttgg gtagtttgca gttttaaaat    4140
tatgttttaa aatggactat catatgctta ccgtaacttg aaagtatttc gatttcttgg    4200
ctttatatat cttgtggaaa ggacgaaaca ccggtgtacc ggaggtttga agatgccgca    4260
```

```
tttctcgaga aatgcggcat cttcaaacct ttttttgaat tctcgaccta gggacaaatg    4320
gcagtattca tccacaattt taaaagaaaa gggggattg ggggtacag tgcagggaa       4380 agaatagtag acataatagc aacagacata caaactaaag aattacaaaa acaaattaca    4440
aaaattcaaa attttcgggt ttattacagg gacagcagag atccactttg gccgcggatc    4500
cgcaacaaat ctgactttgc atgtgcaaac gccttcaaca acagcattat tccagaagac    4560
accttcttcc ccagcccagg taagggcagc tttggtgcct tcgcaggctg tttccttgct    4620
tcaggaatgg ccaggttctg cccagagctc tggtcaatga tgtctaaaac tcctctgatt    4680
ggtggtctcg gccttatcca ttgccaccaa aaccctcttt ttactaagaa acagtgagcc    4740
ttgttctggc agtccagaga atgacacggg aaaaagcag atgaagagaa ggtggcagga    4800
gagggcacgt ggcccagcct cagtctctcc aactgagttc ctgcctgcct gcctttgctc    4860
agactgtttg cccccttactg ctcttctagg cctcattcta agccccttct ccaagttgcc   4920
tctccttatt tctccctgtc tgccaaaaaa tctttcccag ctcactaagt cagtctcacg    4980
cagtcactca ttaacccacc aatcactgat tgtgccggca catgaatgca ccaggtgttg    5040
aagtggagga attaaaaagt cagatgaggg gtgtgcccag aggaagcacc attctagttg    5100
ggggagccca tctgtcagct gggaaaagtc caaataactt cagattggaa tgtgttttaa    5160 ctcaggggttg agaaaacagc caccttcagg acaaaagtca gggaagggct ctctgaagaa   5220
atgctacttg aagataccag ccctaccaag ggcagggaga ggaccaattg atggagttgg    5280
ccactccctc tctgcgcgct cgctcgctca ctgaggccgc ccgggcaaag cccgggcgtc    5340
gggcgacctt tggtcgcccg gcctcagtga gcgagcgagc gcgcagagag ggagtggcca    5400
acggcgcgcc tgcaggtctc aaaaatagct accctctccg gcatgaattt atcagctaga    5460
acggttgaat atcatattga tggtgattg actgtctccg gcctttctca cccgtttgaa     5520 tcttttaccta cacattactc aggcattgca tttaaaatat atgagggttc taaaattttt   5580
tatccttgcg ttgaaataaa ggcttctccc gcaaaagtat tacagggtca taatgttttt    5640
ggtacaaccg atttagcttt atgctctgag gctttattgc ttaattttgc taattctttg    5700
ccttgcctgt atgatttatt ggatgttgga attcctgatg cggtattttc tccttacgca    5760
tctgtgcggt atttcacacc gcatatggtg cactctcagt acaatctgct ctgatgccgc    5820
atagttaagc cagccccgac acccgccaac acccgctgac gcgccctgac gggcttgtct    5880
gctcccggca tccgcttaca gacaagctgt gaccgtctcc gggagctgca tgtgtcagag    5940
gttttcaccg tcatcaccga aacgcgcgag acgaaagggc ctcgtgatac gcctattttt    6000
ataggttaat gtcatgataa taatggtttc ttagacgtca ggtggcactt ttcggggaaa    6060
tgtgcgcgga acccctattt gtttattttt ctaaatacat tcaaatatgt atccgctcat    6120
gagacaataa ccctgataaa tgcttcaata atattgaaaa aggaagagta tgagtattca    6180
acatttccgt gtcgccctta ttccctttt tgcggcattt tgccttcctg ttttgctca     6240 cccagaaacg ctggtgaaag taaaagatgc tgaagatcag ttgggtgcac gagtgggtta    6300
catcgaactg gatctcaaca gcggtaagat ccttgagagt tttcgccccg aagaacgttt    6360
tccaatgatg agcactttta aagttctgct atgtggcgcg gtattatccc gtattgacgc    6420
cgggcaagag caactcggtc gccgcataca ctattctcag aatgacttgg ttgagtactc    6480
accagtcaca gaaaagcatc ttacggatgg catgacagta agagaattat gcagtgctgc    6540
cataaccatg agtgataaca ctgcggccaa cttacttctg acaacgatcg gaggaccgaa    6600
```

```
ggagctaacc gcttttttgc acaacatggg ggatcatgta actcgccttg atcgttggga      6660
accggagctg aatgaagcca taccaaacga cgagcgtgac accacgatgc ctgtagcaat      6720
ggcaacaacg ttgcgcaaac tattaactgg cgaactactt actctagctt cccggcaaca      6780
attaatagac tggatggagg cggataaagt tgcaggacca cttctgcgct cggcccttcc      6840
ggctggctgg tttattgctg ataaatctgg agccggtgag cgtgggtctc gcggtatcat      6900
tgcagcactg gggccagatg gtaagccctc ccgtatcgta gttatctaca cgacggggag      6960
tcaggcaact atggatgaac gaaatagaca gatcgctgag ataggtgcct cactgattaa      7020
gcattggtaa ctgtcagacc aagtttactc atatatactt tagattgatt taaaacttca      7080
tttttaattt aaaaggatct aggtgaagat cctttttgat aatctcatga ccaaaatccc      7140
ttaacgtgag ttttcgttcc actgagcgtc agaccccgta gaaaagatca aaggatcttc      7200
ttgagatcct ttttttctgc gcgtaatctg ctgcttgcaa acaaaaaaac caccgctacc      7260
agcggtggtt tgtttgccgg atcaagagct accaactctt tttccgaagg taactggctt      7320
cagcagagcg cagataccaa atactgtcct tctagtgtag ccgtagttag gccaccactt      7380
caagaactct gtagcaccgc ctacatacct cgctctgcta atcctgttac cagtggctgc      7440
tgccagtggc gataagtcgt gtcttaccgg gttggactca agacgatagt taccggataa      7500
ggcgcagcgg tcgggctgaa cggggggttc gtgcacacag cccagcttgg agcgaacgac      7560
ctacaccgaa ctgagatacc tacagcgtga gctatgagaa agcgccacgc ttcccgaagg      7620
gagaaaggcg gacaggtatc cggtaagcgg cagggtcgga acaggagagc gcacgaggga      7680
gcttccaggg ggaaacgcct ggtatcttta tagtcctgtc gggtttcgcc acctctgact      7740
tgagcgtcga tttttgtgat gctcgtcagg gggcggagc ctatggaaaa acgccagcaa      7800
cgcggccttt ttacggttcc tggccttttg ctggccttttt gctcacatgt tctttcctgc      7860
gttatcccct gattctgtgg ataaccgtat taccgccttt gagtgagctg ataccgctcg      7920
ccgcagccga acgaccgagc gcagcgagtc agtgagcgag gaagcggaag agcgcccaat      7980
acgcaaaccg cctctccccg cgcgttggcc gattcattaa tg                        8022
```

<210> SEQ ID NO 20
<211> LENGTH: 8099
<212> TYPE: DNA
<213> ORGANISM: Artificial Sequence
<220> FEATURE:
<223> OTHER INFORMATION: Synthesized

<400> SEQUENCE: 20

```
cagcagctgg cgtaatagcg aagaggcccg caccgatcgc ccttcccaac agttgcgcag       60
cctgaatggc gaatggaatt ccagacgatt gagcgtcaaa atgtaggtat ttccatgagc      120 gttttttcctg ttgcaatggc tggcggtaat attgttctgg atattaccag caaggccgat      180
agtttgagtt cttctactca ggcaagtgat gttattacta atcaaagaag tattgcgaca      240
acggttaatt tgcgtgatgg acagactctt ttactcggtg gcctcactga ttataaaaac      300
acttctcagg attctggcgt accgttcctg tctaaaatcc ctttaatcgg cctcctgttt      360
agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
cgctacactt gccagcgccc tagcgcccgc tcctttcgct ttcttccctt cctttctcgc      540
cacgttcgcc ggctttcccc gtcaagctct aaatcggggg ctcccttag ggttccgatt      600 tagtgcttta cggcacctcg accccaaaaa acttgattag ggtgatggtt cacgtagtgg      660
```

```
gccatcgccc tgatagacgg ttttccgccc tttgacgttg gagtccacgt tctttaatag      720
tggactcttg ttccaaactg gaacaacact caacccctatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900 cctgttttg gggcttttct gattatcaac cggggtacat atgattgaca tgctagtttt       960
acggcgcgcc gggttggcca ctccctctct gcgcgctcgc tcgctcactg aggccgggcg     1020
accaaaggtc gcccgacgcc cgggctttgc ccgggcggcc tcagtgagcg agcgagcgcg     1080
cagagaggga gtggccaact ccatcactag gggttcctac gcgtagatct catattctgg     1140
cagggtcagt ggctccaact aacatttgtt tggtacttta cagtttatta aatagatgtt     1200
tatatggaga agctctcatt tctttctcag aagagcctgg ctaggaaggt ggatgaggca     1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc ccaacttaat     1440
gccaacatac cataaacctc ccattctgct aatgcccagc ctaagttggg gagaccactc     1500
cagattccaa gatgtacagt ttgctttgct gggcctttt cccatgcctg cctttactct      1560
gccagagtta tattgctggg gttttgaaga agatcctatt aaataaaaga ataagcagta     1620
ttattaagta gccctgcatt tcaggtttcc ttgagtggca ggccaggcct ggccgtgaac     1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc cccgcccttg tccatcactg gcatctggac tccagcctgg     1860
gttggggcaa agagggaaat gagatcatgt cctaaccctg atcctcttgt cccacagata     1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg     2040
tgtatatcac agacaaaact gtgctagaca tgaggtctat ggacttcaag agcaacagtg     2100
ctgtggcctg gagcaactag tgatccagac atgataagat acattgatga gtttggacaa     2160
accacaacta gaatgcagtg aaaaaaatgc tttatttgtg aaatttgtga tgctattgct     2220
ttatttgtaa ccattataag ctgcaataaa caagttaaca acaacaattg cattcatttt     2280
atgtttcagg ttcaggggga ggtgtgggag gttttttaaa gcaagtaaac tggtacctca     2340
tcgaggtggt aaggcttgca tgtgcagcgc gtcgtatgtg tccttggtcg cggtggaaag     2400
cccctggtat aagccgtcgt gtcccttttcc gcgacgtctc tcgcccttca taccaatctc     2460
cgagtacgcc tcagccatct tgtccttctg gagttcgttg tacaggcccct cctggggggtt    2520 ctttctccga ggcttgcctc ccatctccgg gtccctacct ctacgcttgt ctaacacgtc     2580
gtactcctcc cggcgcccca ggtttaactc gttgtatagc tggttctgac cctgctggta     2640
agcgggtgcg tccgcggagc gagagaactt cactctcagt tcgcagctgc cttcttcttc     2700
gctcggcgcg cggcagctgc tcgcatcttc ttcctgcgcg ctgctcgccg ggctcgcaaa     2760 cgggcttta gccgccgccg ccgctttttt gcggctcgct ttgcagtaga gcgttattac     2820
caagctcaac aacaacactc cgcaagtccc ggctagtggt gcccagatgt agatgtcgca     2880
ggcgaagtct agtcctcgcg tgtgaacgga gccgcccgcc gcgggcctgc aagcctcagg     2940
gcgaagagat aagggctgac ttgctatcgt tggagctggc gtgggggggac gtggggctgg     3000
```

```
ggtagtagtg ggcttcgctg gggatacatt tgtagaaaca tttgaaaatg ttccctgggt      3060
aggtaactcg ctggatacgg tcacagaagt gccctgaccc cagtagtcca ttgcgtaact      3120
cccgccgtag tagtagtgct cgcgcagta gtaaatagcg gtgtcgtcag tctggagaga       3180
gttcatcttt aagaaaacct gcgacttact gttgtcctta atgatggtga ggcggctctt      3240
gagagctgag ttgtagtatg tggtttcact tccccagata accccagcc actctaagcc       3300 ctttctaggc ggctgtcgta tccatgatac cccgtagtct gggagactga ctccagacac      3360
agtgcacgtg actgagaggc tctggctagg tgcgaccaag cccggtccgc tctcctgtaa      3420
cttgacctcc gagccgccac ccccgctgcc gccgccaccg ctgccaccgc tccggtaat      3480 ctccagctta gttcccccac cgaatgtgta cgggagcgtg ttgccctgct gacagaagta     3540
ggtggcgatg tcctcctgct caaggttact gattgtcagg ctgtagtccg taccggaacc     3600
ggaacccgaa atcggctag gaacgcctga gtgtaatctc gacgtgtggt aaatgagcaa      3660
cttaactgtt ccgtccggct tctgctgata ccagtttaag tattttgaga tgtcctggct     3720
ggcccggcaa gatattgtta ctcggtcgcc taaagaagca gatagggaag aggtagtctg    3780
agtcatctgt atgtcaggac gagccgcgtg caataataac gccagaggta aaagtaaggc   3840
tgtcactggg agcgccatgg tggctttccg gaacaaacaa gaaccgcgac ccaaatcccg    3900
gctgcgacgg aactagctgt gccacacccg gcgcgtcctt atataatcat cggcgttcac    3960
cgcccattct ccgcccagcc ataaaaggca actttcggaa cggcgcacgc tgattggctc    4020
cgccctaact ccgcccacta gtgcggccgc cccctttcacc gagggcctat ttcccatgat   4080
tccttcatat ttgcatatac gatacaaggc tgttagagag ataattggaa ttaatttgac   4140
tgtaaacaca aagatattag tacaaaatac gtgacgtaga aagtaataat ttcttgggta   4200
gtttgcagtt ttaaaattat gttttaaaat ggactatcat atgcttaccg taacttgaaa    4260
gtatttcgat ttcttggctt tatatatctt gtggaaagga cgaaacaccg gtgtaccgga    4320
ggtttgaaga tgccgcattt ctcgagaaat gcggcatctt caaaccttt tttgaattct     4380 cgacctaggg acaaatggca gtattcatcc acaattttaa aagaaaaggg gggattgggg   4440
ggtacagtgc agggggaaga atagtagaca taatagcaac agacatacaa actaaagaat    4500
tacaaaaaca aattacaaaa attcaaaatt ttcgggttta ttacagggac agcagagatc    4560
cactttggcc gcggatccgc aacaaatctg actttgcatg tgcaaacgcc ttcaacaaca    4620
gcattattcc agaagacacc ttcttcccca gcccaggtaa gggcagcttt ggtgccttcg    4680
caggctgttt ccttgcttca ggaatggcca ggttctgccc agagctctgg tcaatgatgt    4740
ctaaaactcc tctgattggt ggtctcggcc ttatccattg ccaccaaaac cctctttta    4800 ctaagaaaca gtgagccttg ttctggcagt ccagagaatg acacgggaaa aaagcagatg   4860
aagagaaggt ggcaggagag ggcacgtggc ccagcctcag tctctccaac tgagttcctg   4920
cctgcctgcc tttgctcaga ctgtttgccc cttactgctc ttctaggcct cattctaagc   4980
cccttctcca agttgcctct ccttatttct ccctgtctgc caaaaatct ttcccagctc    5040 actaagtcag tctcacgcag tcactcatta acccaccaat cactgattgt gccggcacat    5100
gaatgcacca ggtgttgaag tggaggaatt aaaaagtcag atgagggtg tgcccagagg     5160 aagcaccatt ctagttgggg gagcccatct gtcagctggg aaaagtccaa ataacttcag    5220
attggaatgt gttttaactc agggttgaga aaacagccac cttcaggaca aaagtcaggg    5280
aagggctctc tgaagaaatg ctacttgaag ataccagccc taccaaggc agggagagga    5340 ccaattgatg gagttggcca ctccctctct gcgcgctcgc tcgctcactg aggccgcccg    5400
```

```
ggcaaagccc gggcgtcggg cgacctttgg tcgcccggcc tcagtgagcg agcgagcgcg   5460
cagagaggga gtggccaacg gcgcgcctgc aggtctcaaa aatagctacc ctctccggca   5520
tgaatttatc agctagaacg gttgaatatc atattgatgg tgatttgact gtctccggcc   5580
tttctcaccc gttgaatct ttacctacac attactcagg cattgcattt aaaatatatg    5640
agggttctaa aaatttttat ccttgcgttg aaataaaggc ttctcccgca aaagtattac   5700
agggtcataa tgttttggt acaaccgatt tagctttatg ctctgaggct ttattgctta    5760
attttgctaa ttctttgcct tgcctgtatg atttattgga tgttggaatt cctgatgcgg   5820
tattttctcc ttacgcatct gtgcggtatt tcacaccgca tatggtgcac tctcagtaca   5880
atctgctctg atgccgcata gttaagccag ccccgacacc cgccaacacc cgctgacgcg   5940
ccctgacggg cttgtctgct cccggcatcc gcttacagac aagctgtgac cgtctccggg   6000
agctgcatgt gtcagaggtt ttcaccgtca tcaccgaaac gcgcgagacg aaagggcctc   6060
gtgatacgcc tatttttata ggttaatgtc atgataataa tggtttctta cgtcaggt    6120 ggcactttc ggggaaatgt gcgcggaacc cctatttgtt tattttcta aatacattca    6180 aatatgtatc cgctcatgag acaataaccc tgataaatgc ttcaataata ttgaaaaagg   6240
aagagtatga gtattcaaca tttccgtgtc gcccttattc cctttttgc ggcattttgc    6300 cttcctgttt ttgctcaccc agaaacgctg gtgaaagtaa aagatgctga agatcagttg   6360
ggtgcacgag tgggttacat cgaactggat ctcaacagcg gtaagatcct tgagagtttt   6420
cgccccgaag aacgtttcc aatgatgagc actttaaag ttctgctatg tggcgcggta    6480
ttatcccgta ttgacgccgg gcaagagcaa ctcggtcgcc gcatacacta ttctcagaat   6540
gacttggttg agtactcacc agtcacagaa aagcatctta cggatggcat gacagtaaga   6600
gaattatgca gtgctgccat aaccatgagt gataacactg cggccaactt acttctgaca   6660
acgatcggag gaccgaagga gctaaccgct ttttgcaca acatggggga tcatgtaact    6720
cgccttgatc gttgggaacc ggagctgaat gaagccatac caaacgacga gcgtgacacc   6780
acgatgcctg tagcaatggc aacaacgttg cgcaaactat taactggcga actacttact   6840
ctagcttccc ggcaacaatt aatagactgg atggaggcgg ataaagttgc aggaccactt   6900
ctgcgctcgg cccttccggc tggctggttt attgctgata atctggagc cggtgagcgt    6960 gggtctcgcg gtatcattgc agcactgggg ccagatggta agccctcccg tatcgtagtt   7020
atctacacga cggggagtca ggcaactatg gatgaacgaa atagacagat cgctgagata   7080
ggtgcctcac tgattaagca ttggtaactg tcagaccaag tttactcata tactttag    7140 attgatttaa aacttcattt ttaatttaaa aggatctagg tgaagatcct ttttgataat   7200
ctcatgacca aaatcccta acgtgagttt tcgttccact gagcgtcaga ccccgtagaa    7260
aagatcaaag gatcttcttg agatcctttt tttctgcgcg taatctgctg cttgcaaaca   7320
aaaaaaccac cgctaccagc ggtggtttgt ttgccggatc aagagctacc aactctttt     7380 ccgaaggtaa ctggcttcag cagagcgcag ataccaaata ctgtccttct agtgtagccg   7440
tagttaggcc accacttcaa gaactctgta gcaccgccta catacctcgc tctgctaatc   7500
ctgttaccag tggctgctgc cagtggcgat aagtcgtgtc ttaccgggtt ggactcaaga   7560
cgatagttac cggataaggc gcagcggtcg ggctgaacgg ggggttcgtg cacacagccc   7620
agcttggagc gaacgaccta caccgaactg agatacctac agcgtgagct atgagaaagc   7680
gccacgcttc ccgaagggag aaaggcggac aggtatccgg taagcggcag ggtcggaaca   7740
```

```
ggagagcgca cgagggagct tccaggggga aacgcctggt atctttatag tcctgtcggg    7800
tttcgccacc tctgacttga gcgtcgattt ttgtgatgct cgtcaggggg gcggagccta    7860
tggaaaaacg ccagcaacgc ggccttttta cggttcctgg ccttttgctg gccttttgct    7920
cacatgttct ttcctgcgtt atccctgat  tctgtggata accgtattac cgcctttgag    7980
tgagctgata ccgctcgccg cagccgaacg accgagcgca gcgagtcagt gagcgaggaa    8040
gcggaagagc gcccaatacg caaaccgcct ctccccgcgc gttggccgat tcattaatg     8099
```

```
<210> SEQ ID NO 21
<211> LENGTH: 8039
<212> TYPE: DNA
<213> ORGANISM: Artificial Sequence
<220> FEATURE:
<223> OTHER INFORMATION: Synthesized

<400> SEQUENCE: 21
```

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctcccttag  ggttccgatt    600 tagtgcttta cggcacctcg accccaaaaa acttgattag ggtgatggtt cacgtagtgg    660
gccatcgccc tgatagacgg ttttcgccc  tttgacgttg gagtccacgt tctttaatag    720
tggactcttg ttccaaactg gaacaacact caaccctatc tcggtctatt cttttgattt    780
ataagggatt tgccgatttc ggcctattg  gttaaaaaat gagctgattt aacaaaaatt    840
taacgcgaat tttaacaaaa tattaacgtt tacaatttaa atatttgctt atacaatctt    900 cctgttttg  gggcttttct gattatcaac cggggtacat atgattgaca tgctagtttt    960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtagatct catattctgg    1140
cagggtcagt ggctccaact aacatttgtt tggtacttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacga aggtgttctg atttatagtt    1380
caaaacctct atcaatgaga gagcaatctc ctggtaatgt gatagatttc ccaacttaat    1440
gccaacatac cataaacctc ccattctgct aatgccagc  ctaagttggg gagaccactc    1500
cagattccaa gatgtacagt ttgctttgct gggccttttt cccatgcctg cctttactct    1560
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
```

```
agtccatcac gagcagctgg tttctaagat gctatttccc gtataaagca tgagaccgtg    1800
acttgccagc cccacagagc cccgcccttg tccatcactg gcatctggac tccagcctgg    1860
gttggggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgatccagac atgataagat acattgatga gtttggacaa    2160
accacaacta gaatgcagtg aaaaaaatgc tttatttgtg aaatttgtga tgctattgct    2220
ttatttgtaa ccattataag ctgcaataaa caagttaaca acaacaattg cattcatttt    2280
atgtttcagg ttcaggggga ggtgtgggag gtttttttaaa gcaagtaaac tggtacctca    2340
tcgaggtggt aaggcttgca tgtgcagcgc gtcgtatgtg tccttggtcg cggtggaaag    2400
cccctggtat aagccgtcgt gtcccttttcc gcgacgtctc tcgcccttca taccaatctc    2460
cgagtacgcc tcagccatct tgtccttctg gagttcgttg tacaggccct cctgggggtt    2520
ctttctccga ggcttgcctc ccatctccgg gtccctacct ctacgcttgt ctaacacgtc    2580
gtactcctcc cggcgcccca ggtttaactc gttgtatagc tggttctgac cctgctggta    2640
agcgggtgcg tccgcggagc gagagaactt cactctcagt tcgcagctgc cttcttcttc    2700
gctcggcgcg cggcagctgc tcgcatcttc ttcctgcgcg ctgctcgccg ggctcgcaaa    2760
cgggcttttc gccgccgccg ccgctttttt gcggctcgct ttgcagtaga gcgttattac    2820
caagctcaac aacaacactc cgcaagtccc ggctagtggt gcccagatgt agatgtcgca    2880
ggcgaagtct agtcctcgcg tgtgaacggc gccgcccgcc gcgggcctgc aagcctcagg    2940
gcgaagagat aagggctgac ttgctatcgt tggagctggc gtgggggac gtgggctgg     3000 ggtagtagtg ctggatacgg tcacagaagt gccctgaccc cagtagtcca ttgcgtaact    3060
cccgccgtag tagtagtgct tcgcgcagta gtaaatagcg gtgtcgtcag tctggagaga    3120
gttcatcttt aagaaaacct gcgacttact gttgtcctta atgatggtga ggcggctctt    3180
gagagctgag ttgtagtatg tggtttcact tccccagata accccagcc actctaagcc     3240 ctttctaggc ggctgtcgta tccatgatac cccgtagtct gggagactga ctccagacac    3300
agtgcacgtg actgagaggc tctggctagg tgcgaccaag cccggtccgc tctcctgtaa    3360
cttgacctcc gagccgccac ccccgctgcc gccgccaccg ctgccaccgc ctccggtaat    3420
ctccagctta gttcccccac cgaatgtgta cgggagcgtg ttgccctgct gacagaagta    3480
ggtggcgatg tcctcctgct caaggttact gattgtcagg ctgtagtccg taccggaacc    3540
ggaacccgaa atcggctag gaacgcctga gtgtaatctc gacgtgtggt aaatgagcaa     3600
cttaactgtt ccgtccggct tctgctgata ccagtttaag tattttgaga tgtcctggct    3660
ggcccggcaa gatattgtta ctcggtcgcc taaagaagca gatagggaag aggtagtctg    3720
agtcatctgt atgtcaggac gagccgcgtg caataataac gccagaggta aaagtaaggc    3780
tgtcactggg agcgccatgg tggctttccg gaacaaacaa gaaccgcgac ccaaatcccg    3840
gctgcgacgg aactagctgt gccacacccg gcgcgtcctt atataatcat cggcgttcac    3900
cgcccattct ccgcccagcc ataaaaggca actttcggaa cggcgcacgc tgattggctc    3960
cgccctaact ccgcccacta gtgcggccgc cccttcacc gagggcctat ttcccatgat     4020
tccttcatat ttgcatatac gatacaaggc tgttagagag ataattggaa ttaatttgac    4080
```

```
tgtaaacaca aagatattag tacaaaatac gtgacgtaga aagtaataat ttcttgggta    4140
gtttgcagtt ttaaaattat gttttaaaat ggactatcat atgcttaccg taacttgaaa    4200
gtatttcgat ttcttggctt tatatatctt gtggaaagga cgaaacaccg tgtaccgga     4260 ggtttgaaga tgccgcattt ctcgagaaat gcggcatctt caaaccttttt tttgaattct   4320 cgacctaggg acaaatggca gtattcatcc acaattttaa agaaaaggg gggattgggg     4380 ggtacagtgc aggggaaaga atagtagaca taatagcaac agacatacaa actaaagaat   4440
tacaaaaaca aattacaaaa attcaaaatt tcgggttta ttacagggac agcagagatc     4500
cactttggcc gcggatccgc aacaaatctg actttgcatg tgcaaacgcc ttcaacaaca   4560
gcattattcc agaagacacc ttcttcccca gcccaggtaa gggcagcttt ggtgccttcg   4620
caggctgttt ccttgcttca ggaatggcca ggttctgccc agagctctgg tcaatgatgt   4680
ctaaaactcc tctgattggt ggtctcggcc ttatccattg ccaccaaaac cctcttttta   4740
ctaagaaaca gtgagccttg ttctggcagt ccagagaatg acgggaaa aaagcagatg     4800 aagagaaggt ggcaggagag ggcacgtggc ccagcctcag tctctccaac tgagttcctg   4860
cctgcctgcc tttgctcaga ctgtttgccc cttactgctc ttctaggcct cattctaagc   4920
cccttctcca agttgcctct ccttatttct ccctgtctgc caaaaaatct ttcccagctc   4980
actaagtcag tctcacgcag tcactcatta acccaccaat cactgattgt gccggcacat   5040
gaatgcacca ggtgttgaag tggaggaatt aaaaagtcag atgaggggtg tgcccagagg   5100
aagcaccatt ctagttgggg gagcccatct gtcagctggg aaaagtccaa ataacttcag   5160
attggaatgt gttttaactc agggttgaga aaacagccac cttcaggaca aaagtcaggg   5220
aagggctctc tgaagaaatg ctacttgaag ataccagccc taccaagggc agggagagga   5280
ccaattgatg gagttggcca ctccctctct gcgcgctcgc tcgctcactg aggccgcccg   5340
ggcaaagccc gggcgtcggg cgacctttgg tcgcccggcc tcagtgagcg agcgagcgcg   5400
cagagaggga gtggccaacg gcgcgcctgc aggtctcaaa aatagctacc ctctccggca   5460
tgaatttatc agctagaacg gttgaatatc atattgatgg tgatttgact gtctccggcc   5520
tttctcaccc gtttgaatct ttacctacac attactcagg cattgcattt aaaatatatg   5580
agggttctaa aaatttttat ccttgcgttg aaataaaggc ttctcccgca aaagtattac   5640
agggtcataa tgttttggt acaaccgatt tagcttatg ctctgaggct ttattgctta     5700
attttgctaa ttcttgcct tgcctgtatg atttattgga tgttggaatt cctgatgcgg    5760 tatttctcc ttacgcatct gtgcggtatt tcacaccgca tatggtgcac tctcagtaca    5820
atctgctctg atgccgcata gttaagccag ccccgacacc cgccaacacc cgctgacgcg   5880
ccctgacggg cttgtctgct cccggcatcc gcttacagac aagctgtgac cgtctccggg   5940
agctgcatgt gtcagaggtt ttcaccgtca tcaccgaaac gcgcgagacg aaagggcctc   6000
gtgatacgcc tatttttata ggttaatgtc atgataataa tggtttctta gacgtcaggt   6060 ggcactttt ggggaaatgt gcgcggaacc cctatttgtt tatttttcta aatacattca    6120
aatatgtatc cgctcatgag acaataaccc tgataaatgc ttcaataata ttgaaaaagg   6180
aagagtatga gtattcaaca tttccgtgtc gcccttattc ccttttttgc ggcatttttgc  6240 cttcctgttt ttgctcaccc agaaacgctg gtgaaagtaa aagatgctga agatcagttg   6300
ggtgcacgag tgggttacat cgaactggat ctcaacagcg gtaagatcct tgagagtttt   6360
cgccccgaag aacgttttcc aatgatgagc acttttaaag ttctgctatg tggcgcggta   6420
ttatcccgta ttgacgccgg gcaagagcaa ctcggtcgcc gcatacacta ttctcagaat   6480
```

```
gacttggttg agtactcacc agtcacagaa aagcatctta cggatggcat gacagtaaga      6540
gaattatgca gtgctgccat aaccatgagt gataacactg cggccaactt acttctgaca      6600
acgatcggag gaccgaagga gctaaccgct tttttgcaca acatggggga tcatgtaact      6660
cgccttgatc gttgggaacc ggagctgaat gaagccatac caaacgacga gcgtgacacc      6720
acgatgcctg tagcaatggc aacaacgttg cgcaaactat taactggcga actacttact      6780
ctagcttccc ggcaacaatt aatagactgg atggaggcgg ataaagttgc aggaccactt      6840
ctgcgctcgg cccttccggc tggctggttt attgctgata atctggagcc ggtgagcgt       6900 gggtctcgcg gtatcattgc agcactgggg ccagatggta gccctcccg tatcgtagtt       6960 atctacacga cggggagtca ggcaactatg gatgaacgaa atagacagat cgctgagata      7020
ggtgcctcac tgattaagca ttggtaactg tcagaccaag tttactcata tactttag        7080 attgatttaa aacttcattt ttaatttaaa aggatctagg tgaagatcct ttttgataat      7140
ctcatgacca aaatccctta acgtgagttt cgttccact gagcgtcaga ccccgtagaa       7200
aagatcaaag gatcttcttg agatcctttt tttctgcgcg taatctgctg cttgcaaaca      7260
aaaaaaccac cgctaccagc ggtggttttgt ttgccggatc aagagctacc aactctttttt   7320 ccgaaggtaa ctggcttcag cagagcgcag ataccaaata ctgtccttct agtgtagccg     7380
tagttaggcc accacttcaa gaactctgta gcaccgccta catacctcgc tctgctaatc      7440
ctgttaccag tggctgctgc cagtggcgat aagtcgtgtc ttaccgggtt ggactcaaga      7500
cgatagttac cggataaggc gcagcggtcg ggctgaacgg ggggttcgtg cacacagccc      7560
agcttggagc gaacgaccta caccgaactg agatacctac agcgtgagct atgagaaagc      7620
gccacgcttc ccgaagggag aaaggcggac aggtatccgg taagcggcag gtcggaaca      7680 ggagagcgca cgagggagct ccagggga aacgcctggt atctttatag tcctgtcggg       7740
tttcgccacc tctgacttga gcgtcgattt ttgtgatgct cgtcagggg gcggagccta      7800 tggaaaaacg ccagcaacgc ggcctttta cggttcctgg ccttttgctg gccttttgct      7860
cacatgttct ttcctgcgtt atcccctgat tctgtggata accgtattac cgcctttgag     7920
tgagctgata ccgctcgccg cagccgaacg accgagcgca gcgagtcagt gagcgaggaa     7980
gcggaagagc gcccaatacg caaaccgcct ctccccgcgc gttggccgat tcattaatg      8039
```

<210> SEQ ID NO 22
<211> LENGTH: 8098
<212> TYPE: DNA
<213> ORGANISM: Artificial Sequence
<220> FEATURE:
<223> OTHER INFORMATION: Synthesized

<400> SEQUENCE: 22

```
cagcagctgg cgtaatagcg aagaggcccg caccgatcgc ccttcccaac agttgcgcag       60
cctgaatggc gaatgaatt ccagacgatt gagcgtcaaa atgtaggtat ttccatgagc       120 gttttcctg ttgcaatggc tggcggtaat attgttctgg atattaccag caaggccgat       180
agtttgagtt cttctactca ggcaagtgat gttattacta atcaaagaag tattgcgaca      240
acggttaatt tgcgtgatgg acagactctt ttactcggtg gcctcactga ttataaaaac      300
acttctcagg attctggcgt accgttcctg tctaaaatcc ctttaatcgg cctcctgtttt     360 agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
```

```
cgctacacytt gccagcgccc tagcgcccgc tcctttcgct ttcttcccct cctttctcgc    540
cacgttcgcc ggctttcccc gtcaagctct aaatcggggg ctcccttag ggttccgatt      600 tagtgcttta cggcacctcg accccaaaaa acttgattag ggtgatggtt cacgtagtgg     660
gccatcgccc tgatagacgg ttttcgccc tttgacgttg gagtccacgt tctttaatag      720
tggactcttg ttccaaactg aacaacact caaccctatc tcggtctatt cttttgattt      780
ataagggatt ttgccgattt cggcctattg gttaaaaaat gagctgattt aacaaaaatt     840
taacgcgaat tttaacaaaa tattaacgtt tacaatttaa atatttgctt atacaatctt     900 cctgttttg gggcttttct gattatcaac cggggtacat atgattgaca tgctagtttt      960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtgccaact  ccatcactag gggttcctac gcgtagatct catattctgg    1140
cagggtcagt ggctccaact aacatttgtt tggtacttta cagtttatta aatagatgtt    1200
tatatggaga agctctcatt tctttctcag aagagcctgg ctaggaaggt ggatgaggca    1260
ccatattcat tttgcaggtg aaattcctga gatgtaagga gctgctgtga cttgctcaag    1320
gccttatatc gagtaaacgg tagcgctggg gcttagacgc aggtgttctg atttatagtt    1380
caaaacctct atcaatgaga gagcaatctc ctggtaatgt gatagatttc ccaacttaat    1440
gccaacatac cataaaccct ccattctgct aatgcccagc ctaagttggg gagaccactc    1500
cagattccaa gatgtacagt ttgctttgct gggccttttt cccatgcctg cctttactct    1560
gccagagtta tattgctggg gttttgaaga agatcctatt aaataaaga ataagcagta    1620 ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttggggcaa agagggaaat gagatcatgt cctaaccctg atcctcttgt cccacagata    1920
tccagaaccc tgaccctgcc gtgtaccagc tgagagactc taaatccagt gacagtctg    1980 tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgatccagac atgataagat acattgatga gtttggacaa    2160
accacaacta gaatgcagtg aaaaaaatgc tttatttgtg aaatttgtga tgctattgct    2220
ttatttgtaa ccattataag ctgcaataaa caagttaaca acaacaattg cattcatttt    2280
atgtttcagg ttcaggggga ggtgtgggag gttttttaaa gcaagtaaac tggtacctca    2340
tcgaggtggt aaggcttgca tgtgcagcgc gtcgtatgtg tccttggtcg cggtggaaag    2400 ccctggtat aagccgtcgt gtcccttttcc gcgacgtctc tcgcccttca taccaatctc     2460
cgagtacgcc tcagccatct tgtccttctg gagttcgttg tacaggccct cctgggggtt    2520
ctttctccga ggcttgcctc ccatctccgg gtccctacct ctacgcttgt ctaacacgtc    2580
gtactcctcc cggcgcccca ggtttaactc gttgtatagc tggttctgac cctgctggta    2640
agcgggtgcg tccgcggagc gagagaactt cactctcagt tcgcagctgc cttcttcttc    2700
gctcggcgcg cggcagctgc tcgcatcttc ttcctgcgcg ctgctcgccg ggctcgcaaa    2760 cgggcttta gccgccgccg ccgcttttt gcggctcgct ttgcagtaga gcgttattac    2820
caagctcaac aacaacactc cgcaagtccc ggctagtggt gcccagatgt agatgtcgca    2880
```

```
ggcgaagtct agtcctcgcg tgtgaacggc ccgcccgcc gcgggcctgc aagcctcagg     2940
gcgaagagat aagggctgac ttgctatcgt tggagctggc gtgggggac gtggggctgg     3000 ggtagtagtg ggcttcgctg gggatacatt tgtagaaaca tttgaaaatg ttccctgggt    3060
aggtaactcg ctggatacgg tcacagaagt gccctgaccc cagtagtcca ttgcgtaact    3120
cccgccgtag tagtagtgct tcgcgcagta gtaaatagcg gtgtcgtcag tctggagaga   3180
gttcatcttt aagaaaacct gcgacttact gttgtcctta atgatggtga ggcggctctt    3240
gagagctgag ttgtagtatg tggtttcact tccccagata accccagcc actctaagcc     3300 cttttctaggc ggctgtcgta tccatgatac cccgtagtct gggagactga ctccagacac   3360
agtgcacgtg actgagaggc tctggctagg tgcgaccaag cccggtccgc tctcctgtaa    3420
cttgacctcc gagccgccac cccgctgcc gccgccaccg ctgccaccgc ctccggtaat     3480
ctccagctta gttcccccac cgaatgtgta cgggagcgtg ttgccctgct gacagaagta    3540
ggtggcgatg tcctcctgct caaggttact gattgtcagg ctgtagtccg taccggaacc    3600 ggaaccccgaa atcggctag gaacgcctga gtgtaatctc gacgtgtggt aaatgagcaa    3660
cttaactgtt ccgtccggct tctgctgata ccagtttaag tattttgaga tgtcctggct    3720
ggcccggcaa gatattgtta ctcggtcgcc taaagaagca gatagggaag aggtagtctg    3780
agtcatctgt atgtcaggac gagccgcgtg caataataac gccagaggta aaagtaaggc    3840
tgtcactggg agcgccatgg tggctttccg gaacaaacaa gaaccgcgac ccaaatcccg    3900
gctgcgacgg aactagctgt gccacacccg gcgcgtcctt atataatcat cggcgttcac    3960
cgcccattct ccgcccagcc ataaaaggca actttcggaa cggcgcacgc tgattggctc    4020
cgccctaact ccgcccacta gtgcggccgc gcggccaaag tggatctctg ctgtccctgt    4080
aataaacccg aaaatttga attttgtaa tttgtttttg taattcttta gtttgtatgt       4140
ctgttgctat tatgtctact attctttccc ctgcactgta cccccaatc ccccttttc      4200 tttttaaaatt gtggatgaat actgccattt gtccctaggt cgagaattca aaaaaggtt    4260 tgaagatgcc gcatttctcg agaaatgcgg catcttcaaa cctccggtac accggtgttt    4320
cgtcctttcc acaagatata aaagccaag aaatcgaaat actttcaagt tacggtaagc     4380
atatgatagt ccatttaaa acataatttt aaaactgcaa actacccaag aaattattac    4440
tttctacgtc acgtattttg tactaatatc tttgtgttta cagtcaaatt aattccaatt    4500
atctctctaa cagccttgta tcgtatatgc aaatatgaag gaatcatggg aaataggccc    4560
tcggtgaagg gggatccgca acaaatctga ctttgcatgt gcaaacgcct tcaacaacag    4620
cattattcca gaagacacct tcttccccag cccaggtaag ggcagctttg gtgccttcgc    4680
aggctgtttc cttgcttcag gaatggccag gttctgccca gagctctggt caatgatgtc    4740
taaaactcct ctgattggtg gtctcggcct tatccattgc caccaaaacc ctcttttttac   4800 taagaaacag tgagccttgt tctggcagtc cagagaatga cacggaaaaa aagcagatga   4860
agagaaggtg gcaggagagg gcacgtggcc cagcctcagt ctctccaact gagttcctgc    4920
ctgcctgcct ttgctcagac tgtttgcccc ttactgctct tctaggcctc attctaagcc    4980
ccttctccaa gttgcctctc cttatttctc cctgtctgcc aaaaaatctt tcccagctca    5040
ctaagtcagt ctcacgcagt cactcattaa cccaccaatc actgattgtg ccggcacatg    5100
aatgcaccag gtgttgaagt ggaggaatta aaaagtcaga tgagggtgt gcccagagga    5160 agcaccattc tagttggggg agcccatctg tcagctggga aaagtccaaa taacttcaga   5220
```

```
ttggaatgtg ttttaactca gggttgagaa aacagccacc ttcaggacaa aagtcaggga    5280
agggctctct gaagaaatgc tacttgaaga taccagccct accaagggca gggagaggac    5340
caattgatgg agttggccac tccctctctg cgcgctcgct cgctcactga ggccgcccgg    5400
gcaaagcccg ggcgtcgggc gacctttggt cgcccggcct cagtgagcga gcgagcgcgc    5460
agagagggag tggccaacgg cgcgcctgca ggtctcaaaa atagctaccc tctccggcat    5520
gaatttatca gctagaacgg ttgaatatca tattgatggt gatttgactg tctccggcct    5580
ttctcacccg tttgaatctt tacctacaca ttactcaggc attgcattta aaatatatga    5640
gggttctaaa aatttttatc cttgcgttga aataaaggct tctcccgcaa aagtattaca    5700
gggtcataat gttttttggta caaccgattt agctttatgc tctgaggctt tattgcttaa    5760
ttttgctaat tctttgcctt gcctgtatga tttattggat gttggaattc ctgatgcggt    5820 atttctcct tacgcatctg tgcggtattt cacaccgcat atggtgcact ctcagtacaa    5880
tctgctctga tgccgcatag ttaagccagc cccgacaccc gccaacaccc gctgacgcgc    5940
cctgacgggc ttgtctgctc ccggcatccg cttacagaca agctgtgacc gtctccggga    6000
gctgcatgtg tcagaggttt tcaccgtcat caccgaaacg cgcgagacga aagggcctcg    6060
tgatacgcct atttttatag gttaatgtca tgataataat ggtttcttag acgtcaggtg    6120
gcacttttcg gggaaatgtg cgcggaaccc ctatttgttt attttctaa atacattcaa     6180 atatgtatcc gctcatgaga caataaccct gataaatgct tcaataatat tgaaaaagga    6240
agagtatgag tattcaacat ttccgtgtcg cccttattcc cttttttgcg gcattttgcc    6300
ttcctgtttt tgctcaccca gaaacgctgg tgaaagtaaa agatgctgaa gatcagttgg    6360
gtgcacgagt gggttacatc gaactggatc tcaacagcgg taagatcctt gagagttttc    6420
gccccgaaga acgttttcca atgatgagca cttttaaagt tctgctatgt ggcgcggtat    6480
tatcccgtat tgacgccggg caagagcaac tcggtcgccg catacactat tctcagaatg    6540
acttggttga gtactcacca gtcacagaaa agcatcttac ggatggcatg acagtaagag    6600
aattatgcag tgctgccata accatgagtg ataacactgc ggccaactta cttctgacaa    6660
cgatcggagg accgaaggag ctaaccgctt ttttgcacaa catgggggat catgtaactc    6720
gccttgatcg ttgggaaccg gagctgaatg aagccatacc aaacgacgag cgtgacacca    6780
cgatgcctgt agcaatggca acaacgttgc gcaaactatt aactggcgaa ctacttactc    6840
tagcttcccg gcaacaatta atagactgga tggaggcgga taaagttgca ggaccacttc    6900
tgcgctcggc ccttccggct ggctggttta ttgctgataa atctggagcc ggtgagcgtg    6960
ggtctcgcgg tatcattgca gcactggggc cagatggtaa gccctcccgt atcgtagtta    7020
tctacacgac ggggagtcag gcaactatgg atgaacgaaa tagacagatc gctgagatag    7080
gtgcctcact gattaagcat tggtaactgt cagaccaagt ttactcatat atactttaga    7140
ttgatttaaa acttcatttt taatttaaaa ggatctaggt gaagatcctt tttgataatc    7200
tcatgaccaa aatcccttaa cgtgagtttt cgttccactg agcgtcagac cccgtagaaa    7260
agatcaaagg atcttcttga gatccttttt ttctgcgcgt aatctgctgc ttgcaaacaa    7320
aaaaaccacc gctaccagcg gtggtttgtt tgccggatca agagctacca actctttttc    7380
cgaaggtaac tggcttcagc agagcgcaga taccaaatac tgtccttcta gtgtagccgt    7440
agttaggcca ccacttcaag aactctgtag caccgcctac atacctcgct ctgctaatcc    7500
tgttaccagt ggctgctgcc agtggcgata agtcgtgtct taccgggttg gactcaagac    7560
gatagttacc ggataaggcg cagcggtcgg gctgaacggg gggttcgtgc acacagccca    7620
```

-continued

```
gcttggagcg aacgacctac accgaactga gatacctaca gcgtgagcta tgagaaagcg      7680
ccacgcttcc cgaagggaga aaggcggaca ggtatccggt aagcggcagg gtcggaacag      7740
gagagcgcac gagggagctt ccaggggaa acgcctggta tctttatagt cctgtcgggt       7800
ttcgccacct ctgacttgag cgtcgatttt tgtgatgctc gtcagggggg cggagcctat      7860
ggaaaaacgc cagcaacgcg gcctttttac ggttcctggc cttttgctgg ccttttgctc      7920
acatgttctt tcctgcgtta tcccctgatt ctgtggataa ccgtattacc gcctttgagt      7980
gagctgatac cgctcgccgc agccgaacga ccgagcgcag cgagtcagtg agcgaggaag      8040
cggaagagcg cccaatacgc aaaccgcctc tccccgcgcg ttggccgatt cattaatg        8098
```

<210> SEQ ID NO 23
<211> LENGTH: 8038
<212> TYPE: DNA
<213> ORGANISM: Artificial Sequence
<220> FEATURE:
<223> OTHER INFORMATION: Synthesized

<400> SEQUENCE: 23

```
cagcagctgg cgtaatagcg aagaggcccg caccgatcgc ccttcccaac agttgcgcag        60
cctgaatggc gaatggaatt ccagacgatt gagcgtcaaa atgtaggtat ttccatgagc       120
gttttttcctg ttgcaatggc tggcggtaat attgttctgg atattaccag caaggccgat      180
agtttgagtt cttctactca ggcaagtgat gttattacta atcaaagaag tattgcgaca      240
acggttaatt tgcgtgatgg acagactctt ttactcggtg gcctcactga ttataaaaac      300
acttctcagg attctggcgt accgttcctg tctaaaatcc ctttaatcgg cctcctgttt      360
agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
cgctacactt gccagcgccc tagcgcccgc tcctttcgct ttcttccctt cctttctcgc      540
cacgttcgcc ggctttcccc gtcaagctct aaatcggggg ctcccttag ggttccgatt       600
tagtgcttta cggcacctcg accccaaaaa acttgattag ggtgatggtt cacgtagtgg      660
gccatcgccc tgatagacgg ttttcgccc tttgacgttg gagtccacgt tctttaatag       720
tggactcttg ttccaaactg gaacaacact caaccctatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900
cctgtttttg ggcttttct gattatcaac cggggtacat atgattgaca tgctagtttt      960
acggcgcgcc gggttggcca ctccctctct gcgcgctcgc tcgctcactg aggccgggcg     1020
accaaaggtc gcccgacgcc cgggctttgc ccgggcggcc tcagtgagcg agcgagcgcg     1080
cagagaggga gtggccaact ccatcactag gggttcctac gcgtagatct catattctgg     1140
cagggtcagt ggctccaact aacatttgtt tggtacttta cagtttatta aatagatgtt     1200
tatatggaga agctctcatt tctttctcag aagagcctgg ctaggaaggt ggatgaggca     1260
ccatattcat tttgcaggtg aaattcctga gatgtaagga gctgctgtga cttgctcaag     1320
gccttatatc gagtaaacgg tagcgctggg gcttagacga aggtgttctg atttatagtt     1380
caaaacctct atcaatgaga gagcaatctc ctggtaatgt gatagatttc caacttaat      1440
gccaacatac cataaacctc ccattctgct aatgccagc ctaagttggg gagaccactc       1500
cagattccaa gatgtacagt ttgctttgct gggcctttt cccatgcctg cctttactct       1560
```

```
gccagagtta tattgctggg gttttgaaga agatcctatt aaataaaaga ataagcagta    1620
ttattaagta gccctgcatt tcaggtttcc ttgagtggca ggccaggcct ggccgtgaac    1680
gttcactgaa atcatggcct cttggccaag attgatagct tgtgcctgtc cctgagtccc    1740
agtccatcac gagcagctgg tttctaagat gctatttccc gtataaagca tgagaccgtg    1800
acttgccagc cccacagagc cccgcccttg tccatcactg gcatctggac tccagcctgg    1860
gttgggcaa agagggaaat gagatcatgt cctaaccctg atcctcttgt cccacagata    1920
tccagaaccc tgaccctgcc gtgtaccagc tgagagactc taaatccagt gacaagtctg    1980
tctgcctatt caccgatttt gattctcaaa caaatgtgtc acaaagtaag gattctgatg    2040
tgtatatcac agacaaaact gtgctagaca tgaggtctat ggacttcaag agcaacagtg    2100
ctgtggcctg gagcaactag tgatccagac atgataagat acattgatga gtttggacaa    2160
accacaacta gaatgcagtg aaaaaaatgc tttatttgtg aaatttgtga tgctattgct    2220
ttatttgtaa ccattataag ctgcaataaa caagttaaca acaacaattg cattcatttt    2280
atgtttcagg ttcaggggga ggtgtgggag gttttttaaa gcaagtaaac tggtacctca    2340
tcgaggtggt aaggcttgca tgtgcagcgc gtcgtatgtg tccttggtcg cggtggaaag    2400
cccctggtat aagccgtcgt gtccctttcc gcgacgtctc tcgcccttca taccaatctc    2460
cgagtacgcc tcagccatct tgtccttctg gagttcgttg tacaggccct cctgggggtt    2520
cttttctccga ggcttgcctc ccatctccgg gtccctacct ctacgcttgt ctaacacgtc    2580
gtactcctcc cggcgcccca ggtttaactc gttgtatagc tggttctgac cctgctggta    2640
agcgggtgcg tccgcggagc gagagaactt cactctcagt tcgcagctgc cttcttcttc    2700
gctcggcgcg cggcagctgc tcgcatcttc ttcctgcgcg ctgctcgccg ggctcgcaaa    2760
cgggcttttc gccgccgccg ccgcttttt gcggctcgct ttgcagtaga gcgttattac    2820
caagctcaac aacaacactc cgcaagtccc ggctagtggt gcccagatgt agatgtcgca    2880
ggcgaagtct agtcctcgcg tgtgaacggc gccgccgcc gcgggcctgc aagcctcagg    2940
gcgaagagat aagggctgac ttgctatcgt tggagctggc gtgggggac gtgggctgg    3000
ggtagtagtg ctggatacgg tcacagaagt gccctgaccc cagtagtcca ttgcgtaact    3060
cccgccgtag tagtagtgct tcgcgcagta gtaaatagcg gtgtcgtcag tctggagaga    3120
gttcatcttt aagaaaacct gcgacttact gttgtcctta atgatggtga ggcggctctt    3180
gagagctgag ttgtagtatg tggtttcact tcccagata acccccagcc actctaagcc    3240
ctttctaggc ggctgtcgta tccatgatac cccgtagtct gggagactga ctccagacac    3300
agtgcacgtg actgagaggc tctggctagg tgcgaccaag cccggtccgc tctcctgtaa    3360
cttgacctcc gagccgccac cccgctgccg ccgccaccg ctgccaccgc tccggtaat    3420
ctccagctta gttcccccac cgaatgtgta cgggagcgtg ttgccctgct gacagaagta    3480
ggtggcgatg tcctcctgct caaggttact gattgtcagg ctgtagtccg taccggaacc    3540
ggaacccgaa atcggctag gaacgcctga gtgtaatctc gacgtgtggt aaatgagcaa    3600
cttaactgtt ccgtccggct tctgctgata ccagtttaag tattttgaga tgtcctggct    3660
ggccggcaa gatattgtta ctcggtcgcc taaagaagca gatagggaag aggtagtctg    3720
agtcatctgt atgtcaggac gagccgcgtg caataataac gccagaggta aaagtaaggc    3780
tgtcactggg agcgccatgg tggctttccg gaacaaacaa gaaccgcgac ccaaatcccg    3840
gctgcgacgg aactagctgt gccacacccg gcgcgtcctt atataatcat cggcgttcac    3900
cgcccattct ccgcccagcc ataaaaggca actttcggaa cggcgcacgc tgattggctc    3960
```

```
cgccctaact ccgcccacta gtgcggccgc gcggccaaag tggatctctg ctgtccctgt    4020
aataaacccg aaaattttga attttttgtaa tttgtttttg taattcttta gtttgtatgt    4080
ctgttgctat tatgtctact attctttccc ctgcactgta cccccaatc cccccttttc    4140 ttttaaaatt gtggatgaat actgccattt gtccctaggt cgagaattca aaaaaggtt    4200 tgaagatgcc gcattctctcg agaaatgcgg catcttcaaa cctccggtac accggtgttt    4260
cgtcctttcc acaagatata aaagccaag aaatcgaaat actttcaagt tacggtaagc    4320
atatgatagt ccattttaaa acataatttt aaaactgcaa actacccaag aaattattac    4380
tttctacgtc acgtattttg tactaatatc tttgtgttta cagtcaaatt aattccaatt    4440
atctctctaa cagccttgta tcgtatatgc aaatatgaag gaatcatggg aaataggccc    4500
tcggtgaagg gggatccgca acaaatctga ctttgcatgt gcaaacgcct tcaacaacag    4560
cattattcca gaagacacct tcttccccag cccaggtaag ggcagctttg gtgccttcgc    4620
aggctgtttc cttgcttcag gaatggccag gttctgccca gagctctggt caatgatgtc    4680
taaaactcct ctgattggtg gtctcggcct tatccattgc caccaaaacc ctctttttac    4740
taagaaacag tgagccttgt tctggcagtc cagagaatga cacggaaaaa agcagatga    4800 agagaaggtg gcaggagagg gcacgtggcc cagcctcagt ctctccaact gagttcctgc    4860
ctgcctgcct ttgctcagac tgtttgcccc ttactgctct tctaggcctc attctaagcc    4920
ccttctccaa gttgcctctc cttatttctc cctgtctgcc aaaaaatctt tcccagctca    4980
ctaagtcagt ctcacgcagt cactcattaa cccaccaatc actgattgtg ccggcacatg    5040
aatgcaccag gtgttgaagt ggaggaatta aaaagtcaga tgaggggtgt gcccagagga    5100
agcaccattc tagttggggg agcccatctg tcagctggga aaagtccaaa taacttcaga    5160
ttggaatgtg ttttaactca gggttgagaa aacagccacc ttcaggacaa aagtcaggga    5220
agggctctct gaagaaatgc tacttgaaga taccagccct accaagggca gggagaggac    5280
caattgatgg agttggccac tccctctctg cgcgctcgct cgctcactga ggccgcccgg    5340
gcaaagcccg ggcgtcgggc gacctttggt cgcccggcct cagtgagcga gcgagcgcgc    5400
agagagggag tggccaacgg cgcgcctgca ggtctcaaaa atagctaccc tctccggcat    5460
gaatttatca gctagaacgg ttgaatatca tattgatggt gatttgactg tctccggcct    5520
ttctcacccg tttgaatctt tacctacaca ttactcaggc attgcattta aaatatga    5580 gggttctaaa aattttatc cttgcgttga aataaggct tctcccgcaa agtattaca    5640 gggtcataat gttttggta caaccgattt agctttatgc tctgaggctt tattgcttaa    5700
ttttgctaat tctttgcctt gcctgtatga tttattggat gttggaattc ctgatgcggt    5760
attttctcct tacgcatctg tgcggtattt cacaccgcat atggtgcact ctcagtacaa    5820
tctgctctga tgccgcatag ttaagccagc cccgacaccc gccaacaccc gctgacgcgc    5880
cctgacgggc ttgtctgctc ccggcatccg cttacagaca agctgtgacc gtctccggga    5940
gctgcatgtg tcagaggttt tcaccgtcat caccgaaacg cgcgagacga agggcctcg    6000 tgatacgcct atttttatag gttaatgtca tgataataat ggtttcttag acgtcaggtg    6060
gcacttttcg gggaaatgtg cgcggaaccc ctatttgttt attttctaa atacattcaa    6120 atatgtatcc gctcatgaga caataaccct gataaatgct tcaataatat tgaaaagga    6180 agagtatgag tattcaacat ttccgtgtcg cccttattcc cttttttgcg gcattttgcc    6240
ttcctgtttt tgctcaccca gaaacgctgg tgaaagtaaa agatgctgaa gatcagttgg    6300
```

```
gtgcacgagt gggttacatc gaactggatc tcaacagcgg taagatcctt gagagttttc    6360
gccccgaaga acgttttcca atgatgagca cttttaaagt tctgctatgt ggcgcggtat    6420
tatcccgtat tgacgccggg caagagcaac tcggtcgccg catacactat tctcagaatg    6480
acttggttga gtactcacca gtcacagaaa agcatcttac ggatggcatg acagtaagag    6540
aattatgcag tgctgccata accatgagtg ataacactgc ggccaactta cttctgacaa    6600
cgatcggagg accgaaggag ctaaccgctt ttttgcacaa catggggat catgtaactc      6660 gccttgatcg ttgggaaccg gagctgaatg aagccatacc aaacgacgag cgtgacacca    6720
cgatgcctgt agcaatggca acaacgttgc gcaaactatt aactggcgaa ctacttactc    6780
tagcttcccg gcaacaatta atagactgga tggaggcgga taaagttgca ggaccacttc    6840
tgcgctcggc ccttccggct ggctggttta ttgctgataa atctggagcc ggtgagcgtg    6900
ggtctcgcgg tatcattgca gcactggggc cagatggtaa gccctcccgt atcgtagtta    6960
tctacacgac ggggagtcag gcaactatgg atgaacgaaa tagacagatc gctgagatag    7020
gtgcctcact gattaagcat tggtaactgt cagaccaagt ttactcatat atactttaga    7080
ttgatttaaa acttcatttt taatttaaaa ggatctaggt gaagatcctt tttgataatc    7140
tcatgaccaa aatcccttaa cgtgagtttt cgttccactg agcgtcagac cccgtagaaa    7200
agatcaaagg atcttcttga gatccttttt ttctgcgcgt aatctgctgc ttgcaaacaa    7260
aaaaaccacc gctaccagcg gtggtttgtt tgccggatca agagctacca actcttttc     7320 cgaaggtaac tggcttcagc agagcgcaga taccaaatac tgtccttcta gtgtagccgt    7380
agttaggcca ccacttcaag aactctgtag caccgcctac atacctcgct ctgctaatcc    7440
tgttaccagt ggctgctgcc agtggcgata gtcgtgtct taccgggttg gactcaagac     7500
gatagttacc ggataaggcg cagcggtcgg gctgaacggg gggttcgtgc acacagccca    7560
gcttggagcg aacgacctac accgaactga gatacctaca gcgtgagcta tgagaaagcg    7620
ccacgcttcc cgaagggaga aaggcggaca ggtatccgt aagcggcagg gtcggaacag     7680
gagagcgcac gagggagctt ccaggggga acgcctggta tctttatagt cctgtcgggt     7740
ttcgccacct ctgacttgag cgtcgatttt tgtgatgctc gtcaggggg cggagcctat     7800 ggaaaaacgc cagcaacgcg gcctttttac ggttcctggc cttttgctgg ccttttgctc    7860
acatgttctt tcctgcgtta tcccctgatt ctgtggataa ccgtattacc gcctttgagt    7920
gagctgatac cgctcgccgc agccgaacga ccgagcgcag cgagtcagtg agcgaggaag    7980
cggaagagcg cccaatacgc aaaccgcctc tccccgcgcg ttggccgatt cattaatg      8038
```

<210> SEQ ID NO 24
<211> LENGTH: 8626
<212> TYPE: DNA
<213> ORGANISM: Artificial Sequence
<220> FEATURE:
<223> OTHER INFORMATION: Synthesized

<400> SEQUENCE: 24

```
cagcagctgg cgtaatagcg aagaggcccg caccgatcgc ccttcccaac agttgcgcag       60
cctgaatggc gaatggaatt ccagacgatt gagcgtcaaa atgtaggtat ttccatgagc      120 gttttcctg ttgcaatggc tggcggtaat attgttctgg atattaccag caaggccgat       180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt    360
```

```
agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
cgctacactt gccagcgccc tagcgcccgc tcctttcgct ttcttcccct cctttctcgc      540
cacgttcgcc ggctttcccc gtcaagctct aaatcggggg ctccctttag ggttccgatt      600
tagtgcttta cggcaccctcg accccaaaaa acttgattag ggtgatggtt cacgtagtgg      660
gccatcgccc tgatagacgg ttttcgccc tttgacgttg gagtccacgt tctttaatag      720
tggactcttg ttccaaactg aacaacact caaccctatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900 cctgttttg gggcttttct gattatcaac cggggtacat atgattgaca tgctagtttt      960
acggcgcgcc gggttggcca ctccctctct gcgcgctcgc tcgctcactg aggccgggcg     1020
accaaaggtc gcccgacgcc cgggctttgc ccgggcggcc tcagtgagcg agcgagcgcg     1080
cagagaggga gtgccaact ccatcactag gggttcctac gcgtagatct catattctgg     1140
cagggtcagt ggctccaact aacatttgtt tggtacttta cagtttatta aatagatgtt     1200
tatatggaga agctctcatt tctttctcag aagagcctgg ctaggaaggt ggatgaggca     1260
ccatattcat tttgcaggtg aaattcctga gatgtaagga gctgctgtga cttgctcaag     1320
gccttatatc gagtaaacgg tagcgctggg gcttagacgc aggtgttctg atttatagtt     1380
caaaacctct atcaatgaga gagcaatctc ctggtaatgt gatagatttc ccaacttaat     1440
gccaacatac cataaacctc ccattctgct aatgcccagc ctaagttggg gagaccactc     1500
cagattccaa gatgtacagt ttgctttgct gggcctttt cccatgcctg cctttactct     1560
gccagagtta tattgctggg gttttgaaga agatcctatt aaataaaaga ataagcagta     1620
ttattaagta gccctgcatt tcaggtttcc ttgagtggca ggccaggcct ggccgtgaac     1680
gttcactgaa atcatggcct cttggccaag attgatagct tgtgcctgtc cctgagtccc     1740
agtccatcac gagcagctgg tttctaagat gctatttccc gtataaagca tgagaccgtg     1800
acttgccagc cccacagagc cccgcccttg tccatcactg gcatctggac tccagcctgg     1860 gttgggcaa agaggaaat gagatcatgt cctaaccctg atcctcttgt cccacagata     1920
tccagaaccc tgaccctgcc gtgtaccagc tgagagactc taaatccagt gacaagtctg     1980
tctgcctatt caccgatttt gattctcaaa caaatgtgtc acaaagtaag gattctgatg     2040
tgtatatcac agacaaaact gtgctagaca tgaggtctat ggacttcaag agcaacagtg     2100
ctgtggcctg gagcaactag tgatccagac atgataagat acattgatga gtttggacaa     2160
accacaacta gaatgcagtg aaaaaaatgc tttatttgtg aaatttgtga tgctattgct     2220
ttatttgtaa ccattataag ctgcaataaa caagttaaca acaacaattg cattcatttt     2280
atgtttcagg ttcaggggga ggtgtgggag gttttttaaa gcaagtaaac tggtacctca     2340
tcgaggtggt aaggcttgca tgtgcagcgc gtcgtatgtg tccttggtcg cggtggaaag     2400
cccctggtat aagccgtcgt gtccctttcc gcgacgtctc tcgcccttca taccaatctc     2460
cgagtacgcc tcagccatct tgtccttctg gagttcgttg tacaggcccct cctgggggtt     2520 ctttctccga ggcttgcctc ccatctccgg gtccctacct ctacgcttgt ctaacacgtc     2580
gtactcctcc cggcgcccca ggtttaactc gttgtatagc tggttctgac cctgctggta     2640
agcgggtgcg tccgcggagc gagagaactt cactctcagt tcgcagctgc cttcttcttc     2700
```

-continued

```
gctcggcgcg cggcagctgc tcgcatcttc ttcctgcgcg ctgctcgccg ggctcgcaaa    2760
cgggctttta gccgccgccg ccgcttttt gcggctcgct ttgcagtaga gcgttattac     2820
caagctcaac aacaacactc cgcaagtccc ggctagtggt gcccagatgt agatgtcgca    2880
ggcgaagtct agtcctcgcg tgtgaacggc ccgcccgcc gcgggcctgc aagcctcagg     2940
gcgaagagat aagggctgac ttgctatcgt tggagctggc gtgggggac gtgggctgg      3000 ggtagtagtg ggcttcgctg gggatacatt tgtagaaaca tttgaaaatg ttccctgggt    3060
aggtaactcg ctggatacgg tcacagaagt gccctgaccc cagtagtcca ttgcgtaact    3120
cccgccgtag tagtagtgct tcgcgcagta gtaaatagcg gtgtcgtcag tctggagaga    3180
gttcatcttt aagaaaacct gcgacttact gttgtcctta atgatggtga ggcggctctt    3240
gagagctgag ttgtagtatg tggtttcact tccccagata accccagcc actctaagcc     3300 ctttctaggc ggctgtcgta tccatgatac cccgtagtct gggagactga ctccagacac    3360
agtgcacgtg actgagaggc tctggctagg tgcgaccaag cccggtccgc tctcctgtaa    3420
cttgacctcc gagccgccac ccccgctgcc gccgccaccg ctgccaccgc ctccggtaat    3480
ctccagctta gttcccccac cgaatgtgta cgggagcgtg ttgccctgct gacagaagta    3540
ggtggcgatg tcctcctgct caaggttact gattgtcagg ctgtagtccg taccggaacc    3600
ggaacccgaa aatcggctag gaacgcctga gtgtaatctc gacgtgtggt aaatgagcaa    3660
cttaactgtt ccgtccggct tctgctgata ccagtttaag tattttgaga tgtcctggct    3720
ggcccggcaa gatattgtta ctcggtcgcc taaagaagca gatagggaag aggtagtctg    3780
agtcatctgt atgtcaggac gagccgcgtg caataataac gccagaggta aaagtaaggc    3840
tgtcactggg agcgccatgg tggctttccg gaacaaacaa gaaccgcgac ccaaatcccg    3900
gctgcgacgg aactagctgt gccacacccg gcgcgtcctt atataatcat cggcgttcac    3960
cgcccattct ccgcccagcc ataaaaggca actttcggaa cggcgcacgc tgattggctc    4020
cgccctaact ccgcccacta gtgcggccgc cccttcacc gagggcctat ttcccatgat     4080
tccttcatat ttgcatatac gatacaaggc tgttagagag ataattggaa ttaatttgac    4140
tgtaaacaca aagatattag tacaaaatac gtgacgtaga aagtaataat ttcttgggta    4200
gtttgcagtt ttaaaattat gttttaaaat ggactatcat atgcttaccg taacttgaaa    4260
gtatttcgat ttcttggctt tatatatctt gtggaaagga cgaaacaccg gtgtaccgga    4320
ggtttgaaga tgccgcattt ctcgagaaat gcggcatctt caaaccttt tttgaattct     4380 cgacctaggg acaaatggca gtattcatcc acaattttaa agaaaaggg gggattgggg     4440 ggtacagtgc aggggaaaga atagtagaca taatagcaac agacatacaa actaaagaat    4500
tacaaaaaca aattacaaaa attcaaaatt ttcgggttta ttacagggac agcagagatc    4560
cactttggcc gcggatcccc cttcaccgag ggcctatttc ccatgattcc ttcatatttg    4620
catatacgat acaaggctgt tagagagata attggaatta atttgactgt aaacacaaag    4680
atattagtac aaaatacgtg acgtagaaag taataatttc ttgggtagtt tgcagtttta    4740
aaattatgtt ttaaaatgga ctatcatatg cttaccgtaa cttgaaagta tttcgatttc    4800
ttggctttat atatcttgtg gaaaggacga acaccggtg taccgaggt ttgaagatgc       4860 cgcatttctc gagaaatgcg gcatcttcaa acctttttt gaattctcga cctagggaca     4920
aatggcagta ttcatccaca attttaaaag aaaaggggg attgggggt acagtgcagg      4980 ggaaagaata gtagacataa tagcaacaga catacaaact aaagaattac aaaaacaaat    5040
tacaaaaatt caaaattttc gggtttatta cagggacagc agagatccac tttggccgcg    5100
```

```
gatccgcaac aaatctgact ttgcatgtgc aaacgccttc aacaacagca ttattccaga    5160
agacaccttc ttccccagcc caggtaaggg cagctttggt gccttcgcag gctgtttcct    5220
tgcttcagga atggccaggt tctgcccaga gctctggtca atgatgtcta aaactcctct    5280
gattggtggt ctcggcctta tccattgcca ccaaaaccct cttttacta agaaacagtg    5340 agccttgttc tggcagtcca gagaatgaca cgggaaaaaa gcagatgaag agaaggtggc    5400
aggagagggc acgtggccca gcctcagtct ctccaactga gttcctgcct gcctgccttt    5460
gctcagactg tttgccccct actgctcttc taggcctcat tctaagcccc ttctccaagt    5520
tgcctctcct tatttctccc tgtctgccaa aaaatctttc ccagctcact aagtcagtct    5580
cacgcagtca ctcattaacc caccaatcac tgattgtgcc ggcacatgaa tgcaccaggt    5640
gttgaagtgg aggaattaaa aagtcagatg aggggtgtgc ccagaggaag caccattcta    5700
gttgggggag cccatctgtc agctgggaaa agtccaaata acttcagatt ggaatgtgtt    5760
ttaactcagg gttgagaaaa cagccacctt caggacaaaa gtcagggaag ggctctctga    5820
agaaatgcta cttgaagata ccagccctac caagggcagg gagaggacca attgatggag    5880
ttggccactc cctctctgcg cgctcgctcg ctcactgagg ccgcccggcc aaagcccggg    5940
cgtcgggcga cctttggtcg cccggcctca gtgagcgagc gagcgcgcag agagggagtg    6000
gccaacggcg cgcctgcagg tctcaaaaat agctaccctc tccggcatga atttatcagc    6060
tagaacggtt gaatatcata ttgatggtga tttgactgtc tccggccttt ctcacccgtt    6120
tgaatcttta cctacacatt actcaggcat tgcatttaaa atatatgagg gttctaaaaa    6180
tttttatcct tgcgttgaaa taaaggcttc tcccgcaaaa gtattacagg gtcataatgt    6240
ttttggtaca accgatttag ctttatgctc tgaggcttta ttgcttaatt ttgctaattc    6300
tttgccttgc ctgtatgatt tattggatgt tggaattcct gatgcggtat tttctcctta    6360
cgcatctgtg cggtatttca caccgcatat ggtgcactct cagtacaatc tgctctgatg    6420
ccgcatagtt aagccagccc cgacacccgc caacacccgc tgacgcgccc tgacgggctt    6480
gtctgctccc ggcatccgct tacagacaag ctgtgaccgt ctccgggagc tgcatgtgtc    6540
agaggttttc accgtcatca ccgaaacgcg cgagacgaaa gggcctcgtg atacgcctat    6600
ttttataggt taatgtcatg ataataatgg tttcttagac gtcaggtggc acttttcggg    6660
gaaatgtgcg cggaacccct atttgtttat ttttctaaat acattcaaat atgtatccgc    6720
tcatgagaca ataaccctga taaatgcttc aataatattg aaaaaggaag agtatgagta    6780
ttcaacattt ccgtgtcgcc cttattccct ttttttgcggc attttgcctt cctgtttttg    6840
ctcacccaga aacgctggtg aaagtaaaag atgctgaaga tcagttgggt gcacgagtgg    6900
gttacatcga actggatctc aacagcggta agatccttga gttttttcgc cccgaagaac    6960
gttttccaat gatgagcact tttaaagttc tgctatgtgg cgcggtatta tcccgtattg    7020
acgccgggca agagcaactc ggtcgccgca tacactattc tcagaatgac ttggttgagt    7080
actcaccagt cacagaaaag catcttacgg atggcatgac agtaagagaa ttatgcagtg    7140
ctgccataac catgagtgat aacactgcgg ccaacttact tctgacaacg atcggaggac    7200
cgaaggagct aaccgctttt ttgcacaaca tgggggatca tgtaactcgc cttgatcgtt    7260
gggaaccgga gctgaatgaa gccataccaa acgacgagcg tgacaccacg atgcctgtag    7320
caatggcaac aacgttgcgc aaactattaa ctggcgaact acttactcta gcttcccggc    7380
aacaattaat agactggatg gaggcggata aagttgcagg accacttctg cgctcggccc    7440
```

-continued

| | |
|---|---|
| ttccggctgg ctggtttatt gctgataaat ctggagccgg tgagcgtggg tctcgcggta | 7500 |
| tcattgcagc actggggcca gatggtaagc cctcccgtat cgtagttatc tacacgacgg | 7560 |
| ggagtcaggc aactatggat gaacgaaata gacagatcgc tgagataggt gcctcactga | 7620 |
| ttaagcattg gtaactgtca gaccaagttt actcatatat actttagatt gatttaaaac | 7680 |
| ttcattttta atttaaaagg atctaggtga agatccttt tgataatctc atgaccaaaa | 7740 |
| tcccttaacg tgagttttcg ttccactgag cgtcagaccc cgtagaaaag atcaaaggat | 7800 |
| cttcttgaga tccttttttt ctgcgcgtaa tctgctgctt gcaaacaaaa aaaccaccgc | 7860 |
| taccagcggt ggtttgtttg ccggatcaag agctaccaac tcttttccg aaggtaactg | 7920 |
| gcttcagcag agcgcagata ccaaatactg tccttctagt gtagccgtag ttaggccacc | 7980 |
| acttcaagaa ctctgtagca ccgcctacat acctcgctct gctaatcctg ttaccagtgg | 8040 |
| ctgctgccag tggcgataag tcgtgtctta ccgggttgga ctcaagacga tagttaccgg | 8100 |
| ataaggcgca gcggtcgggc tgaacggggg gttcgtgcac acagcccagc ttggagcgaa | 8160 |
| cgacctacac cgaactgaga tacctacagc gtgagctatg agaaagcgcc acgcttcccg | 8220 |
| aagggagaaa ggcggacagg tatccggtaa gcggcagggt cggaacagga gagcgcacga | 8280 |
| gggagcttcc agggggaaac gcctggtatc tttatagtcc tgtcgggttt cgccacctct | 8340 |
| gacttgagcg tcgatttttg tgatgctcgt caggggggcg gagcctatgg aaaaacgcca | 8400 |
| gcaacgcggc cttttacgg ttcctggcct tttgctggcc ttttgctcac atgttctttc | 8460 |
| ctgcgttatc ccctgattct gtggataacc gtattaccgc ctttgagtga gctgataccg | 8520 |
| ctcgccgcag ccgaacgacc gagcgcagcg agtcagtgag cgaggaagcg gaagagcgcc | 8580 |
| caatacgcaa accgcctctc cccgcgcgtt ggccgattca ttaatg | 8626 |

<210> SEQ ID NO 25
<211> LENGTH: 6827
<212> TYPE: DNA
<213> ORGANISM: Artificial Sequence
<220> FEATURE:
<223> OTHER INFORMATION: Synthesized

<400> SEQUENCE: 25

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctcccttag ggttccgatt | 600 |
| tagtgcttta cggcacctcg accccaaaaa acttgattag ggtgatggtt cacgtagtgg | 660 |
| gccatcgccc tgatagacgg tttttcgccc tttgacgttg gagtccacgt tctttaatag | 720 |
| tggactcttg ttccaaactg gaacaacact caacccatc tcggtctatt cttttgattt | 780 |
| ataagggatt ttgccgattt cggcctattg gttaaaaaat gagctgattt aacaaaaatt | 840 |
| taacgcgaat tttaacaaaa tattaacgtt tacaatttaa atatttgctt atacaatctt | 900 |

```
cctgttttg  gggctttct   gattatcaac  cggggtacat  atgattgaca  tgctagtttt    960
acggcgcgcc  gggttggcca  ctccctctct  gcgcgctcgc  tcgctcactg  aggccgggcg   1020
accaaaggtc  gcccgacgcc  cgggctttgc  ccgggcggcc  tcagtgagcg  agcgagcgcg   1080
cagagaggga  gtggccaact  ccatcactag  gggttcctac  gcgtgggaaa  tgagatcatg   1140
tcctaaccct  gatcctcttg  tcccacagat  atccagaacc  ctgaccctgc  cgtgtaccag   1200
ctgagagact  ctaaatccag  tgacaagtct  gtctgcctat  tcaccgattt  tgattctcaa   1260
acaaatgtgt  cacaaagtaa  ggattctgat  gtgtatatca  cagacaaaac  tgtgctagac   1320
atgaggtcta  tggacttcaa  gagcaacagt  gctgtggcct  ggagcaacta  gtgatccaga   1380
catgataaga  tacattgatg  agtttggaca  aaccacaact  agaatgcagt  gaaaaaaatg   1440
ctttatttgt  gaaatttgtg  atgctattgc  tttatttgta  accattataa  gctgcaataa   1500
acaagttaac  aacaacaatt  gcattcattt  tatgtttcag  gttcaggggg  aggtgtggga   1560
ggtttttaa   agcaagtaaa  ctggtacctc  atcgaggtgg  taaggcttgc  atgtgcagcg   1620
cgtcgtatgt  gtccttggtc  gcggtggaaa  gcccctggta  taagccgtcg  tgtccctttc   1680
cgcgacgtct  ctcgcccttc  ataccaatct  ccgagtacgc  ctcagccatc  ttgtccttct   1740
ggagttcgtt  gtacaggccc  tcctggggt   tctttctccg  aggcttgcct  cccatctccg   1800
ggtccctacc  tctacgcttg  tctaacacgt  cgtactcctc  ccggcgcccc  aggtttaact   1860
cgttgtatag  ctggttctga  ccctgctggt  aagcgggtgc  gtccgcggag  cgagagaact   1920
tcactctcag  ttcgcagctg  ccttcttctt  cgctcggcgc  gcggcagctg  ctcgcatctt   1980
cttcctgcgc  gctgctcgcc  gggctcgcaa  acgggctttt  agccgccgcc  gccgcttttt   2040
tgcggctcgc  tttgcagtag  agcgttatta  ccaagctcaa  caacaacact  ccgcaagtcc   2100
cggctagtgg  tgcccagatg  tagatgtcgc  aggcgaagtc  tagtcctcgc  gtgtgaacgg   2160
cgccgcccgc  cgcgggcctg  caagcctcag  ggcgaagaga  taagggctga  cttgctatcg   2220
ttggagctgg  cgtgggggga  cgtggggctg  gggtagtagt  gggcttcgct  ggggatacat   2280
ttgtagaaac  atttgaaaat  gttccctggg  taggtaactc  gctggatacg  gtcacagaag   2340
tgccctgacc  ccagtagtcc  attgcgtaac  tcccgccgta  gtagtagtgc  ttcgcgcagt   2400
agtaaatagc  ggtgtcgtca  gtctggagag  agttcatctt  taagaaaacc  tgcgacttac   2460
tgttgtcctt  aatgatggtg  aggcggctct  tgagagctga  gttgtagtat  gtggtttcac   2520
ttccccagat  aaccccagc   cactctaagc  cctttctagg  cggctgtcgt  atccatgata   2580
ccccgtagtc  tgggagactg  actccagaca  cagtgcacgt  gactgagagg  ctctggctag   2640
gtgcgaccaa  gcccggtccg  ctctcctgta  acttgacctc  cgagccgcca  ccccgctgc   2700
cgccgccacc  gctgccaccg  cctccggtaa  tctccagctt  agttccccca  ccgaatgtgt   2760
acgggagcgt  gttgccctgc  tgacagaagt  aggtggcgat  gtcctcctgc  tcaaggttac   2820
tgattgtcag  gctgtagtcc  gtaccggaac  cggaacccga  aaatcggcta  ggaacgcctg   2880
agtgtaatct  cgacgtgtgg  taaatgagca  acttaactgt  tccgtccggc  ttctgctgat   2940
accagtttaa  gtattttgag  atgtcctggc  tggcccggca  agatattgtt  actcggtcgc   3000
ctaaagaagc  agatagggaa  gaggtagtct  gagtcatctg  tatgtcagga  cgagccgcgt   3060
gcaataataa  cgccagaggt  aaaagtaagg  ctgtcactgg  gagcgccatg  gtggctttcc   3120
ggaacaaaca  agaaccgcga  cccaaatccc  ggctgcgacg  gaactagctg  tgccacaccc   3180
ggcgcgtcct  tatataatca  tcggcgttca  ccgcccattc  tccgcccagc  cataaaaggc   3240
```

```
aactttcgga acggcgcacg ctgattggct ccgccctaac tccgcccact agtgcggccg    3300
cactgcaaac ccagggctgc cttggaaaag gcgcaacccg ggccccctcg agccggcgcc    3360
aaagtggatc tctgctgtcc ctgtaataaa cccgaaaatt ttgaattttt gtaatttgtt    3420
tttgtaattc tttagtttgt atgtctgttg ctattatgtc tactattctt tcccctgcac    3480 tgtaccccccc aatccccccct tttcttttaa aattgtggat gaatactgcc atttgtctca    3540
agatctagaa ttcaaaaaaa ggtttgaaga tgccgcattt ctcgagaaat gcggcatctt    3600
caaacctccg gtacctcgtc cttttccacaa gatatataaa gccaagaaat cgaaatactt    3660
tcaagttacg gtaagcatat gatagtccat tttaaaacat aattttaaaa ctgcaaacta    3720
cccaagaaat tattactttc tacgtcacgt attttgtact aatatctttg tgtttacagt    3780
caaattaatt ctaattatct ctctaacagc cttgtatcgt atatgcaaat atgaaggaat    3840
catgggaaat aggccctctc tgggtcccct ggatccgcaa caaatctgac tttgcatgtg    3900
caaacgcctt caacaacagc attattccag aagacacctt cttccccagc ccaggtaagg    3960
gcagctttgg tgccttcgca ggctgtttcc ttgcttcagg aatggccagg ttctgcccag    4020
agctctggtc aatgatgtct aaaactcctc tgattggtgg tctcggcccc aattgatgga    4080
gttggccact ccctctctgc gcgctcgctc gctcactgag gccgcccggg caaagcccgg    4140
gcgtcgggcg acctttggtc gcccggcctc agtgagcgag cgagcgcgca gagagggagt    4200
ggccaacggc gcgcctgcag gtctcaaaaa tagctaccct ctccggcatg aatttatcag    4260
ctagaacggt tgaatatcat attgatggtg atttgactgt ctccggcctt tctcacccgt    4320
ttgaatcttt acctacacat tactcaggca ttgcatttaa aatatatgag ggttctaaaa    4380 attttttatcc ttgcgttgaa ataaaggctt ctcccgcaaa agtattacag ggtcataatg    4440 ttttttggtac aaccgattta gctttatgct ctgaggcttt attgcttaat tttgctaatt    4500
ctttgccttg cctgtatgat ttattggatg ttggaattcc tgatgcggta ttttctcctt    4560
acgcatctgt gcggtatttc acaccgcata tggtgcactc tcagtacaat ctgctctgat    4620
gccgcatagt taagccagcc ccgacacccg ccaacacccg ctgacgcgcc ctgacgggct    4680
tgtctgctcc cggcatccgc ttacagacaa gctgtgaccg tctccgggag ctgcatgtgt    4740
cagaggtttt caccgtcatc accgaaacgc gcgagacgaa agggcctcgt gatacgccta    4800
tttttatagg ttaatgtcat gataataatg gtttcttaga cgtcaggtgg cacttttcgg    4860
ggaaatgtgc gcggaacccc tatttgttta ttttttctaaa tacattcaaa tatgtatccg    4920
ctcatgagac aataaccctg ataaatgctt caataatatt gaaaaaggaa gagtatgagt    4980
attcaacatt tccgtgtcgc ccttattccc ttttttgcgg cattttgcct tcctgttttt    5040
gctcacccag aaacgctggt gaaagtaaaa gatgctgaag atcagttggg tgcacgagtg    5100
ggttacatcg aactggatct caacagcggt aagatccttg agagttttcg ccccgaagaa    5160
cgttttccaa tgatgagcac ttttaaagtt ctgctatgtg gcgcggtatt atcccgtatt    5220
gacgccgggc aagagcaact cggtcgccgc atacactatt ctcagaatga cttggttgag    5280
tactcaccag tcacagaaaa gcatcttacg gatggcatga cagtaagaga attatgcagt    5340
gctgccataa ccatgagtga taacactgcg gccaacttac ttctgacaac gatcggagga    5400
ccgaaggagc taaccgcttt tttgcacaac atggggatc atgtaactcg ccttgatcgt    5460
tgggaaccgg agctgaatga agccatacca aacgacgagc gtgacaccac gatgcctgta    5520
gcaatggcaa caacgttgcg caaactatta actggcgaac tacttactct agcttcccgg    5580
caacaattaa tagactggat ggaggcggat aaagttgcag gaccacttct gcgctcggcc    5640
```

```
cttccggctg gctggtttat tgctgataaa tctggagccg gtgagcgtgg gtctcgcggt    5700
atcattgcag cactgggscc agatggtaag ccctcccgta tcgtagttat ctacacgacg    5760
gggagtcagg caactatgga tgaacgaaat agacagatcg ctgagatagg tgcctcactg    5820
attaagcatt ggtaactgtc agaccaagtt tactcatata tactttagat tgatttaaaa    5880
cttcattttt aatttaaaag gatctaggtg aagatccttt ttgataatct catgaccaaa    5940
atcccttaac gtgagttttc gttccactga gcgtcagacc ccgtagaaaa gatcaaagga    6000
tcttcttgag atcctttttt tctgcgcgta atctgctgct tgcaaacaaa aaaaccaccg    6060
ctaccagcgg tggtttgttt gccggatcaa gagctaccaa ctcttttcc gaaggtaact    6120 ggcttcagca gagcgcagat accaaatact gtccttctag tgtagccgta gttaggccac    6180
cacttcaaga actctgtagc accgcctaca tacctcgctc tgctaatcct gttaccagtg    6240
gctgctgcca gtggcgataa gtcgtgtctt accgggttgg actcaagacg atagttaccg    6300
gataaggcgc agcggtcggg ctgaacgggg gttcgtgca cacagcccag cttggagcga    6360
acgacctaca ccgaactgag atacctacag cgtgagctat gagaaagcgc cacgcttccc    6420
gaagggagaa aggcggacag gtatccggta agcggcaggg tcggaacagg agagcgcacg    6480
agggagcttc caggggggaaa cgcctggtat ctttatagtc ctgtcgggtt tcgccacctc    6540
tgacttgagc gtcgattttt gtgatgctcg tcaggggggc ggagcctatg gaaaaacgcc    6600
agcaacgcgg ccttttacg gttcctggcc ttttgctggc cttttgctca catgttcttt    6660
cctgcgttat cccctgattc tgtggataac cgtattaccg cctttgagtg agctgatacc    6720
gctcgccgca gccgaacgac cgagcgcagc gagtcagtga gcgaggaagc ggaagagcgc    6780
ccaatacgca aaccgcctct ccccgcgcgt tggccgattc attaatg               6827
```

<210> SEQ ID NO 26  
<211> LENGTH: 6762  
<212> TYPE: DNA  
<213> ORGANISM: Artificial Sequence  
<220> FEATURE:  
<223> OTHER INFORMATION: Synthesized

<400> SEQUENCE: 26

```
cagcagctgg cgtaatagcg aagaggcccg caccgatcgc ccttcccaac agttgcgcag     60
cctgaatggc gaatggaatt ccagacgatt gagcgtcaaa atgtaggtat ttccatgagc    120
gtttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa agcaaccata    420
gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600
tagtgcttta cggcacctcg accccaaaaa acttgattag ggtgatggtt cacgtagtgg    660
gccatcgccc tgatagacgg ttttcgccc tttgacgttg gagtccacgt tctttaatag    720
tggactcttg ttccaaactg gaacaacact caacccatc tcggtctatt cttttgattt    780
ataagggatt ttgccgattt cggcctattg gttaaaaaat gagctgattt aacaaaaatt    840
```

```
taacgcgaat tttaacaaaa tattaacgtt tacaatttaa atatttgctt atacaatctt    900 cctgttttg gggctttct gattatcaac cggggtacat atgattgaca tgctagtttt     960
acggcgcgcc gggttggcca ctccctctct gcgcgctcgc tcgctcactg aggccgggcg  1020
accaaaggtc gcccgacgcc cgggctttgc ccgggcggcc tcagtgagcg agcgagcgcg  1080
cagagaggga gtggccaact ccatcactag gggttcctac gcgtgggaaa tgagatcatg  1140
tcctaaccct gatcctcttg tcccacagat atccagaacc ctgaccctgc cgtgtaccag  1200
ctgagagact ctaaatccag tgacaagtct gtctgcctat tcaccgattt tgattctcaa  1260
acaaatgtgt cacaaagtaa ggattctgat gtgtatatca cagacaaaac tgtgctagac  1320
atgaggtcta tggacttcaa gagcaacagt gctgtggcct ggagcaacta gtgatccaga  1380
catgataaga tacattgatg agtttggaca aaccacaact agaatgcagt gaaaaaaatg  1440
ctttatttgt gaaatttgtg atgctattgc tttatttgta accattataa gctgcaataa  1500
acaagttaac aacaacaatt gcattcattt tatgtttcag gttcaggggg aggtgtggga  1560 ggtttttaa agcaagtaaa ctggtacctc atcgaggtgg taaggcttgc atgtgcagcg  1620
cgtcgtatgt gtccttggtc gcggtggaaa gccctggta taagccgtcg tgtccctttc  1680
cgcgacgtct ctcgcccttc ataccaatct ccgagtacgc ctcagccatc ttgtccttct  1740
ggagttcgtt gtacaggccc tcctgggggt tctttctccg aggcttgcct cccatctccg  1800
ggtccctacc tctacgcttg tctaacacgt cgtactcctc ccggcgcccc aggtttaact  1860
cgttgtatag ctggttctga ccctgctggt aagcgggtgc gtccgcggag cgagagaact  1920
tcactctcag ttcgcagctg ccttcttctt cgctcggcgc gcggcagctg ctcgcatctt  1980
cttcctgcgc gctgctcgcc gggctcgcaa cgggcttttt agccgccgcc gccgcttttt  2040
tgcggctcgc tttgcagtag agcgttatta ccaagctcaa caacaacact ccgcaagtcc  2100
cggctagtgg tgcccagatg tagatgtcgc aggcgaagtc tagtcctcgc gtgtgaacgg  2160
cgccgcccgc cgcgggcctg caagcctcag ggcgaagaga taagggctga cttgctatcg  2220
ttggagctgg cgtgggggga cgtggggctg gggtagtagt gggcttcgct ggggatacat  2280
ttgtagaaac atttgaaaat gttccctggg taggtaactc gctggatacg gtcacagaag  2340
tgccctgacc ccagtagtcc attgcgtaac tcccgccgta gtagtagtgc ttcgcgcagt  2400
agtaaatagc ggtgtcgtca gtctggagag agttcatctt taagaaaacc tgcgacttac  2460
tgttgtcctt aatgatggtg aggcggctct tgagagctga gttgtagtat gtggtttcac  2520
ttccccagat aaccccagc cactctaagc cctttctagg cggctgtcgt atccatgata  2580
ccccgtagtc tgggagactg actccagaca cagtgcacgt gactgagagg ctctggctag  2640
gtgcgaccaa gcccggtccg ctctcctgta acttgacctc cgagccgcca ccccgctgc  2700 cgccgccacc gctgccaccg cctccggtaa tctccagctt agttccccca ccgaatgtgt  2760 acggagcgt gttgccctgc tgacagaagt aggtggcgat gtcctcctgc tcaaggttac  2820
tgattgtcag gctgtagtcc gtaccggaac cggaacccga aaatcggcta ggaacgcctg  2880
agtgtaatct cgacgtgtgg taaatgagca acttaactgt tccgtccggc ttctgctgat  2940
accagtttaa gtattttgag atgtcctggc tggcccggca agatattgtt actcggtcgc  3000
ctaaagaagc agatagggaa gaggtagtct gagtcatctg tatgtcagga cgagccgcgt  3060
gcaataataa cgccagaggt aaaagtaagg ctgtcactgg gagcgccatg gtggctttcc  3120
ggaacaaaca agaaccgcga cccaaatccc ggctgcgacg gaactagctg tgccacaccc  3180
ggcgcgtcct tatataatca tcggcgttca ccgcccattc tccgcccagc cataaaaggc  3240
```

```
aactttcgga acggcgcacg ctgattggct ccgccctaac tccgcccact agtgcggccg    3300
cgggcccgtt taaacgctag cgagagggcc tatttcccat gattccttca tatttgcata    3360
tacgatacaa ggctgttaga gagataatta gaattaattt gactgtaaac acaaagatat    3420
tagtacaaaa tacgtgacgt agaaagtaat aatttcttgg gtagtttgca gttttaaaat    3480
tatgttttaa aatggactat catatgctta ccgtaacttg aaagtatttc gatttcttgg    3540
ctttatatat cttgtggaaa ggacgaggta ccggaggttt gaagatgccg catttctcga    3600
gaaatgcggc atcttcaaac cttttttga attctagatc ttgagacaaa tggcagtatt     3660
catccacaat tttaaaagaa aagggggat tgggggtac agtgcagggg aaagaatagt      3720
agacataata gcaacagaca tacaaactaa agaattacaa aaacaaatta caaaattca     3780 aaattttcct aggtacgtat ctagtggatc cgcaacaaat ctgactttgc atgtgcaaac    3840
gccttcaaca acagcattat tccagaagac accttcttcc ccagcccagg taagggcagc    3900
tttggtgcct tcgcaggctg tttccttgct tcaggaatgg ccaggttctg cccagagctc    3960
tggtcaatga tgtctaaaac tcctctgatt ggtggtctcg gccccaattg atggagttgg    4020
ccactccctc tctgcgcgct cgctcgctca ctgaggccgc ccgggcaaag cccgggcgtc    4080
gggcgacctt tggtcgcccg gcctcagtga gcgagcgagc gcgcagagag ggagtggcca    4140
acggcgcgcc tgcaggtctc aaaaatagct accctctccg gcatgaattt atcagctaga    4200
acggttgaat atcatattga tggtgatttg actgtctccg gcctttctca cccgtttgaa    4260 tcttaccta cacattactc aggcattgca tttaaaatat atgagggttc taaaaatttt    4320
tatccttgcg ttgaaataaa ggcttctccc gcaaaagtat tacagggtca taatgttttt    4380
ggtacaaccg atttagcttt atgctctgag gctttattgc ttaattttgc taattctttg    4440
ccttgcctgt atgatttatt ggatgttgga attcctgatg cggtattttc tccttacgca    4500
tctgtgcggt atttcacacc gcatatggtg cactctcagt acaatctgct ctgatgccgc    4560
atagttaagc cagccccgac acccgccaac acccgctgac gcgccctgac gggcttgtct    4620
gctcccggca tccgcttaca cacaagctgt gaccgtctcc gggagctgca tgtgtcagag    4680
gttttcaccg tcatcaccga aacgcgcgag acgaaagggc ctcgtgatac gcctattttt    4740
ataggttaat gtcatgataa taatggtttc ttagacgtca ggtggcactt ttcggggaaa    4800
tgtgcgcgga acccctattt gtttattttt ctaaatacat tcaaatatgt atccgctcat    4860
gagacaataa ccctgataaa tgcttcaata atattgaaaa aggaagagta tgagtattca    4920
acatttccgt gtcgccctta ttcccttttt tgcggcattt tgccttcctg tttttgctca    4980
cccagaaacg ctggtgaaag taaaagatgc tgaagatcag ttgggtgcac gagtgggtta    5040
catcgaactg gatctcaaca gcggtaagat ccttgagagt tttcgccccg aagaacgttt    5100
tccaatgatg agcactttta aagttctgct atgtggcgcg gtattatccc gtattgacgc    5160
cgggcaagag caactcggtc gccgcataca ctattctcag aatgacttgg ttgagtactc    5220
accagtcaca gaaaagcatc ttacggatgg catgacagta agagaattat gcagtgctgc    5280
cataaccatg agtgataaca ctgcggccaa cttacttctg acaacgatcg gaggaccgaa    5340
ggagctaacc gcttttttgc acaacatggg ggatcatgta actcgccttg atcgttggga    5400
accggagctg aatgaagcca taccaaacga cgagcgtgac accacgatgc ctgtagcaat    5460
ggcaacaacg ttgcgcaaac tattaactgg cgaactactt actctagctt cccggcaaca    5520
attaatagac tggatggagg cggataaagt tgcaggacca cttctgcgct cggcccttcc    5580
```

```
ggctggctgg tttattgctg ataaatctgg agccggtgag cgtgggtctc gcggtatcat    5640
tgcagcactg gggccagatg gtaagccctc ccgtatcgta gttatctaca cgacggggag    5700
tcaggcaact atggatgaac gaaatagaca gatcgctgag ataggtgcct cactgattaa    5760
gcattggtaa ctgtcagacc aagtttactc atatatactt tagattgatt taaaacttca    5820 ttttttaattt aaaaggatct aggtgaagat cctttttgat aatctcatga ccaaaatccc    5880
ttaacgtgag ttttcgttcc actgagcgtc agacccgta gaaaagatca aaggatcttc    5940
ttgagatcct ttttttctgc gcgtaatctg ctgcttgcaa acaaaaaaac caccgctacc    6000
agcggtggtt tgtttgccgg atcaagagct accaactctt tttccgaagg taactggctt    6060
cagcagagcg cagataccaa atactgtcct tctagtgtag ccgtagttag gccaccactt    6120
caagaactct gtagcaccgc ctacatacct cgctctgcta atcctgttac cagtggctgc    6180
tgccagtggc gataagtcgt gtcttaccgg gttggactca agacgatagt taccggataa    6240
ggcgcagcgg tcgggctgaa cggggggttc gtgcacacag cccagcttgg agcgaacgac    6300
ctacaccgaa ctgagatacc tacagcgtga gctatgagaa agcgccacgc ttcccgaagg    6360
gagaaaggcg gacaggtatc cggtaagcgg cagggtcgga acaggagagc gcacgaggga    6420
gcttccaggg ggaaacgcct ggtatcttta tagtcctgtc gggtttcgcc acctctgact    6480
tgagcgtcga ttttgtgat gctcgtcagg gggcggagc ctatggaaaa acgccagcaa    6540
cgcggccttt ttacgttcc tggccttttg ctggccttt gctcacatgt tctttcctgc    6600
gttatcccct gattctgtgg ataaccgtat taccgccttt gagtgagctg ataccgctcg    6660
ccgcagccga acgaccgagc gcagcgagtc agtgagcgag gaagcggaag agcgcccaat    6720
acgcaaaccg cctctccccg cgcgttggcc gattcattaa tg                      6762
```

<210> SEQ ID NO 27
<211> LENGTH: 7227
<212> TYPE: DNA
<213> ORGANISM: Artificial Sequence
<220> FEATURE:
<223> OTHER INFORMATION: Synthesized

<400> SEQUENCE: 27

```
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttttcctg ttgcaatggc tggcggtaat attgttctgg atattaccag caaggccgat     180
agtttgagtt cttctactca ggcaagtgat gttattacta atcaaagaag tattgcgaca     240
acggttaatt tgcgtgatgg acagactctt ttactcggtg gcctcactga ttataaaaac     300
acttctcagg attctggcgt accgttcctg tctaaaatcc ctttaatcgg cctcctgttt     360
agctcccgct ctgattctaa cgaggaaagc acgttatacg tgctcgtcaa agcaaccata     420
gtacgcgccc tgtagcggcg cattaagcgc ggcgggtgtg gtggttacgc gcagcgtgac     480
cgctacactt gccagcgccc tagcgcccgc tcctttcgct ttcttccctt cctttctcgc     540
cacgttcgcc ggctttcccc gtcaagctct aaatcggggg ctccctttag ggttccgatt     600
tagtgcttta cggcacctcg accccaaaaa acttgattag ggtgatggtt cacgtagtgg     660
gccatcgccc tgatagacgg ttttcgccc tttgacgttg gagtccacgt tctttaatag     720
tggactcttg ttccaaactg gaacaacact caacccctatc tcggtctatt cttttgattt     780
ataagggatt ttgccgattt cggcctattg gttaaaaaat gagctgattt aacaaaaatt     840
taacgcgaat tttaacaaaa tattaacgtt tacaatttaa atatttgctt atacaatctt     900
```

```
cctgtttttg gggcttttct gattatcaac cggggtacat atgattgaca tgctagtttt     960
acggcgcgcc gggttggcca ctccctctct gcgcgctcgc tcgctcactg aggccgggcg    1020
accaaaggtc gcccgacgcc cgggctttgc ccgggcggcc tcagtgagcg agcgagcgcg    1080
cagagaggga gtggccaact ccatcactag gggttcctac gcgtgggaaa tgagatcatg    1140
tcctaaccct gatcctcttg tcccacagat atccagaacc ctgaccctgc cgtgtaccag    1200
ctgagagact ctaaatccag tgacaagtct gtctgcctat tcaccgattt tgattctcaa    1260
acaaatgtgt cacaaagtaa ggattctgat gtgtatatca cagacaaaac tgtgctagac    1320
atgaggtcta tggacttcaa gagcaacagt gctgtggcct ggagcaacta gtgatccaga    1380
catgataaga tacattgatg agtttggaca aaccacaact agaatgcagt gaaaaaaatg    1440
ctttatttgt gaaatttgtg atgctattgc tttatttgta accattataa gctgcaataa    1500
acaagttaac aacaacaatt gcattcattt tatgtttcag gttcaggggg aggtgtggga    1560
ggttttttaa agcaagtaaa ctggtacctc atcgaggtgg taaggcttgc atgtgcagcg    1620
cgtcgtatgt gtccttggtc gcggtggaaa gcccctggta taagccgtcg tgtccctttc    1680
cgcgacgtct ctcgcccttc ataccaatct ccgagtacgc ctcagccatc ttgtccttct    1740
ggagttcgtt gtacaggccc tcctgggggt tctttctccg aggcttgcct cccatctccg    1800
ggtccctacc tctacgcttg tctaacacgt cgtactcctc ccggcgcccc aggtttaact    1860
cgttgtatag ctggttctga ccctgctggt aagcgggtgc gtccgcggag cgagagaact    1920
tcactctcag ttcgcagctg ccttcttctt cgctcggcgc gcggcagctg ctcgcatctt    1980
cttcctgcgc gctgctcgcc gggctcgcaa acgggctttt agccgccgcc gccgcttttt    2040
tgcggctcgc tttgcagtag agcgttatta ccaagctcaa caacaacact ccgcaagtcc    2100
cggctagtgg tgcccagatg tagatgtcgc aggcgaagtc tagtcctcgc gtgtgaacgg    2160
cgccgcccgc cgcgggcctg caagcctcag ggcgaagaga taagggctga cttgctatcg    2220
ttggagctgg cgtgggggga cgtggggctg gggtagtagt gggcttcgct ggggatacat    2280
ttgtagaaac atttgaaaat gttccctggg taggtaactc gctggatacg gtcacagaag    2340
tgccctgacc ccagtagtcc attgcgtaac tcccgccgta gtagtagtgc ttcgcgcagt    2400
agtaaatagc ggtgtcgtca gtctggagag agttcatctt taagaaaacc tgcgacttac    2460
tgttgtcctt aatgatggtg aggcggctct tgagagctga gttgtagtat gtggtttcac    2520
ttccccagat aaccccagc cactctaagc cctttctagg cggctgtcgt atccatgata    2580
cccgtagtc tgggagactg actccagaca cagtgcacgt gactgagagg ctctggctag    2640
gtgcgaccaa gcccggtccg ctctcctgta acttgacctc cgagccgcca ccccgctgc    2700
cgccgccacc gctgccaccg cctccggtaa tctccagctt agttcccca ccgaatgtgt    2760
acgggagcgt gttgccctgc tgacagaagt aggtggcgat gtcctcctgc tcaaggttac    2820
tgattgtcag gctgtagtcc gtaccggaac cggaacccga aaatcggcta ggaacgcctg    2880
agtgtaatct cgacgtgtgg taaatgagca acttaactgt tccgtccggc ttctgctgat    2940
accagtttaa gtattttgag atgtcctggc tggcccggca agatattgtt actcggtcgc    3000
ctaaagaagc agatagggaa gaggtagtct gagtcatctg tatgtcagga cgagccgcgt    3060
gcaataataa cgccagaggt aaaagtaagg ctgtcactgg gagcgccatg gtggctttcc    3120
ggaacaaaca agaaccgcga cccaaatccc ggctgcgacg gaactagctg tgccacaccc    3180
ggcgcgtcct tatataatca tcggcgttca ccgcccattc tccgcccagc cataaaaggc    3240
```

```
aactttcgga acggcgcacg ctgattggct ccgccctaac tccgcccact agtgcggccc    3300
gtttaaacgc tagcgagagg gcctatttcc catgattcct tcatatttgc atatacgata    3360
caaggctgtt agagagataa ttagaattaa tttgactgta aacacaaaga tattagtaca    3420
aaatacgtga cgtagaaagt aataatttct tgggtagttt gcagttttaa aattatgttt    3480
taaaatggac tatcatatgc ttaccgtaac ttgaaagtat ttcgatttct tggctttata    3540
tatcttgtgg aaaggacgag gtaccggagg tttgaagatg ccgcatttct cgagaaatgc    3600
ggcatcttca aaccttttt tgaattctag atcttgagac aaatggcagt attcatccac    3660
aattttaaaa gaaaggggg gattgggggg tacagtgcag gggaaagaat agtagacata    3720
atagcaacag acatacaaac taagaattca caaaacaaa ttacaaaat tcaaattt    3780 cctagcgaga gggcctattt ccatgattc cttcatattt gcatatacga tacaaggctg    3840
ttagagagat aattagaatt aatttgactg taaacacaaa gatattagta caaaatacgt    3900
gacgtagaaa gtaataattt cttgggtagt ttgcagtttt aaaattatgt tttaaaatgg    3960
actatcatat gcttaccgta acttgaaagt atttcgattt cttggcttta tatatcttgt    4020
ggaaaggacg aggtaccgga ggtttgaaga tgccgcattt ctcgagaaat gcggcatctt    4080
caaacctttt tttgaattct agatcttgag acaaatggca gtattcatcc acaattttaa    4140
aagaaaaggg gggattgggg ggtacagtgc aggggaaaga atagtagaca taatagcaac    4200
agacatacaa actaaagaat tacaaaaaca aattacaaaa attcaaaatt ttcctaggta    4260
cgtatctagt ggatccgcaa caaatctgac tttgcatgtg caaacgcctt caacaacagc    4320
attattccag aagacacctt cttccccagc ccaggtaagg gcagctttgg tgccttcgca    4380
ggctgtttcc ttgcttcagg aatggccagg ttctgcccag agctctggtc aatgatgtct    4440
aaaactcctc tgattggtgg tctcggcccc aattgatgga gttggccact ccctctctgc    4500
gcgctcgctc gctcactgag gccgcccggg caaagcccgg gcgtcgggcg acctttggtc    4560
gcccggcctc agtgagcgag cgagcgcgca gagagggagt ggccaacggc gcgcctgcag    4620
gtctcaaaaa tagctaccct ctccggcatg aatttatcag ctagaacggt tgaatatcat    4680
attgatggtg atttgactgt ctccggcctt tctcacccgt ttgaatcttt acctacacat    4740
tactcaggca ttgcatttaa aatatatgag ggttctaaaa atttttatcc ttgcgttgaa    4800
ataaaggctt ctcccgcaaa agtattacag ggtcataatg ttttttggtac aaccgattta    4860 gctttatgct ctgaggcttt attgcttaat tttgctaatt ctttgccttg cctgtatgat    4920
ttattggatg ttggaattcc tgatgcggta ttttctcctt acgcatctgt gcggtatttc    4980
acaccgcata tggtgcactc tcagtacaat ctgctctgat gccgcatagt taagccagcc    5040
ccgacacccg ccaacacccg ctgacgcgcc ctgacgggct tgtctgctcc cggcatccgc    5100
ttacagacaa gctgtgaccg tctccgggag ctgcatgtgt cagaggtttt caccgtcatc    5160
accgaaacgc gcgagacgaa agggcctcgt gatacgccta ttttataggt taatgtcat    5220 gataataatg gtttcttaga cgtcaggtgg cacttttcgg ggaaatgtgc gcggaacccc    5280
tatttgttta ttttctaaa tacattcaaa tatgtatccg ctcatgagac aataaccctg    5340
ataaatgctt caataatatt gaaaaaggaa gagtatgagt attcaacatt tccgtgtcgc    5400
ccttattccc ttttttgcgg cattttgcct tcctgttttt gctcacccag aaacgctggt    5460
gaaagtaaaa gatgctgaag atcagttggg tgcacgagtg ggttacatcg aactggatct    5520
caacagcggt aagatccttg agagttttcg ccccgaagaa cgttttccaa tgatgagcac    5580
ttttaaagtt ctgctatgtg gcgcggtatt atcccgtatt gacgccgggc aagagcaact    5640
```

```
cggtcgccgc atacactatt ctcagaatga cttggttgag tactcaccag tcacagaaaa    5700
gcatcttacg gatggcatga cagtaagaga attatgcagt gctgccataa ccatgagtga    5760
taacactgcg gccaacttac ttctgacaac gatcggagga ccgaaggagc taaccgcttt    5820
tttgcacaac atgggggatc atgtaactcg ccttgatcgt tgggaaccgg agctgaatga    5880
agccatacca aacgacgagc gtgacaccac gatgcctgta gcaatggcaa caacgttgcg    5940
caaactatta actggcgaac tacttactct agcttcccgg caacaattaa tagactggat    6000
ggaggcggat aaagttgcag gaccacttct gcgctcggcc cttccggctg gctggtttat    6060
tgctgataaa tctggagccg gtgagcgtgg gtctcgcggt atcattgcag cactggggcc    6120
agatggtaag ccctcccgta tcgtagttat ctacacgacg gggagtcagg caactatgga    6180
tgaacgaaat agacagatcg ctgagatagg tgcctcactg attaagcatt ggtaactgtc    6240
agaccaagtt tactcatata actttagat tgatttaaaa cttcattttt aatttaaaag    6300
gatctaggtg aagatccttt ttgataatct catgaccaaa atcccttaac gtgagttttc    6360
gttccactga gcgtcagacc ccgtagaaaa gatcaaagga tcttcttgag atccttttt    6420 tctgcgcgta atctgctgct tgcaaacaaa aaaaccaccg ctaccagcgg tggtttgttt    6480
gccggatcaa gagctaccaa ctcttttcc gaaggtaact ggcttcagca gagcgcagat    6540
accaaatact gtccttctag tgtagccgta gttaggccac cacttcaaga actctgtagc    6600
accgcctaca tacctcgctc tgctaatcct gttaccagtg gctgctgcca gtggcgataa    6660
gtcgtgtctt accgggttgg actcaagacg atagttaccg gataaggcgc agcggtcggg    6720
ctgaacgggg ggttcgtgca cacagcccag cttggagcga acgacctaca ccgaactgag    6780
atacctacag cgtgagctat gagaaagcgc cacgcttccc gaaggagaa aggcggacag    6840 gtatccggta agcggcaggg tcggaacagg agagcgcacg agggagcttc caggggaaa    6900 cgcctggtat ctttatagtc ctgtcgggtt tcgccacctc tgacttgagc gtcgatttt    6960 gtgatgctcg tcagggggc ggagcctatg gaaaaacgcc agcaacgcgg cctttttacg    7020
gttcctggcc ttttgctggc cttttgctca catgttcttt cctgcgttat ccctgattc    7080 tgtggataac cgtattaccg cctttgagtg agctgatacc gctcgccgca gccgaacgac    7140
cgagcgcagc gagtcagtga gcgaggaagc ggaagagcgc ccaatacgca aaccgcctct    7200
ccccgcgcgt tggccgattc attaatg                                        7227

<210> SEQ ID NO 28
<211> LENGTH: 118
<212> TYPE: DNA
<213> ORGANISM: Artificial Sequence
<220> FEATURE:
<223> OTHER INFORMATION: Synthetic sequence

<400> SEQUENCE: 28
ttttaaaaga aaaggggga ttggggggta cagtgcaggg gaaagaatag tagacataat       60
agcaacagac atacaaacta aagaattaca aaaacaaatt acaaaaattc aaaatttt       118
```